US010555792B2

(12) United States Patent
Kopelman et al.

(10) Patent No.: US 10,555,792 B2
(45) Date of Patent: Feb. 11, 2020

(54) DIRECT FABRICATION OF ORTHODONTIC APPLIANCES WITH ELASTICS

(71) Applicant: ALIGN TECHNOLOGY, INC., San Jose, CA (US)

(72) Inventors: Avi Kopelman, Palo Alto, CA (US); Jeeyoung Choi, Sunnyvale, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 15/202,392

(22) Filed: Jul. 5, 2016

(65) Prior Publication Data
US 2016/0310236 A1 Oct. 27, 2016

Related U.S. Application Data

(63) Continuation-in-part of application No. 14/609,970, filed on Jan. 30, 2015, which is a continuation-in-part
(Continued)

(51) Int. Cl.
*A61C 3/00* (2006.01)
*A61C 7/00* (2006.01)
(Continued)

(52) U.S. Cl.
CPC ............... *A61C 7/002* (2013.01); *A61C 7/08* (2013.01); *A61C 7/14* (2013.01); *G06F 17/50* (2013.01)

(58) Field of Classification Search
CPC .. A61C 7/002; A61C 7/08; A61C 7/14; G06F 17/50
See application file for complete search history.

(56) References Cited

U.S. PATENT DOCUMENTS

| 2,467,432 A | 4/1949 | Kesling |
| 3,237,305 A | 3/1966 | Hegedus |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Nicholas D Lucchesi
(74) *Attorney, Agent, or Firm* — Wilson Sonsini Goodrich & Rosati

(57) ABSTRACT

Improved orthodontic appliances, along with related systems and methods, are provided. In one aspect, an appliance includes a shell having a plurality of cavities shaped to receive teeth, a discontinuity formed in the shell, and an elastic member positioned to interact with the discontinuity. In another aspect, an appliance includes a plurality of discrete shell segments joined by an elastic material to form a single appliance shell. In another aspect, an appliance includes a shell having an exterior layer and an interior layer having a stiffness less than a stiffness of the exterior layer, and a discontinuity formed in the exterior layer. In another aspect, an appliance includes a shell comprising an interior surface and an exterior surface, and an elastic coating covering at least a portion of one or more of the interior surface or exterior surface of the shell.

21 Claims, 65 Drawing Sheets

Related U.S. Application Data of application No. 14/610,027, filed on Jan. 30, 2015, which is a continuation-in-part of application No. 14/610,060, filed on Jan. 30, 2015, which is a continuation-in-part of application No. 14/610,108, filed on Jan. 30, 2015.

(60) Provisional application No. 61/934,657, filed on Jan. 31, 2014, provisional application No. 61/969,023, filed on Mar. 21, 2014, provisional application No. 61/015,170, filed on Jun. 20, 2014, provisional application No. 62/015,217, filed on Jun. 20, 2014, provisional application No. 62/189,269, filed on Jul. 7, 2015, provisional application No. 62/189,272, filed on Jul. 7, 2015, provisional application No. 62/189,279, filed on Jul. 7, 2015, provisional application No. 62/189,284, filed on Jul. 7, 2015.

(51) Int. Cl.
*A61C 7/08* (2006.01)
*A61C 7/14* (2006.01)
*G06F 17/50* (2006.01)

(56) References Cited

U.S. PATENT DOCUMENTS

| | | |
|---|---|---|
| 3,334,417 A | 8/1967 | Spengeman |
| 3,407,500 A | 10/1968 | Kesling |
| 3,593,421 A | 7/1971 | Brader |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,762,050 A | 10/1973 | Dal Pont |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 3,988,832 A | 11/1976 | Wallshein |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,413,978 A | 11/1983 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |

(56) References Cited

U.S. PATENT DOCUMENTS

| | | | |
|---|---|---|---|
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,178,967 B1 | 1/2001 | Barnes, Sr. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,293,790 B1 | 9/2001 | Hilliard | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,386,864 B1 | 5/2002 | Kuo | |
| 6,398,548 B1 | 6/2002 | Muhammad et al. | |
| 6,402,707 B1 | 6/2002 | Ernst | |
| 6,450,807 B1 | 9/2002 | Chishti et al. | |
| 6,454,565 B2 | 9/2002 | Phan et al. | |
| 6,471,511 B1 | 10/2002 | Chishti et al. | |
| 6,482,298 B1 | 11/2002 | Bhatnagar | |
| 6,524,101 B1 | 2/2003 | Phan et al. | |
| 6,554,611 B2 | 4/2003 | Shishti et al. | |
| 6,572,372 B1 | 6/2003 | Phan et al. | |
| 6,629,840 B2 | 10/2003 | Chishti et al. | |
| 6,702,575 B2 | 3/2004 | Hilliard | |
| 6,705,863 B2 | 3/2004 | Phan et al. | |
| 6,722,880 B2 | 4/2004 | Chishti et al. | |
| 6,830,450 B2 | 12/2004 | Knopp et al. | |
| 7,077,646 B2 | 7/2006 | Hilliard | |
| 7,553,157 B2 | 6/2009 | Abolfathi et al. | |
| 7,637,262 B2 | 12/2009 | Bailey | |
| 7,810,503 B2 | 10/2010 | Magnin | |
| 7,831,322 B2 | 11/2010 | Liu et al. | |
| 7,878,801 B2 | 2/2011 | Abolfathi et al. | |
| 7,892,474 B2 | 2/2011 | Shkolnik et al. | |
| 8,118,592 B2 | 2/2012 | Tortorici | |
| 8,439,672 B2 | 5/2013 | Matov et al. | |
| 8,439,674 B2 | 5/2013 | Li et al. | |
| 8,444,412 B2 | 5/2013 | Baughman et al. | |
| 8,517,726 B2 | 8/2013 | Kakavand et al. | |
| 8,758,009 B2 | 6/2014 | Chen et al. | |
| 8,858,226 B2 * | 10/2014 | Phan | A61C 7/00 433/6 |
| 8,899,976 B2 | 12/2014 | Chen et al. | |
| 8,899,977 B2 | 12/2014 | Cao et al. | |
| 9,655,691 B2 | 5/2017 | Li et al. | |
| 9,795,460 B2 * | 10/2017 | Martz | A61C 7/08 |
| 10,299,894 B2 | 5/2019 | Tanugula et al. | |
| 2001/0041320 A1 | 11/2001 | Phan et al. | |
| 2002/0006597 A1 | 1/2002 | Andreiko et al. | |
| 2002/0051951 A1 | 5/2002 | Chishti et al. | |
| 2002/0187451 A1 | 12/2002 | Phan et al. | |
| 2002/0192617 A1 * | 12/2002 | Phan | A61C 7/00 433/6 |
| 2003/0009252 A1 | 1/2003 | Pavlovskaia et al. | |
| 2003/0139834 A1 | 7/2003 | Nikolskiy et al. | |
| 2003/0190575 A1 * | 10/2003 | Hilliard | A61C 7/00 433/6 |
| 2003/0198911 A1 * | 10/2003 | Knopp | A61C 7/00 433/6 |
| 2003/0198912 A1 | 10/2003 | Mah | |
| 2003/0207224 A1 | 11/2003 | Lotte | |
| 2003/0224311 A1 | 12/2003 | Cronauer | |
| 2004/0067463 A1 | 4/2004 | Rosenberg | |
| 2004/0128010 A1 | 7/2004 | Pavlovskaia et al. | |
| 2004/0166462 A1 * | 8/2004 | Phan | A61C 7/146 433/24 |
| 2004/0209218 A1 | 10/2004 | Chishti et al. | |
| 2004/0229185 A1 | 11/2004 | Knopp | |
| 2005/0048433 A1 | 3/2005 | Hilliard | |
| 2005/0055118 A1 | 3/2005 | Nikolskiy et al. | |
| 2005/0100853 A1 * | 5/2005 | Tadros | A61C 19/063 433/6 |
| 2005/0186524 A1 | 8/2005 | Abolfathi et al. | |
| 2005/0186526 A1 | 8/2005 | Stewart et al. | |
| 2005/0208450 A1 | 9/2005 | Sachdeva et al. | |
| 2005/0233276 A1 | 10/2005 | Kopelman et al. | |
| 2006/0068353 A1 | 3/2006 | Abolfathi et al. | |
| 2006/0078841 A1 | 4/2006 | Desimone et al. | |
| 2006/0093992 A1 * | 5/2006 | Wen | A61C 9/002 433/213 |
| 2006/0199142 A1 | 9/2006 | Liu et al. | |
| 2006/0199153 A1 * | 9/2006 | Liu | A61C 8/0089 433/213 |
| 2007/0231765 A1 | 10/2007 | Phan et al. | |
| 2007/0275340 A1 | 11/2007 | Kopelman et al. | |
| 2008/0050692 A1 * | 2/2008 | Hilliard | A61C 7/002 433/24 |
| 2008/0254402 A1 * | 10/2008 | Hilliard | A61C 7/08 433/24 |
| 2008/0268400 A1 * | 10/2008 | Moss | A61C 7/00 433/24 |
| 2009/0014013 A1 | 1/2009 | Magnin | |
| 2009/0061375 A1 | 3/2009 | Yamamoto et al. | |
| 2009/0098500 A1 | 4/2009 | Diaz Rendon | |
| 2009/0191502 A1 * | 7/2009 | Cao | A61C 7/08 433/24 |
| 2010/0068671 A1 | 3/2010 | Kakavand et al. | |
| 2010/0075268 A1 | 3/2010 | Duran Von Arx | |
| 2010/0086890 A1 | 4/2010 | Kuo | |
| 2010/0092905 A1 | 4/2010 | Martin | |
| 2010/0138025 A1 | 6/2010 | Morton et al. | |
| 2010/0151404 A1 * | 6/2010 | Wu | A61C 7/00 433/24 |
| 2010/0279245 A1 | 11/2010 | Navarro | |
| 2011/0039223 A1 * | 2/2011 | Li | A61C 7/08 433/6 |
| 2011/0185525 A1 | 8/2011 | Stapelbroek et al. | |
| 2011/0269091 A1 | 11/2011 | Li et al. | |
| 2011/0269092 A1 * | 11/2011 | Kuo | A61C 7/002 433/6 |
| 2011/0281229 A1 | 11/2011 | Abolfathi | |
| 2012/0082950 A1 | 4/2012 | Li et al. | |
| 2012/0150494 A1 * | 6/2012 | Anderson | A61C 7/002 703/1 |
| 2012/0270173 A1 | 10/2012 | Pumphrey et al. | |
| 2012/0282565 A1 | 11/2012 | Adell | |
| 2013/0078594 A1 | 3/2013 | Leslie-Martin et al. | |
| 2013/0089828 A1 * | 4/2013 | Borovinskih | A61C 7/08 433/6 |
| 2013/0095446 A1 | 4/2013 | Andreiko et al. | |
| 2013/0122448 A1 * | 5/2013 | Kitching | A61C 7/002 433/24 |
| 2013/0157213 A1 | 6/2013 | Arruda | |
| 2013/0204583 A1 | 8/2013 | Matov et al. | |
| 2013/0244194 A1 | 9/2013 | Bergersen | |
| 2013/0302742 A1 | 11/2013 | Li et al. | |
| 2013/0323665 A1 | 12/2013 | Dinh et al. | |
| 2014/0011162 A1 | 1/2014 | Zegarelli | |
| 2014/0178829 A1 | 6/2014 | Kim | |
| 2014/0193767 A1 | 7/2014 | Li et al. | |
| 2014/0300676 A1 | 10/2014 | Miller et al. | |
| 2014/0363779 A1 | 12/2014 | Kopelman et al. | |
| 2015/0157421 A1 | 6/2015 | Martz et al. | |
| 2015/0216627 A1 | 8/2015 | Kopelman | |
| 2015/0238283 A1 * | 8/2015 | Tanugula | A61C 7/002 433/6 |
| 2015/0257856 A1 | 9/2015 | Martz et al. | |
| 2015/0265376 A1 | 9/2015 | Kopelman | |
| 2015/0305832 A1 | 10/2015 | Patel | |
| 2015/0366637 A1 * | 12/2015 | Kopelman | A61C 7/08 433/6 |
| 2015/0366638 A1 | 12/2015 | Kopelman et al. | |

(56) References Cited

U.S. PATENT DOCUMENTS

| | | | |
|---|---|---|---|
| 2016/0081769 | A1 | 3/2016 | Kimura et al. |
| 2016/0128803 | A1 | 5/2016 | Webber et al. |
| 2016/0135925 | A1* | 5/2016 | Mason .................. A61C 7/002 703/2 |
| 2017/0007367 | A1* | 1/2017 | Li ......................... B29C 64/386 |
| 2017/0007368 | A1* | 1/2017 | Boronkay .............. A61C 7/002 |
| 2017/0007371 | A1* | 1/2017 | Robichaud .............. A61C 7/08 |
| 2017/0100210 | A1* | 4/2017 | Wen ........................ A61C 7/002 |
| 2017/0367792 | A1* | 12/2017 | Raby ....................... A61C 7/002 |
| 2017/0367793 | A1* | 12/2017 | Veis ......................... A61C 7/08 |
| 2018/0000564 | A1* | 1/2018 | Cam ........................ A61C 7/08 |

FOREIGN PATENT DOCUMENTS

| | | |
|---|---|---|
| AU | 5598894 A | 6/1994 |
| CA | 1121955 A | 4/1982 |
| CN | 1575782 A | 2/2005 |
| CN | 1655731 A | 8/2005 |
| CN | 1684638 A | 10/2005 |
| CN | 101188981 A | 5/2008 |
| CN | 101404952 A | 4/2009 |
| CN | 202589687 U | 12/2012 |
| CN | 103340690 A | 10/2013 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1806064 A1 | 7/2007 |
| EP | 2000110 A2 | 12/2008 |
| EP | 2138124 A1 | 12/2009 |
| ES | 463897 A1 | 1/1980 |
| FR | 2369828 A1 | 6/1978 |
| FR | 2652256 A1 | 3/1991 |
| FR | 2872406 A1 | 1/2006 |
| GB | 1550777 A | 8/1979 |
| GB | 15500777 | 8/1979 |
| JP | S5358191 A | 5/1978 |
| JP | H0428359 A | 1/1992 |
| JP | 08508174 | 9/1996 |
| JP | H08508174 A | 9/1996 |
| JP | 2004016632 A | 1/2004 |
| JP | 2007260158 A | 10/2007 |
| JP | 4184427 B1 | 11/2008 |
| JP | 2013123626 A | 6/2013 |
| KR | 200465679 Y1 | 3/2013 |
| TW | M464148 U | 11/2013 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0180764 A1 | 11/2001 |
| WO | WO-2006044012 A1 | 4/2006 |
| WO | WO-2006096558 A2 | 9/2006 |
| WO | WO-2007110071 A1 | 10/2007 |
| WO | WO-2008073766 A2 | 6/2008 |
| WO | WO-2015114450 A1 | 8/2015 |
| WO | WO-2015140614 A1 | 9/2015 |
| WO | WO-2015193709 A1 | 12/2015 |
| WO | WO-2015193710 A1 | 12/2015 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237- 253 (1984).

Biggerstaff, "Computerized Diagnostic Setups and Simulations," Angle Orthod., 40(1):28- 36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

(56) References Cited

OTHER PUBLICATIONS

Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Carbon3D. Clip Technology. A new appraoch to 3D printing. 2015. http://carbon3d.com/ Accessed Jul. 1, 2015. 1 page.
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Composite material. Wikipedia. Last modified Jun. 22, 2015. https://en.wikipedia.org/wiki/Composite_material. 3 pages.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Desimone. What if 3D printing was 100% faster? TEDtalk. Mar. 2015. http://www.ted.com/talks/joe_desimone_what_if_3d_printing_was_25x_faster. 11 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese lnformatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98-Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Halterman. A path to the future—continuous composite 3D printing. Nov. 12, 2014. http://www.3dprinterworld.com/article/path-future-continuous-composite-3d-printing. 4 pages.
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hipolite. Helios One 3D Printer—New Heliolithography Technology Could Eventually Replace SLA and FDM. Jul. 2, 2014. http://3dprint.com/7958/orange-maker-helio-one-3d/ 28 pages.
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
International search report and written opinion dated May 19, 2015 for PCT/IB2015/000112.
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.

(56) References Cited

OTHER PUBLICATIONS

Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Objet Geometries. Wikipedia. Last modified Jul. 17, 2014. https://en.wikipedia.org/wiki/Objet_Geometries. 3 pages.
Orange Maker. High resolution 3D printing technology. 2015. http://www.orangemaker.com/. Accessed Jul. 1, 2015. 9 pages.
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Rapid prototyping. Protosys Technologies. 2005. http://www.protosystech.com/rapid-prototyping.htm. Accessed Jul. 1, 2015. 2 pages.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.

(56) References Cited

OTHER PUBLICATIONS

Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Orange Maker Spins the Plate to Make Better 3D Prints. Newloop Tech and Gadgets. YouTube. Jul. 11, 2014. https://www.youtube.com/watch?v=MpzPWURWfZk. 2 pages.
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Appl. No. 14/610,027, filed Jan. 30, 2015.
U.S. Appl. No. 14/610 060, filed Jan. 30, 2015.
U.S. Appl. No. 14/610,108, filed Jan. 30, 2015.
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
Written opinion of the international preliminary examining authority dated Jan. 14, 2016 for PCT/IB2015/000112.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).
International search report and written opinion dated Apr. 23, 2015 for PCT/IB2015/000104.
International search report and written opinion dated May 13, 2015 for PCT/IB2015/000108.
International search report and written opinion dated Jul. 31, 2015 for PCT/IB2015/000106.

* cited by examiner

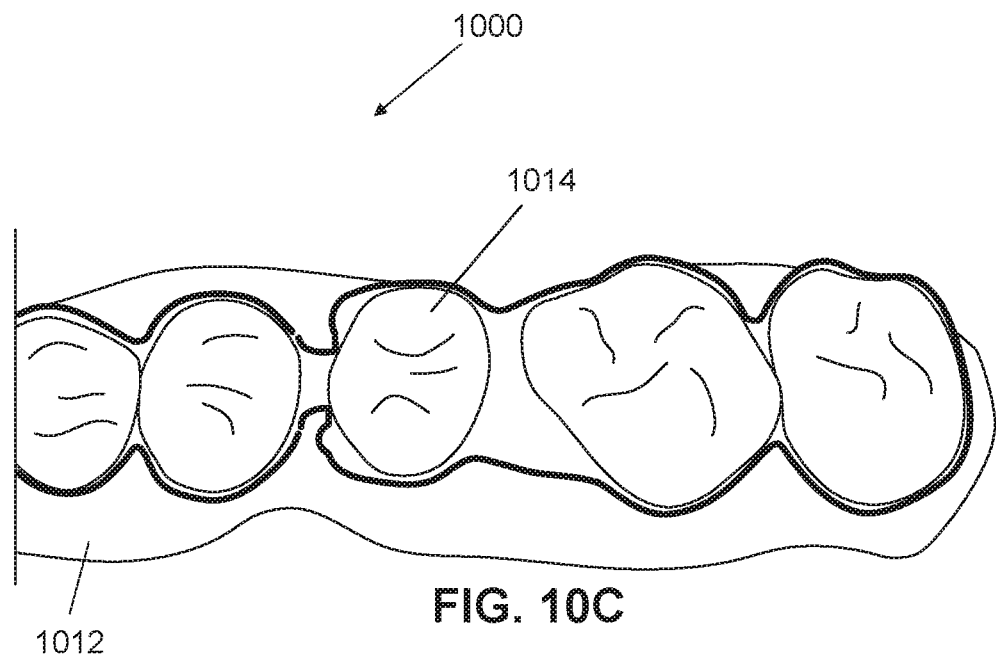
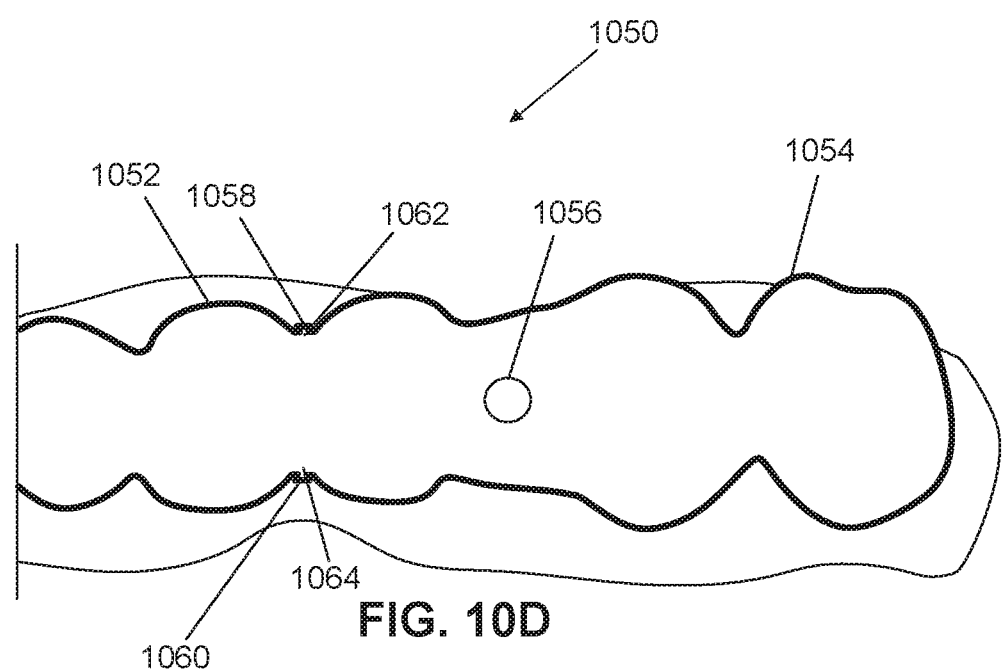

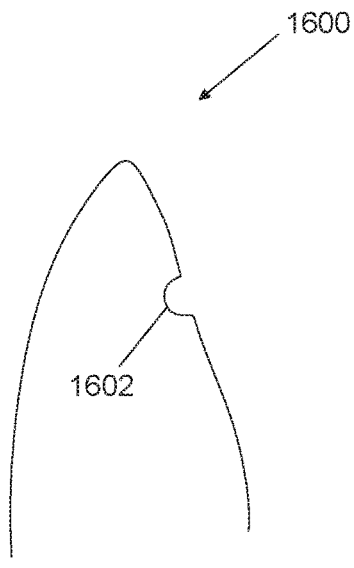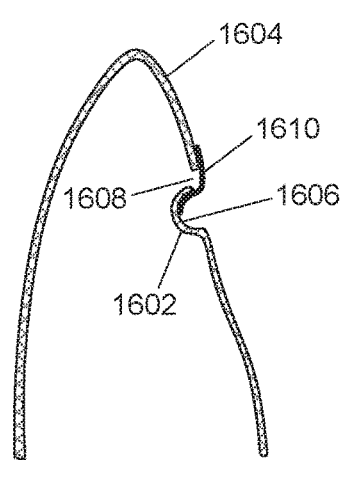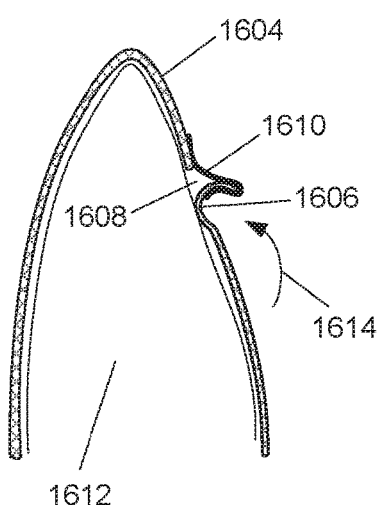
FIG. 16A  FIG. 16B  FIG. 16C
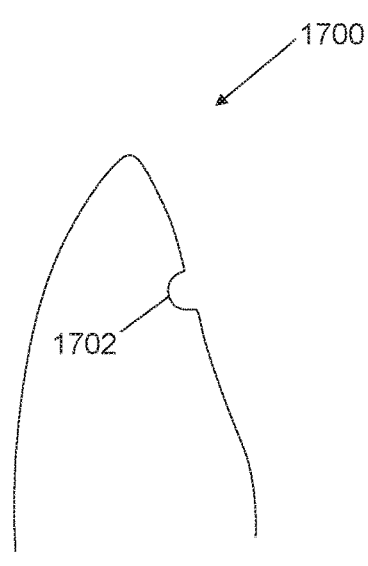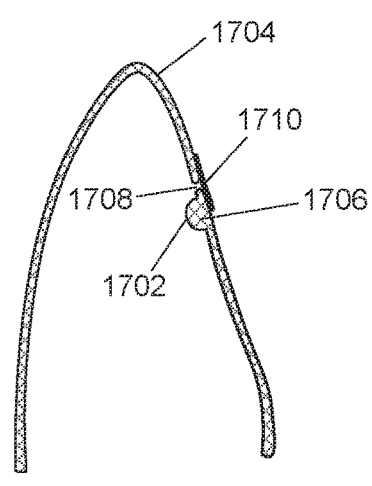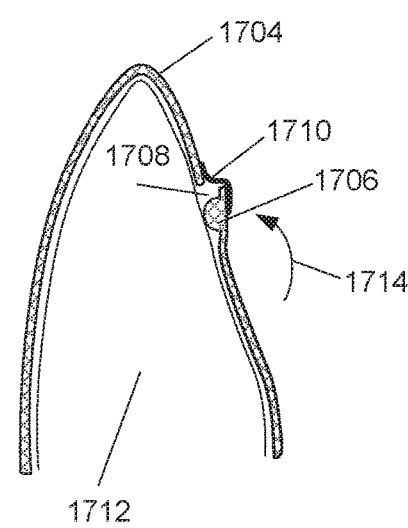
FIG. 17A  FIG. 17B  FIG. 17C

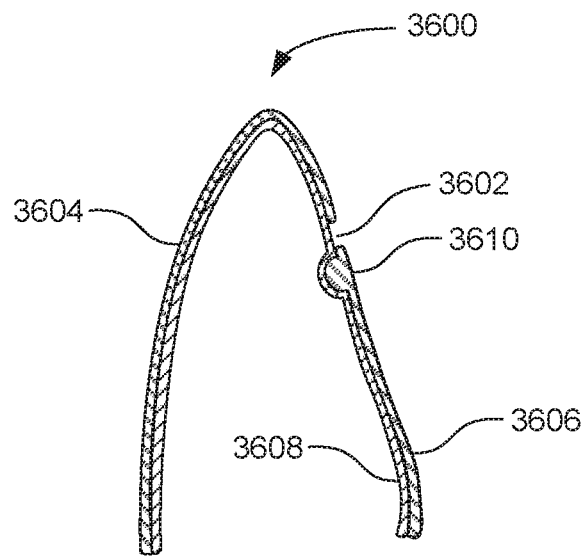
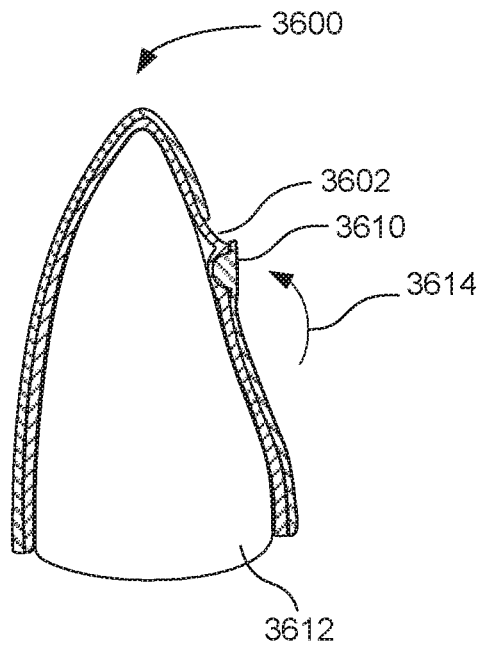
FIG. 36A  FIG. 36B
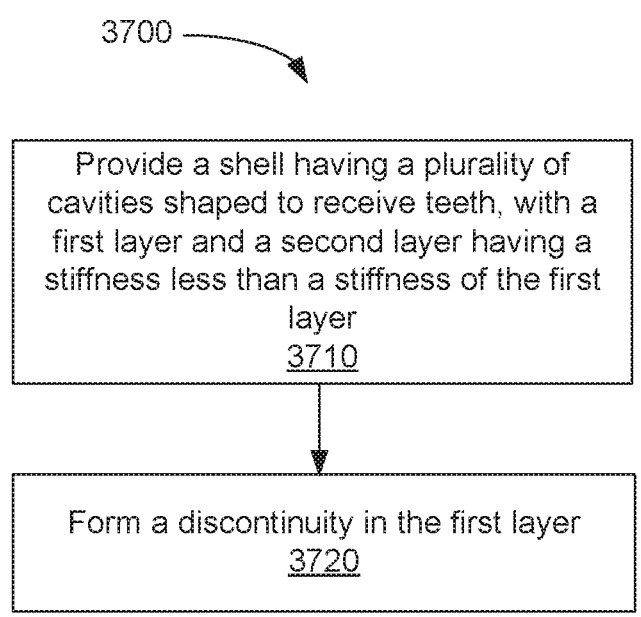
FIG. 37

DIRECT FABRICATION OF ORTHODONTIC APPLIANCES WITH ELASTICS

CROSS-REFERENCE

This application is a continuation-in-part of U.S. application Ser. No. 14/609,970, filed Jan. 30, 2015, which claims the benefit of U.S. Provisional Application No. 61/934,657, filed Jan. 31, 2014; a continuation-in-part of U.S. application Ser. No. 14/610,027, filed Jan. 30, 2015, which claims the benefit of U.S. Provisional Application No. 61/969,023, filed Mar. 21, 2014; a continuation-in-part of U.S. application Ser. No. 14/610,060, filed Jan. 30, 2015, which claims the benefit of U.S. Provisional Application No. 62/015,170, filed Jun. 20, 2014; a continuation-in-part of U.S. application Ser. No. 14/610,108, filed Jan. 30, 2015, which claims the benefit of U.S. Provisional Application No. 62/015,217, filed Jun. 20, 2014; and claims the benefit of U.S. Provisional Application No. 62/189,269, filed Jul. 7, 2015, U.S. Provisional Application No. 62/189,272, filed Jul. 7, 2015, U.S. Provisional Application No. 62/189,279, filed Jul. 7, 2015, and U.S. Provisional Application No. 62/189,284, filed Jul. 7, 2015, the disclosures of each of which are incorporated herein by reference in their entirety.

BACKGROUND

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner. The appliance is configured to exert force on one or more teeth in order to effect desired tooth movements. The application of force can be periodically adjusted by the practitioner (e.g., by altering the appliance or using different types of appliances) in order to incrementally reposition the teeth to a desired arrangement.

In some instances, however, current orthodontic appliances may not be able to effectively generate the forces needed to achieve the desired tooth repositioning, or may not afford sufficient control over the forces applied to the teeth. The prior orthodontic approaches may often employ a single appliance shell with homogeneous and/or continuous material properties, which can provide less than ideal movement and comfort. Additionally, the rigidity of some existing appliances may interfere with the ability of the appliance to be coupled to the patient's teeth and may increase patient discomfort.

SUMMARY

Improved orthodontic appliances, as well as related systems and methods, are provided. The appliances described herein provide enhanced control over forces exerted onto the teeth, thus enabling improved orthodontic treatment procedures. In some embodiments, the appliances described herein are manufactured using direct fabrication techniques enabling facile production of the complex appliance structures and heterogeneous material properties described herein.

In some embodiments, an orthodontic appliance configured to be worn on a patient's teeth includes a discontinuity and an elastic member interacting with or configured to interact with the discontinuity.

In some embodiments, an orthodontic appliance configured to be worn on a patient's teeth includes a plurality of discrete shell segments joined by an elastic material.

In some embodiments, an orthodontic appliance configured to be worn on a patient's teeth includes a shell having an exterior layer and an interior layer, with the exterior layer having a greater stiffness than the interior layer, and a discontinuity formed in the exterior layer. When placed on a patient's teeth, the interaction of the interior layer with the discontinuity can exert forces on the underlying teeth to elicit one or more desired tooth movements.

In some embodiments, an orthodontic appliance includes a thin, flexible shell covered by an elastic coating. The properties of the elastic coating may dictate the overall properties of the appliance, such as the stiffness of the appliance. When worn by a patient, the appliance may apply forces onto the underlying teeth via the elastic coating in order to reposition the teeth.

Accordingly, in one aspect, an orthodontic appliance is provided. The appliance includes a shell having a plurality of cavities shaped to receive teeth and a discontinuity formed in the shell. In some embodiments, an elastic member is directly coupled to the shell at first and second attachment points and positioned to interact with the discontinuity.

In another aspect, an orthodontic appliance includes a plurality of discrete shell segments, each including one or more cavities shaped to receive at least portions of teeth. The discrete shell segments are joined by an elastic material to form a single appliance shell.

In another aspect, an orthodontic appliance can include a shell having a plurality of cavities shaped to receive a patient's teeth. The shell can include an exterior layer and an interior layer having a stiffness less than that of the exterior layer. A discontinuity can be formed in the exterior layer.

In another aspect, an orthodontic appliance includes a shell having a plurality of cavities shaped to receive a patient's teeth and comprising an interior surface and an exterior surface, and an elastic coating covering at least a portion of one or more of the interior surface or exterior surface of the shell. A stiffness of a portion of the orthodontic appliance corresponding to the portion of the shell covered by the elastic coating is determined by a stiffness of the elastic coating.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10C illustrates the appliance of FIG. 10B after tooth repositioning has occurred;

FIG. 10D illustrates an appliance divided into discrete shell segments, in accordance with some embodiments.

FIG. 16A is a cross-sectional view of the internal surface profile of an orthodontic appliance including a protrusion, in accordance with some embodiments.

FIG. 16B is a cross-sectional view of a shell of the appliance of FIG. 16A;

FIG. 16C illustrates the shell of FIG. 16B when placed over a tooth;

FIG. 17A is a cross-sectional view of the internal surface profile of another exemplary orthodontic appliance including a protrusion, in accordance with some embodiments.

FIG. 17B is a cross-sectional view of a shell of the appliance of FIG. 17A;

FIG. 17C illustrates the shell of FIG. 17B when placed over a tooth;

FIG. 36A illustrates a layered orthodontic appliance having a discontinuity, in accordance with some embodiments.

FIG. 36B illustrates the appliance of FIG. 36A when placed over a patient's teeth, in accordance with some embodiments.

FIG. 37 illustrates a method for fabricating an orthodontic appliance, in accordance with some embodiments.

DETAILED DESCRIPTION

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein A and/or B encompasses one or more of A or B, and combinations thereof such as A and B.

The orthodontic appliances described herein, along with related systems and methods, can be employed as part of an orthodontic treatment procedure in order to reposition one or more teeth, maintain a current position of one or more teeth, or suitable combinations thereof.

Figure 1A:
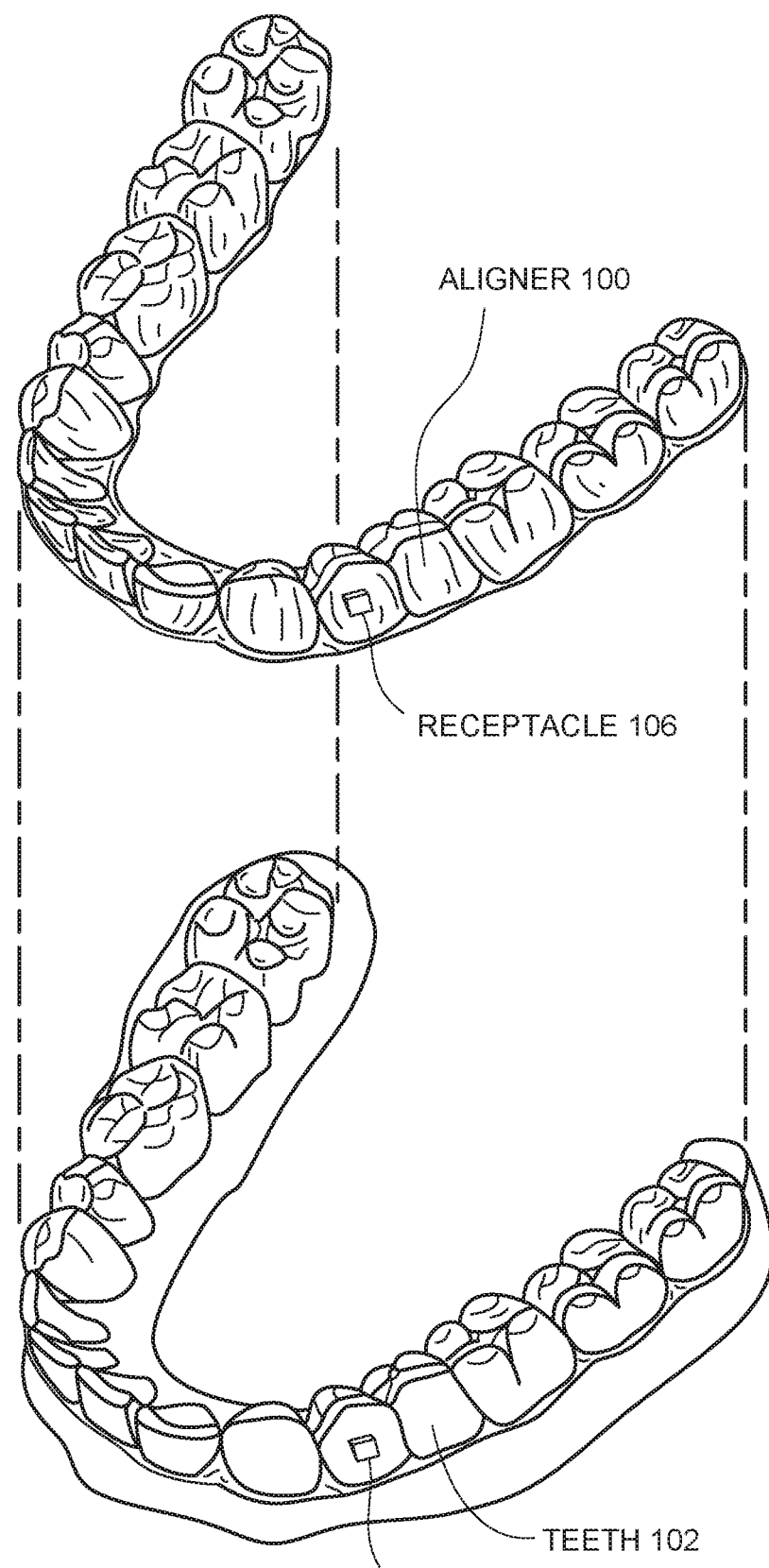
FIG. 1A illustrates a tooth repositioning appliance, in accordance with some embodiments.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some instances, a physical appliance is directly fabricated, e.g., using additive manufacturing fabrication techniques, from a digital model of an appliance, as discussed further herein. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments 104 or other anchoring elements on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
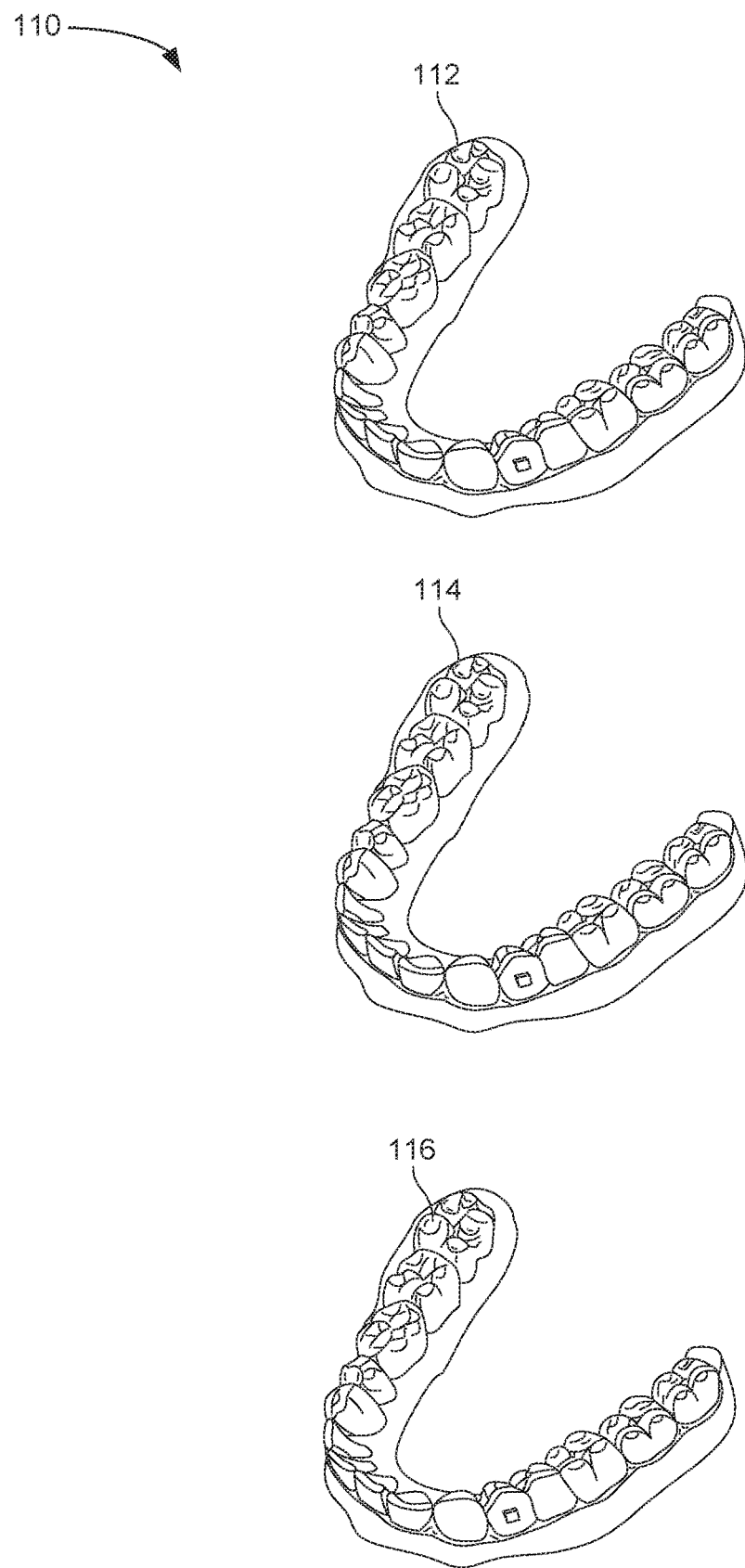
FIG. 1B illustrates a tooth repositioning system, in accordance with some embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
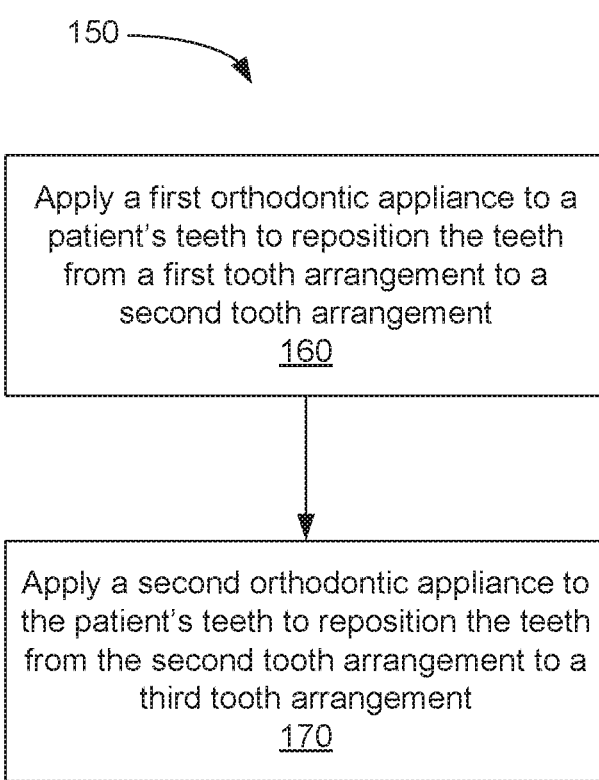
FIG. 1C illustrates a method of orthodontic treatment using a plurality of appliances, in accordance with some embodiments.

FIG. 1C illustrates a method 150 of orthodontic treatment using a plurality of appliances, in accordance with some embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Although the above steps show a method 150 of orthodontic treatment using a plurality of appliances in accordance with embodiments, a person of ordinary skill in the art will recognize many variations based on the teaching described herein. Some of the steps may comprise sub-steps. Many of the steps may be repeated as often as beneficial to the treatment. One or more steps of the method 150 may be applied to any suitable orthodontic appliance, such as the embodiments described herein.

Orthodontic Appliance with Elastics and Discontinuity

In some embodiments, orthodontic appliances of the present disclosure include a shell shaped to receive the patient's teeth, with the geometry of the shell being selected to exert appropriate forces on the teeth in order to achieve the desired positioning of teeth. In some embodiments, the orthodontic appliances described herein utilize one or more elastic members (also referred to herein as "elastics") acting in conjunction with one or more discontinuities formed in the shell to apply orthodontic forces to the teeth. The geometry and configuration of the one or more discontinuities and/or the one or more elastic members can be selected to control the magnitude and direction of the applied forces. In contrast to existing approaches, in which one or more elastics are fastened to the teeth or to one or more attachments mounted onto the teeth, the appliances disclosed herein employ one or more elastic members directly coupled to the shell and exerting force on the teeth via interaction with the discontinuity. Such appliances may be used to generate larger and/or more precisely controlled forces for orthodontic applications. Furthermore, the geometry and configuration of the one or more discontinuities and/or the one or more elastics can be used to adjust the local compliance of the appliance, thus improving appliance fit and reducing patient discomfort. Additionally, by locally controlling the compliance of the shell, the techniques described herein can be used to ensure that some or all points on the appliance intended to exert forces on the teeth (also known as "active points") maintain sufficient contact with the teeth throughout the treatment process, thus improving the precision and efficiency of repositioning. The amount of force exerted on the teeth at each active point can vary based on the compliance of the shell, as well as on the configuration of the discontinuities and/or elastics.

Thus, in one aspect, an orthodontic appliance can include a shell having a plurality of cavities shaped to receive teeth, and a discontinuity formed in the shell. The appliance also includes an elastic member having a first portion directly coupled to the shell at a first attachment point and a second portion directly coupled to the shell at a second attachment point. The elastic member can be positioned to interact with the discontinuity. For example, the elastic member can interact with regions of the shell on opposing sides of the discontinuity, thereby accommodating changes in configuration and/or size of the discontinuity during mounting of the appliance onto teeth and/or during resulting repositioning of one or more teeth.

An orthodontic appliance can be configured to accommodate an attachment coupled to a tooth. A portion of the elastic member between the first and second attachment points can be engaged or engageable with the attachment.

An orthodontic appliance can be configured to reduce one or more spaces between teeth. For example, an orthodontic appliance can include one or more elastic members and one or more discontinuities that are configured to elicit a movement of the teeth that reduces the size of an interproximal space between the teeth when the appliance is worn on the teeth.

Any suitable configuration and/or number of discontinuities can be employed. For example, the discontinuity can be or include an aperture in the shell, a cut in the shell, or a deformation of the shell.

In some embodiments, a portion of the elastic member between the first and second attachment points extends along a surface of the shell such that the portion spans a plurality of the cavities. The discontinuity can include a plurality of openings in the shell disposed between the first and second attachment points. Each of the plurality of openings can be adjacent to or near an interproximal region of the teeth when the appliance is worn on the teeth.

In some embodiments, a mesial-distal arch length of the shell is shorter or adapted to be shorter when the appliance is not being worn on the teeth and is longer or adapted to be longer when the appliance is being worn on the teeth. For example, the orthodontic appliance can include one or more discontinuities and one or more elastics such that the arch length of the shell depends on whether or not the appliance is being worn on the teeth. As another example, the discontinuity can divide the shell into discrete segments with one or more elastics coupling the segments, such that the segments are movable relative to each other to enable the arch length of the shell to change depending on whether or not the appliance is being worn on the teeth.

The orthodontic appliance may include one or more elastics that span a discontinuity. For example, an orthodontic appliance can include a discontinuity in the form of an elongate opening in the shell, with a portion of the elastic member between the first and second attachment points spanning the elongate opening.

In some embodiments, the first and second attachment points are disposed on the shell, such that a portion of the elastic member between the first and second attachment points is adjacent to or near an interproximal region of the teeth when the appliance is worn on the teeth. For example, the first attachment point can be disposed on a lingual surface of the shell and the second attachment point can be disposed on a buccal surface of the shell. In another example, the first and second attachment points can each be disposed on a lingual surface of the shell. As a further example, the first and second attachment points can each be disposed on a buccal surface of the shell.

In some embodiments, an appliance includes one or more guide features formed in the shell and configured to guide relative movement between portions of the shell, wherein the relative movement results from a force applied by the elastic member. The one or more guide features can affect at least one of magnitude or direction of the force applied by the elastic member. In some instances, the one or more guide features can include telescopic features formed in the shell.

The appliance may include one or more retention features formed in the shell and configured to retain a portion of the elastic member at a specified position relative to the shell. The one or more retention features can include a groove formed in the shell, with the portion of the elastic member retained within the groove.

In some embodiments, at least one of the first and second attachment points includes a hook formed in the shell, the hook being configured to fasten the elastic member to the shell. A portion of the elastic member can extend between the first and second attachment points.

In some embodiments, the discontinuity forms a flap in a location of the shell configured to accommodate an attachment mounted on a tooth received or receivable within a cavity of the shell. A portion of the elastic member between the first and second attachment points can extend around the flap to engage the attachment, such that the elastic member imparts a force directly on the attachment. As another example, a portion of the elastic member extending between the first and second attachment points can span the flap, such that the elastic member imparts a force on the attachment through the flap.

In another aspect, a method of orthodontic treatment includes providing an orthodontic appliance including a shell having a plurality of cavities shaped to receive teeth and a discontinuity formed in the shell. An elastic member can be directly coupled to the shell in a position interacting with the discontinuity, wherein a first portion of the elastic member is directly coupled to the shell at a first attachment point and a second portion of the elastic member is directly coupled to the shell at a second attachment point. The appliance can be placed on a patient's teeth. Force can be applied to the teeth via the interaction of the elastic member with the discontinuity.

In some embodiments, the elastic member and the discontinuity are configured to elicit a movement of the teeth reducing the size of an interproximal space between the teeth. The discontinuity can be an aperture in the shell, a cut in the shell, or a deformation of the shell. In some instances, a portion of the elastic member between the first and second attachment points extends along a surface of the shell such that the portion spans a plurality of cavities.

In some embodiments, a mesial-distal arch length of the shell is shorter or adapted to be shorter when the appliance is not being worn on the teeth and is longer or adapted to be longer when the appliance is being worn on the teeth. One or more guide features can be formed in the shell and configured to guide movement of a portion of the shell, wherein the movement results from a force applied to the portion by the elastic member.

In another aspect, an orthodontic system includes a plurality of orthodontic appliances each having a shell including a plurality of cavities shaped to receive teeth. The appliances can be adapted to be successively worn by a patient to move one or more teeth from a first arrangement to a second arrangement. At least one of the appliances includes a discontinuity formed in the shell and an elastic member positioned to interact with the discontinuity. The elastic member can have a first portion directly coupled to the shell at a first attachment point and a second portion directly coupled to the shell at a second attachment point.

In some embodiments, the discontinuity includes an elongate opening in the shell, with a portion of the elastic member between the first and second attachment points spanning the elongate opening. The first and second attachment points can be disposed on the shell, such that a portion of the elastic member between the first and second attachment points is adjacent to or near an interproximal region of the teeth when the appliance is worn on the teeth.

In some embodiments, one or more retention features are formed in the shell and configured to retain a portion of the elastic member at a specified position relative to the shell. In some instances, at least one of the first and second attachment points includes a hook formed in the shell, the hook being configured to fasten the elastic member to the shell.

In some embodiments, a portion of the elastic member extends between the first and second attachment points. The discontinuity can form a flap in a location of the shell configured to accommodate an attachment mounted on a tooth received or receivable within a cavity of the shell.

In another aspect, a method of designing an orthodontic appliance is provided. The method can comprise generating a digital model of the orthodontic appliance. The digital model can comprises a digital representation of a shell including a plurality of cavities shaped to receive teeth, a digital representation of a discontinuity formed in the shell, and a digital representation of an elastic member. Optionally, the elastic member can have a first portion directly coupled to the shell at a first attachment point and a second portion directly coupled to the shell at a second attachment point. The elastic member can be positioned to interact with the discontinuity. The method can further comprise generating instructions for fabricating the orthodontic appliance comprising the shell, the discontinuity, and the elastic member by a direct fabrication technique, based on the digital model.

Various types of direct fabrication techniques are suitable for use with the embodiments herein. For example, the direct fabrication technique can comprise one or more of: vat photopolymerization, material jetting, binder jetting, material extrusion, powder bed fusion, sheet lamination, or directed energy deposition. In some embodiments, the direct fabrication technique comprises a continuous direct fabrication technique. Optionally, the direct fabrication technique comprises a multi-material direct fabrication technique.

The use of direct fabrication as discussed herein permits the various components of the orthodontic appliance to be fabricated concurrently in a single manufacturing step, without requiring additional steps to form and/or couple additional components. For example, in some embodiments, the instructions are configured to cause a fabrication machine to form the discontinuity concurrently with the shell. The instructions can be configured to cause a fabrication machine to concurrently fabricate the shell and the discontinuity using the direct fabrication technique. The instructions can be configured to cause the fabrication machine to couple the elastic member to the shell after fabricating the shell and the discontinuity. The digital model can further comprise a digital representation of an interface shaped to facilitate coupling of the elastic member to the shell. As another example, the instructions can be configured to cause a fabrication machine to form the elastic member concurrently with the shell.

In some embodiments, the instructions are configured to cause a fabrication machine to fabricate the shell from a first material and the elastic member from a second material. The first material can have a greater stiffness than the second material.

In some embodiments, the discontinuity includes an aperture or cut in the shell. A portion of the elastic member can span the aperture or cut.

In some embodiments, the digital model further comprises a digital representation of one or more auxiliary components. The one or more auxiliary components can include one or more of a channel, a guide feature, a fastening feature, a flap, a receptacle, a retention feature, a telescoping feature, an interproximal feature, or a biasing feature. Optionally, the instructions are configured to cause a fabrication machine to form the one or more auxiliary components concurrently with the shell. Alternatively or in combination, the digital model can further include a digital representation of an interface shaped to facilitate coupling of the elastic member or the one or more auxiliary components to the shell, and the elastic member or the one more auxiliary components can be coupled to the shell in a separate manufacturing step via the interface.

In another aspect, a method for fabricating an orthodontic appliance includes: fabricating a shell including a plurality of cavities shaped to receive teeth; fabricating a discontinuity in the shell; and fabricating an elastic member positioned to interact with the discontinuity. At least one of the shell, discontinuity, or the elastic member can be fabricated using a direct fabrication technique.

In some embodiments, the direct fabrication technique includes one or more of: vat photopolymerization, material jetting, binder jetting, material extrusion, powder bed fusion, sheet lamination, or directed energy deposition.

In some embodiments, the shell and the discontinuity are fabricated concurrently using the direct fabrication technique. Fabricating the elastic member can involve coupling the elastic member to the shell after fabricating the shell and the discontinuity. The method can further include fabricating an interface in the shell, the interface being shaped to facilitate the coupling of the elastic member of the shell.

In some embodiments, the shell and the elastic member are fabricated concurrently using the direct fabrication technique.

In some embodiments, the shell is fabricated from a first material and the elastic member is fabricated from a second material. The first material can have a greater stiffness than the second material.

In some embodiments, the discontinuity comprises an aperture or cut in the shell. A portion of the elastic member can span the aperture or cut.

In some embodiments, the method further includes fabricating one or more auxiliary components formed in or coupled to the shell, the one or more auxiliary components including one or more of: a channel, a guide feature, a fastening feature, a flap, a receptacle, a retention feature, a telescoping feature, an interproximal feature, or a biasing feature.

The orthodontic appliances of the present disclosure can include one or more elastic members. The elastic member can be a band, cord, strip, loop, wire, spring, mesh, membrane, scaffold, layer, or any other suitable elastic connecting element, and can be fabricated from materials such as one or more polymers, one or more metals, or composites. In some embodiments, the elastic member can be fabricated by extrusion, additive manufacturing, spraying, thermoforming, or suitable combinations thereof. The elastic member can be fabricated from a single type of elastic material, or a plurality of different elastic material types. The characteristics of the elastic material (e.g., length, width, thickness, area, shape, cross-section, stiffness, etc.) can be selected based on the desired properties for the elastic member, e.g., magnitude and/or direction of forces to be applied by the elastic member.

An orthodontic appliance can include a shell having teeth receiving cavities as previously described herein and one or more elastic members coupled to the shell. Various configurations for coupling an elastic member to a shell are possible. One or more portions of the elastic member (e.g., portions at or near each end of the elastic member) can be coupled to the shell at a suitable number of attachment points (e.g., one, two, three, four, or more). Alternatively or in addition, one or more portions of the elastic member can be coupled to the shell over a continuous attachment region. Any description herein pertaining to attachment points can also be applied to attachment regions, and vice-versa. Each of the attachment points can be situated on any suitable portion of the shell, such as on a buccal surface, lingual surface, occlusal surface, gingival surface, internal surface (e.g., surface adjacent to or near the teeth), external surface (e.g., surface away from the teeth), or suitable combinations thereof. The position of the attachment points can be selected in order to control the forces (e.g., force magnitude and/or trajectory) applied to the teeth. In some embodiments, the elastic member is directly coupled to the attachment points on the shell without utilizing intervening attachment elements or fasteners. For example, the elastic member can be directly coupled to the shell by adhesives and/or bonding. As another example, the attachment points on the shell can be formed (e.g., integrally formed as a unitary or monolithic piece) with or into one or more hooks, protrusions, apertures, tabs, or other such features suitable for directly fastening the elastic member to the shell. In alternative embodiments, the elastic member may be indirectly coupled to the shell (e.g., via attachment elements or fasteners that are not integrally formed with the shell as a unitary or monolithic piece). In some instances, the elastic member is permanently affixed to the shell. Conversely, the elastic member can be removably coupled or otherwise detachable from the shell. In some embodiments, the elastic member is coupled only to the shell, and not to the teeth of the patient or an attachment mounted on the teeth.

The orthodontic appliance described herein can include one or more discontinuities formed in the shell. The one or more discontinuities can include one or more cuts, flaps, apertures (e.g., openings, windows, gaps, notches), and/or deformations (e.g., protrusions, indentations, reliefs) formed in any suitable portion of the shell (e.g., in a buccal, lingual, occlusal, and/or gingival surface). Exemplary geometries for such discontinuities are described in further detail herein. The discontinuities provided herein can be used to control the forces applied to a patient's teeth by an orthodontic appliance. In some embodiments, one or more discontinuities are used in combination with one or more elastic members in order to produce the desired forces. In alternative embodiments, an orthodontic appliance can include one or more discontinuities without using any elastic members, such that the forces applied to the teeth are modulated through the use of discontinuities alone.

In some embodiments, one or more elastic members are positioned to interact with one or more discontinuities in the appliance shell. In some instances, a discontinuity is located between two or more attachment points for an elastic member, such that a portion of the elastic member extending between the attachment points spans the discontinuity (or at least a part of the discontinuity). Alternatively or additionally, a portion of an elastic member between attachment points can extend around the discontinuity (e.g., around the periphery of an aperture or flap of the discontinuity). An elastic member can interact with a discontinuity by exerting forces directly on the discontinuity (e.g., pressing or pulling against a flap, deformation, etc.), as well as by exerting forces on portions of the shell adjacent to the discontinuity (e.g., applying force to portions of the shell surrounding a cut, aperture). Such interactions may comprise, for example, the elastic member applying a force on or in the region of the discontinuity when the appliance is worn (e.g., such that the resulting force is in a direction suitable to change the form of the discontinuity) and/or the elastic member applying a force on the discontinuity when the appliance is not being worn. In some embodiments, the applied force is at least partially generated by deformation (e.g., stretching, compressing, bending, flexing) of the elastic member. In some instances, the deformation of the elastic member can be caused by deformations of the corresponding discontinuity and/or shell, such as deformations occurring when the appliance is placed over teeth, as described in further detail below.

The interaction of the elastic member with the discontinuity can result in the application of forces on portions of the appliance shell. Associated resulting forces can be transmitted to the underlying teeth via the shell to elicit tooth movements (e.g., extrusion, intrusion, rotating, torqueing, tipping, and/or translating) towards a specified tooth arrangement. As the teeth move towards the specified arrangement, the deformation of the discontinuity may decrease, until the teeth reach the arrangement and the discontinuity fully reverts to its undeformed state (also known as the "fully expressed" state). In some embodiments, the shell includes a predetermined amount of internal space (e.g., in the teeth-receiving cavities of the shell) to accommodate tooth movements from an arrangement to a subsequent specified arrangement. The size of the internal space can be used to control the extent to which the teeth move. For example, the teeth can be prevented from moving further once they have traversed the available internal space and come into contact with an internal surface of the shell (e.g., the wall of a tooth-receiving cavity). Additionally, the geometry of the discontinuity (e.g., size) can also influence the extent of tooth movement, in that no more tooth movements are produced once the discontinuity has been fully expressed. In some instances, one or more portions of the internal surface can be fabricated from a more rigid material than the rest of the shell to ensure that the teeth are retained at the desired configuration.

The magnitude and/or direction of the forces applied to the teeth can be at least partially controlled by, influenced by, or based on the geometry of the discontinuity, as well as its positioning relative to the elastic member. The dimensions (e.g., length, width, depth, surface area, etc.) and/or the shape of the discontinuity can be calculated, for instance, to achieve a specified degree of appliance compliance. For example, portions of the shell adjacent to the discontinuity may be more compliant, while portions of the shell away from the discontinuity may be more rigid. In some embodiments, the discontinuity is configured to be deformable (e.g., changeable in shape, size) and/or displaceable, thereby increasing the local compliance of the appliance. The local compliance of various portions of the shell can be used to control the resulting forces exerted on the underlying teeth.

The forces applied to the teeth can also be influenced by characteristics of the elastic member (e.g., length, width, thickness, area, shape, cross-section, number, elastic coefficient and other material properties, etc.). Any suitable combination of characteristics can be used in order to elicit the desired tooth movements, and such characteristics can be homogeneous or variable within the elastic. In some embodiments, the elasticity of the elastic member can vary based on the direction of deformation of the elastic member (anisotropic elasticity). For example, an elastic member can be configured to be more compliant when deformed along one or more specified directions (e.g., longitudinal, lateral, etc.), and less compliant (or noncompliant) when deformed along all other directions, or vice-versa. The directionality of the elasticity can be used to control the resultant forces applied to the teeth.

Optionally, the elastic member can be deformed before being coupled to the appliance and/or before the appliance is worn by the patient (e.g., due to the placement of the attachment points and/or discontinuity), such that there is an initial "pre-loading" force or tension in the elastic member. The use of pre-loading can be used to produce a substantially constant force on the teeth throughout the treatment duration. Moreover, the use of pre-loading can ensure that sufficient force is applied to the teeth, e.g., in accordance with a desired treatment plan. Alternatively, the elastic member can be relaxed prior to attachment to the appliance and/or wearing of the appliance, such that there is no pre-loading force before the appliance is placed on the teeth.

Figure 2A:
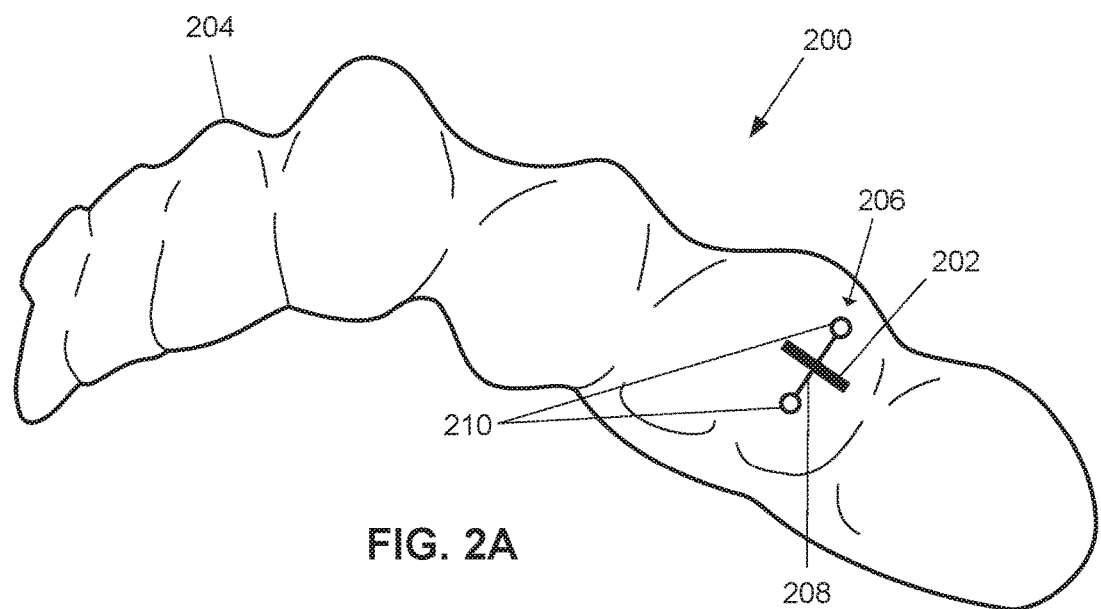
FIG. 2A illustrates an exemplary orthodontic appliance with a coupled elastic member and a discontinuity, in accordance with some embodiments.
Figure 2B:
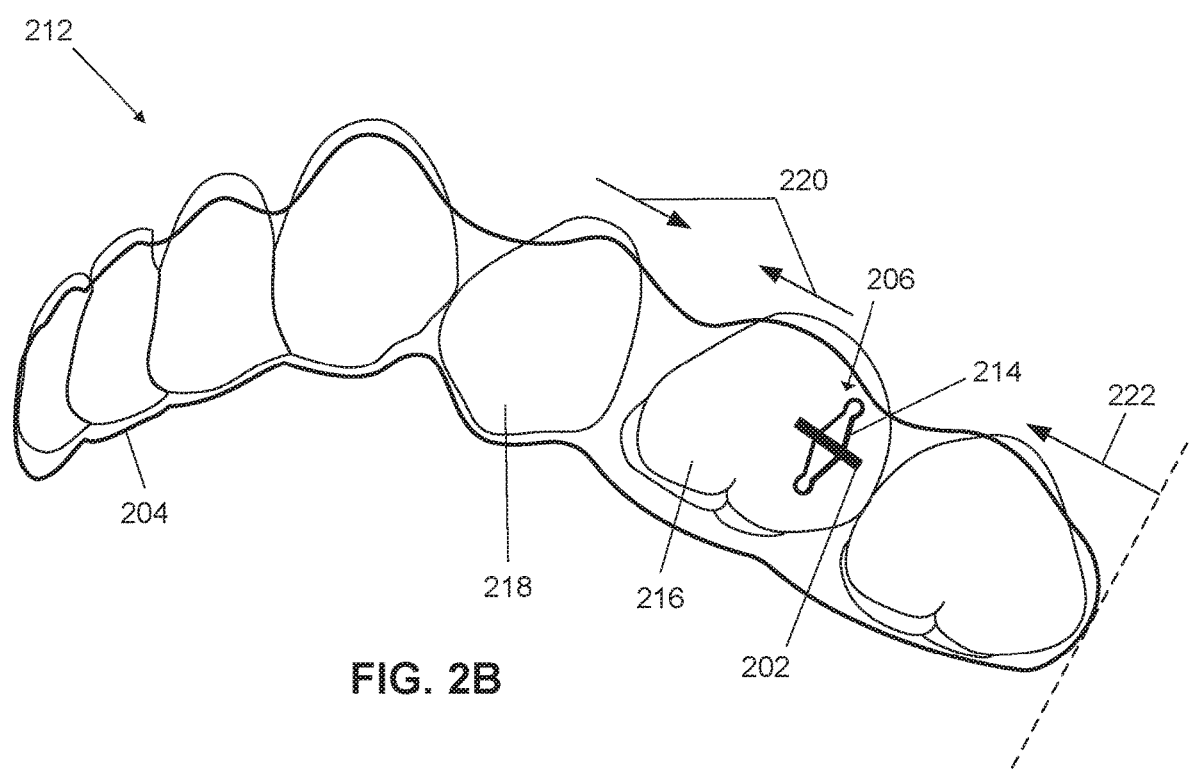
FIG. 2B illustrates the appliance of FIG. 2A when placed over the teeth.

FIG. 2A and FIG. 2B illustrate an orthodontic appliance 200 with a coupled elastic member 202, in accordance with some embodiments. The elastic member 202 is depicted as an elongate band or strip having two opposing ends. The ends of the elastic member 202 are attached to the exterior of a shell 204 shaped to receive teeth of a single dental arch. In FIG. 2A and FIG. 2B, the elastic member 202 spans a discontinuity 206 formed in the shell 204, with the ends of the elastic member 202 attached to the shell 204 on either side of the discontinuity 206. The discontinuity 206 includes an elongate cut 208 which optionally terminates at either end in a circular aperture 210. The circular apertures 210 can be used to prevent undesirable lengthening of the cut 208 when force is applied on the shell 204. In alternative embodiments, other types of aperture shapes (e.g., oval apertures) can be used instead of circular apertures. In some embodiments, when the appliance 200 is placed on the teeth of a patient's dental arch 212 (as illustrated in FIG. 2B), at least some portions of the shell 204 are deformed by the forces generated by the deliberately designed mismatch between the patient's current tooth configuration and the tooth arrangement specified by the geometry of the appliance 200, resulting in a corresponding deformation of the discontinuity 206. For example, stretching of the shell 204 can cause the elongate cut 208 to widen into an elongate aperture 214. The deformation of the discontinuity causes the geometry of the appliance to more easily comply with the current positions of the patient's teeth, thereby reducing the discomfort experienced by the patient when wearing the appliance. Additionally, the deformation of the discontinuity can enable the appliance to accommodate the patient's teeth even in situations where the teeth are not in an ideal arrangement relative to the configuration of the appliance (e.g., due to inaccuracies in appliance fabrication, inaccurate measurement data of the initial teeth arrangement, tooth movements lagging behind or not conforming to the treatment plan, etc.). Furthermore, the deformation can allow the appliance to effect larger tooth movements, thus enabling the appliance to be used for a longer time.

The deformation of the discontinuity 206 and/or shell 204 generally results in deformation of the elastic member 202. For example, the elastic member 202 can be stretched by the widening of the discontinuity 206. The tension in the elastic member 202 generated by such deformation can be reacted to as a continuous force by portions of the shell 204, such as portions of the shell 204 adjacent the discontinuity 206, in some embodiments. Associated resulting forces can be transmitted by the shell 204 to the underlying teeth so as to elicit tooth movements repositioning the teeth to a desired predetermined arrangement. For example, since the discontinuity 206 is situated adjacent the tooth 216, the appliance 200 can exert forces on the tooth 216 and its neighbor 218, causing them to move towards each other (see, e.g., arrows 220). This movement can reduce the interproximal space between the teeth 216, 218, thereby shortening the mesial-distal length of the arch 212 (see, e.g., arrow 222). The deformation of the shell 204, discontinuity 206, and/or elastic member 202 can decrease as the repositioning of the teeth reduces the mismatch between the tooth arrangement and appliance geometry, thus diminishing the amount of force expressed on the teeth by the appliance 200.

Figure 2C:
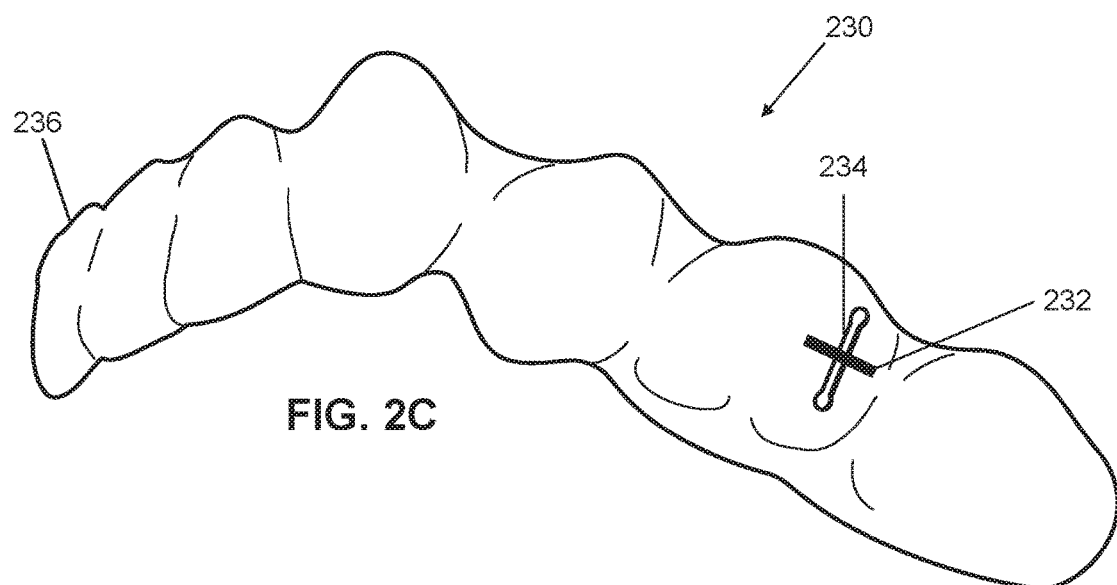
FIG. 2C illustrates another example of an orthodontic appliance with a coupled elastic member and a discontinuity, in accordance with some embodiments.
Figure 2D:
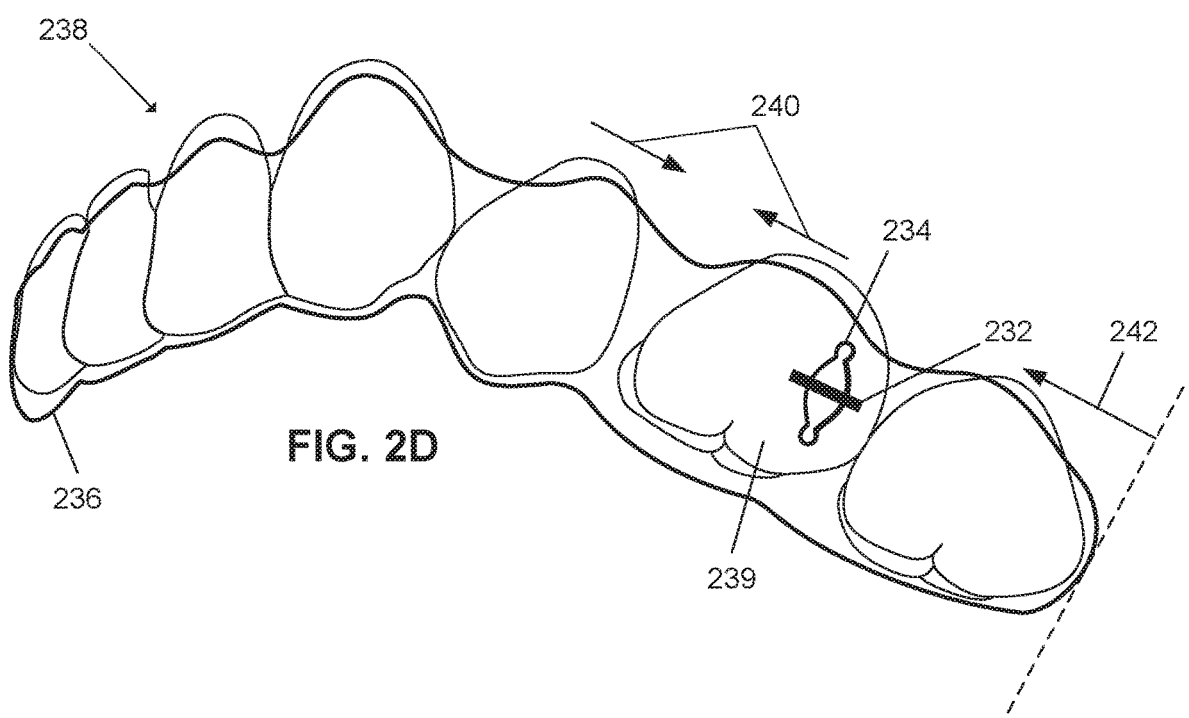
FIG. 2D illustrates the appliance of FIG. 2C when placed over the teeth.

FIG. 2C and FIG. 2D illustrate an orthodontic appliance 230 with a coupled elastic member 232 and a discontinuity 234 formed within a shell 236, in accordance with some embodiments. The discontinuity 234 is similar to the discontinuity 206 of FIG. 2A, except that the cut 208 is replaced with a narrow elongate aperture, which can be formed in any suitable manner, such as by removing material from the shell 236. As used herein, narrow may mean, for example, that the aperture has an extension in one direction of more than twice, e.g., more than four times, its dimension in a second, e.g., perpendicular, direction. When placed on a patient's arch 238, as depicted in FIG. 2D, the discontinuity 234 and the elastic member 232 are situated adjacent to a tooth 239. The elongate aperture of the discontinuity 234 can be deformed when worn (e.g., the size of the aperture increases), generating tension in the elastic member 232 and causing it to exert forces on portions of the shell 236 disposed on opposite sides of the discontinuity 234. Associated resulting forces can be applied to the underlying teeth to close an interproximal space (see, e.g., arrows 240) and thereby reduce the overall arch length (see, e.g., arrow 242).

Figure 2E:
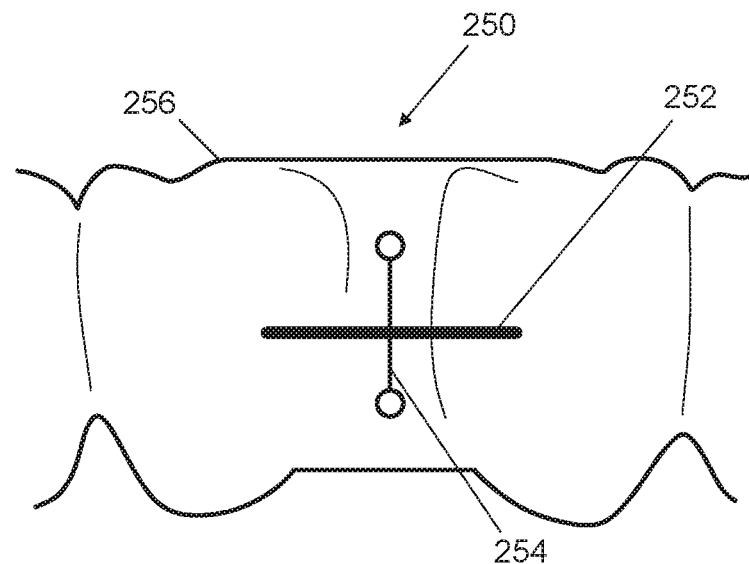
FIG. 2E illustrates yet another example of an orthodontic appliance with a coupled elastic member and a discontinuity, in accordance with some embodiments.
Figure 2F:
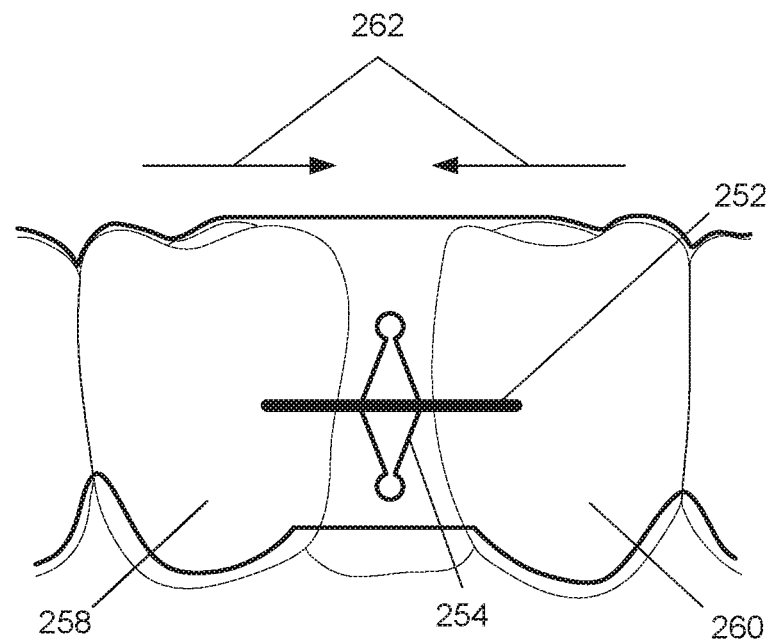
FIG. 2F illustrates the appliance of FIG. 2E when placed over the teeth.

FIG. 2E and FIG. 2F illustrate an orthodontic appliance 250 with a coupled elastic member 252 and a discontinuity 254, in accordance with some embodiments. The discontinuity 254 can be formed as an elongated cut in the shell 256, similar to the discontinuity 206 of the appliance 200. When the appliance 250 is worn (as depicted in FIG. 2F), the discontinuity 254 can be situated adjacent the interproximal space between tooth 258 and tooth 260. The elastic member 252 can be attached to the shell 256 at attachment points adjacent the teeth 258, 260 when the appliance 250 is worn. The principle of operation of the appliance 250 is similar to that of the appliances 200, and 230, in that the elastic member 252 interacts with the discontinuity 254 to elicit tooth movements (see, e.g., arrows 262) that reduce the interproximal space between the teeth 258, 260.

Figure 2G:
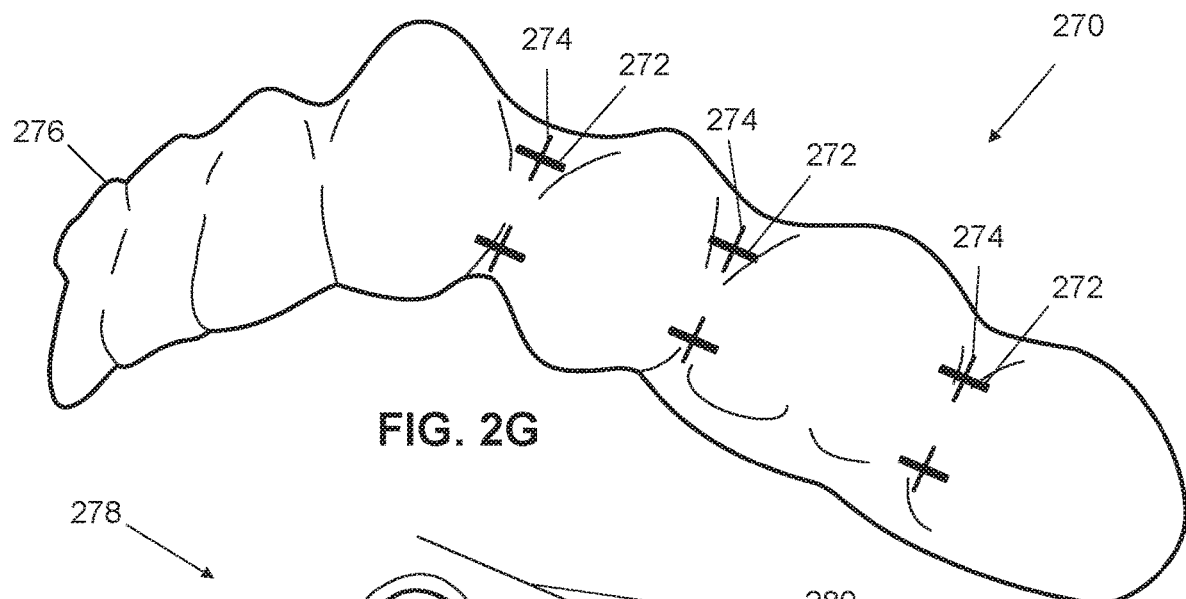
FIG. 2G illustrates an example of an orthodontic appliance having a plurality of elastic members and discontinuities, in accordance with some embodiments.
Figure 2H:
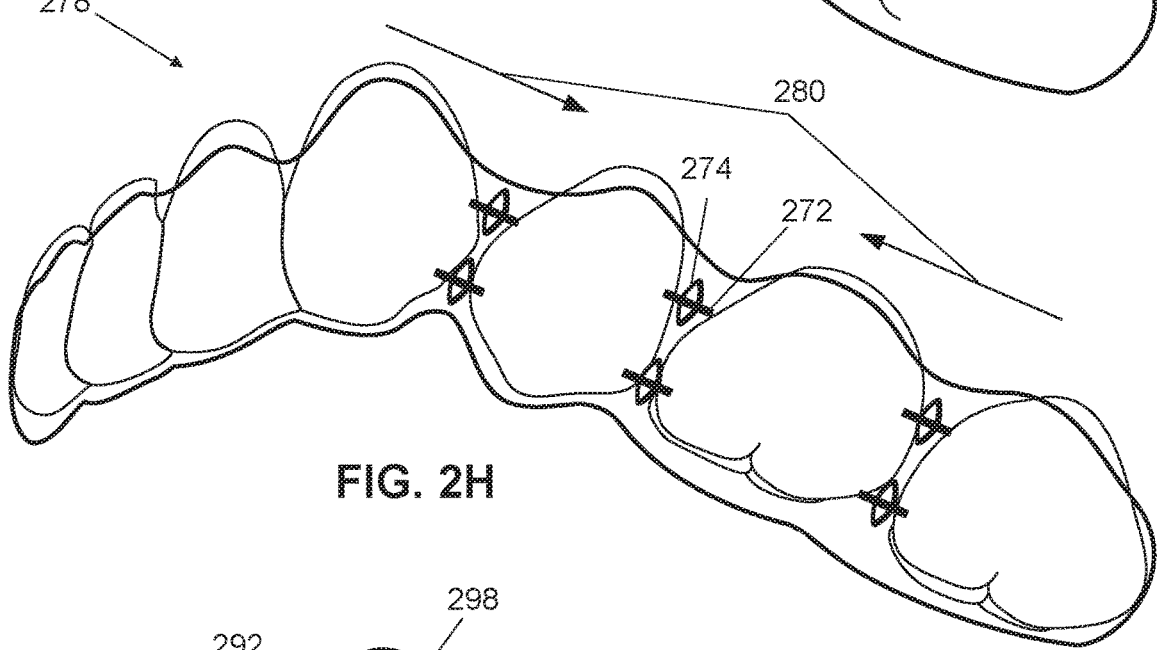
FIG. 2H illustrates the appliance of the FIG. 2G when placed over the teeth.

FIG. 2G and FIG. 2H illustrate an example of an orthodontic appliance 270 having a plurality of elastic members 272 and discontinuities 274 formed within a shell 276. Each elastic member 272 is positioned to span one of the plurality of discontinuities 274, which are depicted as cuts in the shell 276. The discontinuities 274 are disposed adjacent to the interproximal regions when the appliance 270 is worn over the arch 278 (as illustrated in FIG. 2H). The interactions between the elastic members 272 and discontinuities 274 can produce forces for repositioning the teeth to reduce an interproximal space (see, e.g., arrows 280). Although the elastic members 272 and discontinuities 274 are depicted in FIG. 2G and FIG. 2H as situated solely on the buccal surface of the appliance, they can also be situated on other surfaces, such as on the lingual surface or on the occlusal surface, as well as combinations of any these surfaces. For example, an appliance can include some discontinuities and elastics situated on a lingual surface and some discontinuities and elastics situated on a buccal surface. In this configuration, forces are applied to the underlying teeth via both surfaces of the shell, thereby increasing the repositioning efficiency. One, two, three or more discontinuities may additionally or alternatively be disposed in other regions than the regions adjacent to the interproximal regions, and each discontinuity may optionally be spanned by none, one, or more elastic members.

Figure 2I:
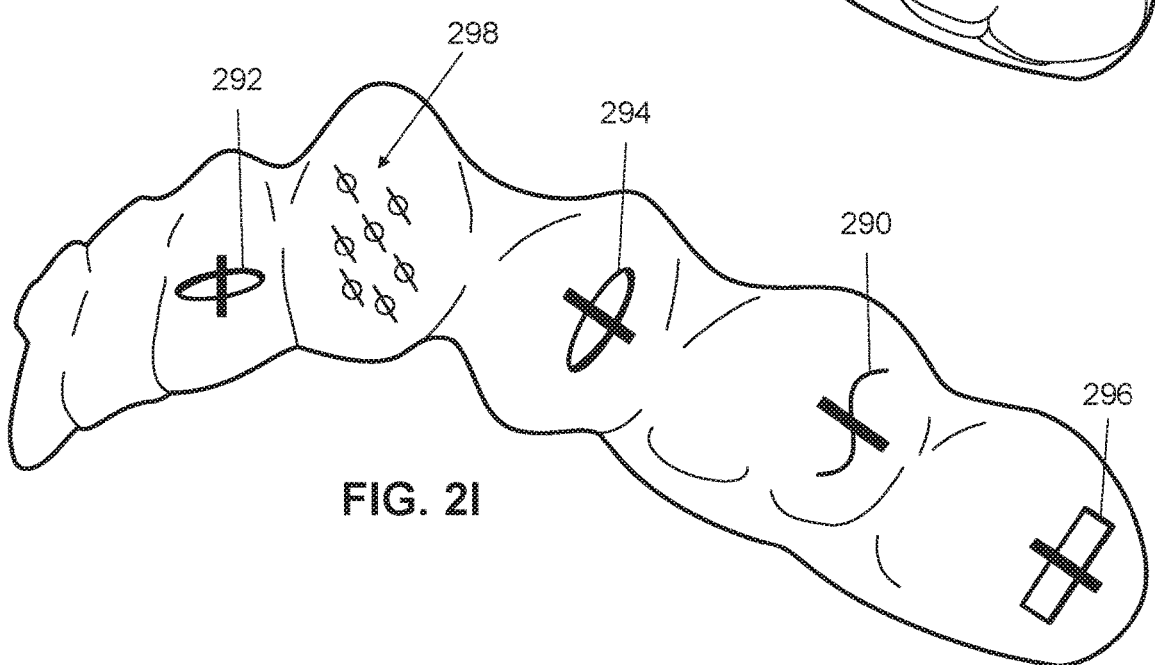
FIG. 2I illustrates additional exemplary geometries for a discontinuity in an orthodontic appliance, in accordance with some embodiments.

FIG. 2I illustrates additional example geometries for one or more discontinuities in an orthodontic appliance shell, in accordance with some embodiments. As previously mentioned, a discontinuity can have any suitable configuration, for example, such as a cut, flap, aperture, deformation, and the like. For example, a discontinuity can include a cut in the shell, and the cut can include linear portions and/or curved portions (e.g., curvilinear cut 290). As another example, the discontinuity can include an aperture formed in a suitable shape, such as a circle, ellipse (e.g., elliptical apertures 292, 294), triangle, square, rectangle (e.g., rectangular aperture 296), or other polygonal shape, and/or suitable combinations thereof. The discontinuities and/or elastics can be positioned in any suitable orientation. For example, the elastic member can extend vertically (along a occlusal-gingival direction), horizontally or longitudinally (along a mesial-distal direction), or any other suitable orientation. Similarly, the discontinuity may extend vertically (e.g., discontinuities 290, 294, 296), horizontally or longitudinally (e.g., discontinuity 292), or any other suitable orientation. The orientation of the elastic member and/or discontinuity can be selected based on the desired tooth movements. In some instances, different orientations can be used to produce different types of movements.

In some embodiments, a discontinuity can be composed of a plurality of individual elements arranged in a suitable configuration (e.g., plurality of circular apertures 298). An appliance can incorporate any suitable number and type of discontinuities, and the discontinuities can interact with any suitable number of elastic members. For example, a single elastic member can be paired with a single discontinuity. Alternatively, a plurality of elastic members can interact with a single discontinuity. Conversely or additionally, a single elastic member can interact with a plurality of discontinuities. The discontinuities described herein, along with their corresponding elastic member(s), can be arranged on the shell in any suitable manner relative to the underlying dentition (e.g., adjacent to one or more teeth, one or more interproximal regions, etc.) and to each other.

Figure 3A:
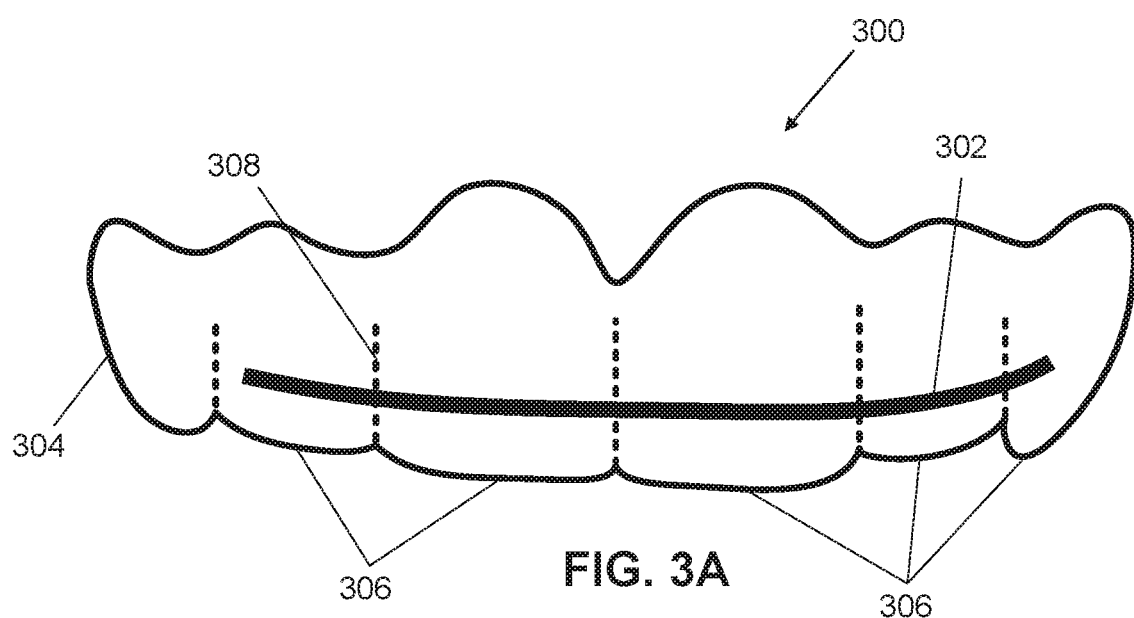
FIG. 3A illustrates an orthodontic appliance for repositioning teeth, in accordance with some embodiments.
Figure 3B:
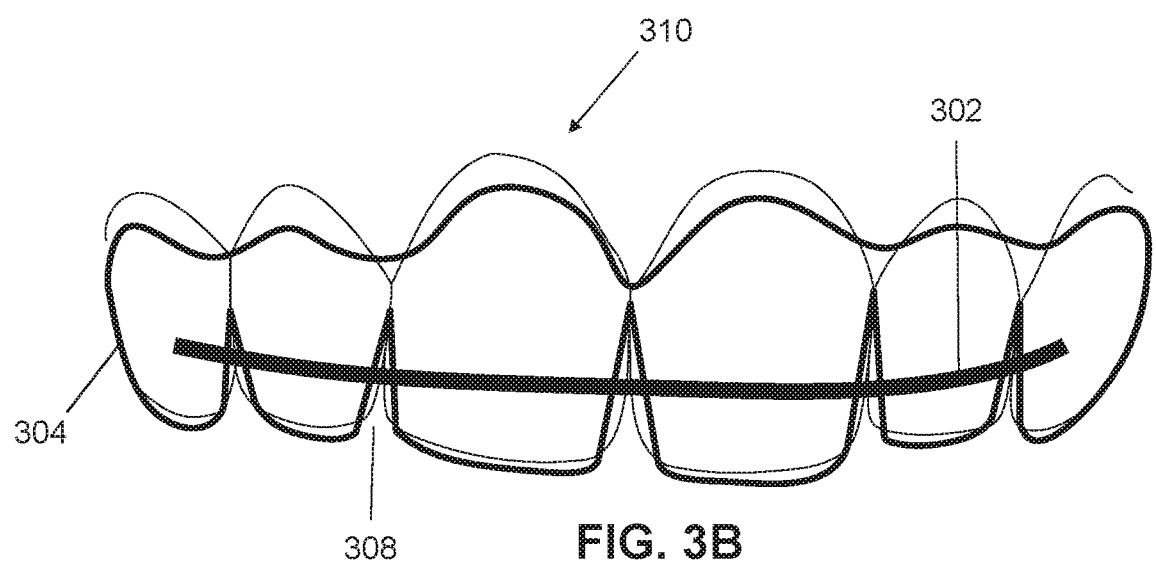
FIG. 3B illustrates the appliance of FIG. 3A when placed over the teeth.

FIG. 3A and FIG. 3B illustrate an orthodontic appliance 300 for repositioning teeth 310, in accordance with some embodiments. For example, the appliance 300 can be used to reduce interproximal space between the teeth 310. The orthodontic appliance 300 includes a shell 304 and an elastic member 302 coupled with the shell 304. The shell 304 has a plurality of discontinuities 308 formed in the shell. The length of the elastic member 302 extends along the surface of the shell 304 spanning a plurality of teeth-receiving cavities 306. The elastic member 302 spans the discontinuities 308, depicted herein as cuts, although other geometries can also be used. When placed on the teeth 310 of the patient as depicted in FIG. 3B, the discontinuities 308 can deform to form a plurality of openings. The orthodontic appliance 300 can be configured such that each of the openings of discontinuities 308 is positioned over or adjacent to a respective interproximal region of the teeth 310. The elastic member 302 can exert forces on the shell 304 such that resulting associated forces are applied to the teeth 310, thereby eliciting tooth movements to reduce the size of the interproximal space(s) between the teeth 310.

In some embodiments, the appliance includes one or more retention features that are formed in the shell (e.g., grooves, ridges, protrusions, indentations, etc.) to retain the elastic member (or suitable portions thereof) at a specified position relative to the shell. The retention features may be beneficial in instances where the elastic member is relatively long and therefore more prone to slippage relative to the shell 304. For instance, the shell 304 of the appliance 300 can include a groove (not shown) configured to constrain the elastic member 302 to a configuration spanning the teeth-receiving cavities 306 and the discontinuities 308. Such retention features can be used to prevent the accidental displacement or release of the elastic member from the desired position, thereby ensuring that the appropriate therapeutic force is maintained.

Figure 4A:
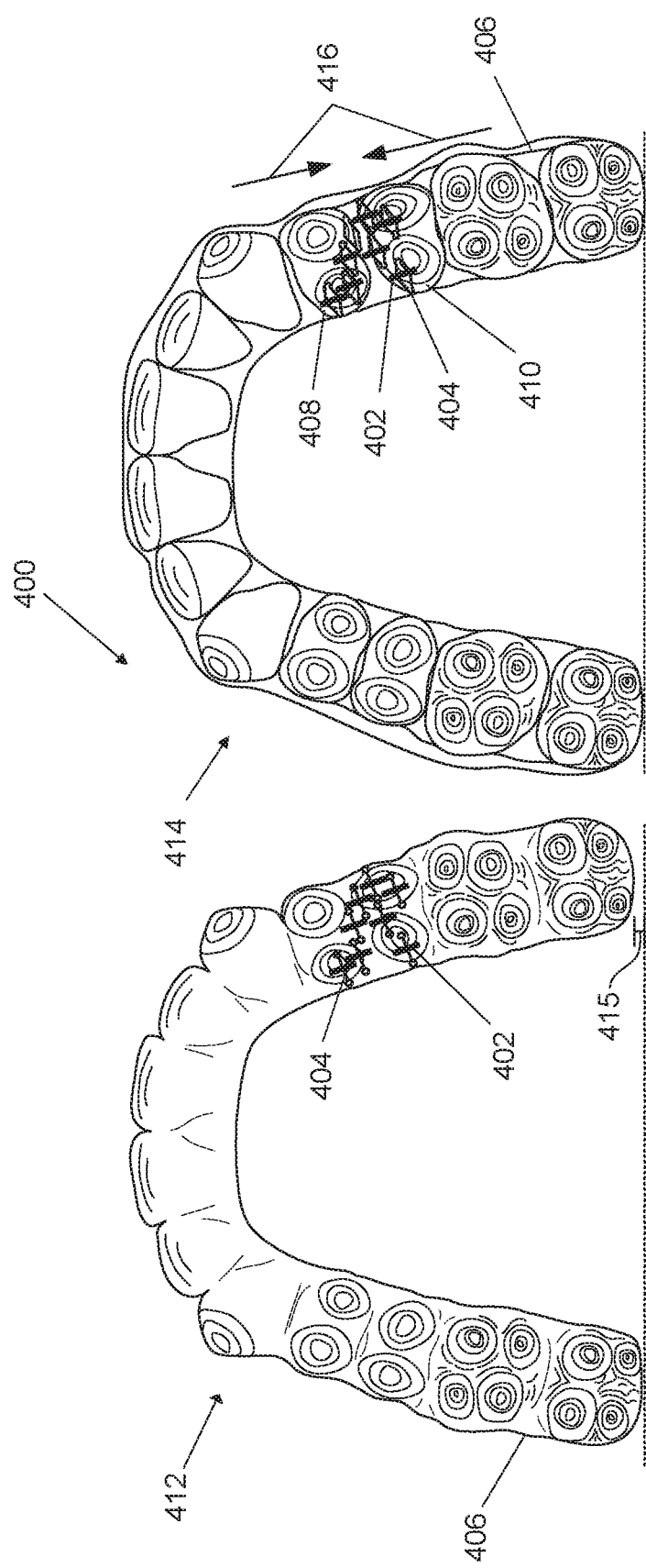
FIG. 4A illustrates an orthodontic appliance for repositioning teeth, in accordance with some embodiments.

FIG. 4A illustrates configurations of an orthodontic appliance 400 for repositioning teeth, in accordance with some embodiments. For example, the appliance 400 can be used to reduce interproximal space between teeth. The appliance 400 includes a shell 406, a plurality of elastic members 402, each of which spans one of a plurality of discontinuities 404 (depicted as cuts terminating in circular apertures) formed in the shell 406. The elastic members 402 and discontinuities 404 are situated on the occlusal surface of the shell 406 near the interproximal region between teeth 408 and 410. The appliance 400 is configured to reduce the size of the interproximal space between teeth 408, 410. In some embodiments, the mesial-distal arch length of the shell 406 is shorter when the appliance is not being worn by a patient (configuration 412) compared to when it is being worn (configuration 414), e.g., by an amount 415, due to the increased interproximal space in the patient's initial tooth arrangement versus the tooth positions of the appliance 400. The discontinuities 404 can be deformable to contribute to the compliance of the appliance 400 and relieve some of the initial forces generated by the mismatch between the geometry of the patient's teeth and the geometry of the appliance 400. Similar to the other embodiments described herein, the elastic members 402 can apply a continuous force between portions of the shell 406 to elicit tooth movements (see, e.g., arrows 416) that reduce and may eliminate the interproximal space between teeth 408, 410.

Figure 4B:
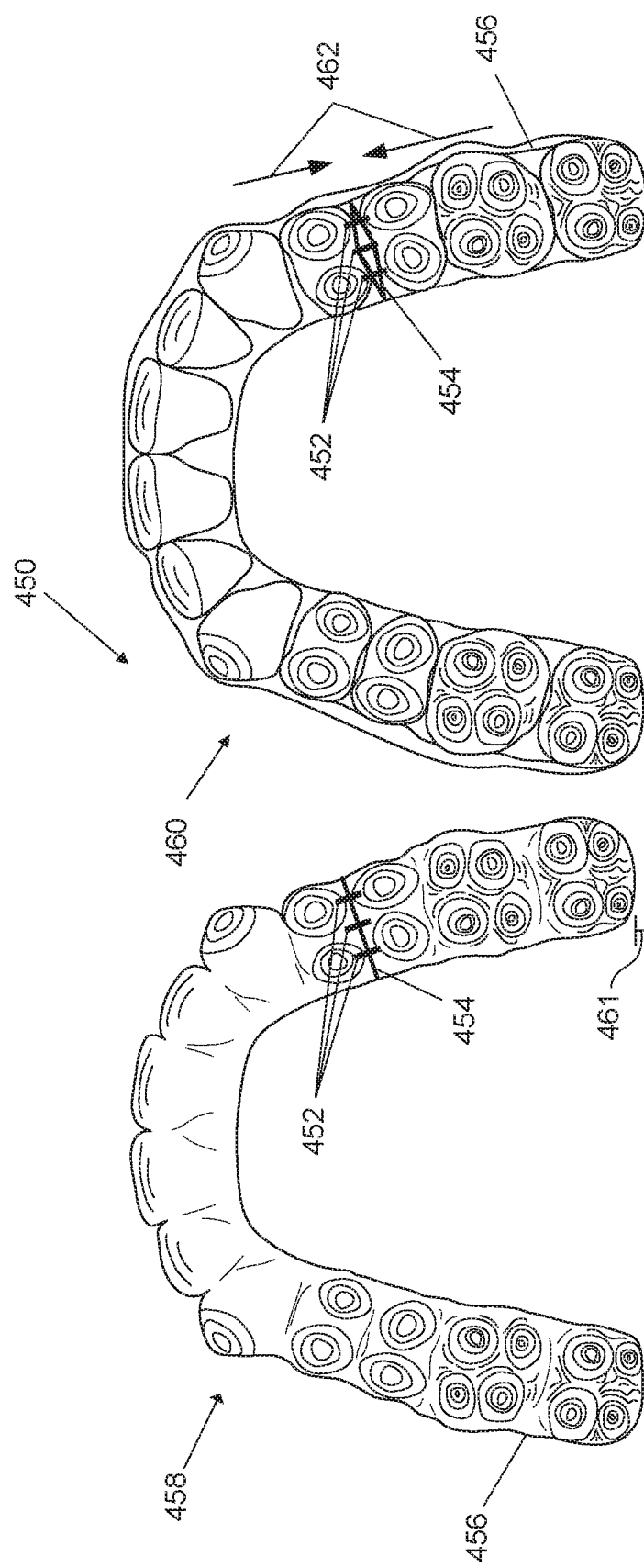
FIG. 4B illustrates another orthodontic appliance for repositioning teeth, in accordance with some embodiments.

FIG. 4B illustrates configurations of an orthodontic appliance 450 for reducing an interproximal space between teeth, in accordance with some embodiments. The appliance 450 includes a shell 456 and a plurality of elastic members 452 spanning a single discontinuity 454 (depicted as a single cut) formed in the shell 456. The discontinuity 454 can be a complete cut in the shell 456 separating it into discrete segments, or it can be a partial cut such that the shell 456 remains a single segment. Similar to the appliance 400, the discontinuity 454 can be deformed (e.g., widened from a cut into an elongate aperture) when the appliance 450 is placed on the teeth of a patient, such that the mesial-distal arch length of the shell 456 is shorter in the unworn configuration 458 than in the worn configuration 460, e.g., by an amount 461. As previously described, the elastic members 452 exert repositioning forces causing closure of the interproximal space (see, e.g., arrows 462).

Figure 5A:
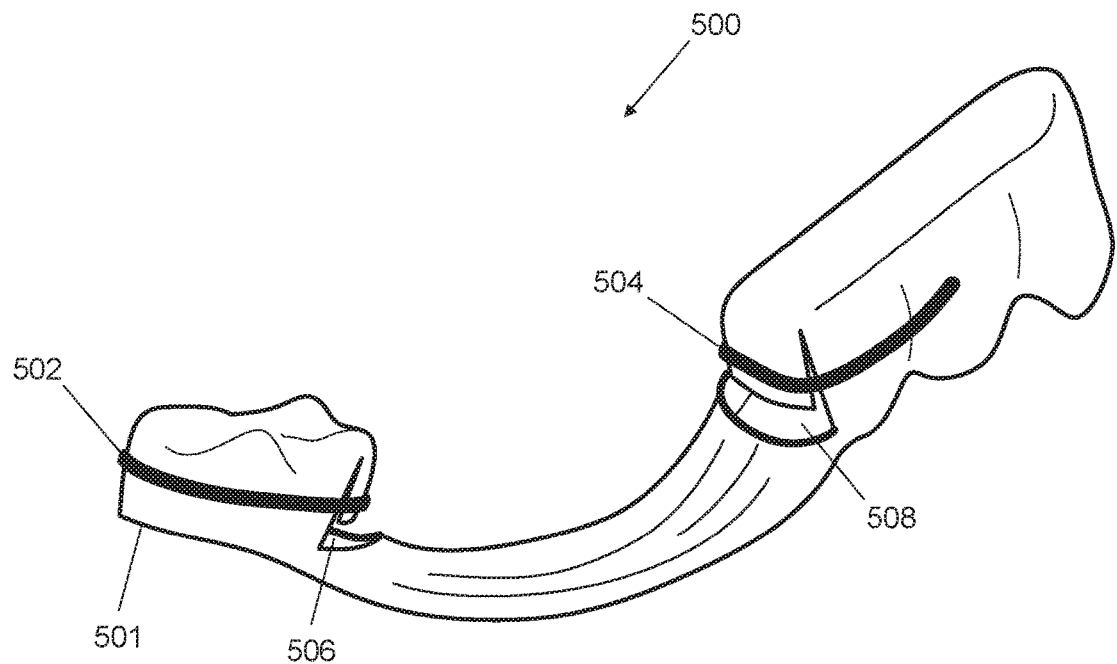
FIG. 5A illustrates an orthodontic appliance for repositioning teeth, in accordance with some embodiments.
Figure 5B:
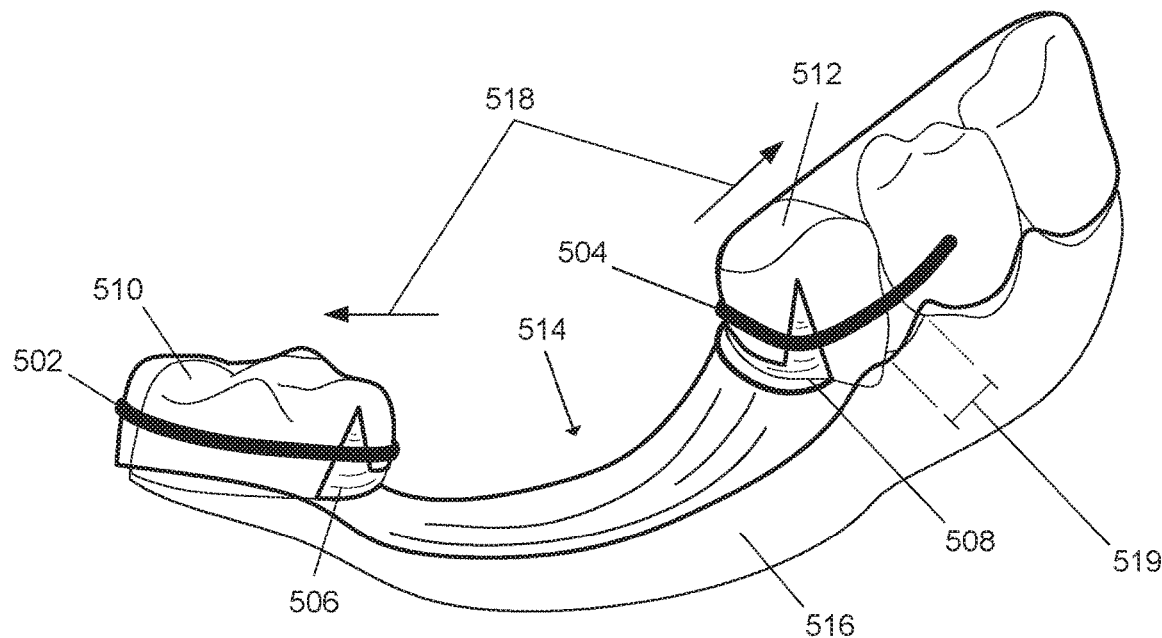
FIG. 5B illustrates the appliance of FIG. 5A when placed over the teeth.
Figure 5C:
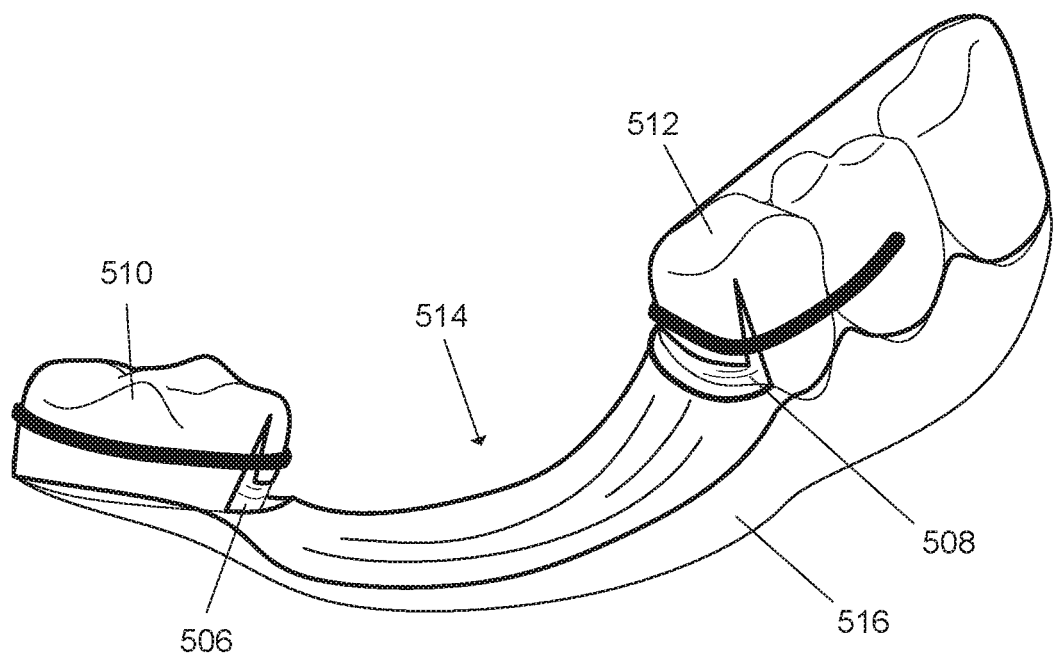
FIG. 5C illustrates the appliance of FIG. 5B after tooth repositioning has occurred.

FIG. 5A through FIG. 5C illustrate an orthodontic appliance 500 for repositioning teeth of a dental arch, in accordance with some embodiments. In the depiction of FIG. 5A through FIG. 5C, the appliance 500 is configured to increase a space between teeth of a lower dental arch, although the concepts presented herein can also be applied to space expansions in the upper dental arch. Space expansion (which can involve expansion of interproximal spaces between adjacent teeth, as well as expansion of spaces resulting from tooth removal) can be beneficial for various dental procedures (e.g., implants, treatment of impacted teeth). The techniques disclosed herein, however, can also be used for other applications, such as decreasing a space between teeth, moving a tooth, tipping a tooth, rotating a tooth, and so on. Any description herein referring to space expansion can also be applied to other types of orthodontic repositioning, and vice-versa. The appliance 500 includes a shell 501 and first and second elastic members 502, 504, interacting respectively with first and second discontinuities 506, 508 formed in the shell 501. In alternative embodiments, instead of one elastic member per discontinuity, two or more elastic members may be used for each discontinuity. The elastic members 502, 504 and associated respective discontinuities 506, 508 can be situated over teeth 510, 512 immediately adjacent to a space 514 when the appliance 500 is placed on a patient's lower arch 516 (depicted in FIG. 5B). The elastic members and the discontinuities can be configured in any manner suitable for producing space-expanding tooth movements. For example, as illustrated in FIG. 5A through FIG. 5C, the discontinuities 506, 508 can each be configured as an aperture positioned over the tooth surfaces adjacent to the space 514. Each aperture extends towards the crown of each tooth and is spanned by the elastic member. The respective elastic member can extend around the entire circumference of the tooth and be attached to the shell over the same tooth (see, e.g., elastic member 502), or extend partially around the circumference of the tooth and be attached to the shell over an adjacent tooth (see, e.g., elastic member 504). In either case, the ends of the elastic member 504 can be respectively attached to the buccal and lingual sides of the shell 501 such that the teeth 510, 512 are moved to increase the space between the teeth 510, 512 (e.g., in the direction indicated by arrows 518). For example, the tooth 512 can be moved so as to reduce and often eliminate an interproximal space 519 between the tooth 512 and the adjacent tooth so as to reposition the teeth as illustrated in FIG. 5C.

When the appliance 500 is placed over the arch 516, the elastic members 502, 504 interact with the discontinuities 506, 508 to apply forces on the teeth 510, 512, thereby moving the teeth 510, 512 in desired directions (see, e.g., arrows 518) so as to expand the space 514. In some embodiments, the extent of the movement can be varied based on the size of the discontinuities 506, 508. FIG. 5C illustrates the tooth configuration of the lower arch 516 after repositioning, with an expanded space 514. The repositioning of the teeth 510, 512 reduces the mismatch between the patient's teeth arrangement and the appliance geometry, thereby causing the deformation of the discontinuities 506, 508 to be reduced relative to the previous configuration depicted in FIG. 5B.

Figure 6:
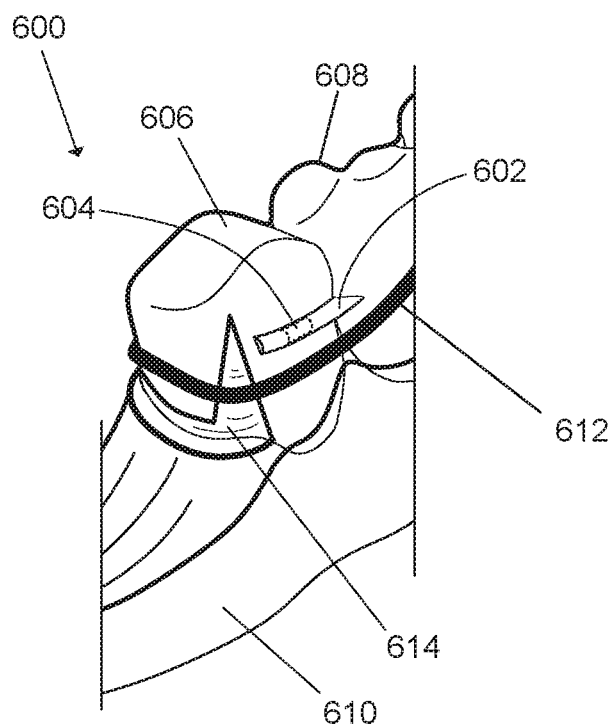
FIG. 6 illustrates an orthodontic appliance including a channel accommodating an attachment on a tooth, in accordance with some embodiments.

FIG. 6 illustrates an orthodontic appliance 600 including a channel 602 accommodating an attachment 604 mounted on a tooth 606, in accordance with some embodiments. The channel 602 can be formed within the internal cavity of the shell 608 of the appliance 600, such that the attachment 604 is received within the channel 602 when the appliance 600 is placed over the patient's arch 610. The channel 602 can be configured to guide the movement of the tooth 606 as it is repositioned due to forces applied by the elastic member 612 on and/or near the discontinuity 614. For example, the geometry of the channel 602 can be used to constrain the movement of the tooth 606 along a predetermined trajectory (e.g., a trajectory substantially parallel to the channel 602). Additionally, the channel 602 can be used to produce intrusion or extrusion of the tooth as it moves along the trajectory. Although the channel 602 is depicted herein as extending along a mesial-distal direction, other orientations can also be used, such as an occlusal-gingival direction (e.g., to produce intrusion, extrusion, leveling, etc.). In some embodiments, an appliance may include a plurality of channels receiving a plurality of corresponding attachments, such as a buccal channel and a lingual channel respectively accommodating a buccal attachment and a lingual attachment on the underlying tooth. The use of multiple channel-attachment pairs can be used to increase the efficiency and accuracy of tooth repositioning. Furthermore, the materials of the channels and attachments can be selected to optimize force expression and tooth repositioning. For example, the channel and the attachment can each be fabricated from different materials. In some embodiments, the materials can be selected to minimize the frictional coefficient between the channel and attachment, so that the attachment can be moved freely within the channel.

Figure 7A:
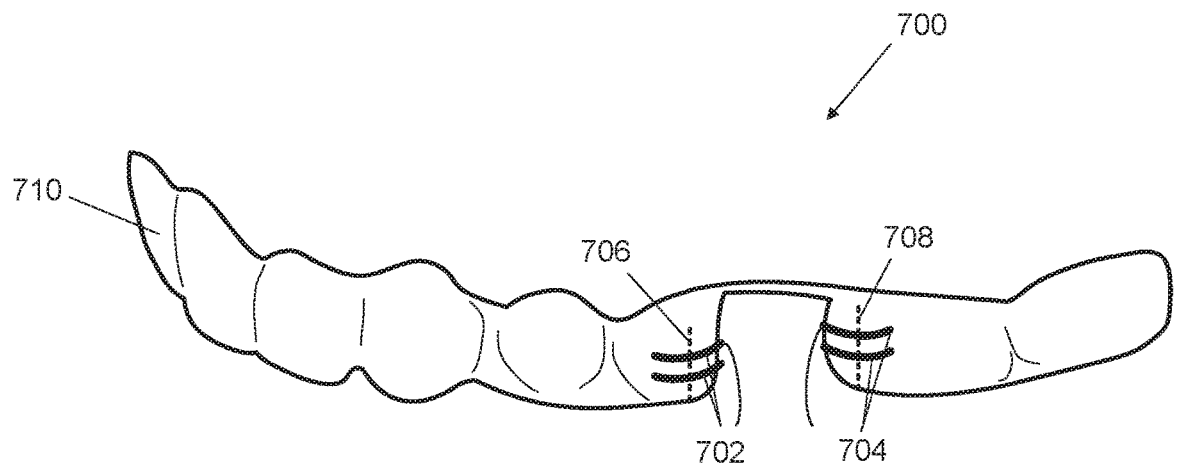
FIG. 7A illustrates another example of an orthodontic appliance for repositioning teeth, in accordance with some embodiments.
Figure 7B:
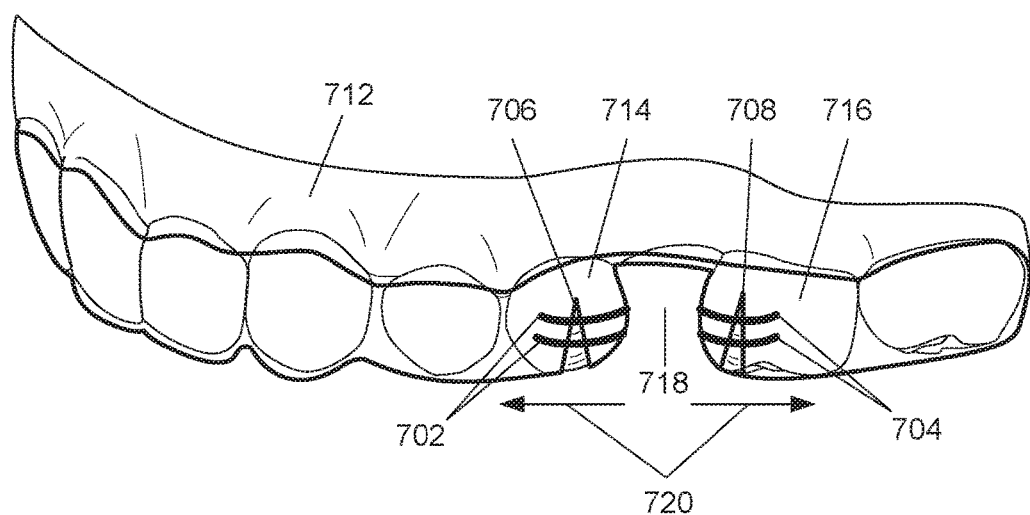
FIG. 7B illustrates the appliance of FIG. 7A when placed over the teeth.
Figure 7C:
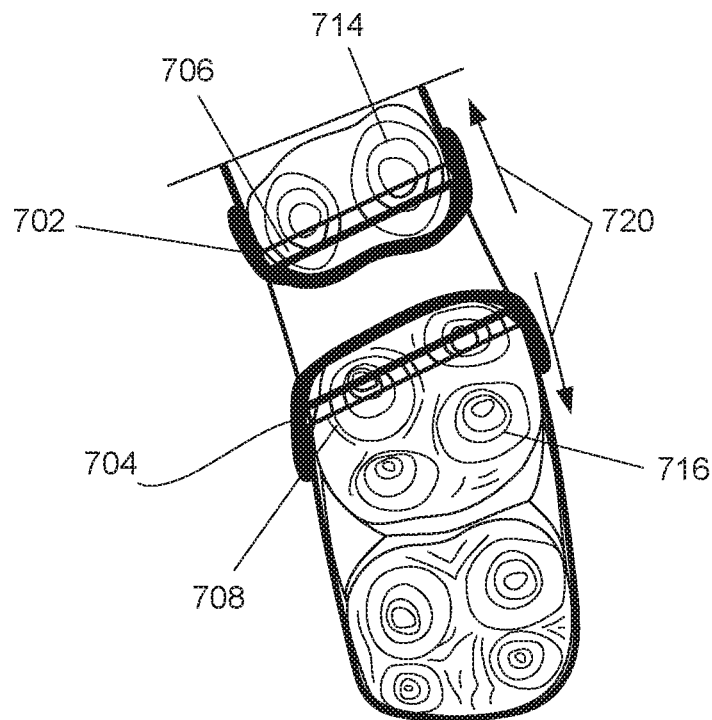
FIG. 7C illustrates the occlusal surface of the appliance of FIG. 7A.
Figure 7D:
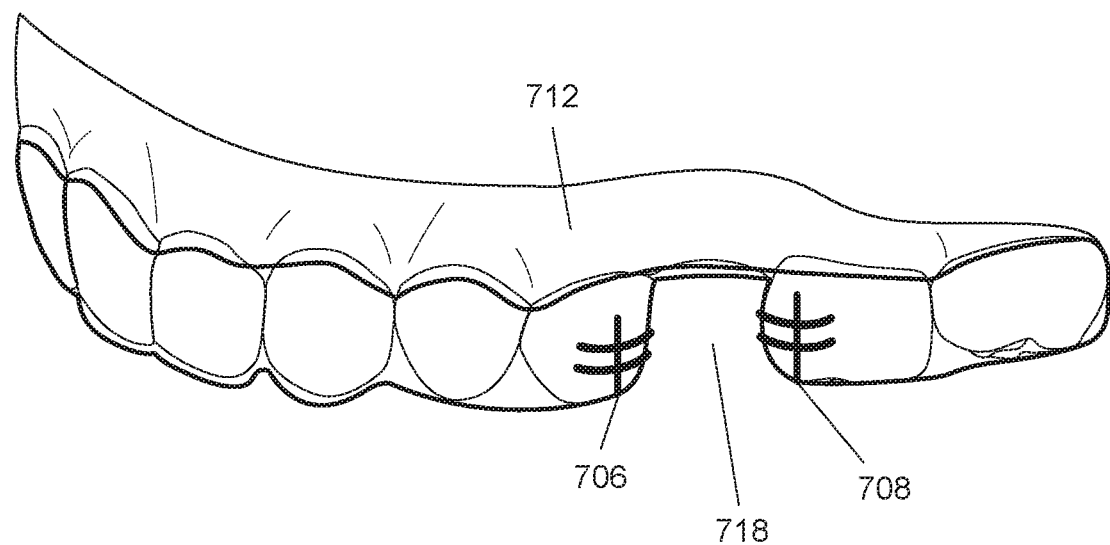
FIG. 7D illustrates the appliance of FIG. 7B after tooth repositioning has occurred.

FIG. 7A through FIG. 7D illustrate an orthodontic appliance 700 for repositioning teeth of a dental arch, in accordance with some embodiments. The appliance 700 includes a shell 710 and first and second pairs of elastic members 702, 704, which interact respectively with the first and second discontinuities 706, 708 formed in the shell 710. In alternative embodiments, a different number of elastic members can be used for each discontinuity, e.g., a single elastic member, or more than two elastic members. When the appliance 700 is placed on the arch 712 (depicted in FIG. 7B), the elastic member pairs 702, 704 and the discontinuities 706, 708 are situated on the teeth 714, 716 immediately flanking the space 718. As illustrated in FIG. 7C, when the appliance 700 is worn, the discontinuities 706, 708 are deformed to form gaps in the shell 710 extending over the occlusal surfaces of the teeth 714, 716, and the elastic members 702, 704 extend from the lingual surfaces to the buccal surfaces of the teeth 714, 716. The interaction between the elastic members 702, 704 and the discontinuities 706, 708 result in tooth movements (see, e.g., arrows 720) expanding the size of the space 718. As previously described, the magnitude of the tooth movements can be influenced by the size of the discontinuities 706, 708. FIG. 7D illustrates the repositioned arch 712, in which the space 718 has been expanded and the discontinuities 706, 708 have reverted to their respective undeformed configuration (the fully expressed state).

In some embodiments, the orthodontic appliances presented herein can include a shell that is separated into two or more discrete segments, which may be referred to as "segmented orthodontic appliances." A shell can be separated into any suitable number of segments, e.g., two, three, four, five, or more. The shell can be separated into two or more horizontal (mesial-distal) segments. Alternatively or in addition, the shell can be separated into two or more vertical (occlusal-gingival) segments. Each shell segment can receive a different subset of the patient's teeth. Different segments can receive different numbers of teeth. Alternatively, some or all of the segments can receive the same number of teeth. The shell segments can be joined to each other via one or more elastic members so as to form a single orthodontic appliance. The elastic members can permit movement of the shell segments relative to each other, and the direction of permitted movement can be determined based on the desired tooth movements to be achieved (e.g., extrusion, intrusion, translation, etc.). In some embodiments, the segments can move relative to each other along a plurality of different directions. Alternatively, the segments may be constrained to move along a single direction. For example, the shell segments can be movable relative to each other only along a horizontal (mesial-distal) direction, only along a vertical (occlusal-gingival) direction, or any suitable intermediate angle. Constrained movement can be achieved using various techniques, such as guide features that define the permissible direction(s) of motion. In some embodiments, such guide features include a first element (e.g., a channel or groove) located on a first shell segment and a second element (e.g., a protrusion that first into the channel or groove) located on a second shell segment, such that the shell segments are only permitted to move along certain directions (e.g., along the length of the channel) when the two elements are engaged with each other. Moreover, the guide features can include elastic elements (e.g., spring elements) that apply forces on the segments to displace them relative to each other (e.g., towards each other or away from each other).

FIG. 8A through FIG. 8C and FIG. 8G illustrate an orthodontic appliance 800 that includes a first shell segment 806 and a second shell segment 808, which can be viewed as being separated by a discontinuity 804 (e.g., the separation between the two segments 806, 808). As depicted herein, the segments 806, 808 of the appliance 800 are horizontal (mesial-distal) segments. The first and second shell segments 806, 808 have guide features 802. The first and second segments 806, 808 are movable relative to each other. A plurality of elastic members 810 spans the discontinuity 804 and is coupled to the first and second segments 806, 808. In some embodiments, the first and second segments 806, 808 are configured to overlap, with a portion of the first segment 806 positioned over a portion of the second segment 808, such that the two segments 806, 808 can telescopically slide relative to each other.

The guide features 802 formed in the segments 806, 808 are configured to guide the movement of the segments 806, 808 relative to each other. For example, the guide features can include mating telescopic features (e.g., protrusions 812 sliding within channels 814) that constrain the relative motion between the segments 806, 808 along a specified direction. FIG. 8H and FIG. 8I illustrate a top view and side view, respectfully, of an exemplary telescopic guide feature 870 including a piston element 872 and spring element 874, in accordance with some embodiments. The piston 872 can slide telescopically within a channel 876. The spring 874 can be any suitable elastic piece or element. In some embodiments, the spring 874 is disposed within the channel 876, with its ends coupled respectively to the interior of the channel 876 and one end of the piston 872, such that the elasticity of the spring 874 controls the amount of force needed to displace the piston 872 relative to the channel 876 (e.g., inwards and/or outwards).

The guide features described herein can be integrally formed with the appliance shell, or provided as separate elements that are attached to the shell. In some embodiments, the guide feature 870 can be installed within the channels 814 of the appliance 800. Alternatively or in addition, the guide feature 870 can be installed on the shell segments 806, 808 of the appliance 800 without requiring the channels 814. For example, the guide feature 870 may be provided as a separate element and fastened to the appliance 800 using one or more fasteners 878 (e.g., rivets, screws, pins, etc.). Any suitable configuration and/or number of telescopic features (or other guide features) can be used in conjunction with any suitable configuration and/or number of elastic members and discontinuities. FIG. 8G illustrates a cross-section of segment 806 in which the telescopic channels 814 and the elastic members 810 are interspersed with each other. The guide features and the elastic members can be situated on any suitable portion of the appliance, such as the lingual, occlusal, and/or buccal surfaces of the appliance.

Figure 8A:
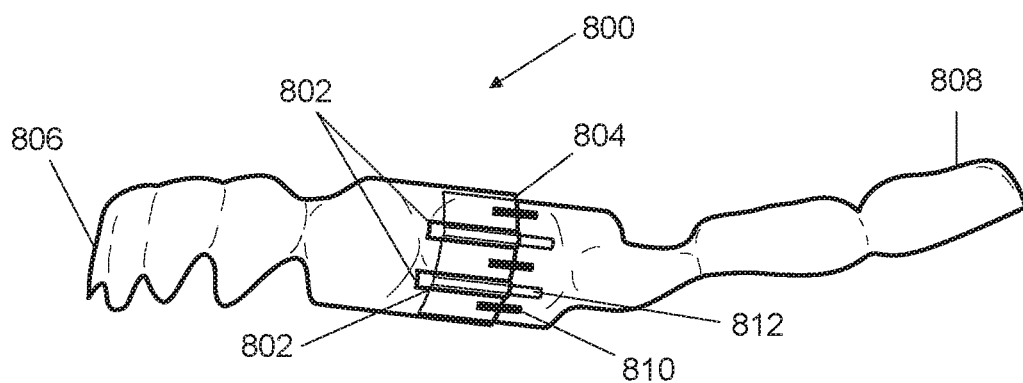
FIG. 8A illustrates an orthodontic appliance having elastics and associated guide features, in accordance with some embodiments.
Figure 8B:
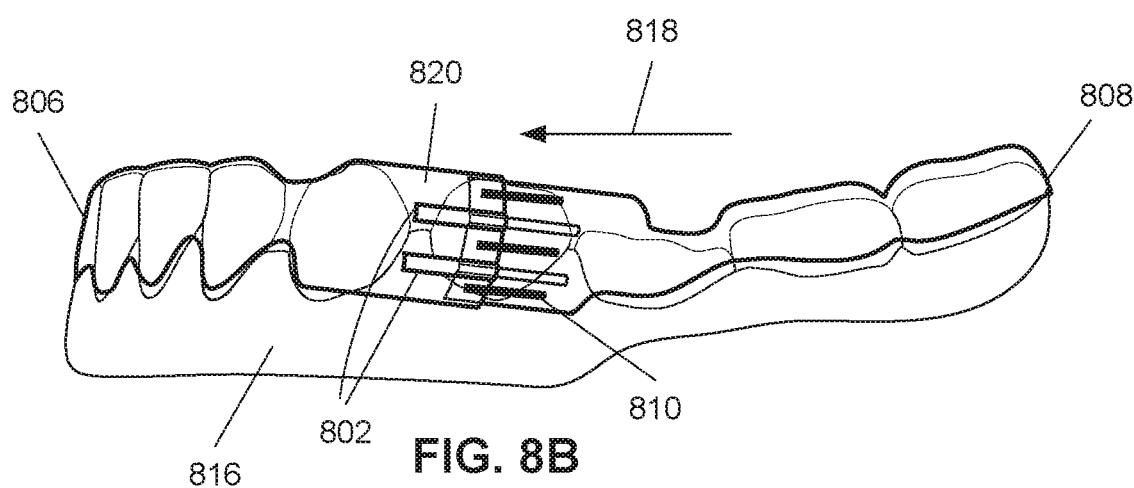
FIG. 8B illustrates the appliance of FIG. 8A when placed over the teeth.
Figure 8C:
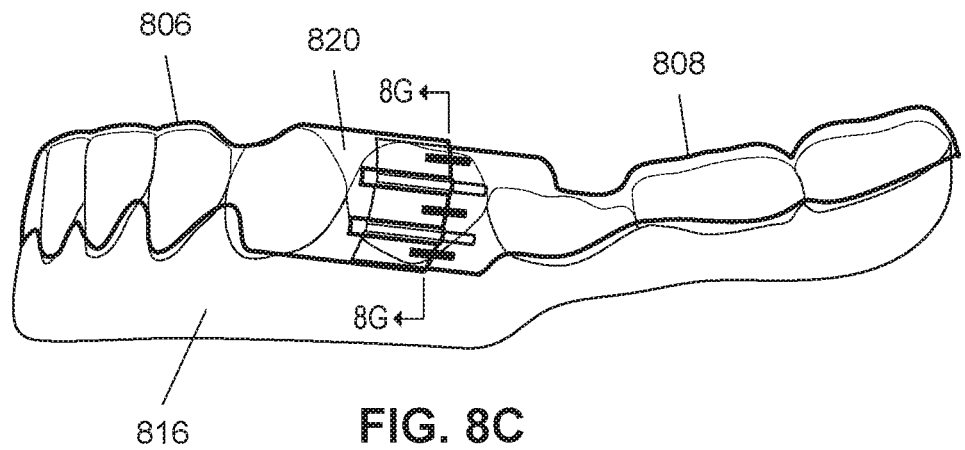
FIG. 8C illustrates the appliance of FIG. 8B after tooth repositioning has occurred.

When the appliance 800 is placed over an arch 816 (as illustrated in FIG. 8B), the segments 806, 808 may be displaced relative to each other (e.g., moved apart). The elastic members 810 can exert a force on the segments 806, 808 resisting the displacement and pulling the segments 806, 808 toward each other. The resulting associated forces applied to the teeth induce repositioning of the teeth of the arch 816 (see, e.g., arrow 818) so as to reduce the arch length (e.g., by closing the interproximal space 820). The guide features 802 can act in parallel with the elastic members 810 to control the magnitude and/or direction of the forces expressed on the teeth. FIG. 8C illustrates the teeth of the arch 816 after repositioning, with the space 820 closed and the two segments 806, 808 returned to the original configuration of FIG. 8A.

Figure 8D:
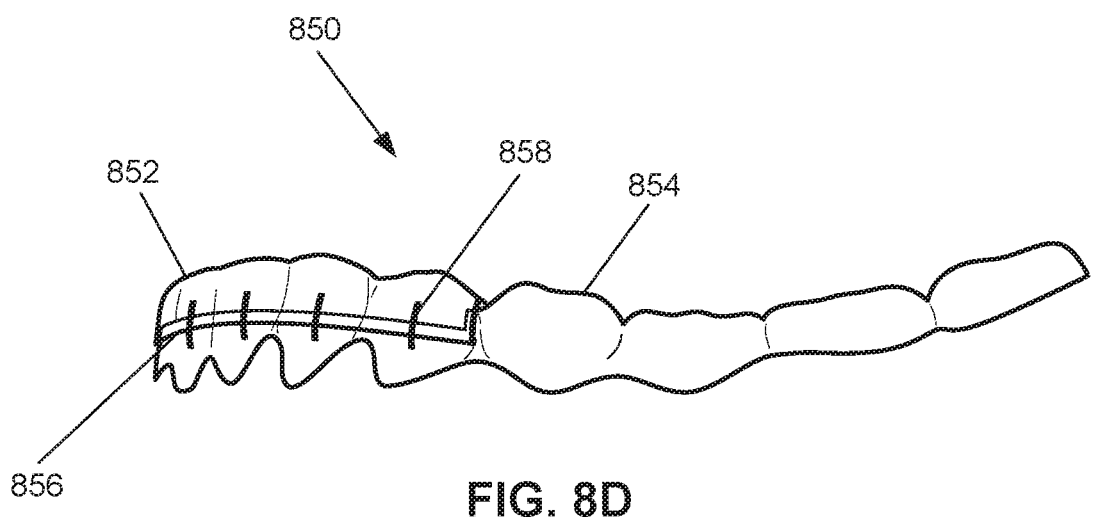
FIG. 8D illustrates an orthodontic appliance having telescopic shell segments, in accordance with some embodiments.
Figure 8E:
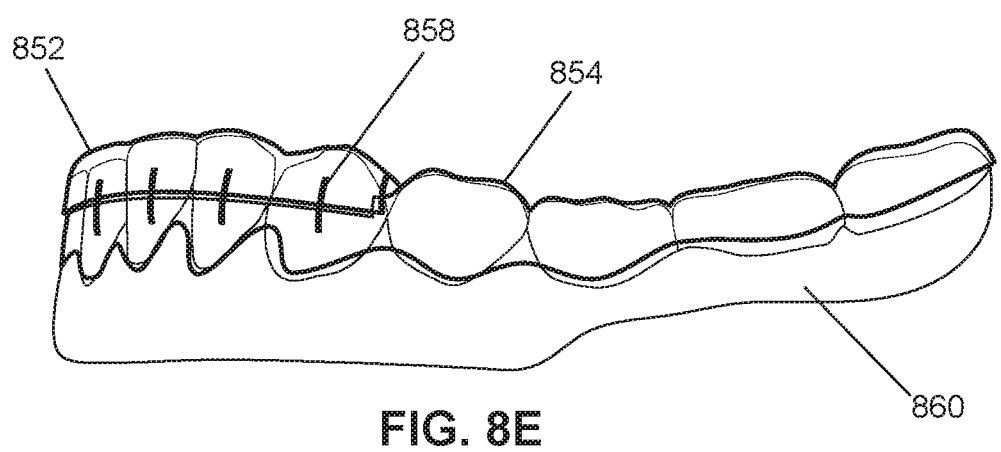
FIG. 8E illustrates the appliance of FIG. 8D when placed over the teeth.
Figure 8F:
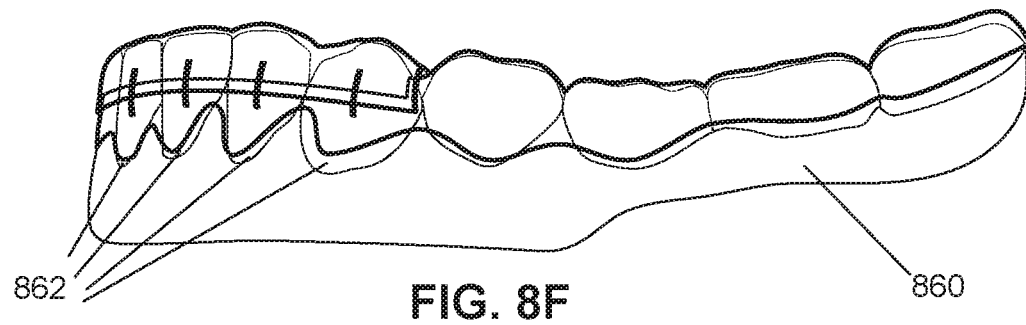
FIG. 8F illustrates the appliance of FIG. 8E after tooth repositioning has occurred.
Figure 8G:
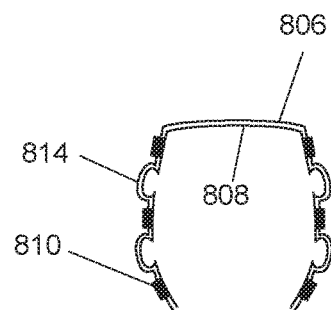
FIG. 8G is a cross-sectional view of a segment of the appliance of FIG. 8C.
Figure 8H:
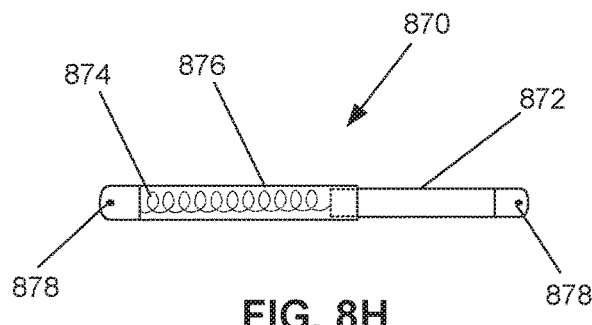
FIG. 8H is a top view of a telescopic guide feature, in accordance with some embodiments.
Figure 8I:
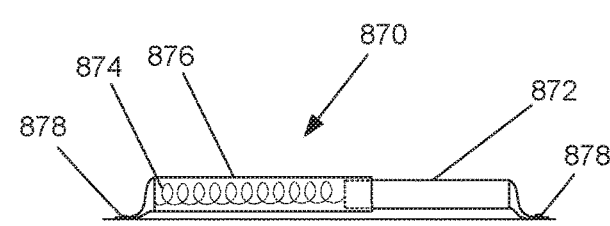
FIG. 8I is a side view of the telescopic guide feature of FIG. 8H.

FIG. 8D through FIG. 8F illustrate an orthodontic appliance 850 with telescopic shell segments 852, 854, in accordance with some embodiments. The shell segments 852, 854 are depicted herein as being vertical (occlusal-gingival) segments. The first shell segment 852 and the second shell segment 854, which can be viewed as being separated by a discontinuity 856, are movable relative to each other, such that the first segment 852 overlaps and slides telescopically over the second segment 854. A plurality of elastic members 858 spans the discontinuity 856 and is coupled to the first and second segments 852, 854. When the appliance 850 is placed over an arch 860 (as illustrated in FIG. 8E), the segments 852, 854 may be displaced relative to each other (e.g., moved apart). The elastic members 858 can resist the displacement and pull the segments 852, 854 towards each other, causing repositioning of the teeth of the arch 860 (e.g., intrusion of the teeth, as illustrated in FIG. 8F). In some embodiments, the orthodontic appliance 850 can include one or more of the guide features described herein in order to more precisely direct the relative movements of the segments 852, 854.

Figure 25A:
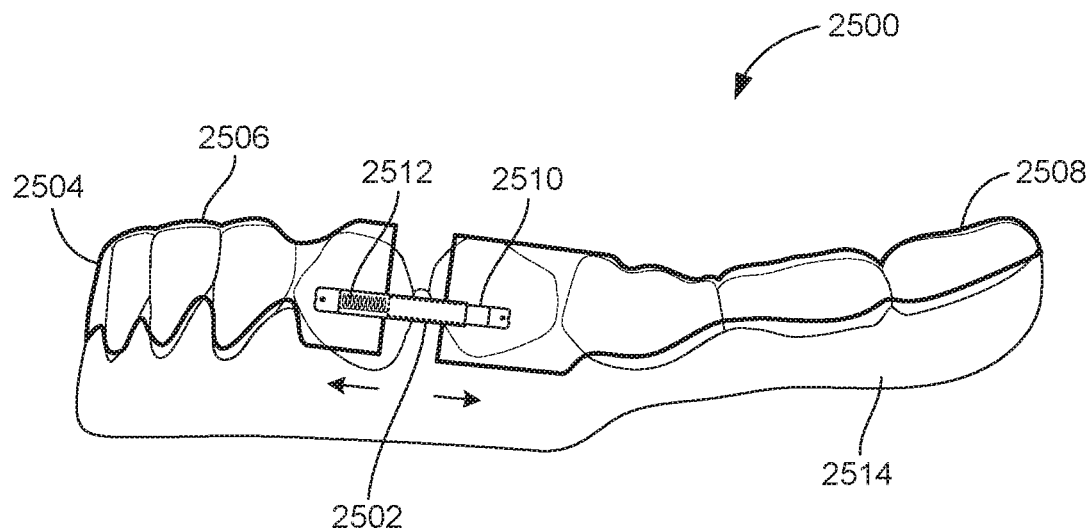
FIGS. 25A and 25B illustrate orthodontic appliances having telescopic guide features, in accordance with some embodiments.

FIG. 25A illustrates an orthodontic appliance 2500 having a telescopic guide feature 2502, in accordance with some embodiments. The appliance 2500 includes a shell 2504 that is separated into discrete segments 2506, 2508, with the guide feature 2502 joining the two segments, 2506, 2508. The two segments 2506, 2508 can be configured to move relative to each other without sliding telescopically over each other. In alternative embodiments, the segments 2506, 2508 can be configured for telescopic sliding, similar to the embodiments of FIGS. 8A through 8F. The guide feature 2502 can be used to constrain the relative movement of the shell segments 2506, 2508 along a specified direction of motion. In some embodiments, the guide feature 2502 includes an elastic member (e.g., a spring element) that provides the force for eliciting tooth movements. For example, the guide feature 2502, can include a slidable piston element 2510 coupled to an elastic spring element 2512, similar to the guide features previously described herein with respect to FIGS. 8H and 8I. The guide feature 2502 can be arranged such that when the appliance 2500 is placed on the teeth 2514, the spring element 2512 is compressed by the piston 2510, and thus exerts forces (indicated by arrows) to displace the shell segments 2506, 2508 away from each other. The resultant forces exerted on the teeth 2514 can be used to move teeth apart, e.g., to increase a space between teeth.

Figure 25B:
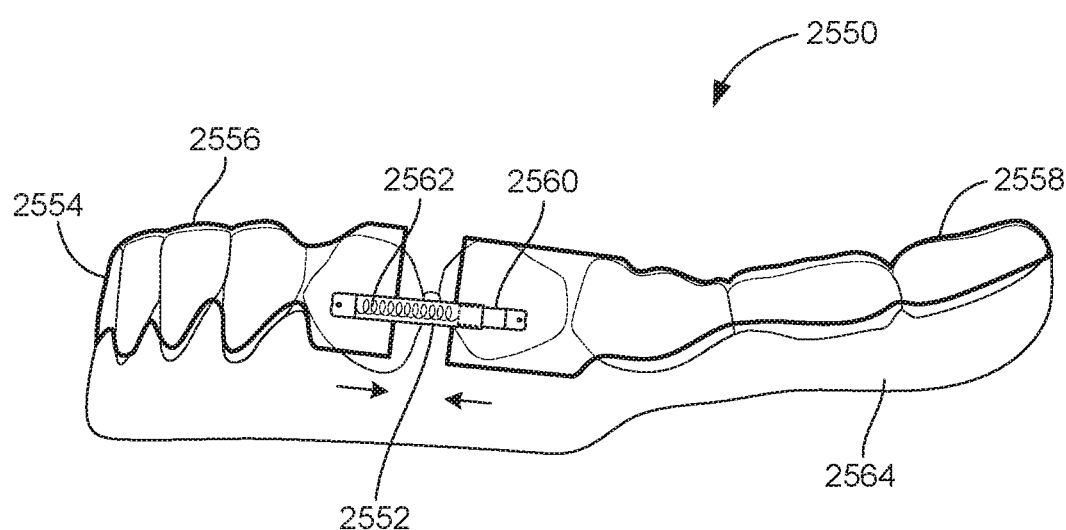

FIG. 25B illustrates an orthodontic appliance 2550 having a telescopic guide feature 2552, in accordance with some embodiments. Similar to the appliance 2500, the appliance 2550 includes a shell 2554 having discrete segments 2556, 2558 joined by the guide feature 2552. The guide feature can include a slidable piston element 2560 coupled to a spring element 2562. The guide feature 2552 can be arranged such that when the appliance 2550 is placed on the teeth 2564, the spring element 2562 is stretched by the piston 2560, and thus exerts forces (indicated by arrows) to displace the shell segments 2556, 2558 towards each other. The resultant forces exerted on the teeth 2564 can be used to move teeth together, e.g., to reduce a space between teeth.

In some embodiments, the orthodontic appliances described herein can be configured to maintain a current position of a patient's teeth, rather than repositioning the teeth. Such tooth retaining appliances, also known as retainers, are generally similar to the tooth repositioning appliances described herein, except that the appliance geometry is selected to exert forces on the teeth without causing repositioning of the teeth. In such embodiments, the tooth arrangement specified by the appliance geometry can be substantially similar to the current tooth arrangement of the patient. A retaining appliance may be worn by a patient, for instance, after orthodontic treatment is complete, in order to reduce or prevent movement of the teeth away from the corrected configuration. Any description herein relating to tooth repositioning appliances can also be applied to tooth retaining appliances, and vice-versa.

Figure 9:
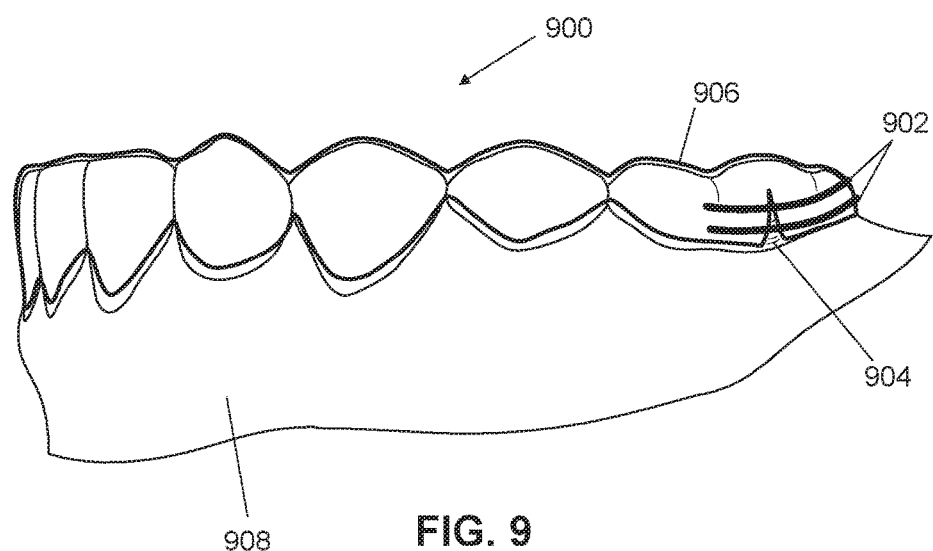
FIG. 9 illustrates an orthodontic appliance for maintaining a current position of the patient's teeth, in accordance with some embodiments.

FIG. 9 illustrates an orthodontic appliance 900 configured to maintain a current position of the patient's teeth, in accordance with some embodiments. The appliance 900 includes a shell 906 and one or more elastic members 902 interacting with a discontinuity 904 formed in the shell 906. For example, the discontinuity 904 can include one or more cuts in the shell 906. The discontinuity 904, e.g., cuts, may extend to a peripheral edge of the shell 906 (e.g., a gingival edge). As illustrated in FIG. 9, the elastic members 902 can be attached on the lingual and buccal surfaces of the shell 906 and span the discontinuity 904. When worn on an arch 908, the appliance 900 can exert a continuous force on one or more teeth to prevent the teeth from moving out of their current arrangement. The magnitude of such forces can be smaller than the magnitude of forces for eliciting tooth movements. Furthermore, the elastic members 902 can function as clasps to prevent the appliance 900 from moving or becoming dislodged from the teeth. The configuration of the shell, elastic members and/or the discontinuity can be selected to prevent inadvertent tooth repositioning.

In some embodiments, in order to improve control over the forces applied to teeth by an orthodontic appliance, the appliance shell can include features such as dimples, ridges, protrusions, etc. that contact teeth at a specified point or region so as to selectively apply force to that point or region. This approach can increase control over the magnitude and/or direction of force application to the teeth, thereby producing more controlled tooth movements and enabling the application of more complex force systems.

Figure 10A:
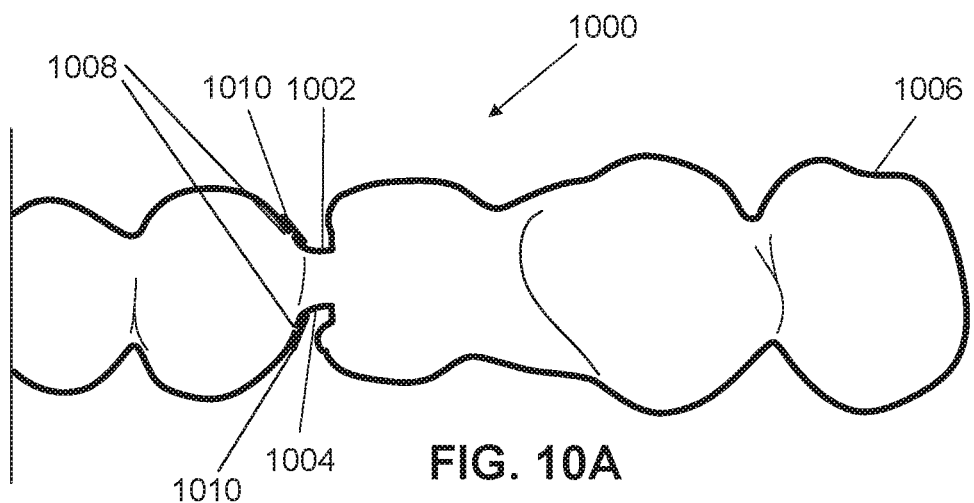
FIG. 10A illustrates an orthodontic appliance with protrusions, in accordance with some embodiments.
Figure 10B:
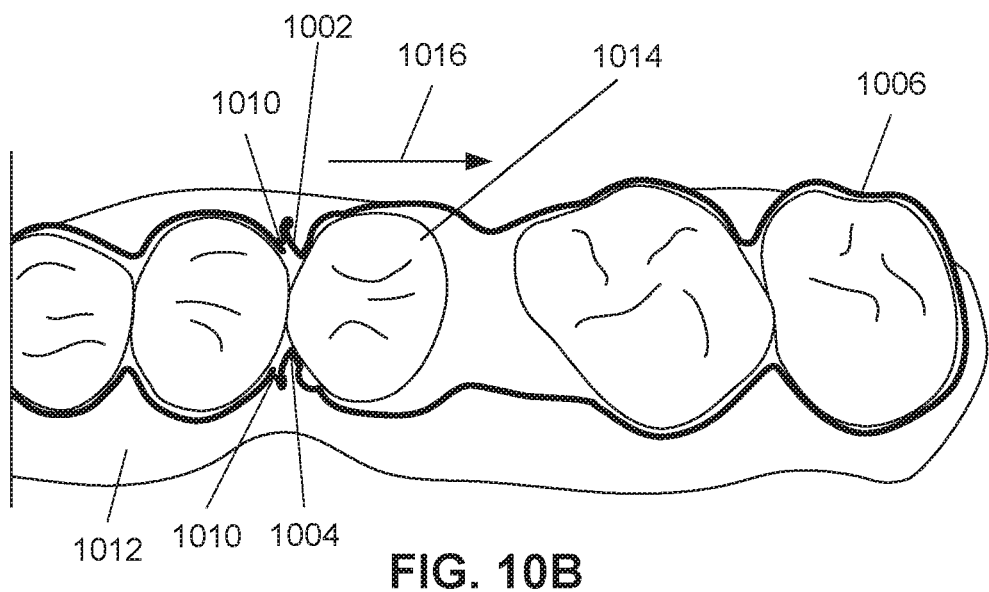
FIG. 10B illustrates the appliance of FIG. 10A when placed over the teeth.

FIG. 10A through FIG. 10C illustrate an orthodontic appliance 1000 with a lingual 1002 and buccal protrusion 1004, in accordance with some embodiments. The lingual protrusion 1002 and buccal protrusion 1004 are formed as curved surfaces on the lingual and buccal surfaces of the shell 1006, respectively, and protrude into the internal cavity of the shell 1006. The shell 1006 can include a pair of discontinuities 1008 formed on the lingual and buccal surfaces, respectively. Each of the discontinuities 1008 can be formed as a cut in the shell 1006 defining a flap surrounding the corresponding protrusion (as illustrated in FIG. 10G) and can be spanned by a pair of elastic members 1010. When placed on an arch 1012 of a patient (as illustrated in FIG. 10B), the protrusions 1002, 1004 are deflected outwards by the underlying tooth 1014. The elastic members 1010 can resist the deflection by exerting forces that are applied inwards against the tooth 1014 by the protrusions 1002, 1004, thereby causing tooth movement (see, e.g., arrow 1016). FIG. 10C illustrates the appliance 1000 and the arch 1012 after repositioning of the tooth 1014 has occurred.

Figure 10E:
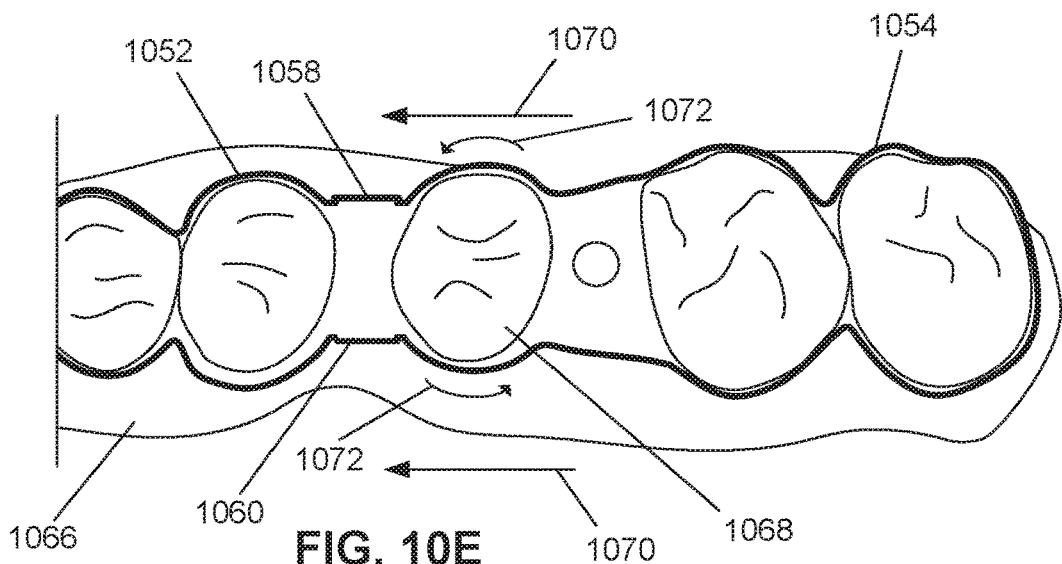
FIG. 10E illustrates the appliance of FIG. 10D when placed over the teeth.
Figure 10F:
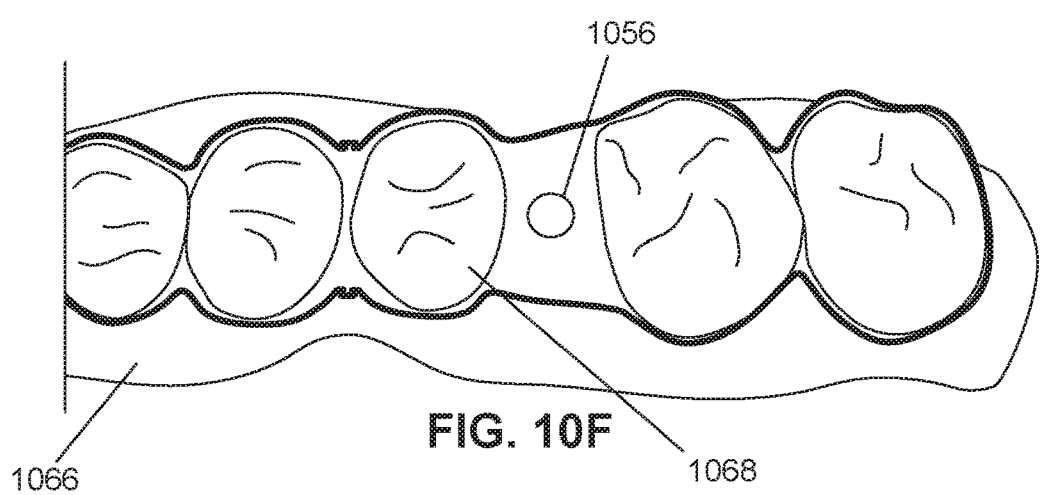
FIG. 10F illustrates the appliance of FIG. 10E after tooth repositioning has occurred.
Figure 10G:
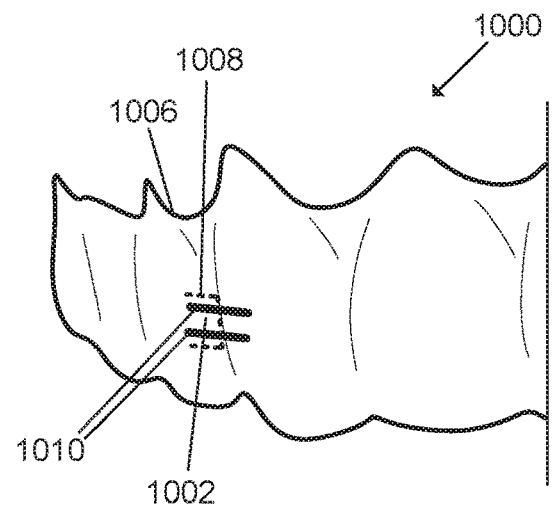
FIG. 10G is a perspective view of the appliance of FIG. 10C.

FIG. 10D through FIG. 10F illustrate an orthodontic appliance 1050 divided into discrete shell segments 1052, 1054, in accordance with some embodiments. The appliance 1050 can be used to increase the size of a space between teeth, for instance, to accommodate installation of a dental prosthesis such as an implant 1056. The shell segments 1052, 1054 are coupled to each other by elastic members 1058, 1060 spanning the discontinuities 1062, 1064, respectively. When placed on an arch 1066 (as illustrated in FIG. 10E), the segments 1052, 1054 are moved apart from each other due to the arrangement of the underlying teeth, thereby stretching the elastics 1058, 1060. The tension in the elastics 1058, 1060 can result in application of repositioning forces to the teeth. For example, the tooth 1068 can be repositioned to increase space for the implant 1056. In some embodiments, the shell segments, discontinuities, and elastic members can be configured to reposition the tooth 1068 in a plurality of phases. In a first phase, the tooth 1068 can be translated along a mesial direction (see, e.g., arrows 1070). In a second phase, the tooth 1068 can be rotated (see, e.g., arrows 1072). The phases may occur sequentially, such that the tooth 1068 is first translated then rotated, or vice-versa. Alternatively, in some instances, the first and second phases can overlap or occur simultaneously, such the tooth 1068 is translated and rotated at the same time. FIG. 10F illustrates the arch 1066 after repositioning, in which the tooth 1068 has been moved to expand the space available for the implant 1056.

FIG. 16A through FIG. 16C illustrate an orthodontic appliance 1600 including a protrusion 1602 for applying force to a tooth, in accordance with some embodiments. As illustrated in FIG. 16A, the internal surface profile of the appliance 1600 has a curved surface that forms the protrusion 1602, which extends into the interior of the appliance. FIG. 16B illustrates a cross-sectional view of a shell 1604 of the appliance 1600, in which the protrusion 1602 is implemented as a curved portion 1606 of the shell 1604. The curved portion 1606 is situated adjacent to or near a discontinuity 1608 in the shell 1604, depicted herein as a cut formed in the shell 1604. An elastic member 1610 is coupled to the shell 1604 spanning the discontinuity 1608, such that one end of the elastic member 1610 is attached to or near the curved portion 1606. FIG. 16C illustrates a tooth 1612 received within the shell 1604 and displacing the curved portion 1606 outward relative to its initial configuration. The elastic member 1610 can exert force on the curved portion 1606 resisting the displacement (see, e.g., arrow 1614). In some embodiments, the exerted force results in associated force being transmitted to the tooth 1612 at a contact point by the curved portion 1606. Application of force to the contact point can be used, for example, to elicit a tipping movement of the tooth 1612.

FIG. 17A through FIG. 17C illustrate an orthodontic appliance 1700 including a protrusion 1702 for applying force to a tooth, in accordance with some embodiments. FIG. 17A illustrates the internal surface profile of the appliance 1700, including the curved protrusion 1702, and is similar to the embodiment of FIG. 16A. FIG. 17B illustrates a cross-sectional view of a shell 1704 of the appliance 1700 in which the protrusion 1702 is implemented as a knob or button 1706 formed on the interior of the shell 1704. Similar to the appliance 1600, the appliance 1700 includes a discontinuity 1708 (e.g., a cut) adjacent to or near the knob 1706, and an elastic member 1710 spanning the discontinuity 1708 and attached at one end to or near the knob 1706. When the appliance receives a tooth 1712, the elastic member 1710 can apply force to the tooth 1712 (see, e.g., arrow 1714) at a contact point via the knob 1706.

Figure 18A:
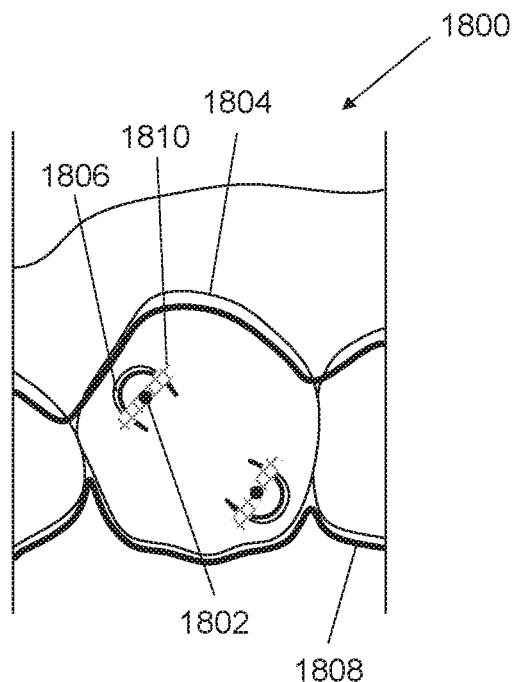
FIGS. 18A through 18C illustrate exemplary orthodontic appliances including protrusions and elastics, in accordance with some embodiments.
Figure 18B:
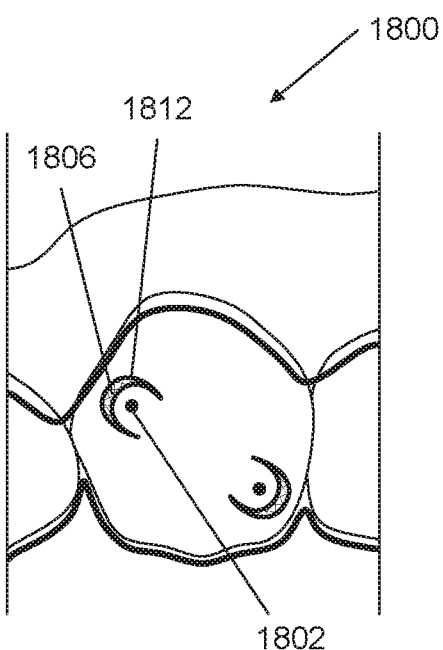
Figure 18C:
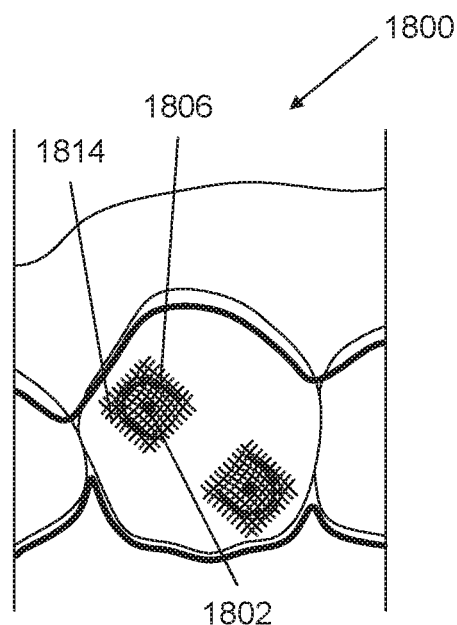
Figure 19:
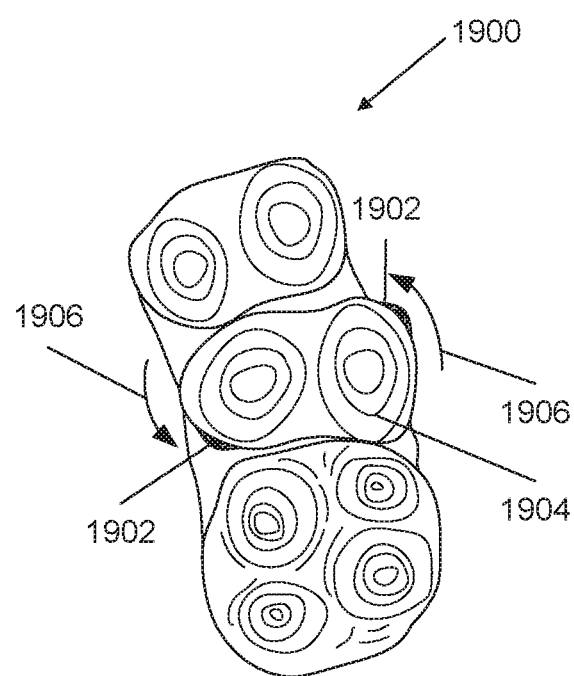
FIG. 19 illustrates another exemplary orthodontic appliance including protrusions, in accordance with some embodiments.

FIG. 18A through FIG. 18C and FIG. 19 illustrate orthodontic appliances that include protrusions for applying forces to teeth, in accordance with some embodiments. The protrusions can be any suitable feature extending from the shell surface to apply force to a tooth via contact between the protrusion and the tooth, such as the embodiments previously described herein (e.g., curved surface 1606, knob 1706). FIG. 18A illustrates an appliance 1800 including a pair of protrusions 1802 situated over a tooth 1804. Each of the protrusions 1802 is positioned near a discontinuity, depicted herein as a cut forming a curved flap 1806 in the shell 1808, such that the protrusion is disposed on the underside of the flap 1806 (extending into the interior of the shell 1808 towards the tooth 1804). An elastic member, depicted herein as a band or strip 1810, is attached to the shell 1808 on opposing sides of the flap 1806 and extends over the flap 1806. FIG. 18B illustrates an alternative configuration for the appliance 1800, in which the elastic member is implemented as an elastic membrane or elastic mesh 1812 that connects the edges of the flap 1806 to the adjacent edges of the shell 1804. FIG. 18C illustrates another exemplary configuration for the appliance 1800, in which the elastic member includes an elastic membrane or elastic mesh 1814 that is positioned over the entirety of the flap 1806 and a portion 1804 of the shell adjacent to the flap 1806. In each of the previous examples, the elastic member can generate forces that are applied to the flap 1806 and thereby generate forces that are applied by the protrusion 1802 against the tooth 1804. The positioning of the protrusions 1802 can be configured to control the tooth movements resulting from the application of these forces. For example, as depicted in FIG. 19, an appliance 1900 can include a pair of protrusions 1902 situated on different sides of a tooth 1904 (e.g., on a buccal surface and a lingual surface, respectively). The positioning of the protrusions 1902, when combined with a suitable set of elastic members and discontinuities (not shown), can be used, for instance, to elicit a rotational tooth movement (see, e.g., arrows 1906). The elastics described herein can be coupled to the shell and/or flap using any suitable method. For example, the elastics can be extruded, sprayed, or otherwise directly adhered onto the shell and/or flap.

Figure 20A:
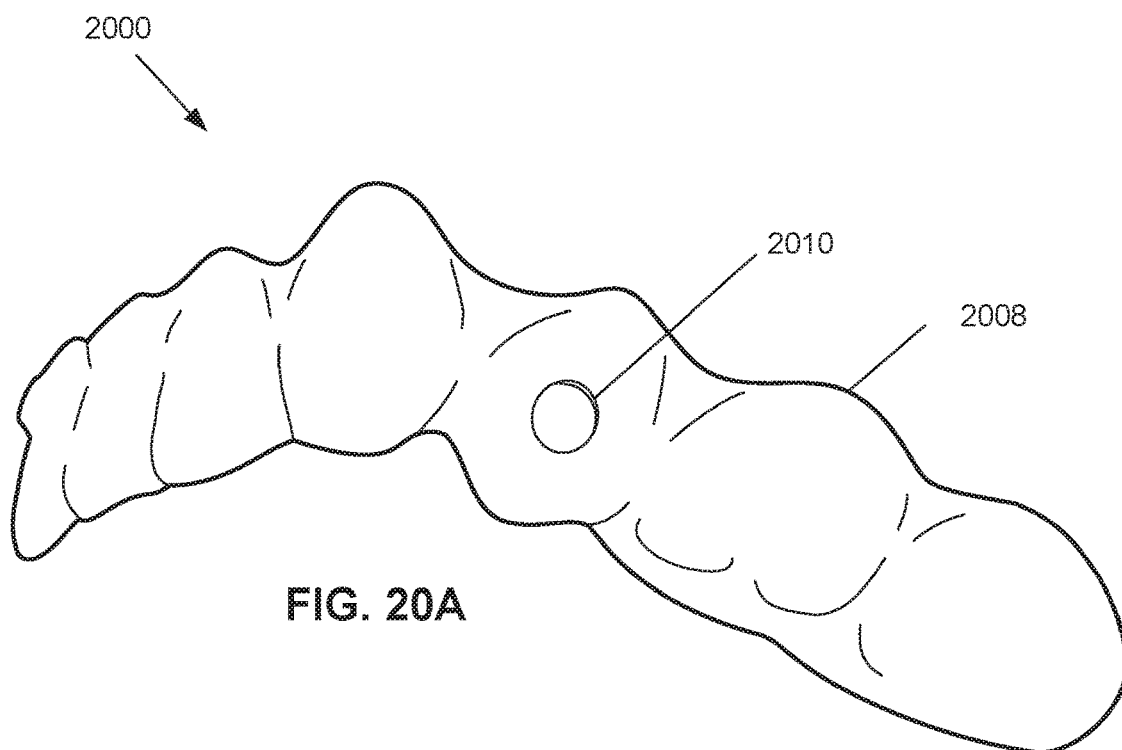
FIG. 20A illustrates an orthodontic appliance shell used with an elastic member and attachment, in accordance with some embodiments.
Figure 20B:
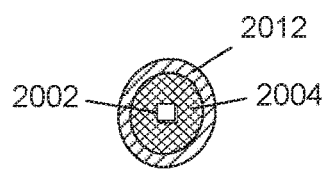
FIG. 20B illustrates an elastic member with an attachment, in accordance with some embodiments.
Figure 20C:
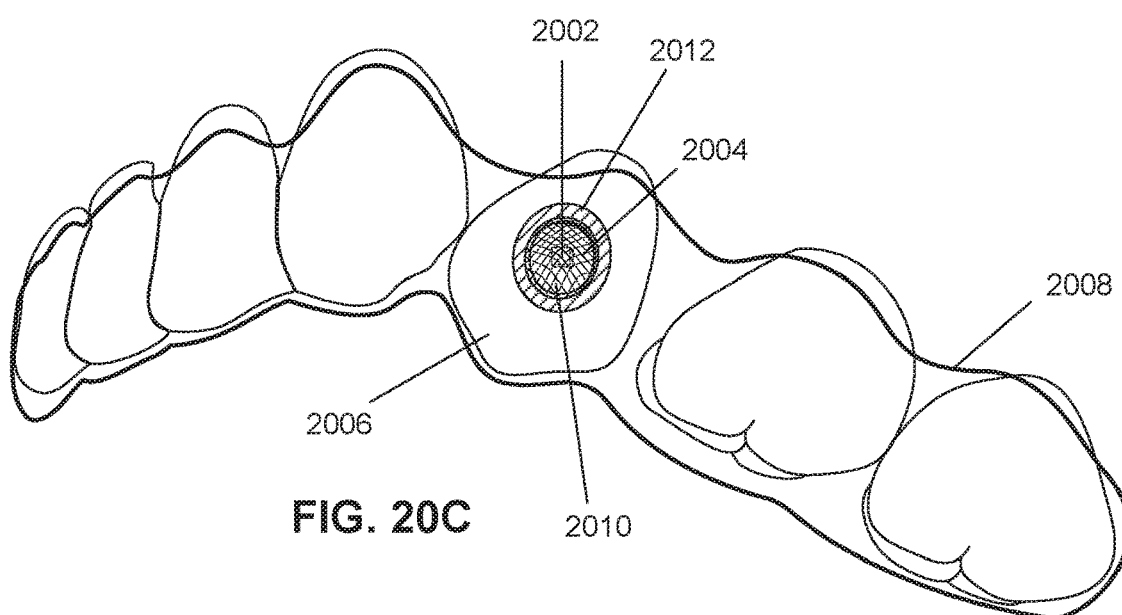
FIG. 20C illustrates the elastic member of FIG. 20B coupled to the appliance of FIG. 20A.

FIG. 20A through FIG. 20C illustrate an orthodontic appliance 2000 including an elastic member with an attachment 2002, in accordance with some embodiments. The elastic member, depicted herein as a mesh or membrane 2004, is formed with or coupled to an attachment 2002. The attachment 2002 (e.g., a protrusion, post, stud, button, etc.) is configured to engage and apply force to a tooth 2006. In some embodiments, the attachment 2002 contacts the tooth 2006 through a discontinuity formed in the shell 2008 of the appliance 2000, depicted herein as an aperture 2010. The attachment 2002 can contact the tooth 2006 directly, or indirectly (e.g., via an attachment mounted on the tooth). The elastic member can be coupled to the shell 2008 in a position spanning the discontinuity such that the attachment 2002 extends into the interior of the shell 2008 through the discontinuity. For example, the mesh 2004 is shaped to cover the aperture 2010 and includes an adhesive perimeter 2012 enabling the mesh 2004 to be directly coupled to the shell 2008. When the mesh 2004 is attached to the shell 2008, the attachment 2002 protrudes through the aperture 2010 towards the tooth 2006.

In some embodiments, the orthodontic appliance is configured to exert force on a tooth via one or more attachments mounted to the tooth. As previously described herein, an attachment can be coupled to the surface of one or more teeth to transmit forces exerted by the appliance onto the teeth. The geometry of the attachment and its position on the tooth can influence the magnitude and/or direction of the forces applied to the tooth. In some embodiments, the attachment is configured to elicit tooth movements that may be difficult to achieve with the appliance alone (e.g., extrusion).

The interactions between the appliance (e.g., an elastic member, a shell, a flap formed in the shell, etc.), attachment (e.g., mounted on a tooth), and teeth can be influenced by friction between these elements. In some embodiments, the frictional coefficient between the appliance and attachment is configured to be smaller than the frictional coefficient between the appliance and the tooth. This arrangement can enable the attachment to move freely relative to the appliance, while increasing the force applied onto the teeth by the appliance. The frictional coefficient can be a function of the material and/or surface properties. In some embodiments, the appliance and the attachment are fabricated using different types of materials, and such materials may be selected based on their material and/or surface properties. Furthermore, the frictional coefficient can be increased or decreased by application of suitable coatings, films, texturing, and the like.

Figure 11A:
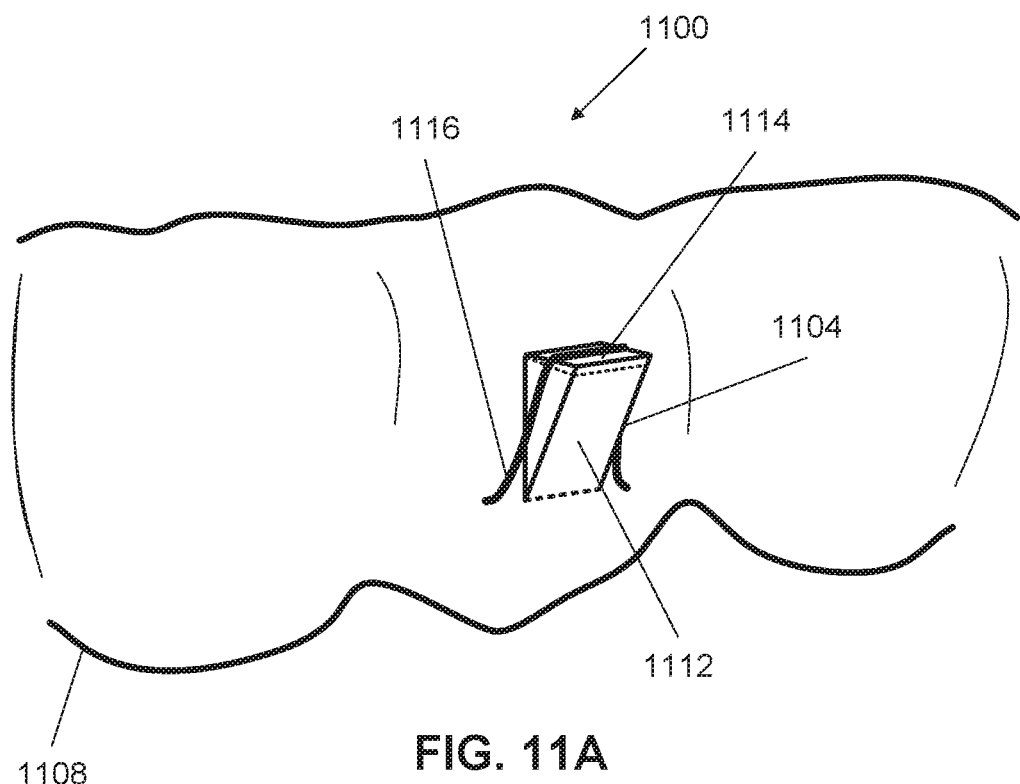
FIG. 11A illustrates an orthodontic appliance configured to engage an attachment, in accordance with some embodiments.
Figure 11B:
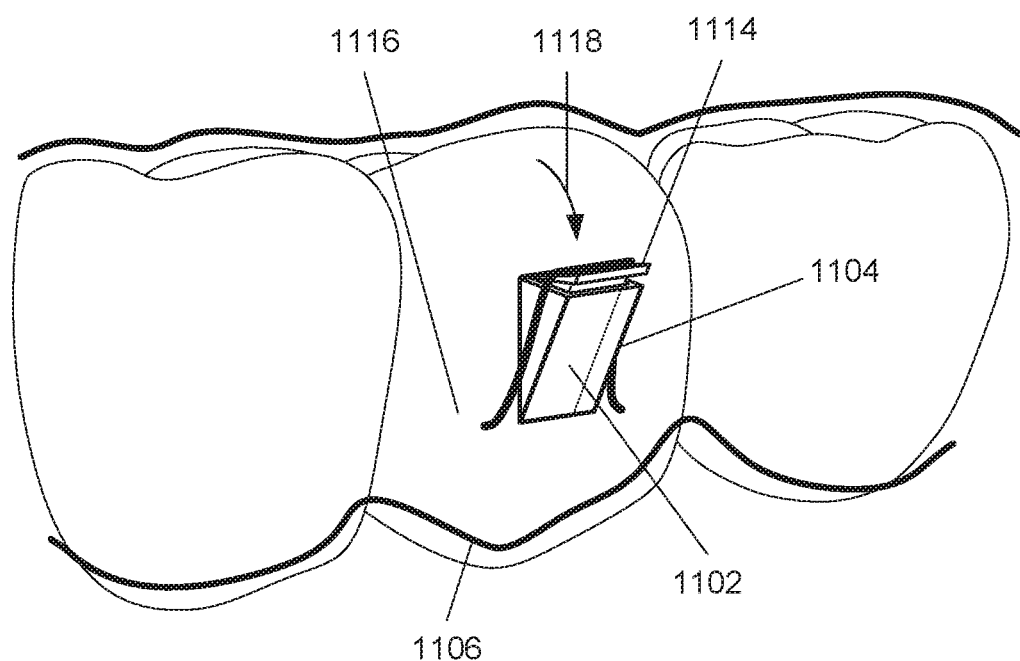
FIG. 11B illustrates the appliance of FIG. 11A when placed over the teeth.

FIG. 11A through FIG. 11B illustrate an orthodontic appliance 1100 configured to engage an attachment 1102 on a tooth 1106, in accordance with some embodiments. The appliance 1100 includes a receptacle 1104 that is configured to accommodate the attachment 1102 coupled to the tooth 1106. For example, the receptacle 1104 can be a protrusion extending outward from the surface of the shell 1108, with an interior space shaped to receive the attachment 1102. In some embodiments, the receptacle 1104 is also shaped to accommodate and/or guide the movement of the attachment relative to the shell 1108, such as movements corresponding to repositioning of the underlying tooth. The receptacle 1104 can include, for example, a sloped lateral wall 1112 along which the attachment 1102 can slide as the tooth 1106 moves upwards or downwards (along a gingival-occlusal axis).

The appliance 1100 further includes a discontinuity formed in the shell 1108, e.g., so as to form a flap 1114, which can be positioned over and/or against the open upper surface of the receptacle 1104. An elastic member 1116 is attached to the shell 1108 at attachment points, e.g., on either side of the receptacle 1104, and can extend over the top of the receptacle 1104 to hold the flap 1114 in place. When the appliance 1100 is placed over the teeth (as illustrated in FIG. 11B), the attachment 1102 is positioned within the receptacle 1104 and can protrude at least partially from the open upper surface, causing the flap 1114 to be displaced from its initial configuration. The elastic member 1116 can push against the flap 1114, thus imparting a downwards force on the attachment 1102 (see, e.g., arrow 1118) that is transmitted to the underlying tooth 1106, eliciting an intrusive tooth movement.

Figure 12A:
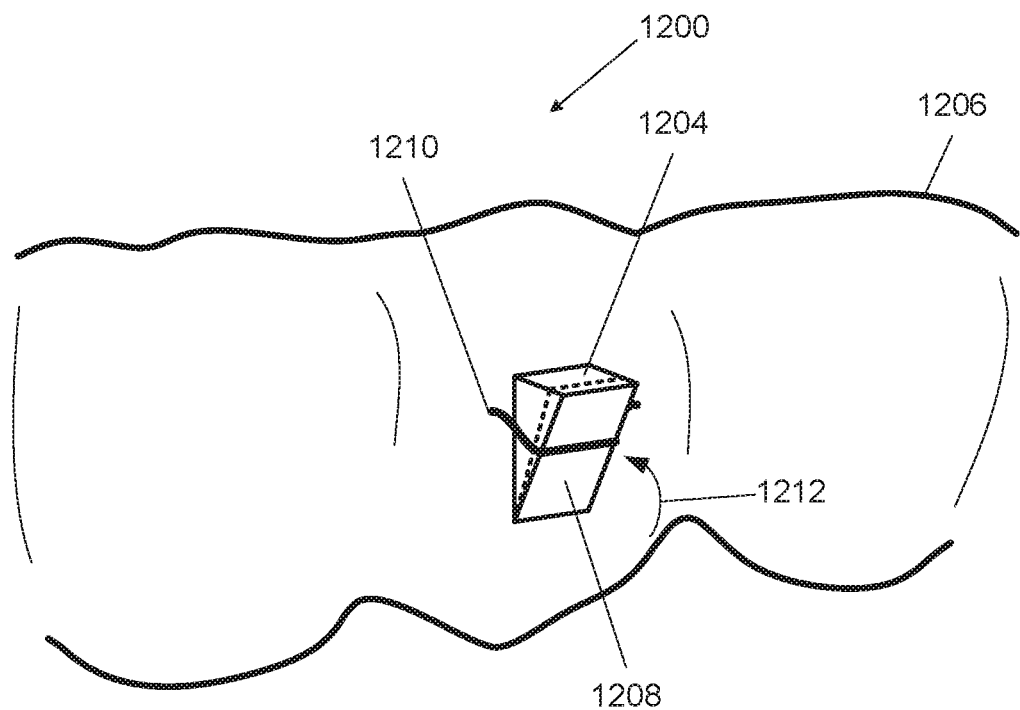
FIG. 12A illustrates another exemplary orthodontic appliance configured to engage an attachment, in accordance with some embodiments.
Figure 12B:
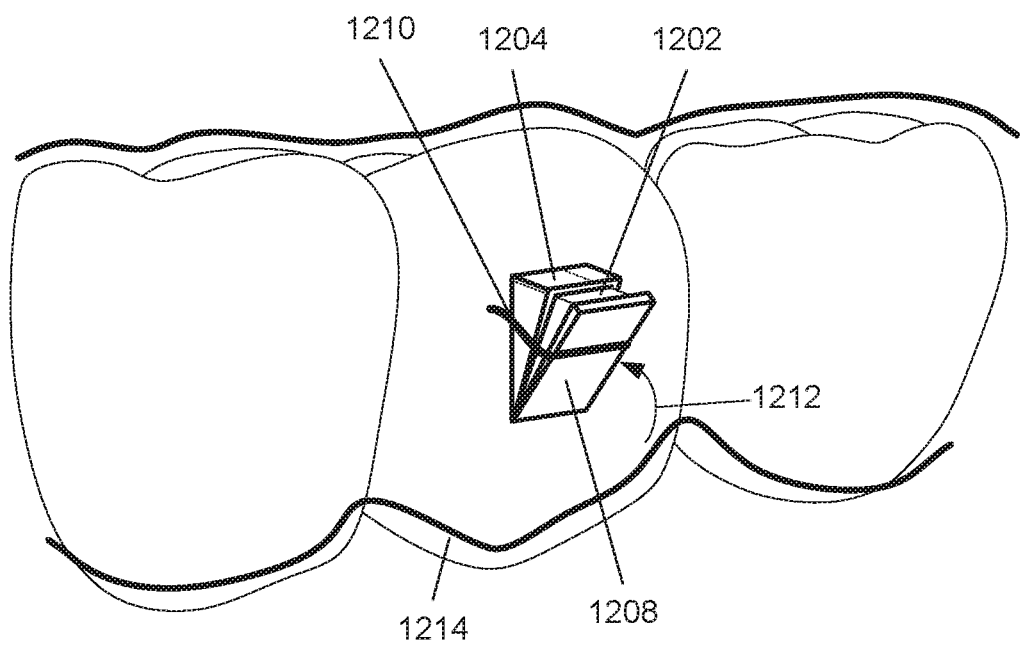
FIG. 12B illustrates the appliance of FIG. 12A when placed over the teeth.

FIG. 12A through FIG. 12B illustrate an orthodontic appliance 1200 configured to engage an attachment 1202, in accordance with some embodiments. The appliance 1200 includes a shell 1206 and a receptacle 1204 formed in the shell 1206 and shaped to receive the attachment 1202. The receptacle 1204 can include an open lateral surface from which the attachment 1202 can protrude. In some embodiments, the appliance 1200 includes a discontinuity that forms a flap 1208, which can be positioned over the open lateral surface of the receptacle 1204. An elastic member 1210 is coupled to the shell 1206 at attachment points situated on opposite sides of the receptacle 1204 and extends over the lateral surface of the receptacle 1204 to hold the flap 1208 in place. Similar to the appliance 1100, when the appliance 1200 is placed over the teeth, the attachment 1202 protrudes from the lateral surface of the receptacle 1204, displacing the flap 1208. The elastic member 1210 exerts a force against the flap 1208 to urge the flap 1208 to its closed configuration (see, e.g., arrow 1212), thereby imparting a force onto the attachment 1202 to elicit movement of the underlying tooth 1214.

Figure 13A:
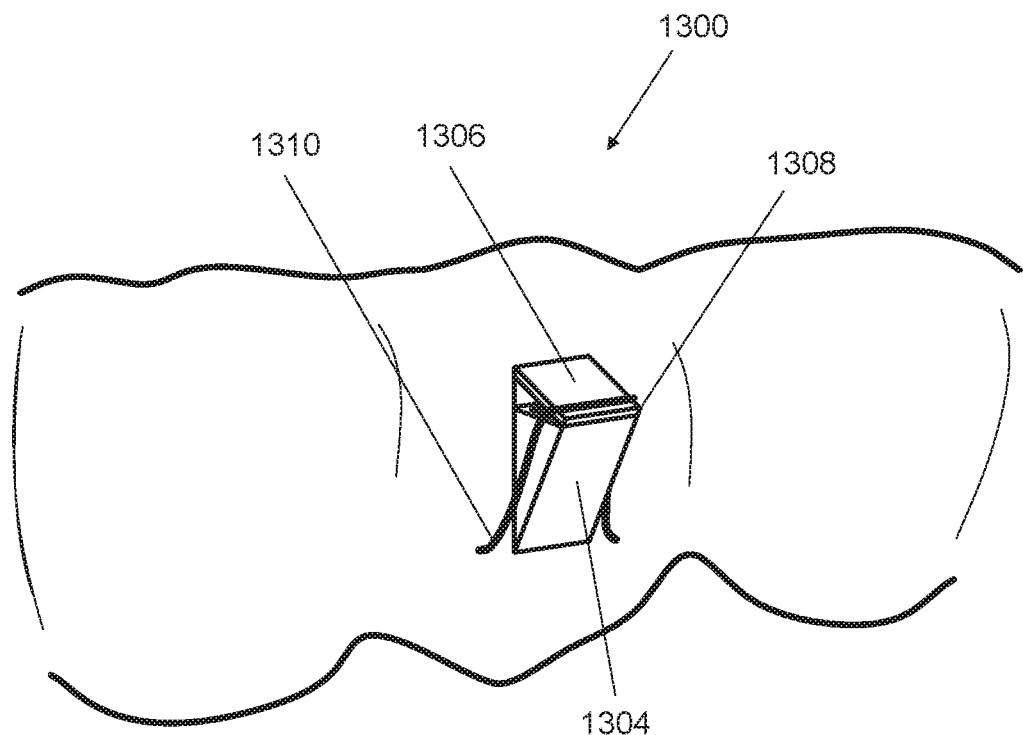
FIG. 13A illustrates yet another orthodontic appliance configured to engage an attachment, in accordance with some embodiments.
Figure 13B:
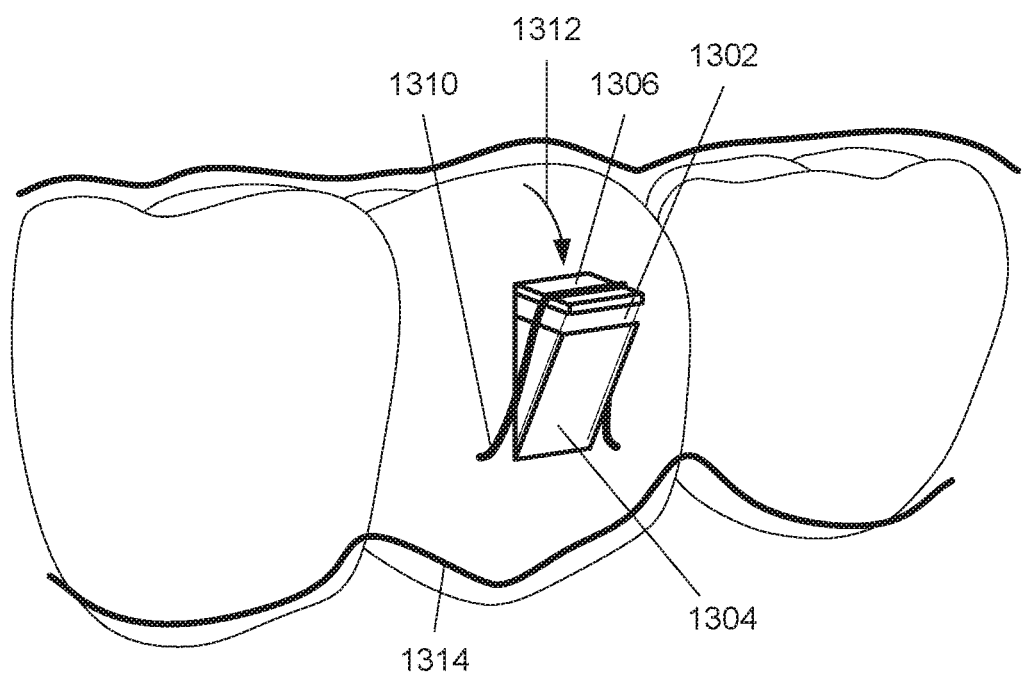
FIG. 13B illustrates the appliance of FIG. 13A when placed over the teeth.

FIG. 13A and FIG. 13B illustrate an orthodontic appliance 1300 configured to engage an attachment 1302, in accordance with some embodiments. Similar to the appliance 1100, the appliance 1300 includes a receptacle 1304 with an open upper surface for accommodating the attachment 1302. A discontinuity of the appliance 1300 can form a flap 1306 positioned over the upper surface of the receptacle 1304. The flap 1306 is vertically offset from the receptacle 1304 such that only the distal edge 1308 of the flap 1306 contacts the receptacle 1304 when the appliance 1300 is not placed over teeth. The elastic member 1310 is similar to the elastic member 1116 in that it extends over the top of the receptacle 1304 to hold the flap 1306 in place. When the appliance 1300 is placed over the teeth (as illustrated in FIG. 13B), the attachment 1302 is received in receptacle 1304 and protrudes from the upper surface of the receptacle 1304 to displace the flap 1306. The elastic member 1310 can impart a downwards force on the flap 1306 (see, e.g., arrow 1312), thereby imparting a downwards force on the attachment 1302 to reposition the tooth 1314.

Figure 14A:
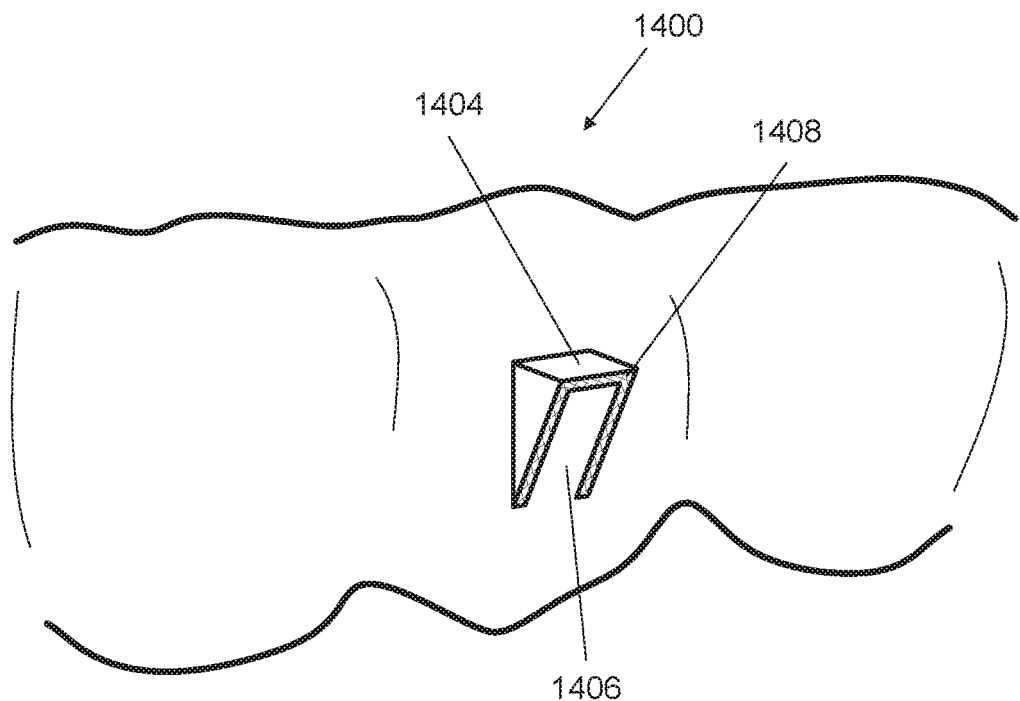
FIG. 14A illustrates an orthodontic appliance configured to engage an attachment, in accordance with some embodiments.
Figure 14B:
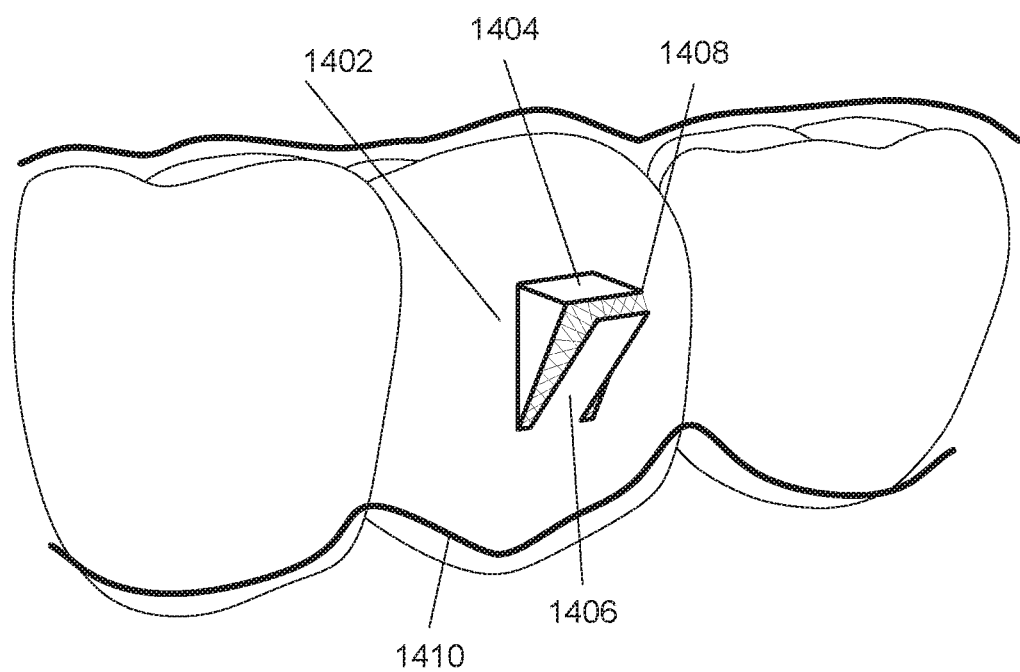
FIG. 14B illustrates the appliance of FIG. 14A when placed over the teeth.

FIG. 14A and FIG. 14B illustrate an orthodontic appliance 1400 configured to engage an attachment 1402, in accordance with some embodiments. Similar to the appliance 1200, the appliance 1400 includes a receptacle 1404 with an open lateral surface for accommodating the attachment 1402. The appliance 1400 includes a discontinuity that forms a flap 1406 positioned over the open lateral surface of the receptacle 1404. An elastic member 1408 of the appliance 1400 is configured as an elastic membrane or elastic mesh joining the edges of the flap 1406 to the corresponding edges of the lateral surface of the receptacle 1404. When the appliance 1400 is worn by the patient (as illustrated in FIG. 14B), the attachment 1404 protrudes through the lateral surface of the receptacle 1404, displacing the flap 1406. The resulting stretching of the elastic member 1408 generated by the displacement of the flap 1406 generates a tooth repositioning force that is applied to the tooth 1410 via the attachment 1404.

Figure 14C:
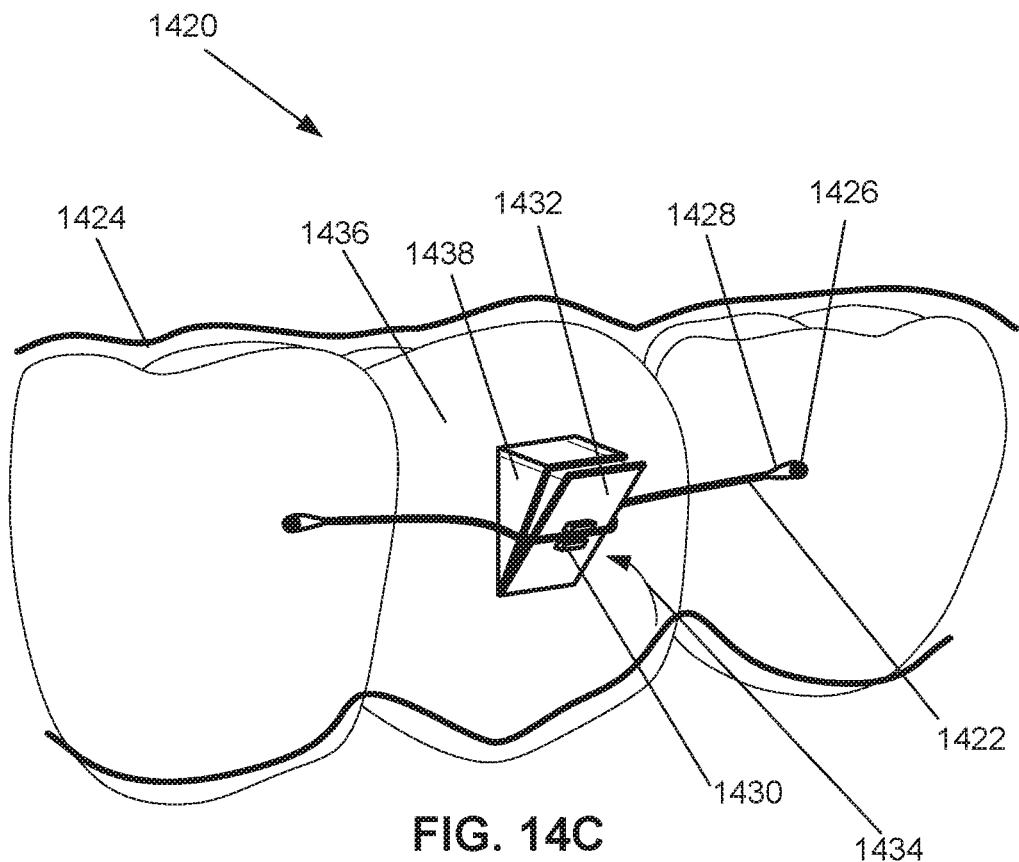
FIG. 14C illustrates an orthodontic appliance including features for securing an elastic member, in accordance with some embodiments.
Figure 14D:
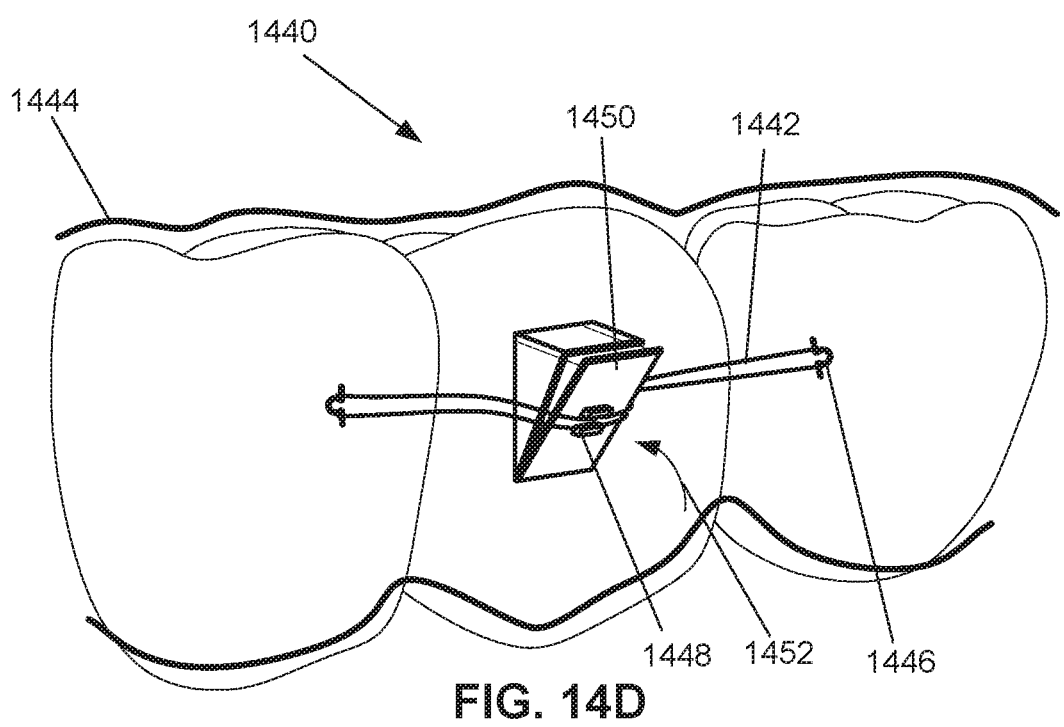
FIG. 14D illustrates another orthodontic appliance including features for securing an elastic member, in accordance with some embodiments.

FIG. 14C illustrates an orthodontic appliance 1420 including features for securing an elastic member 1422, in accordance with some embodiments. The appliance 1420 includes fastening features for coupling the elastic member 1422 to the shell 1424, exemplarily depicted herein as a pair of posts 1426. The elastic member 1422 can engage and be secured to the posts 1426 by loops 1428. The posts 1426 can be formed with the shell 1424, such that the elastic member 1422 is directly coupled to the shell 1424 by the posts 1426. The loops 1428 can be situated at any suitable portion of the elastic member 1422, such as at the ends. Furthermore, the appliance 1420 includes retention features for the elastic member 1422, depicted herein as a pair of tabs or protrusions 1430 situated on the flap 1432. As previously described, the retention features can secure the elastic member 1422 at a specified position relative to the shell 1424. For example, the protrusions 1430 can engage the elastic member 1422 to ensure that at least a portion of its length passes over the flap 1432, so that the appropriate force (see, e.g., arrow 1434) is exerted on the underlying tooth 1436 via the attachment 1438. FIG. 14D illustrates an orthodontic appliance 1440 including features for securing an elastic member 1442, in accordance with some embodiments. The elastic member 1442, depicted herein as an elastic loop, is coupled to the shell 1444 by hooks 1446 formed in the shell 1444. Similar to the appliance 1420, the appliance 1440 includes a pair of protrusions 1448 configured to retain the elastic member 1442 in a position spanning the flap 1450 to ensure that the desired force (see, e.g., arrow 1452) is applied.

Figure 15A:
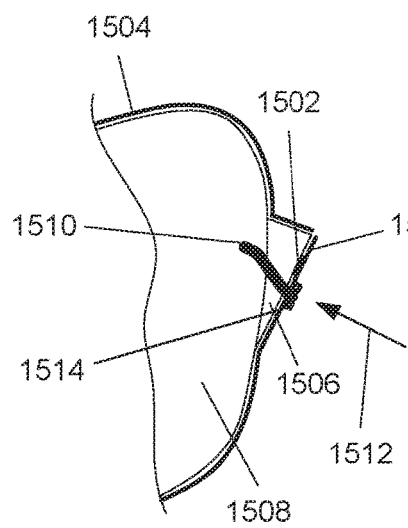
FIGS. 15A through 15D illustrate exemplary flap geometries for orthodontic appliances configured to engage an attachment, in accordance with some embodiments.
Figure 15B:
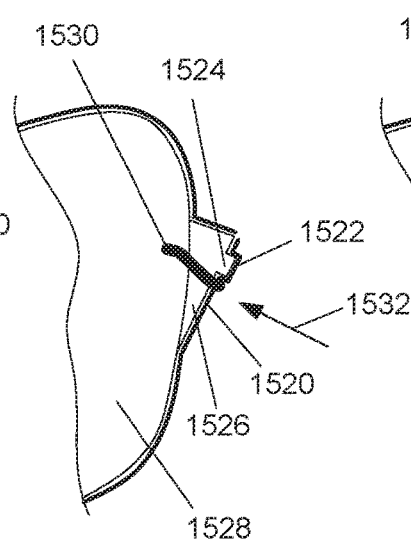
Figure 15C:
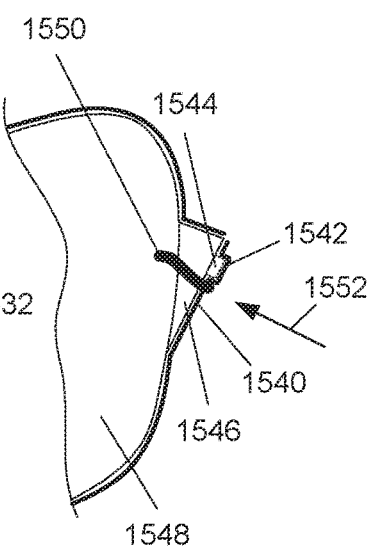
Figure 15D:
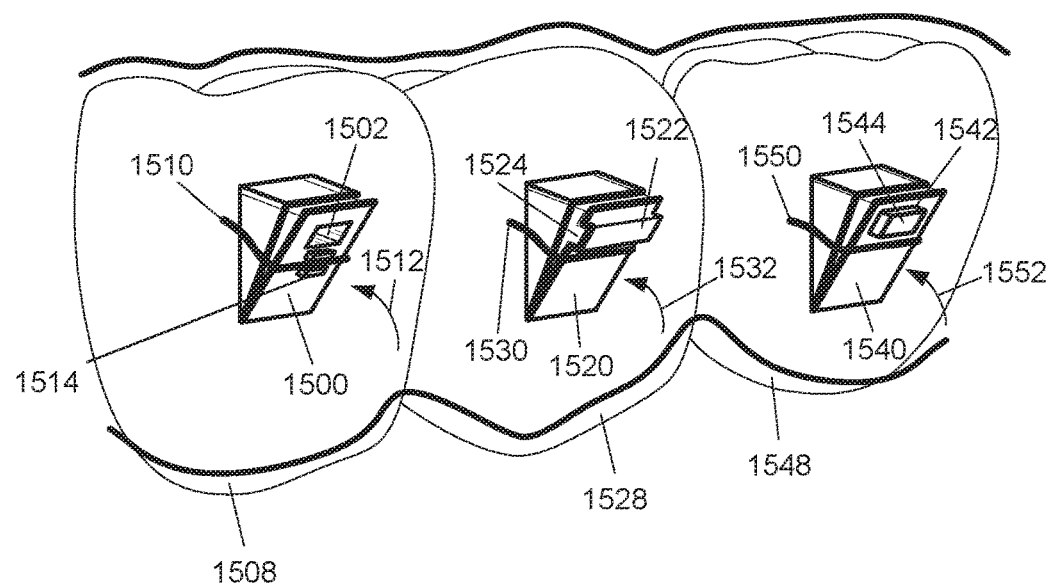

FIG. 15A through FIG. 15D illustrate example flap geometries for orthodontic appliances, in accordance with some embodiments. Similar to the embodiments discussed with respect to FIG. 11A through FIG. 14B, the flaps described herein can be formed via a discontinuity in a shell and positioned over an attachment. The flaps can include one or more features for engaging the attachment. For example, in FIG. 15A, a flap 1500 includes a protrusion 1502 extending towards the interior of a shell 1504 to contact an attachment 1506 mounted on a tooth 1508. The elastic member 1510 is held against the flap 1500 by retention features 1514 so that a repositioning force (see, e.g., arrow 1512) is applied to the attachment 1506 via the flap 1500. As another example, in FIG. 15B, a flap 1520 includes a relief 1522 shaped to accommodate a corresponding protrusion 1524 on an attachment 1526 of a tooth 1528. The ends of the elastic member 1530 can be positioned higher than the protrusion 1524, such that the middle portion of the elastic member 1530 engages the underside of the relief 1522 to apply a force (see, e.g., arrow 1532) to the attachment 1526 via the flap 1520. In a further example, in FIG. 15C, a flap 1540 includes an aperture 1542 into which a protrusion 1544 on an attachment 1546 of a tooth 1548 can extend. Similar to the elastic member 1530, the ends of the elastic member 1550 can be positioned such that the middle portion of the elastic member 1550 engages the protrusion 1544 of the attachment 1546, producing a corresponding force (see, e.g., arrow 1552) directly against the attachment 1546. Similar to other embodiments of flaps described herein, an appliance can include any suitable number and configuration of flaps. For example, as depicted in FIG. 15D, a single appliance can include a plurality of different flap geometries interacting with various types of attachments.

Figure 15E:
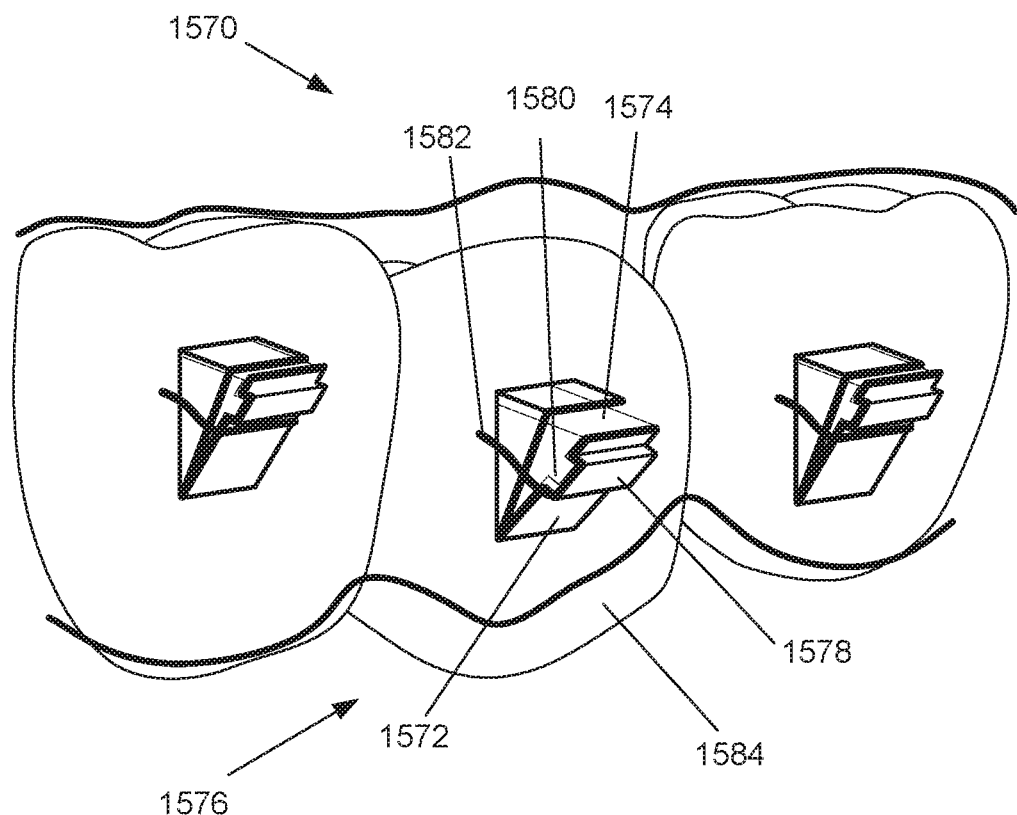
FIG. 15E illustrates an orthodontic appliance including a plurality of flaps for engaging a plurality of attachments on teeth, in accordance with some embodiments.
Figure 15F:
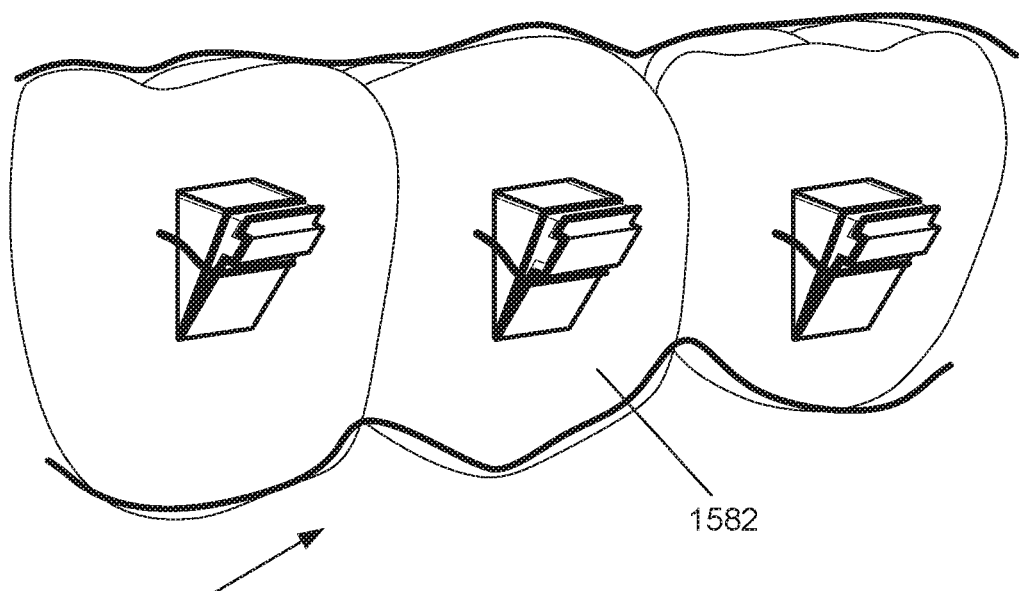
FIG. 15F illustrates the appliance of FIG. 15E after tooth repositioning has occurred.

FIG. 15E and FIG. 15F illustrate an orthodontic appliance 1570 including a plurality of flaps 1572 for engaging a plurality of attachments 1574 mounted on the teeth 1576. Each flap 1572 can include a relief 1578 shaped to accommodate a protrusion 1580 on the corresponding attachment 1574. In some instances, the protrusion 1580 is sized to fit tightly within the relief 1578 with little or no room for movement. Alternatively, the relief 1578 can be larger than the protrusion 1580, such that the relief 1578 includes sufficient space to accommodate movement of the protrusion 1580 within the relief 1578 (e.g., due to movement of the underlying tooth 1584). Each of the plurality of elastic members 1582 is angled upwards to pull against the relief 1578, thereby applying force on the attachment 1574 via the flap 1572. In some embodiments, the portion of the elastic member 1582 engaging the relief 1578 can be secured to the flap 1572 by adhesives, bonding, retention features, and the like. The configuration of the flaps, attachments, and elastics can be customized for each tooth, such that the applied force and/or resultant tooth movements vary per tooth. For example, the appliance 1570 can be configured to elicit an extrusive movement of the tooth 1584 relative to the other teeth. Similar to a conventional wire-bracket system, after the teeth 1576 have been repositioned (as illustrated in FIG. 15F), the attachments 1582 can be positioned collinearly (or approximately collinearly) with each other along a mesial-distal direction.

Although embodiments depicted in FIGS. 11 through 15 are shown as eliciting intrusive tooth movements, it shall be understood that the configurations presented herein can be modified as necessary in order to produce other types of tooth movements along different directions (e.g., occlusal-gingival, mesial-distal, buccal-lingual). Such modifications can involve changing an orientation, location, size, and/or shape of the various features provided herein. For example, referring again to FIGS. 11A and 11B, the orientation of the attachment 1102, receptacle 1104, and flap 1114 can be rotated by any amount (e.g., by 180°) to produce tooth movement in other directions (e.g., tooth extrusion instead of intrusion).

Figure 21A:
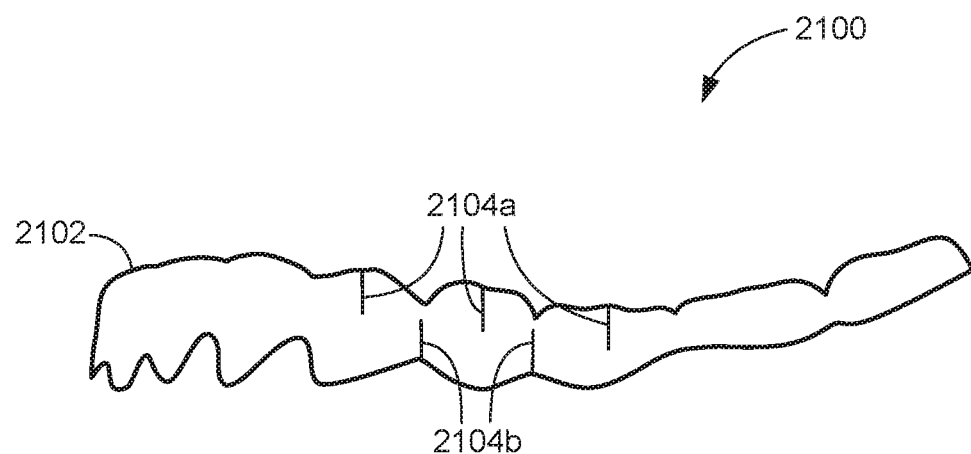
FIGS. 21A through 21F illustrate an orthodontic appliance with a plurality of discontinuities, in accordance with some embodiments.
Figure 21B:
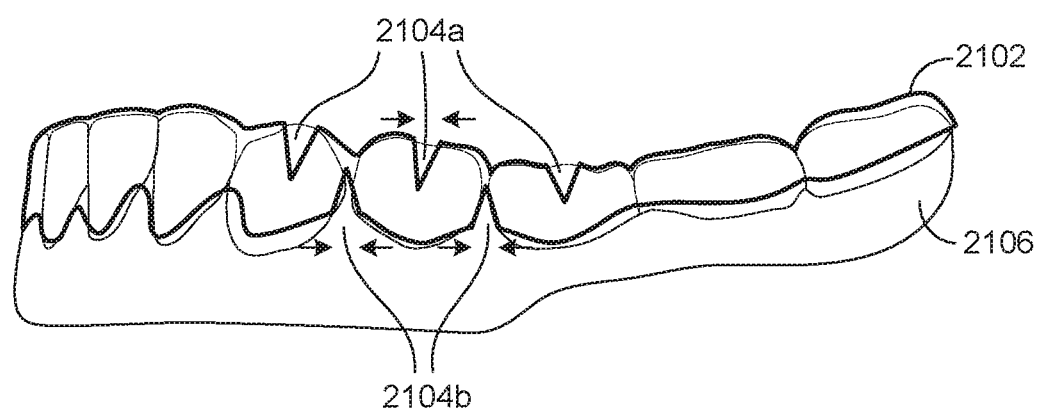
Figure 21C:
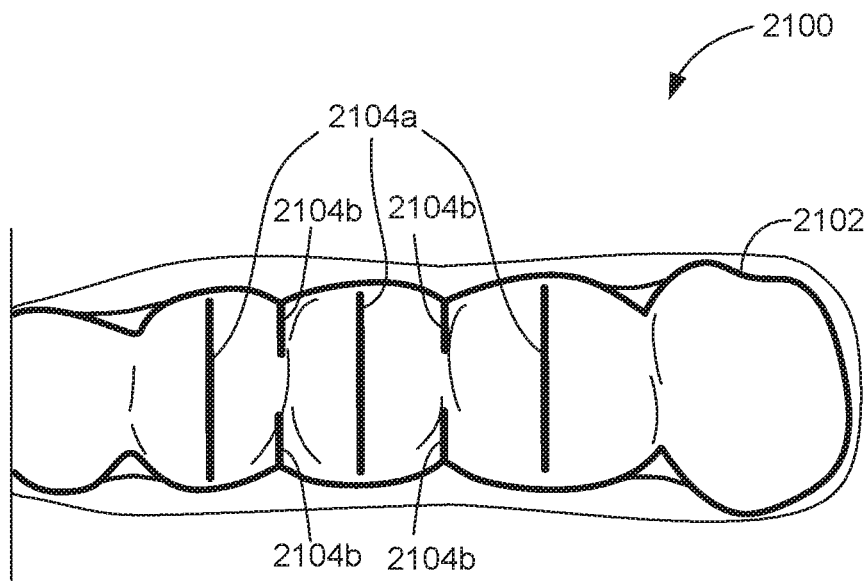
Figure 21D:
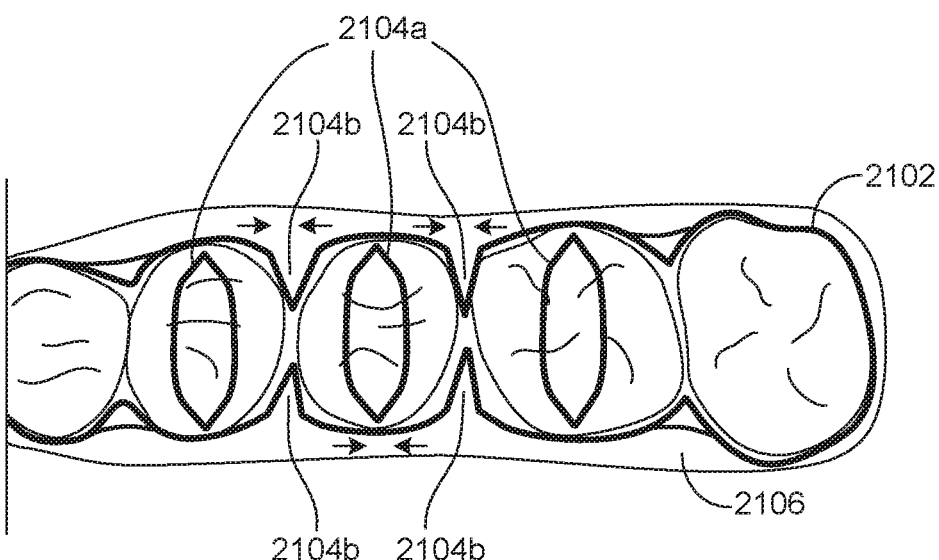
Figure 21E:
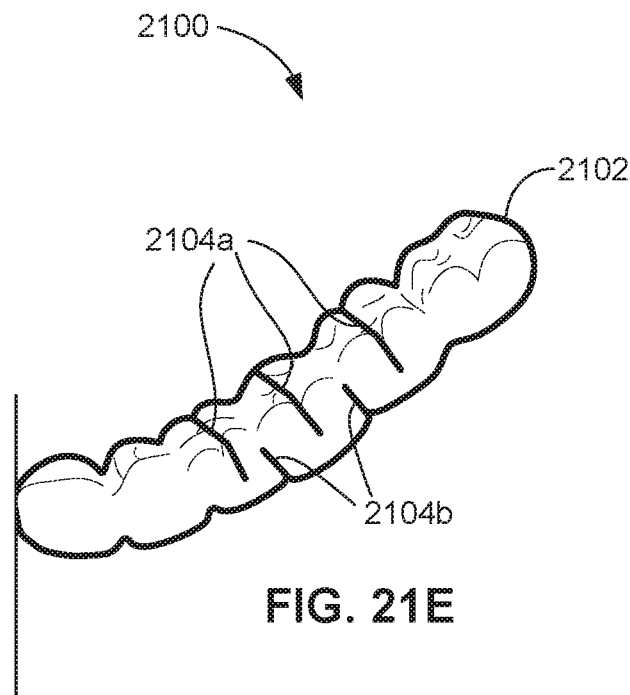
Figure 21F:
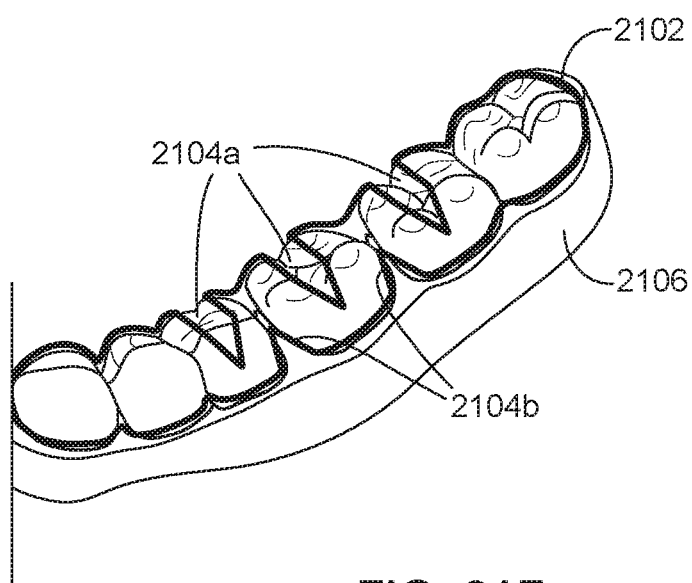

FIGS. 21A through 21F illustrate an orthodontic appliance 2100 with a plurality of discontinuities, in accordance with some embodiments. FIGS. 21A and 21B depict a side view, FIGS. 21C and 21D depict a top view, and FIGS. 21E and 21F depict a perspective view. The appliance 2100 includes a shell 2102 with a first plurality of elongate cuts 2104a and a second plurality of elongate cuts 2104b. The cuts 2104a, 2104b can be substantially parallel to each other. In some embodiments, the cuts 2104a are located primarily on the occlusal surfaces of the appliance 2100 and the cuts 2104b are located primarily on the lingual or buccal surfaces of the appliance 2100. Optionally, some portions of the cuts 2104a and/or 2104b can also extend to other surfaces of the appliance 2100, e.g., some portions of each cut 2104a can extend to the buccal and/or lingual surfaces and portions of each cut 2104b can extend to the occlusal surface. The positioning of the cuts 2104a, 2104b relative to the teeth 2106 received by the shell 2102 can be varied as desired. In the depicted embodiments, the cuts 2104a are located adjacent to occlusal regions of the teeth 2106 while the cuts 2104b are located adjacent to interproximal regions of the teeth 2106. The cuts 2104a can be interspersed with the cuts 2104b along the mesial-distal axis of the appliance 2100, so as to form an expandable "accordion" configuration that allows for mesial-distal elongation of the shell 2102 when placed on the teeth 2106 (depicted in FIGS. 21B, 21D, and 21F). The deformation of the cuts 2104a, 2104b when worn over the teeth 2106 can produce forces (e.g., opposing pairs of mesial-distal forces indicated by arrows) to elicit tooth movements that reduce spaces between teeth. Although FIGS. 21A through 21F depict an appliance 2100 without any elastic members, it shall be understood that alternative embodiments can include one or more elastic members that interact with the cuts 2104a and/or 2104b (e.g., spanning the cuts 2104a and/or 2104b) as previously described herein in order to modulate the forces applied to the teeth 2106.

In some embodiments, the directionality of an elastic member influences the directionality of the resultant forces applied to teeth. For example, in embodiments where the elastic member is elongate (e.g., a band or strip) the forces exerted by the elastic member onto the appliance and/or underlying teeth may be aligned with (e.g., substantially parallel to) the length of the elastic member. Moreover, the directionality of the elastic member relative to a discontinuity can influence the forces applied to teeth via the interaction of the elastic member and discontinuity. The directionality of an elastic member can be varied as desired in order to influence the direction of tooth movement, as well as control the portion(s) of teeth the force is exerted upon. For instance, in some instances it may be desirable to apply forces closer to the crown tip of a tooth (e.g., to produce tipping), while in other instances it may be desirable to apply forces closer to the root center of a tooth (e.g., to avoid tipping).

Figure 22A:
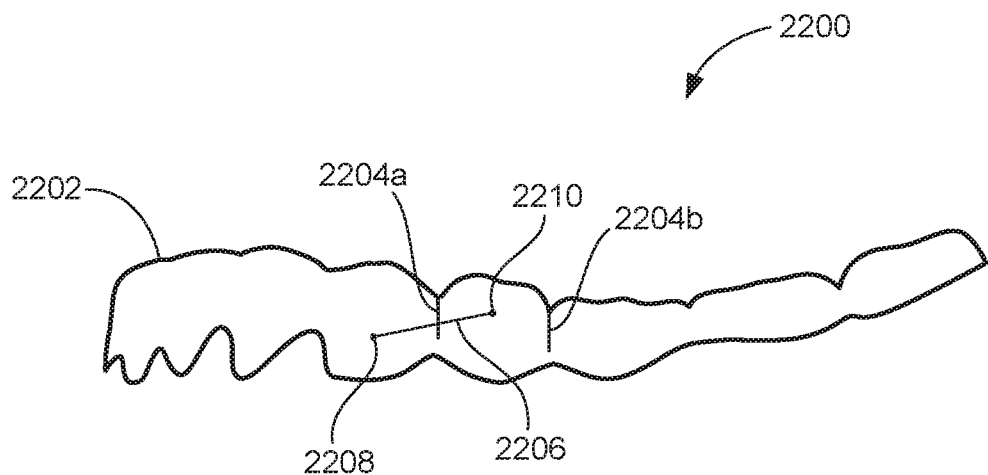
FIGS. 22A through 22D illustrate directionality of an elastic member influencing the forces applied to teeth, in accordance with some embodiments.
Figure 22B:
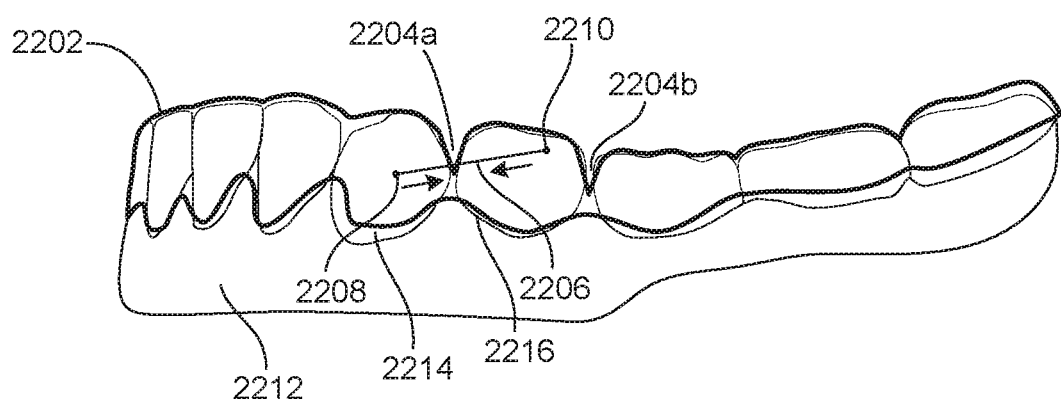

FIGS. 22A through 22D illustrate directionality of an elastic member influencing the forces applied to teeth, in accordance with some embodiments. An appliance 2200 includes a shell 2202 and at least one discontinuity 2204*a-b* formed in the shell 2202, depicted herein as elongate cuts spanning at least the occlusal and buccal surfaces of the appliance 2200. An elastic member 2206, depicted herein as an elongate band, is coupled to the buccal surface of the shell 2202 in a position spanning the discontinuity 2204*a*. In the embodiment of FIGS. 22A and 22B, the elastic member 2206 includes a mesial end 2208 that that is closer to the gingival edge of the shell 2202 and a distal end 2210 that is closer to the occlusal surface of the shell 2202, such that the length of elastic member 2206 is at an angle relative to the mesial-distal axis of the shell 2202 (e.g., is not parallel to the mesial-distal axis). The elastic member 2206 can be arranged such that the length of the elastic member 2206 is non-orthogonal to the length of the discontinuity 2204. Accordingly, when the appliance 2200 is placed on a patient's teeth 2212, the forces exerted on the teeth 2212 (indicated by arrows) are applied closer to the root center of tooth 2214 and closer to the crown tip of tooth 2216.

Figure 22C:
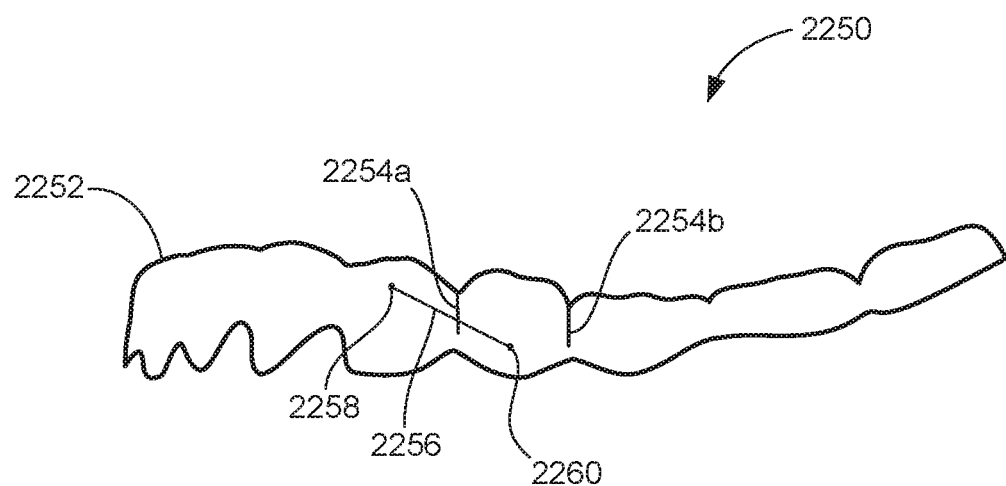
Figure 22D:
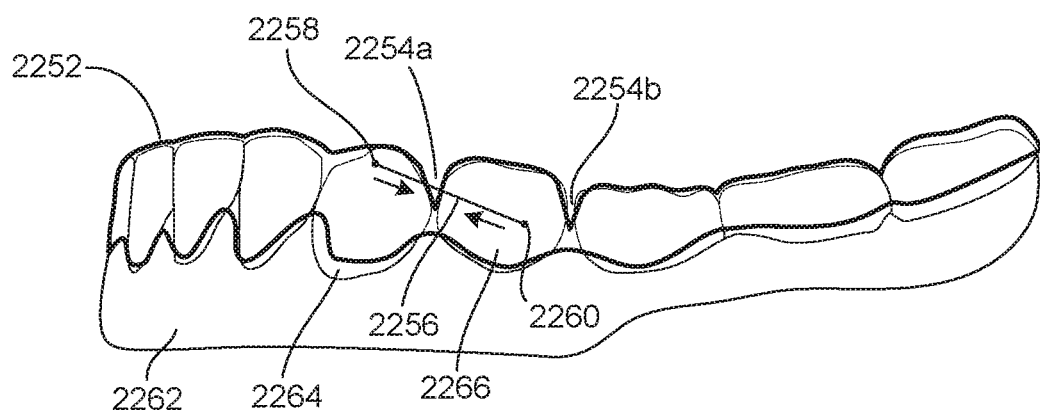

FIGS. 22C and 22D illustrate an orthodontic appliance 2250 having a shell 2252, discontinuities 2254*a-b* formed in the shell, and an elastic member 2256 spanning the discontinuity 2254*a*. The components of the appliance 2250 are substantially similar to those of the appliance 2200, except that the mesial end 2258 of the elastic member 2256 is closer to the occlusal surface of the shell 2252 while the distal end 2260 is closer to the gingival edge. Accordingly, when the appliance 2250 is placed over the teeth 2262, the resultant forces (indicated by arrows) are applied closer the crown tip of tooth 2264 and closer to the root center of tooth 2266.

In some embodiments, two or more elastic members can be used in conjunction with each other to apply a plurality of forces having different magnitudes and/or directions. For example, a pair of elastic members coupled to opposite sides of a shell can be used to produce a force couple to elicit tooth rotation. The use of multiple elastic members can allow for the generation of more complex force systems to improve control over tooth movement and/or produce more complicated tooth movements.

Figure 23A:
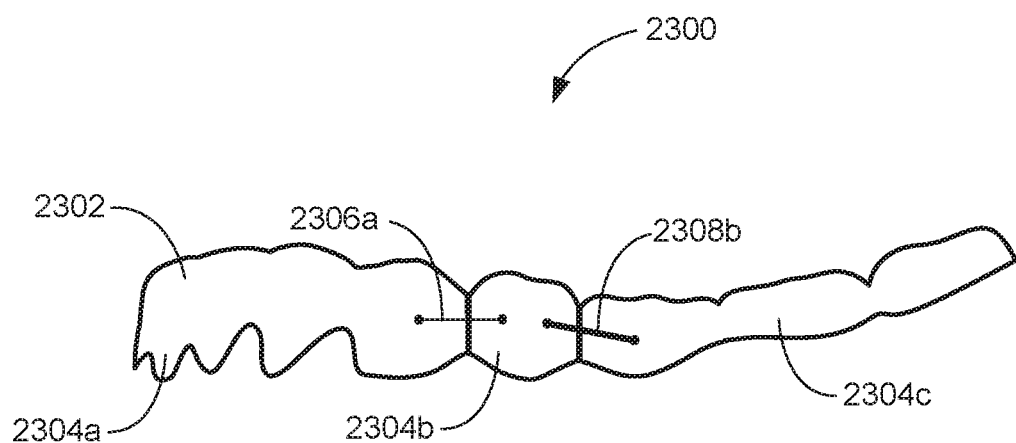
FIGS. 23A through 23D illustrate an orthodontic appliance configured to produce tooth rotation, in accordance with some embodiments.
Figure 23B:
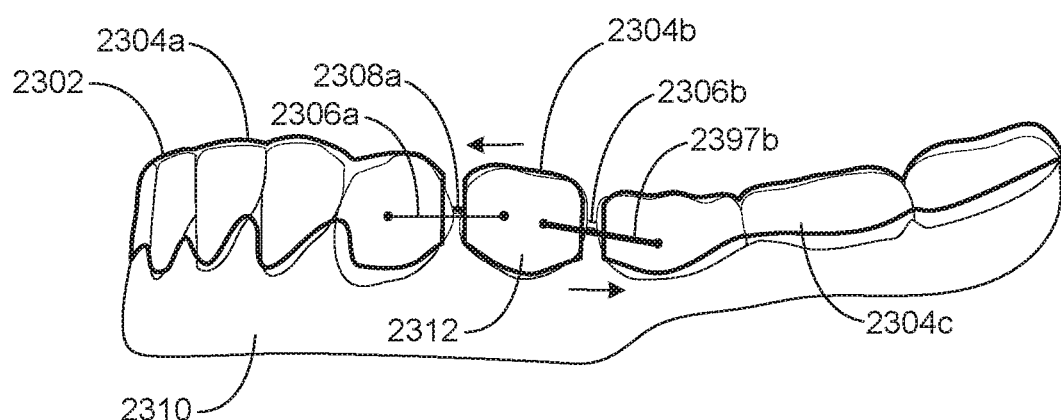
Figure 23C:
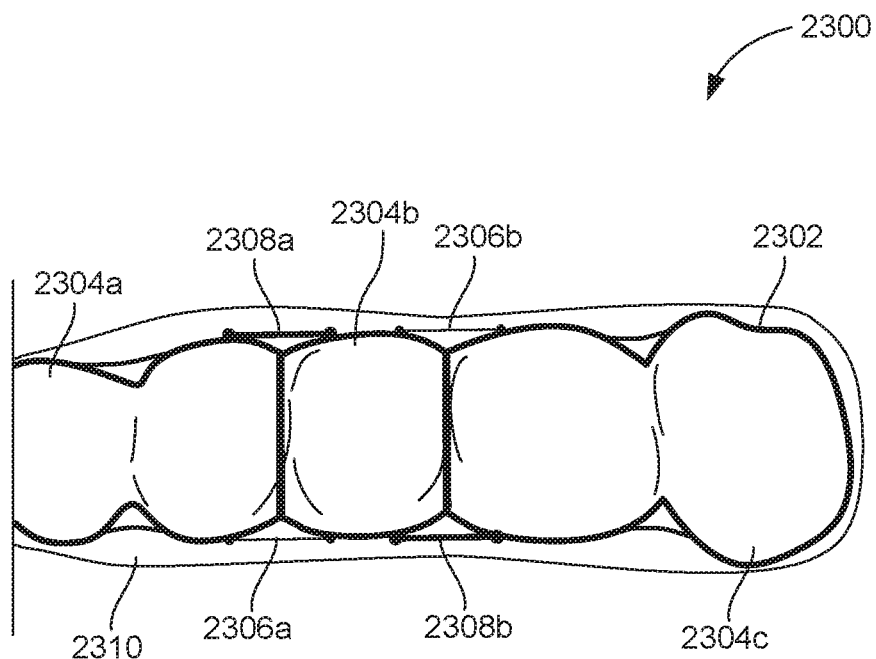
Figure 23D:
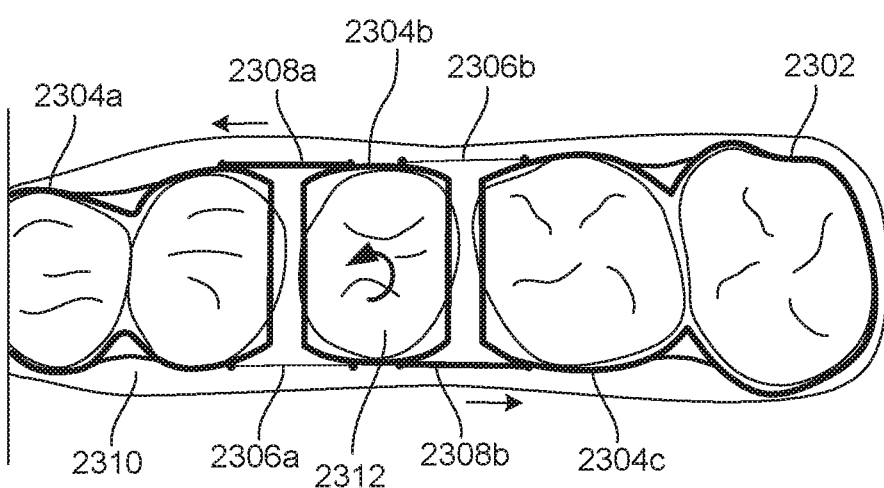
Figure 24A:
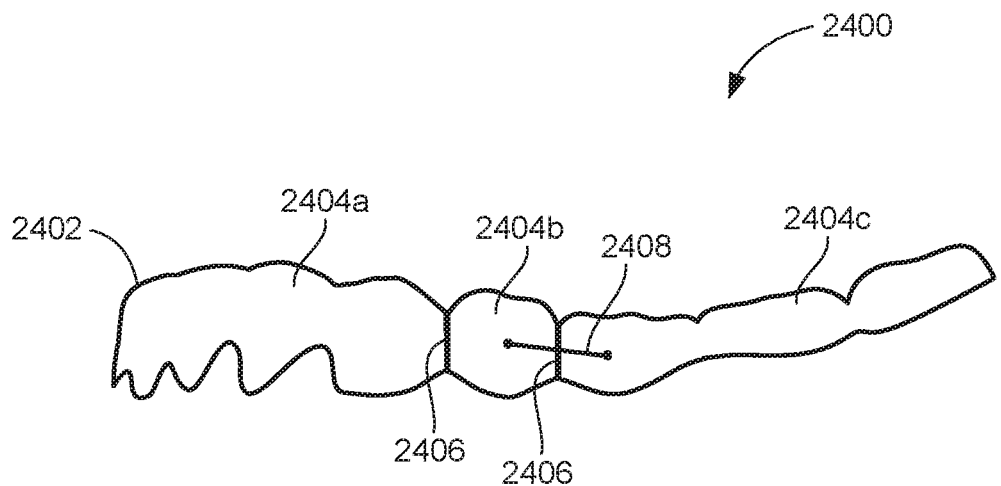
FIGS. 24A through 24D illustrate an orthodontic appliance configured to produce tooth rotation, in accordance with some embodiments.
Figure 24B:
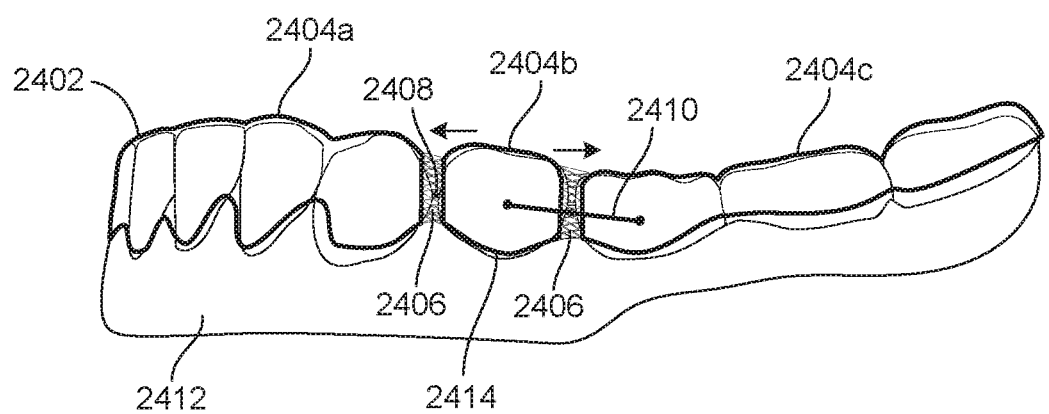
Figure 24C:
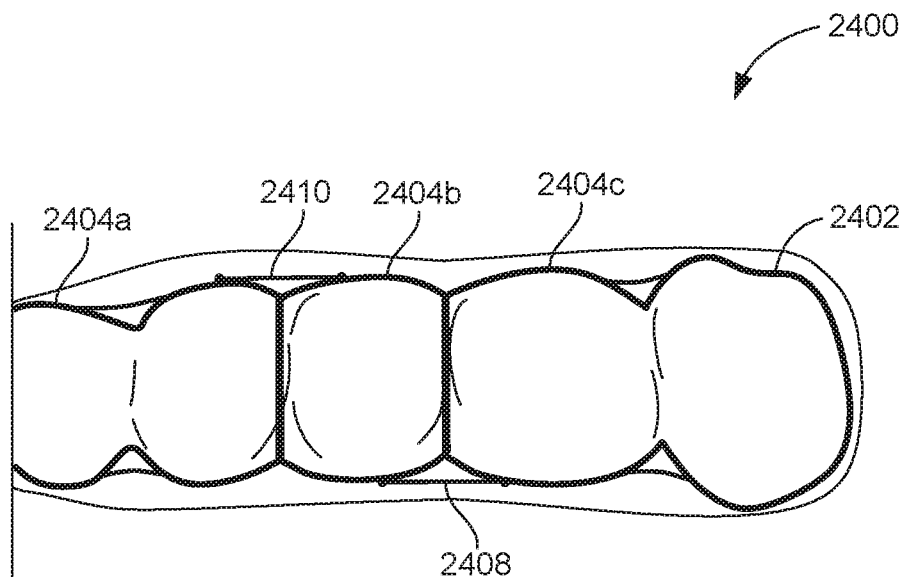
Figure 24D:
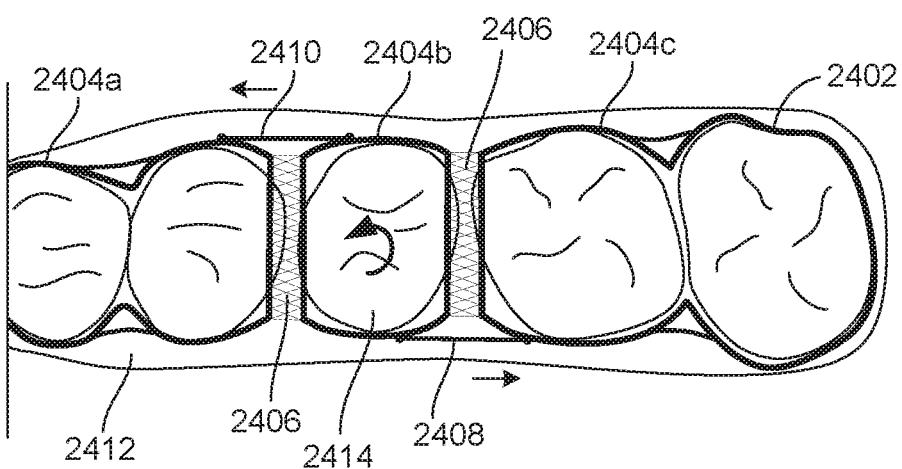

FIGS. 23A through 23D illustrate an orthodontic appliance 2300 configured to produce tooth rotation, in accordance with some embodiments. The appliance 2300 includes a shell 2302 that is separated into a plurality of discrete segments 2304*a-c*. The segments 2304*a-c* can be joined to each other by a first pair of elastic members 2306*a-b* and a second pair of elastic members 2308*a-b*, thereby forming a single appliance in which the segments 2304*a-c* can move relative to each other. In some embodiments, the segment 2304*a* is coupled to the segment 2304*b* by elastic members 2306*a*, 2308*a* and the segment 2304*b* is coupled to the segment 2304*c* by elastic members 2306*b*, 2308*b*. The properties (e.g., stiffness, thickness, material type, etc.) of the elastic members 2306*a-b* can differ from the properties of the elastic members 2308*a-b*. For example, the stiffnesses (elastic moduli) of the elastic members 2306*a-b* can be less than the stiffnesses (elastic moduli) of the elastic members 2308*a-b*. Accordingly, when the appliance 2300 is worn on the patient's teeth 2310 (as depicted in FIGS. 23B, 23D), the forces applied to the teeth by the elastic members 2308*a-b* can be greater in magnitude than the forces applied by the elastic members 2306*a-b*. In some embodiments, the difference in force magnitudes applied by the respective pairs of elastic members results in application of a force couple on the tooth 2312, thereby eliciting rotation of the tooth 2312.

FIGS. 24A through 24D illustrate an orthodontic appliance 2400 configured to produce tooth rotation, in accordance with some embodiments. Similar to the appliance 2300, the appliance 2400 includes a shell 2402 that is separated into discrete segments 2404*a-c*. The segments 2404*a-c* are joined by a first elastic member 2406, depicted herein as a mesh or sheet, in order to form a single appliance 2400 and permit relative movement of the segments 2404*a-c*. Additionally, the appliance 2400 includes a second elastic member 2408 coupled to a first side of the appliance 2400 (e.g., a buccal surface) and a third elastic member 2410 coupled to a second, opposing side of the appliance 2400 (e.g., a lingual surface). The second and third elastic members 2406, 2408 can be arranged such that when the appliance 2400 is placed on the teeth 2412, the second and third elastic members 2406, 2408 apply a force couple onto the tooth 2414, thereby eliciting rotation of the tooth 2414.

In order to improve control over the deformation of an orthodontic appliance (e.g., when worn by a patient), biasing features such as perforations, grooves, parallel lines, engraved shapes, and the like can be formed in the shell in order to define specific locations where desired deformations (e.g., bending, flexing, stretching, compression) should occur. The biasing features may penetrate only partially through the thickness of the shell (e.g., a groove) or may penetrate through the entire thickness (e.g., a cut or aperture). Such features can increase the local compliance of the shell to reduce its resistance to deformation at the specified locations and cause it to preferentially deform at those locations when appropriate forces are applied. In some embodiments, one or more biasing features are used in combination with one or more discontinuities (e.g., flaps, cuts, apertures, etc.) in order to modulate the deformation of the discontinuity when the appliance is placed on patient's teeth. For example, a perforated or engraved line can be used to define a hinge for a flap formed in an appliance. As another example, a plurality of parallel perforated or engraved lines can be used to define a compliant region in the shell that accommodates deformations of the shell (e.g., as force is applied by an elastic member).

Figure 26A:
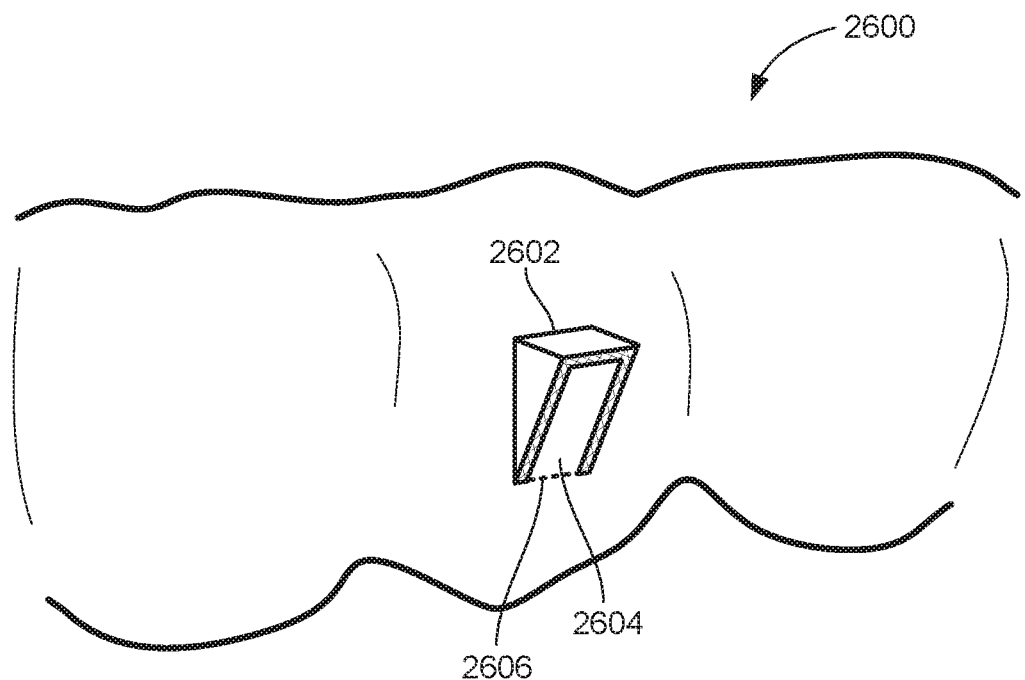
FIGS. 26A through 26D illustrate orthodontic appliances with biasing features, in accordance with some embodiments.
Figure 26B:
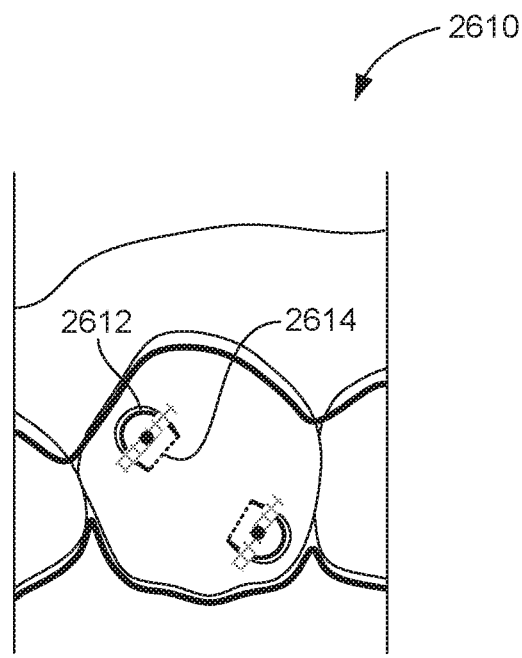
Figure 26C:
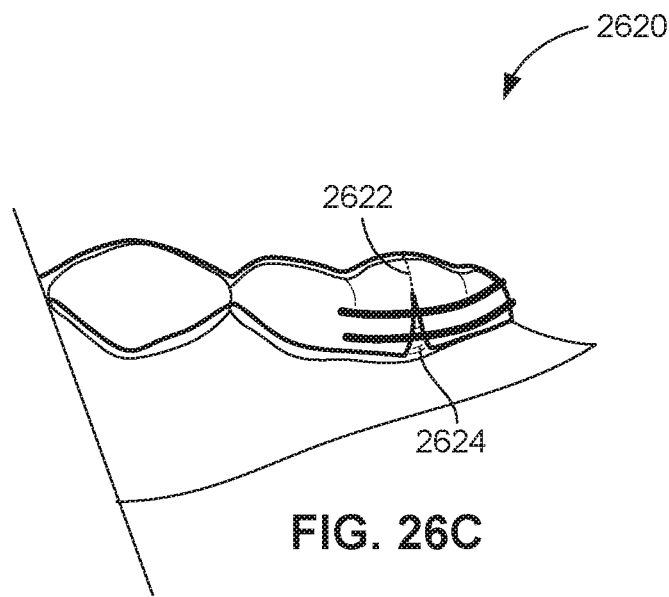
Figure 26D:
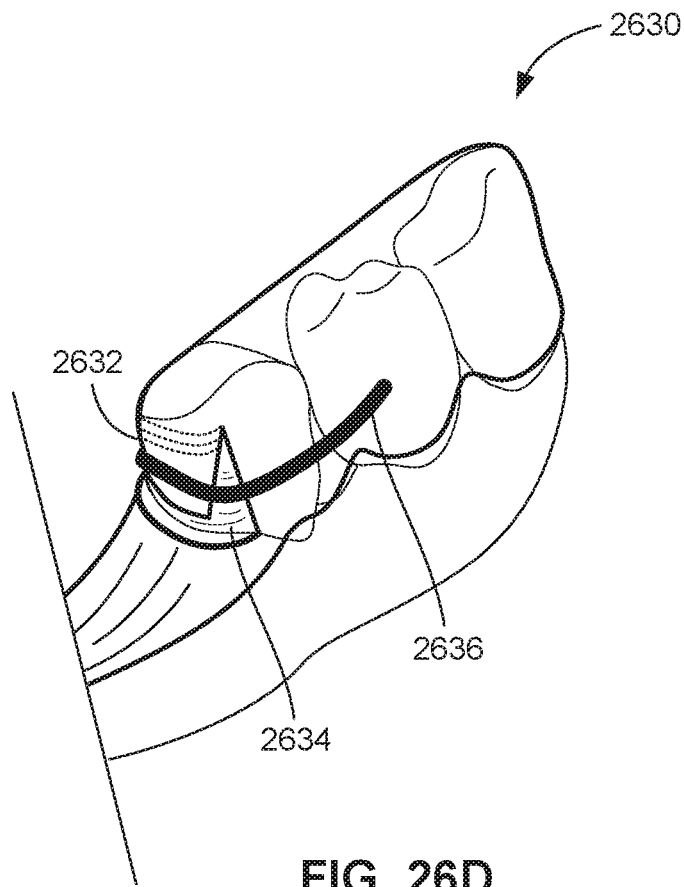

FIGS. 26A through 26D illustrate orthodontic appliances with biasing features, in accordance with some embodiments. Although the biasing features are depicted herein as perforated lines, it shall be understood that various alternative embodiments of biasing features provided herein can also be used. FIG. 26A illustrates an orthodontic appliance 2600 having a receptacle 2602 and a flap 2604. A biasing feature 2606 is formed at the hinge of the flap 2604 in order to ensure that the flap 2604 will preferentially bend at that location. Similarly, FIG. 26B illustrates an orthodontic appliance 2610 having a pair of flaps 2612, with a respective biasing feature 2614 defining the hinge of each flap 2612. FIG. 26C illustrates an appliance 2620 in which a biasing feature 2622 contacts and extends from one end of a discontinuity 2624 (depicted herein as a cut). The biasing feature 2622 can be aligned with the length of the discontinuity 2624 so as to facilitate deformation of the discontinuity 2624 (e.g., widening) when the appliance 2620 is placed on teeth. FIG. 26D illustrates an orthodontic appliance 2630 in which a plurality of biasing features 2632 are used to define a region of increased compliance near a discontinuity 2634 (depicted herein as an aperture). Accordingly, when the elastic member 2636 applies force to the appliance near the discontinuity 2634, the appliance 2630 can preferentially bend at the region of increased compliance in order to apply forces to the tooth, rather than at other locations where force application is not desired.

Figure 27:
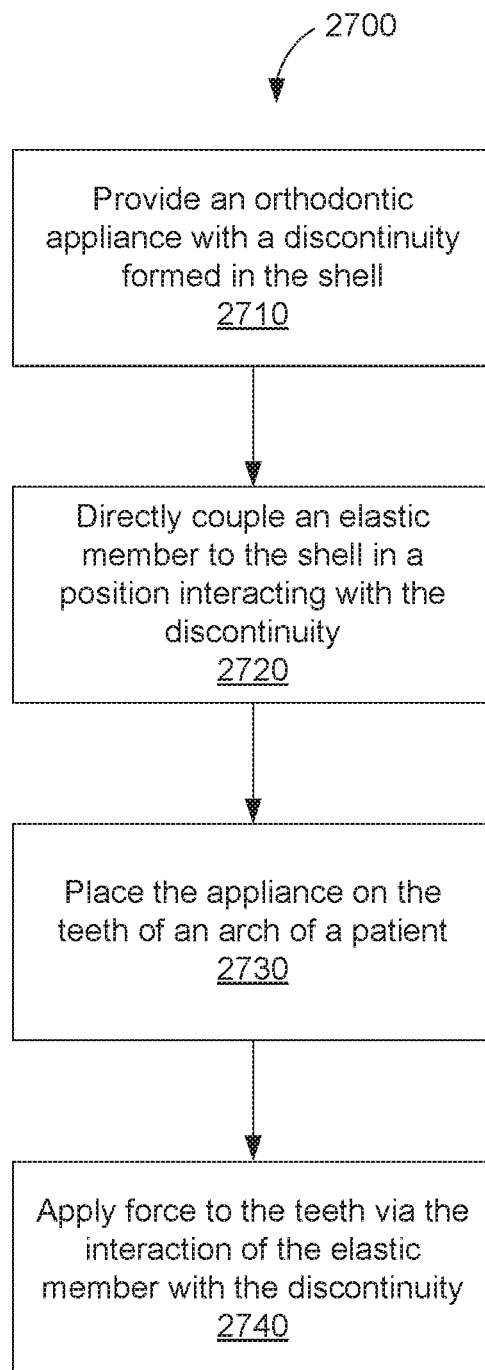
FIG. 27 illustrates a method for orthodontic treatment, in accordance with some embodiments.

FIG. 27 is a schematic illustration by way of block diagram of a method 2700 for orthodontic treatment, in accordance with some embodiments. The method 2700 can be applied to reposition one or more of a patient's teeth, maintain one or more of a patient's teeth in a current configuration, or suitable combinations thereof. The method 2700 can be practiced using any suitable orthodontic appliance, such as suitable orthodontic appliances described herein.

In step 2710, an orthodontic appliance with a discontinuity formed in the shell is provided. The discontinuity can include any embodiments of the various types of discontinuities described herein. In some embodiments, the discontinuity can be formed in the shell (e.g., by cutting, removal of material, deforming a portion of the shell, etc.) after the shell has been fabricated, e.g., in accordance with the indirect fabrication methods discussed herein. Alternatively, the discontinuity can be formed simultaneously with the fabrication of the shell, e.g., in accordance with the direct fabrication methods discussed herein.

In step 2720, an elastic member is directly coupled to the shell in a position interacting with the discontinuity. Any embodiment of the elastic members described herein can be combined with any suitable discontinuity. As previously mentioned, the elastic member can be directly coupled to the shell without the use of intervening attachment elements (e.g., fasteners provided separately and coupled to the shell, such as hooks, screws, nails, pins, etc.). The coupling of the elastic member can be performed by an orthodontic practitioner prior to applying the appliance to the teeth. Alternatively, the coupling can be performed by a manufacturer of the appliance, such that the appliance is provided to the practitioner with the coupled elastic member. In some embodiments, the step 2720 is optional, such as where the orthodontic appliance is already provided with the coupled elastic member. For example, the step 2720 can be omitted if direct fabrication is used to produce an orthodontic appliance with the elastic member integrally formed with the appliance shell.

In step 2730, the appliance is placed on the teeth of an arch of the patient. In some embodiments, the appliance is designed to receive teeth from a single dental arch. One or more of the teeth can be coupled to a previously mounted attachment (e.g., FIG. 11A through FIG. 15D). Alternatively, the appliance can be placed on teeth without any attachments. As previously described herein, placement of the appliance can involve deformation of one or more of the shell, the discontinuity, and the elastic member in order to accommodate the teeth. In some instances, the discontinuity and/or a portion of shell near the discontinuity is displaced when the appliance is worn. For example, the discontinuity can form a flap (e.g., FIGS. 11-19) that is pushed outwards when the appliance is placed on the teeth. As another example, where the appliance includes separate shell segments (e.g., FIG. 8 and FIG. 10), the segments can be moved relative to each other when the appliance is placed on teeth. In some instances, the step 2730 can be performed prior to the step 2720, such that the appliance is placed on the teeth before the elastic member is coupled to the shell.

In step 2740, force is applied to the teeth via the interaction of the elastic member with the discontinuity. As described elsewhere herein, the elastic member can exert a continual force on the shell, and this force can be transmitted via the shell to the underlying teeth. In some embodiments, the force is applied to the teeth via an attachment mounted on one or more of the teeth (e.g., FIGS. 11-15). The applied force can result in repositioning of one or more teeth, as previously described herein. Alternatively, the force can be applied to maintain a current arrangement of the teeth, such that no tooth movements occur.

Figure 28:
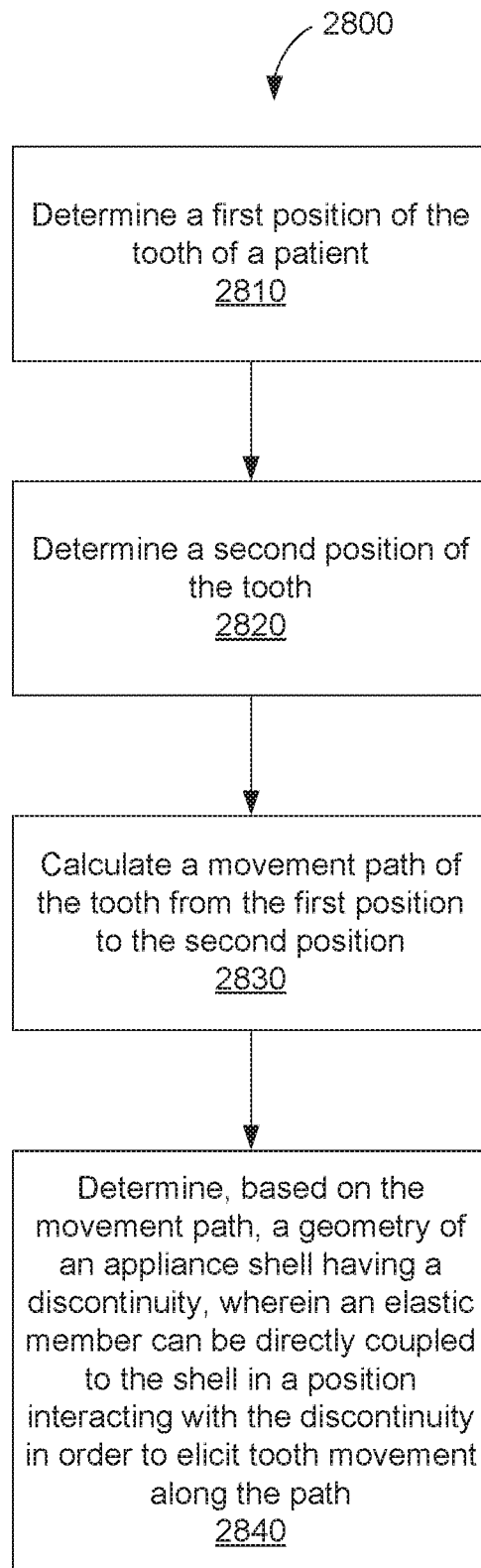
FIG. 28 illustrates a method for designing an orthodontic appliance, in accordance with some embodiments.

FIG. 28 is a schematic illustration by way of block diagram of a method 2800 for designing an orthodontic appliance, in accordance with some embodiments of the present invention. The steps of the method 2800 can be performed by a suitable system, such as the data processing system described elsewhere herein.

In step 2810, a first position of a tooth of a patient is determined. The first position can be, for example an initial position of the tooth (e.g., the current position of the tooth within the patient's arch). The position can be determined based on measurement data of the current tooth arrangement of the patient, such as measurement data obtained by scanning of the patient's teeth or a model of the patient's teeth. The measurement data can be used to generate a digital representation (e.g., a digital model) of the dentition, from which the first position of the tooth can be determined.

In step 2820, a second position of the tooth is determined. In some embodiments, the second position represents an intermediate or final position of the tooth after orthodontic treatment (e.g., repositioning) has occurred. The second position can, for instance, be selected based on an intermediate or final tooth arrangement specified by an orthodontic practitioner for correcting one or more malocclusions.

In step 2830, a movement path of the tooth from the first position to the second position is calculated. In some embodiments, the movement path is calculated using one or more suitable computer programs, which can take digital representations of the first and second positions as input, and provide a digital representation of the movement path as output. The movement path may also be calculated based on the positions and/or movement paths of other teeth in the patient's dentition, and such information can also be provided as digital representations. For example, the movement path can be optimized based on minimizing the total distance moved, preventing collisions with other teeth, avoiding tooth movements that are more difficult to achieve, or any other suitable criteria. In some instances, the movement path can be provided as a series of incremental tooth movements that, when performed in sequence, result in repositioning of the tooth from the first position to the second position.

In step 2840, geometry of an appliance shell having a discontinuity is determined based on the movement path, such that an elastic member can be directly coupled to the shell in a position interacting with the discontinuity in order to elicit tooth movement along the movement path. The geometry can be determined by one or more suitable computer programs, such as a computer program configured to accept a digital representation of the movement path as input and provide a digital representation of the shell, discontinuity, and/or elastic member geometry as output (e.g., as digital models). In some instances, the output can be provided to a manufacturing system in order to fabricate a physical model of the shell with the discontinuity, such as a suitable computer-aided manufacturing system.

The geometry of the shell, discontinuity, and elastic member can be configured in any manner suitable for generating the tooth movement, such as any of the embodiments described herein. In some embodiments, one or more portions of the shell (e.g., tooth receiving cavities of the shell) can be adapted to include a suitable amount of additional space to accommodate the tooth movement, as previously described herein. In some instances, the step 2840 can further include calculating the geometry of an attachment to be coupled to the tooth, such that the elastic member interacts with the attachment to effect movement of the underlying tooth.

Segmented Orthodontic Appliance with Elastics

In some embodiments, the orthodontic appliances provided herein include a plurality of discrete shell segments that are movable relative to each other. Such appliances can be referred to as "segmented" orthodontic appliances. Each shell segment can be shaped to receive at least a portion of a tooth, a single tooth or a plurality of adjacent teeth. For example, a segment can include a portion of a tooth receiving cavity, a single tooth receiving cavity, a plurality of tooth receiving cavities, or combinations thereof. In some embodiments, adjacent shell segments receive adjacent teeth, such that the shell segments collectively cover a continuous span of teeth of a single dental arch (e.g., an upper or lower arch). The separations between the shell segments can correspond approximately to the natural separations between teeth, e.g., are located at or near the interproximal regions of the tooth receiving cavities.

The shell segments can be joined together by an elastic material in order to form a single orthodontic appliance shell that receives a continuous span of teeth. Exemplary elastic materials suitable for use with the embodiments provided herein include but are not limited to isoprene rubber, polyurethane, copolyester, styrenic block copolymer, styrene-butadiene rubber, silicone rubber, or combinations thereof. Many different configurations of the elastic material and shell segments can be used. For example, the elastic material can include a plurality of discrete portions, each attached to and coupling only a subset of the shell segments (e.g., each discrete portions joins only two, three, four, or more adjacent segments). As another example, the elastic material can be a single continuous piece that is attached to and couples all of the shell segments. The elastic material can be attached to the shell segments at one or more discrete attachment points, or over one or more continuous attachment regions. The attachment points and/or regions can be located on any suitable portion of the shell segments, such as the buccal surface, lingual surface, occlusal surface, or combinations thereof.

The elastic material can be deformable (e.g., by stretching, compression, bending, flexing) to allow the segments to move relative to each other. The configuration and/or properties of the elastic material can influence the extent to which relative movement is possible, e.g., constrain the direction of movement, prevent the segments from being displaced more than a certain distance apart or less than a certain distance together, etc. In some embodiments, the elastic material joins the shell segments so as to form a single appliance shell having a geometry corresponding to a target tooth arrangement and is configured to resist displacement of the shell segments away from a target arrangement. Accordingly, when the appliance is worn by a patient having a tooth arrangement different from the target arrangement specified by the appliance, the shell segments may be displaced away from their original positions in the target arrangement, thereby producing deformation of the elastic material. The stiffness of the shell segments can be greater than the stiffness of the elastic material, such that deformations occur primarily in the elastic material rather than in the shell segments. For example, a shell segment can have an elastic modulus within a range from about 10,000 psi to about 700,000 psi, and the elastic material can have an elastic modulus within a range from about 100 psi to about 8000 psi, or from about 100 psi to about 50,000 psi. The resistance of the elastic material to such deformation can generate forces that are transmitted to the underlying teeth in order to elicit tooth repositioning towards the target arrangement specified by the appliance.

Figure 29A:
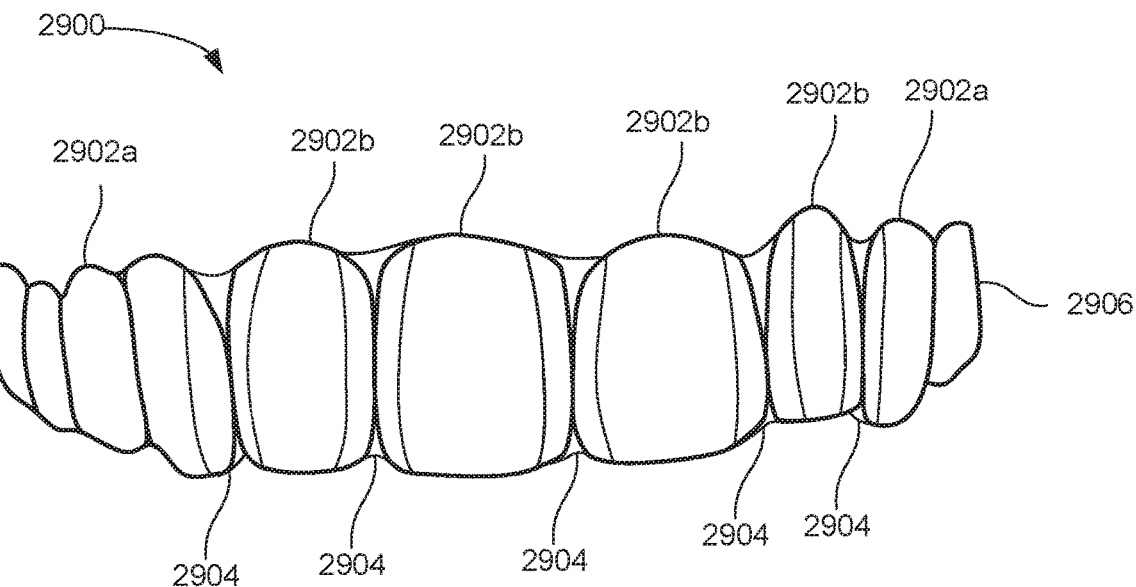
FIG. 29A illustrates a segmented orthodontic appliance, in accordance with some embodiments.
Figure 29B:
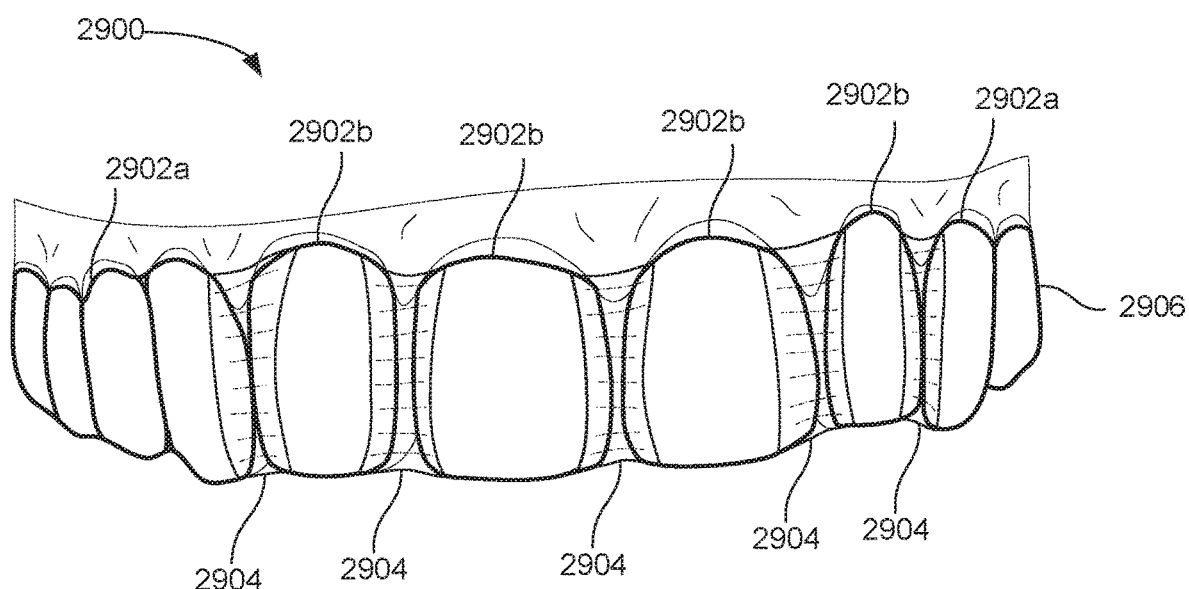
FIG. 29B illustrates the appliance of FIG. 29A placed over the teeth of a patient.
Figure 29C:
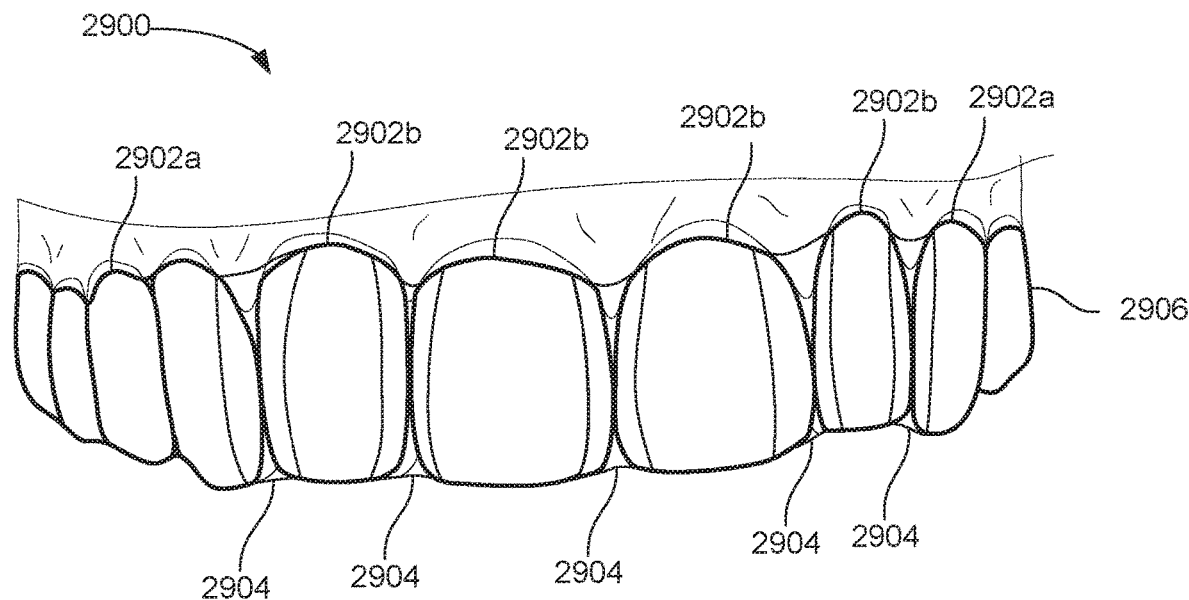
FIG. 29C illustrates the appliance of FIG. 29B after tooth repositioning has occurred.

FIGS. 29A through 29C illustrate a segmented orthodontic appliance 2900, in accordance with some embodiments. The appliance 2900 includes a plurality of discrete shell segments 2902a, 2902b and a plurality of discrete elastic segments 2904 coupled together to form a single appliance shell 2906. The shell segments, such as those shown as 2902a, 2902b, can include cavities shaped to each receive one or more of the teeth (or portions of the teeth) of a patient's dental arch. As non-limiting examples, illustrated segments 2902b each receive a single tooth, whereas segments 2902a each span a plurality of teeth. In additional embodiments, an orthodontic appliance can include segments spanning a single tooth, segments spanning a plurality of teeth, as well as various combinations thereof. In appliance construction, segments that span a single tooth, as well as those that span a plurality are not limited to any particular location within the arch, but the location can be selected in appliance design.

Some of the shell segments may receive a plurality of teeth (e.g., shell segments 2902a), while others may receive a single tooth (e.g., shell segments 2902b). In some embodiments, the shell segments 2902a, 2902b receive a continuous span of teeth and are separated from each other at or near the interproximal regions of the teeth. The elastic segments 2904 are interspersed between the shell segments 2902a, 2902b at or near the aforementioned interproximal regions and couple neighboring shell segments to each other, thus forming a single appliance shell 2906. In some embodiments, the resultant appliance shell 2906 is translucent or transparent, so as to improve the overall aesthetics of the appliance 2900 when worn by a patient.

The elastic segments 2904 can be permanently affixed to the shell segments 2902a, 2902b so that the shell segments 2902a, 2902b and elastic segments 2904 cannot be nondestructively detached from each other. The appliance shell 2906 may be a continuous shell in which the coupled shell segments 2902a, 2902b and elastic segments 2904 are joined without leaving any gaps or apertures between neighboring shell segments. For example, the elastic segments 2904 may extend across the buccal, occlusal, and lingual surfaces of the appliance 2900, thus forming a shell 2906 with a continuous exterior surface. Alternatively, some of the elastic segments 2904 may extend only partially across these surfaces (e.g., only across the buccal and lingual surfaces, only across the lingual and occlusal surfaces, only across the lingual surface, etc.) such that the shell 2906 includes one or more gaps or apertures in its exterior surface.

The shell segments 2902a, 2902b can be formed from relatively rigid materials, such that the stiffness of the shell segments 2902a, 2902b is greater than the stiffness of the elastic segments 2904. The shell segments 2902a, 2902b can be shaped to conform to the current topography of the patient's teeth. In such embodiments, when the shell 2906 is placed over the teeth of a patient's arch, as depicted in FIG. 29B, the shell segments 2902a, 2902b are rigidly connected to the underlying teeth and therefore do not generate tooth repositioning forces. Conversely, the elastic segments 2904 are not rigidly connected to the teeth and can therefore generate forces for eliciting movements of the underlying teeth. At least some of these forces can be generated by deformation (e.g., stretching) of the elastic segments 2904 when the shell 2906 is worn by the patient, due to intentional mismatch between the geometry of the shell 2906 (e.g., the spatial disposition of the shell segments 2902a, 2902b and/or elastic segments 2904) and the current arrangement of the patient's teeth. For example, when the shell 2906 is worn by the patient, some of the shell segments 2902a, 2902b may be displaced from their original positions, thereby stretching the intervening elastic segments 2904. The elastic segments 2904 can be deformed before being coupled the shell and/or before the appliance is worn by the patient, such that there is an initial "pre-loading" force or tension in the elastics. Alternatively, the elastic segments 2904 can be relaxed prior to wearing of the appliance, such that there is no pre-loading force before the appliance is placed on the teeth. The resistance of the elastic segments 2904 to deformation may exert forces on the shell segments 2902a, 2902b that are transmitted to the teeth, thereby eliciting movements of one or more teeth with respect to up to six degrees of freedom of motion (e.g., translation, rotation, intrusion, extrusion, tipping, torqueing, etc.). As the teeth are repositioned, the shell segments 2902a, 2902b can return to their original positions, decreasing the extent of deformation of the elastic segments 2904 and thus reducing the forces applied to the teeth (FIG. 29C).

In some embodiments, an orthodontic appliance can include a plurality of discrete shell segments embedded in or coated with an elastic material, such that the elastic material substantially covers or surrounds the segments. The shell segments include tooth receiving cavities, in a similar manner as described in connection with other embodiments herein. The elastic material coats or surrounds the shell segments so as to hold the segments in a desired positioning relative to other segments. When in use, teeth are received in the cavities of the appliance, including those formed by the shell segments. The elastic material may stretch or deform to allow movement of the shell segments relative to each other upon placement of the appliance over the patient's teeth. The stretched or deformed elastic material can then exert forces that are transmitted to the teeth received in the shell segments.

Figure 30:
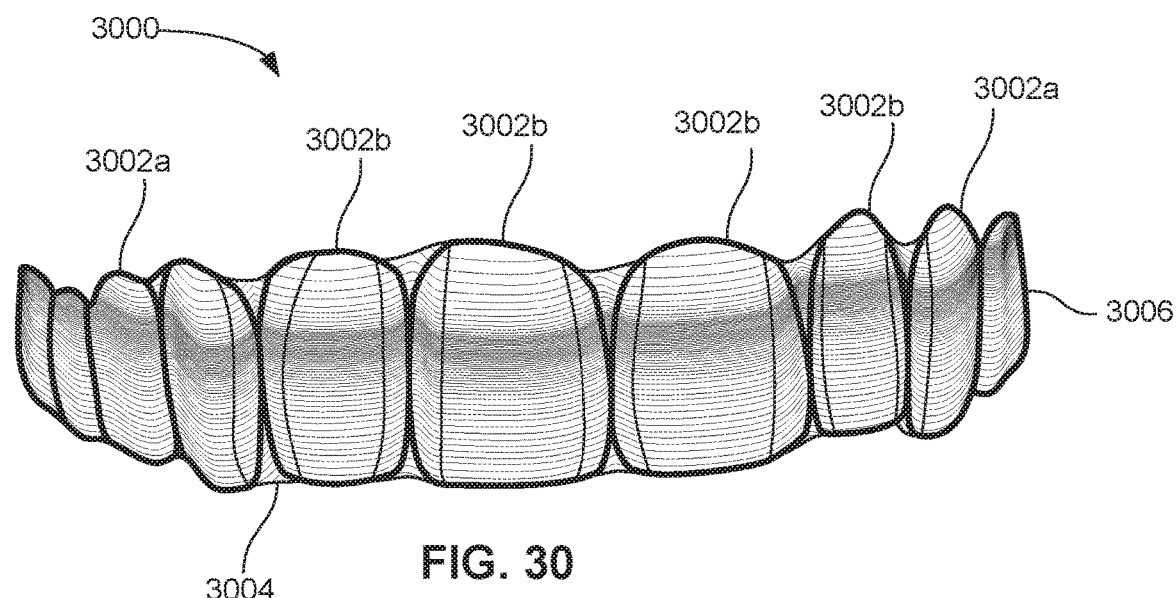
FIG. 30 illustrates another segmented orthodontic appliance, in accordance with some embodiments.

FIG. 30 illustrates a segmented orthodontic appliance 3000, in accordance with some embodiments. Similar to the appliance 2900, the appliance 3000 includes a plurality of discrete shell segments 3002a, 3002b, each shaped to receive one or more teeth and separated from each other at or near the interproximal regions. The shell segments 3002a, 3002b are embedded in a layer of elastic material 3004 which surrounds the shell segments 3002a, 3002b (e.g., coats the exterior and/or interior surfaces), joining them to each other at or near the interproximal regions to form a single appliance shell 3006. Although the elastic material 3004 is depicted in FIG. 30 as covering the entire appliance 3000, in other embodiments, the elastic material 3004 may cover only a portion of the appliance 3000, such as the portions at or adjacent to the interproximal regions. As previously described herein, when the shell 3006 is worn on the patient's teeth, the elastic material 3004 can exert forces that are transmitted to the underlying teeth via the shell segments 3002a, 3002b for eliciting tooth movements. In some embodiments, the appliance 3000 enables larger tooth movements to be produced with fewer shell segments.

Various different embodiments or configurations may be considered for an appliance having elastic material surrounding shell segments in the manner described. For example, an appliance may accommodate various different configurations for elastic materials, including different compositions and/or structures of elastic materials. Elastic material forming a layer may include a single continuous layer of elastic material or multiple layers of the same elastic material, different materials, or a combination of some layers of the same material and one or more layers of different material(s). Properties of the elastic material layer such as resiliency, elasticity, hardness/softness, color, and the like can be determined, at least partially, based on the selected material, layers of material, and/or elastic layer thickness. In some instances, the elastic material or layer can be configured such that one or more properties are uniform along a length or portion of the elastic (or entire elastic). Additionally or alternatively, one or more properties of the elastic material or layer may vary along a length or portion of the elastic (or entire elastic). Vary (or variable) may for example mean that the variations of the one or more properties are higher than 10%, higher than 25%, or higher than 50% of the highest value of the corresponding property or properties of the elastic material. For example, an elastic material or layer may have substantially uniform thickness along a length or portion (or entire elastic), or may vary along a length/portion (or entire elastic). Substantially uniform may mean that the variations (e.g., the absolute value of the difference between any two values of one property with regard to the appliance) of the one or more properties is no higher than 50%, no higher than 25%, or no higher than 10% of the highest value of the corresponding property/properties of the elastic material. As will be appreciated, characteristics of the elastic or layer may be selected so as to affect the force application to the patient's teeth or tooth movement aspects of a particular treatment desired.

Figure 31:
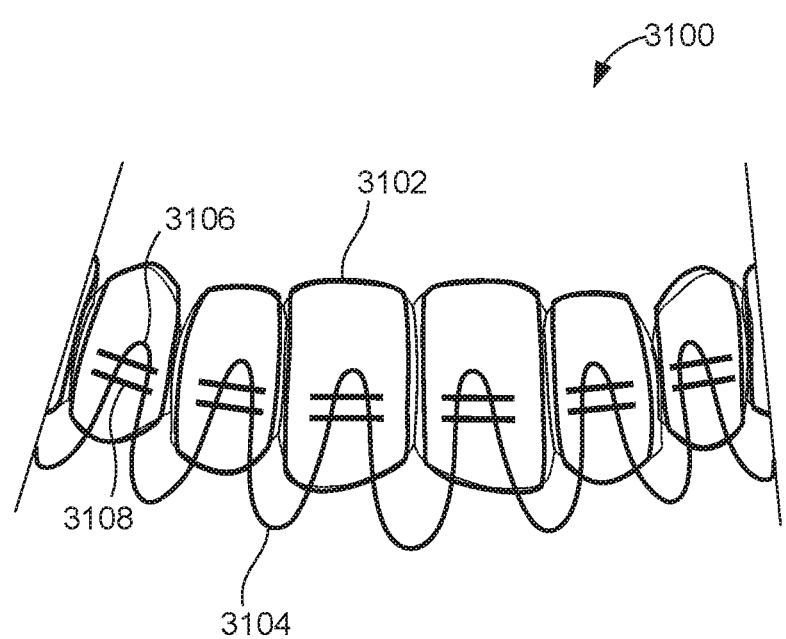
FIG. 31 illustrates a segmented orthodontic appliance with shape memory properties, in accordance with some embodiments.

FIG. 31 illustrates a segmented orthodontic appliance 3100 with shape memory properties, in accordance with some embodiments. The appliance 3100 includes a plurality of discrete shell segments 3102. In some embodiments, each shell segment 3102 is shaped to receive a single tooth. In alternative embodiments, the orthodontic appliance 3100 can include segments spanning a single tooth, segments spanning a plurality of teeth, as well as various combinations thereof. The segments 3102 can be coupled to each other to form a single appliance 3100 by an elastic material 3104, depicted in FIG. 31 as a wire. The elastic material 3104 can include a plurality of attachment portions 3106, with each portion 3106 being coupled to a respective segment 3102, e.g., via suitable adhesive or fastening elements 3108 (depicted herein as pairs of bands). In the embodiment of FIG. 31, the elastic material 3104 has a serpentine shape, with the attachment portions 3106 being located near the occlusal portions of the serpentine shape. In alternative embodiments, the elastic material 3104 can be formed with other geometries, e.g., linear, arcuate, curvilinear, etc., and the location of the attachment portions 3106 can be varied as desired.

In some embodiments, the elastic material 3104 is a material with shape memory properties, such as a shape memory wire, alloy, or polymer. Exemplary shape memory alloys include but are not limited to nickel-titanium, copper-aluminum-nickel, or combinations thereof. Exemplary shape memory polymers include but are not limited to polyurethane, epoxies, polyolefins, polyesters, or combinations thereof. The appliance 3100 can be fabricated with the elastic material 3104 having an initial, undeformed geometry that places the attached shell segments 3102 in an arrangement corresponding to a target arrangement for the patient's teeth. When the appliance 3100 is worn by a patient, differences between the patient's current tooth arrangement and the target arrangement can cause displacement of the shell segments 3102 and therefore deformation of the elastic material 3104 away from the initial geometry. The elastic material 3104 can be triggered to return to its initial geometry upon application of an appropriate shape memory stimulus (e.g., temperature change, exposure to light, application of electricity), which can apply forces to the shell segments 3102 and teeth to move the teeth towards the target tooth arrangement defined by the initial geometry.

The appliances described herein can be used in combination with one or more attachments mounted onto one or more of the received teeth. Accordingly, the topography of the shell segment can be modified to accommodate the attachment (e.g., with a suitable receptacle for receiving the attachment). The attachment can engage the shell segments and/or elastics to transmit repositioning forces to the underlying teeth, as previously described herein. Alternatively or in addition, the attachment can be used to retain the appliance on the patient's teeth and prevent it from inadvertently becoming dislodged. For example, teeth with no undercuts (e.g., central teeth, lateral teeth) may require an attachment to ensure correct engagement of the attachment onto the teeth, while teeth with natural undercuts (e.g., molars) may not require an attachment. The attachment can be mounted onto any suitable portion of the tooth, such as on a buccal or lingual surface of the tooth.

The appliances described herein may apply forces to some or all of the received teeth. For example, as previously described herein, some of the teeth received by the appliance can serve as anchors for holding the appliance in place (e.g., teeth received by shell segments 302a, 402a), while other teeth can be repositioned by the appliance (e.g., teeth received by shell segments 302b, 402b). Furthermore, the magnitude and direction of the forces applied to the teeth (and thus the magnitude and direction of the resultant tooth movements) can be determined based on the properties of the shell segments and/or elastics, such as number, geometry, configuration, and/or material characteristics, as described in further detail herein.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell or a plurality of discrete shell segments, cutting an appliance shell into a plurality of discrete shell segments, and/or joining the plurality of discrete shell segments with an elastic material.

Figure 32A:
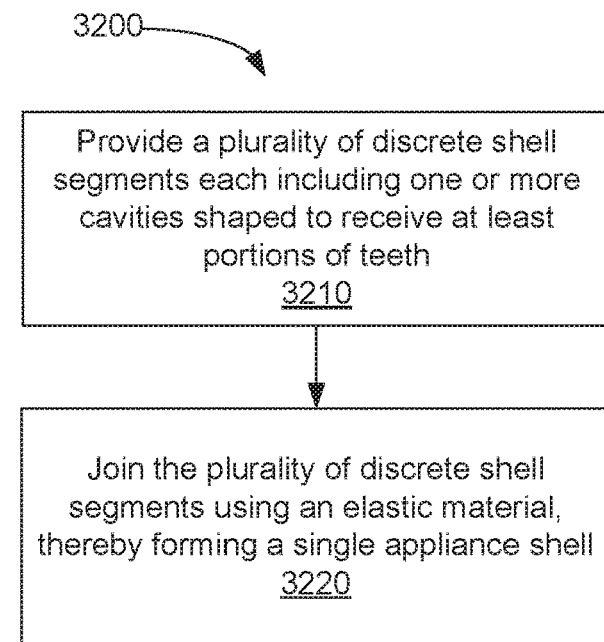
FIGS. 32A and 32B illustrate methods for creating an orthodontic appliance, in accordance with some embodiments.

FIG. 32A illustrates a method 3200 for creating an orthodontic appliance, in accordance with some embodiments. The method 3200 can be applied to any embodiment of the orthodontic appliances described herein. FIGS. 33A through 33D illustrate fabrication of an orthodontic appliance, in accordance with some embodiments.

Figure 32B:
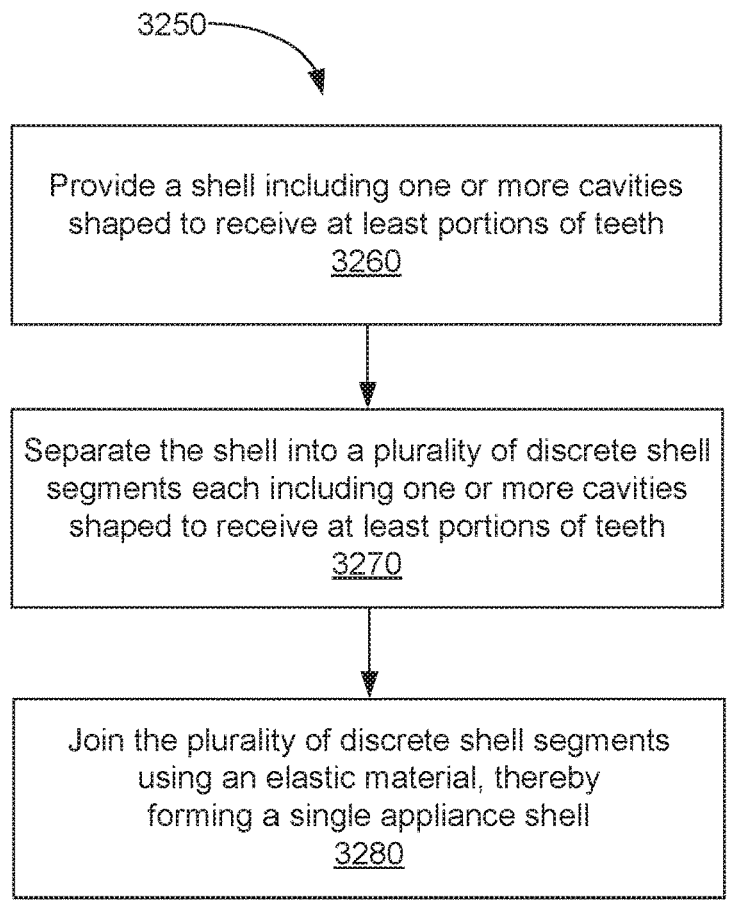
Figure 33A:
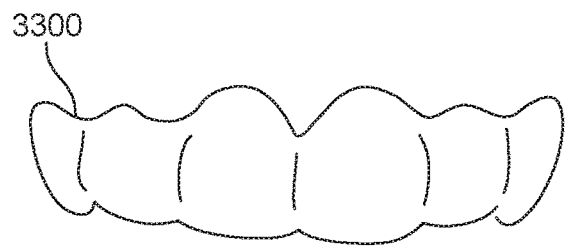
FIGS. 33A through 33D illustrate fabrication of an orthodontic appliance, in accordance with some embodiments.
Figure 33B:
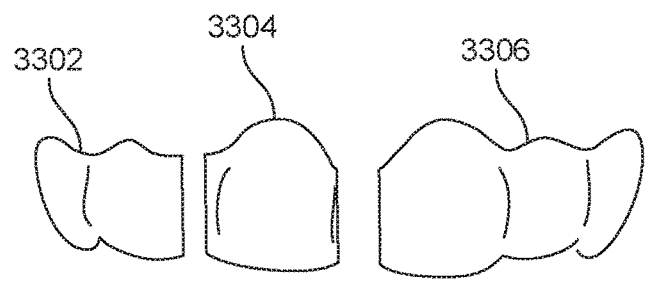
Figure 33C:
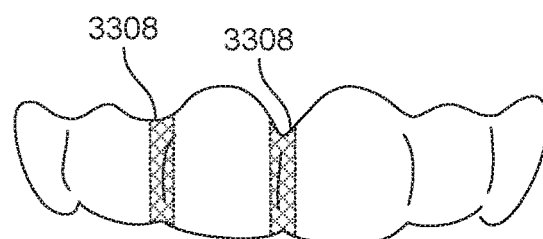
Figure 33D:
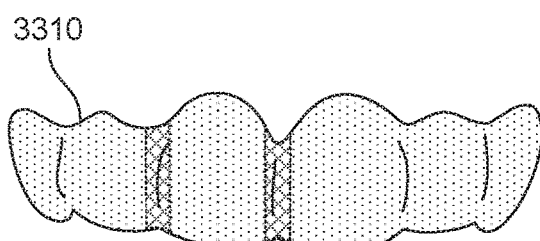

In step 3210, a plurality of discrete shell segments are provided, each including one or more cavities shaped to receive at least portions of teeth (see, e.g., shell segments 3202, 3204, and 3206 of FIG. 32B). The shell segments can collectively receive a continuous span of teeth, with separations between shell segments located at or near the interproximal regions. The number and/or shape of the shell segments can be selected to accommodate the desired tooth movements. The shell segments can be individually fabricated and provided as discrete components, or separated from a larger shell as described below. Exemplary methods for fabricating shells or discrete shell segments include thermoforming, additive manufacturing, or computer numerical control (CNC) milling. In some embodiments, the shells or discrete shell segments are fabricated using direct fabrication, as discussed further herein. The material of the shell or shell segments can be translucent, such as a translucent polymer. Alternatively, the shell or shell segments can be transparent, opaque, or any other suitable level of optical clarity. The shell or shell segments can be fabricated based on a physical or digital model of the patient's teeth. The model can be generated from dental impressions or scanning (e.g., of the patient's intraoral cavity, of a positive or negative model of the patient's intraoral cavity, or of a dental impression formed from the patient's intraoral cavity).

In step 3220, the plurality of discrete shell segments are joined using an elastic material, thereby forming a single appliance shell. As previously mentioned, the elastic material can be provided as a plurality of discrete segments (see, e.g., elastic segments 3208 of FIG. 32C), as a layer or coating (see, e.g., elastic layer 3210 of FIG. 32D), as an elongate serpentine wire, or any other suitable configuration. The elastic material can have varying levels of optical clarity. In some embodiments, the elastic material is transparent, translucent, or opaque. The elastic material can be provided as wires, strips, bands, sheets, meshes, coatings, layers, or suitable combinations thereof, and can be fabricated from any suitable material. Exemplary fabrication methods for elastics include extrusion, additive manufacturing, spraying, thermoforming, or suitable combinations thereof. Optionally, the elastics can be fabricated using direct fabrication, as discussed further herein. The characteristics of the elastic material (e.g., length, width, thickness, area, shape, cross-section, stiffness, etc.) may be homogeneous or substantially homogeneous throughout the bulk of the elastic material, or may be variable. Substantially homogeneous may mean that the variations of the one or more properties is no higher than 50%, no higher than 25%, or no higher than 10% of the highest value of the corresponding property/properties of the elastic material. For example, different portions of the elastic layer 3210 may have different thicknesses (e.g., differing by more than 10%, more than 25%, or more than 50% of the maximum thickness of the elastic layer), thereby altering the local compliance of the appliance shell. Furthermore, in some instances, the elastic can have anisotropic characteristics. As an example, the elastic may be relatively compliant along a first direction, and less compliant (or noncompliant) along a second direction. The directionality of the elastic can be used to control the direction of the resultant forces applied to the teeth. The appliances described herein may utilize a single type of elastic, or a plurality of different types of elastics. For instance, the elastic segments 3208 may have different stiffnesses, thus altering the amount of force applied to each tooth (or group of teeth).

The elastic material can be coupled to the shell segments using suitable adhesives or bonding agents. In some instances, the elastic material may have adhesive properties, thus enabling the elastic to be directly coupled to the shell segments without the use of additional external agents. Exemplary methods of attaching the elastics to the shell segments include extrusion, spraying, coating, dipping, gluing, thermoforming, mechanically connecting, stitching, riveting, weaving, or suitable combinations thereof.

FIG. 32B illustrates a method 3250 for creating an orthodontic appliance, in accordance with some embodiments. The method 3250 can be applied to any embodiment of the orthodontic appliances described herein. In step 3260, a shell including one or more cavities shaped to receive at least portions of teeth is provided (see, e.g., shell 3200 of FIG. 32A). The shell can be fabricated based on the patient's teeth and using any suitable method, as discussed above. In step 3270, the shell is separated into a plurality of discrete shell segments, each including one or more cavities shaped to receive at least portions of teeth (see, e.g., shell segments 3202, 3204, and 3206 of FIG. 32B). The number and shape of the shell segments can be selected to accommodate the desired tooth movements. In some embodiments, the shell is separated into discrete segments by cutting the shell, e.g., at or near one or more interproximal regions.

In step 3280, the plurality of discrete shell segments are joined using an elastic material, thereby forming a single appliance shell (see, e.g., FIGS. 32C and 32D), as previously described herein with respect to step 3220 of FIG. 32A. FIG. 32C shows an appliance including a segments joined by elastic 3208. FIG. 32D shows an appliance including segments having a layer/coating 3210 so as to join the segments. The geometry of the recoupled appliance shell may be different than the geometry of the initial shell provided in step 3260. For example, the geometry of the initial shell may match the current arrangement of the patient's teeth, while the recoupled shell may match a desired tooth arrangement. As previously described herein, the deliberate mismatch between the desired and current arrangement can cause deformation of the elastics when the appliance is worn, thereby producing forces for repositioning the teeth to the desired arrangement.

Orthodontic Appliance with Elastic Layer

In some embodiments, an orthodontic appliance of the present disclosure includes an exterior layer and an interior layer. The exterior layer can be formed from a relatively rigid material while the interior layer can be formed from a relatively elastic material, such that the exterior layer is stiffer than the interior layer. One or more discontinuities can be formed in the exterior layer while leaving the interior layer intact. The geometry and configuration of the discontinuity can be selected such that when the appliance is worn by a patient, the discontinuity interacts with the elastic interior layer so as to generate forces suitable for repositioning one or more of the patient's teeth. In some embodiments, the interior layer resists deformation, deflection, and/or displacement of the discontinuity, thereby causing forces to be applied to one or more teeth. The material properties (e.g., stiffness) of the appliances described herein can be varied via the discontinuities and/or elastic interior layer, thus affording different force application to different teeth of the patient's arch and, in some instances, more precise application or delivery of one or more forces to teeth with decreased patient discomfort. Vary (varied) may mean that the variations (e.g., differences in the values present in an appliance) in the corresponding material properties are more than 10%, more than 25%, or more than 50% of the highest value of the corresponding material property present in the appliance. Additionally, the techniques described herein can be used to adjust the local compliance of the appliance, therefore improving appliance fit and reducing patient discomfort.

Thus, in one aspect, an orthodontic appliance can include a shell having a plurality of cavities shaped to receive a patient's teeth. The shell can include an exterior layer and an interior layer having a stiffness less than a stiffness of the exterior layer. A discontinuity can be formed in the exterior layer. In some embodiments, the exterior layer has an elastic modulus within a range from about 10,000 psi to about 700,000 psi and the interior layer has an elastic modulus within a range from about 100 psi to about 8000 psi. In alternative embodiments, the interior layer has an elastic modulus within a range from about 100 psi to about 50,000 psi.

The design of the discontinuity can be varied as desired to elicit the appropriate tooth movements. For example, the discontinuity can include a cut formed in the exterior layer. The cut may extend at least partially around a protrusion formed in the exterior layer. In some instances, the cut may be a closed cut, such as a cut enclosing a region of the shell. The cut may extend from a buccal surface of the exterior layer to a lingual surface of the exterior layer. Alternatively or in addition, the discontinuity can include a plurality of cuts in the exterior layer, such as a plurality of cuts that are parallel to each other. The discontinuity can include a cut defining a flap in the exterior layer and a plurality of perforations near a joint portion of the flap.

The elements of the appliances described herein can be fabricated using any suitable method. The exterior and interior layers may have been thermoformed, for example. The discontinuity may have been etched or engraved in the exterior layer. In some instances, the discontinuity can include a shape etched in the exterior layer.

In another aspect, an orthodontic appliance can include a shell having a plurality of cavities shaped to receive a patient's teeth, the shell including a first layer and a second layer having a stiffness less than a stiffness of the first layer. A discontinuity can be formed in the first layer. In some embodiments, the first layer has an elastic modulus within a range from about 10,000 psi to about 700,000 psi and the second layer has an elastic modulus within a range from about 100 psi to about 8000 psi. In alternative embodiments, the second layer has an elastic modulus within a range from about 100 psi to about 50,000 psi. The first layer can comprise an exterior layer of the shell and the second layer can comprise an interior layer of the shell. Alternatively, the first layer can comprise an interior layer of the shell and the second layer can comprise an exterior layer of the shell.

The design of the discontinuity can be varied as desired. For example, the discontinuity can include a cut formed in the first layer. The cut may extend at least partially around a protrusion formed in the first layer. In some instances, the cut may be a closed cut, such as a cut enclosing a region of the shell. The cut may extend from a buccal surface of the first layer to a lingual surface of the first layer. Alternatively or in addition, the discontinuity can include a plurality of cuts in the first layer, such as a plurality of cuts that are parallel to each other. The discontinuity can include a cut defining a flap in the first layer and a plurality of perforations near a joint portion of the flap.

The components of the appliances described herein can be produced in a variety of ways. The first and second layers may have been thermoformed, for example. The discontinuity may have been etched or engraved in the first layer. In some instances, the discontinuity can include a shape etched in the first layer.

In another aspect, an appliance as described herein may be included in a series of appliances so as to provide an orthodontic system for positioning teeth. Such an orthodontic system can include a plurality of orthodontic appliances each comprising a shell including one or more cavities shaped to receive a patient's teeth. The appliances may be successively worn or wearable by the patient to move one or more teeth from a first arrangement to a second arrangement. One or more of the appliances can include layered appliance as described herein. For example, a layered appliance of the system can include an appliance shell having a plurality of cavities shaped to receive the patient's teeth. The shell can include an exterior layer and an interior layer having a stiffness less than a stiffness of the exterior layer. A discontinuity can be formed in the exterior layer. In some embodiments, the exterior layer has an elastic modulus within a range from about 10,000 psi to about 700,000 psi and the interior layer has an elastic modulus within a range from about 100 psi to about 8000 psi. In alternative embodiments, the interior layer has an elastic modulus within a range from about 100 psi to about 50,000 psi.

The geometry and configuration of the discontinuity can be selected so as to enable the application of one or more forces to a patient's teeth. The discontinuity can include a cut formed in the exterior layer. For instance, the cut may extend at least partially around a protrusion formed in the exterior layer. As another example, the cut may be a closed cut, such as a cut enclosing a region of the shell. The cut may extend from a buccal surface of the exterior layer to a lingual surface of the exterior layer. In some instances, the discontinuity can include a plurality of cuts in the exterior layer, such as a plurality of cuts that are parallel to each other. The discontinuity can include a cut defining a flap in the exterior layer and a plurality of perforations near a joint portion of the flap.

The exterior and interior layers of an appliance may have been thermoformed so as to form an appliance shell. The discontinuity may have been etched or engraved in the exterior layer. For example, the discontinuity can include a shape etched in the exterior layer.

In another aspect, an orthodontic system for repositioning a patient's teeth is provided. The orthodontic system can include a plurality of orthodontic appliances each comprising a shell including one or more cavities shaped to receive the patient's teeth. The appliances may be successively worn or wearable by the patient to move one or more teeth from a first arrangement to a second arrangement. One or more of the appliances can include a layered appliance as described herein. For example, a layered appliance can include an appliance shell having a plurality of cavities shaped to receive the patient's teeth. The appliance shell can include an first layer and an second layer having a stiffness less than a stiffness of the first layer. A discontinuity can be formed in the first layer. In some embodiments, the first layer has an elastic modulus within a range from about 10,000 psi to about 700,000 psi and the second layer has an elastic modulus within a range from about 100 psi to about 8000 psi. In alternative embodiments, the second layer has an elastic modulus within a range from about 100 psi to about 50,000 psi. The first layer can comprise an exterior layer of the appliance shell and the second layer can comprise an interior layer of the appliance shell. Alternatively, the first layer can comprise an interior layer of the appliance shell and the second layer can comprise an exterior layer of the appliance shell.

The geometry and configuration of the discontinuity can be selected based on forces desired to be applied to a patient's teeth. The discontinuity can include a cut formed in the first layer. For instance, the cut may extend at least partially around a protrusion formed in the first layer. As another example, the cut may be a closed cut, such as a cut enclosing a region of the shell. The cut may extend from a buccal surface of the first layer to a lingual surface of the first layer. In some instances, the discontinuity can include a plurality of cuts in the first layer, such as a plurality of cuts that are parallel to each other. The discontinuity can include a cut defining a flap in the first layer and a plurality of perforations near a joint portion of the flap.

The first and second layers of an appliance may have been thermoformed so as to form an appliance shell. The discontinuity may have been etched or engraved in the first layer. For example, the discontinuity can include a shape etched in the first layer.

In another aspect, a method for creating an orthodontic appliance as described herein can include providing a shell having a plurality of cavities shaped to receive a patient's teeth. The shell can include an exterior layer and an interior layer having a stiffness less than a stiffness of the exterior layer. In some embodiments, the exterior layer has an elastic modulus within a range from about 10,000 psi to about 700,000 psi and the interior layer has an elastic modulus within a range from about 100 psi to about 8000 psi. In alternative embodiments, the interior layer has an elastic modulus within a range from about 100 psi to about 50,000 psi. The exterior and interior layers of the shell may have been thermoformed. A discontinuity can be formed in the exterior layer. The process of forming the discontinuity may include creating a cut in the exterior layer, such as a cut extending at least partially around a protrusion formed in the exterior layer. The cut may be a closed cut. In some instances, the cut may extend from a buccal surface of the exterior layer to a lingual surface of the exterior layer. The discontinuity may also be formed by creating a plurality of cuts in the exterior layer, and the plurality of cuts may be parallel to each other. The discontinuity can include a cut defining a flap in the exterior layer and a plurality of perforations near a joint portion of the flap. As another example, forming the discontinuity may include etching or engraving the discontinuity in the exterior layer. The etching of the discontinuity in the exterior layer may include etching a shape in the exterior layer.

In another aspect, a method for creating an orthodontic appliance as described herein is provided. The method can include providing a shell having a plurality of cavities shaped to receive a patient's teeth. The shell can include a first layer and a second layer having a stiffness less than a stiffness of the first layer. In some embodiments, the first layer has an elastic modulus within a range from about 10,000 psi to about 700,000 psi and the second layer has an elastic modulus within a range from about 100 psi to about 8000 psi. In alternative embodiments, the second layer has an elastic modulus within a range from about 100 psi to about 50,000 psi. The first layer can comprise an exterior layer of the shell and the second layer can comprise an interior layer of the shell. Alternatively, the first layer can comprise an interior layer of the shell and the second layer can comprise an exterior layer of the shell.

The first and second layers of the shell may have been thermoformed. A discontinuity can be formed in the first layer. The process of forming the discontinuity may include creating a cut in the first layer, such as a cut extending at least partially around a protrusion formed in the first layer. The cut may be a closed cut. In some instances, the cut may extend from a buccal surface of the first layer to a lingual surface of the first layer. The discontinuity may also be formed by creating a plurality of cuts in the first layer, and the plurality of cuts may be parallel to each other. The discontinuity can include a cut defining a flap in the first layer and a plurality of perforations near a joint portion of the flap. As another example, forming the discontinuity may include etching or engraving the discontinuity in the first layer. The etching of the discontinuity in the first layer may include etching a shape in the first layer.

In another aspect, a method of designing an orthodontic appliance is provided. The method can comprise generating a digital model of the orthodontic appliance. The digital model can comprises a digital representation of a shell including a plurality of cavities shaped to receive teeth. The shell can comprise a first layer and a second layer having a stiffness less than a stiffness of the first layer. The digital model can comprise a digital representation of a discontinuity formed in the first layer. The method can further comprise generating instructions for fabricating the orthodontic appliance comprising the shell and the discontinuity by a direct fabrication technique, based on the digital model.

Various types of direct fabrication techniques are suitable for use with the embodiments herein. For example, the direct fabrication technique can comprise one or more of: vat photopolymerization, material jetting, binder jetting, material extrusion, powder bed fusion, sheet lamination, or directed energy deposition. In some embodiments, the direct fabrication technique comprises a continuous direct fabrication technique. Optionally, the direct fabrication technique comprises a multi-material direct fabrication technique.

The use of direct fabrication as discussed herein permits the various components of the orthodontic appliance to be fabricated concurrently in a single manufacturing step, without requiring additional steps to form and/or couple additional components. For example, in some embodiments, the instructions are configured to cause a fabrication machine to form the first layer concurrently with the second layer. The instructions can be configured to cause a fabrication machine to form the discontinuity concurrently with the first layer.

Various embodiments and configurations of appliances can be considered for the orthodontic systems and treatments described herein. For example, an appliance can include a plurality of layers, including at least one relatively elastic layer and at least one relatively rigid layer. Herein, "relatively elastic" and "relatively rigid" may indicate that the relatively rigid layer is more rigid (stiff) than the relatively elastic layer. For example, the (relatively) rigid layer may have an elastic modulus within a range from about 10,000 psi to about 700,000 psi, and the (relatively) elastic layer may have an elastic modulus within a range from about 100 psi to about 8000 psi, or from about 100 psi to about 50,000 psi. The elastic and rigid layers can be arranged in any suitable manner to form an appliance, such as with the elastic layer on the interior of the appliance and the rigid layer on the exterior of the appliance. "Interior" may be used herein to refer to portions of an appliance that are adjacent to or approximately adjacent to the received teeth when the appliance is worn, while "exterior" may be used to refer to portions of an appliance opposite from or approximately opposite from the received teeth when the appliance is worn. "Interior" and "exterior" may also be used herein to denote relative positioning rather than absolute positioning. In alternative embodiments, other configurations can be used, e.g., the appliance can be formed with the elastic layer on the exterior and the rigid layer on the interior.

The number of layers within a layered orthodontic appliance can be varied as desired. The appliance can include only a single elastic layer and only a single rigid layer. Alternatively, the appliance can include other layers in addition to the elastic layer and rigid layer, e.g., intermediate layers interspersed between the elastic and rigid layers. Optionally, the appliance can include a plurality of elastic layers and a plurality of rigid layers. As will be appreciated, the layered appliances described herein can impart forces on one or more of the patient's teeth so as to elicit various tooth movements in accordance with a desired treatment procedure.

Figure 34A:
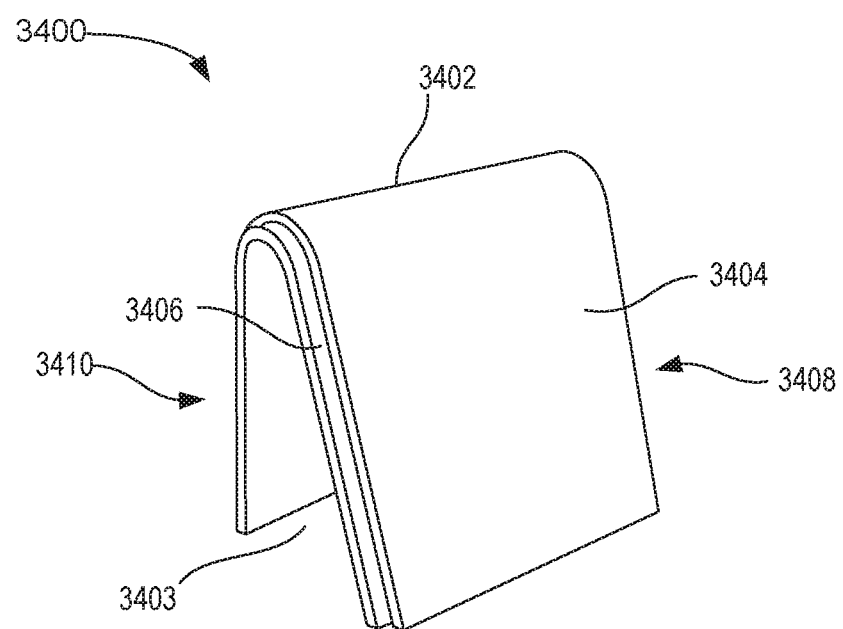
FIG. 34A illustrates a portion of a layered orthodontic appliance, in accordance with some embodiments.

FIG. 34A illustrates a portion of a layered orthodontic appliance 3400, in accordance with some embodiments. The appliance 3400 can include a shell 3402 having one or more teeth-receiving cavities 3403 shaped to accommodate a patient's teeth. The shell 3402 can include an exterior layer 3404 and interior layer 3406. Accordingly, when the appliance 3400 is worn over a patient's teeth, the interior layer 3406 may contact the teeth, while the exterior layer 3404 may not be in contact with the teeth. In some instances, the inner surface of the interior layer 3406 may be covered by one or more additional layers of material (not shown), such that the interior layer 3406 does not directly contact the teeth. These additional layers may be provided primarily as an interface for improving the contact between the shell 3402 and the teeth and/or gingiva, and thus may be relatively thin compared to the exterior and interior layers 3404, 3406. Optionally, one or more additional layers can also be situated at other locations of the shell 3402, e.g., between the exterior layer 3404 and interior layer 3406, over the outer surface of the exterior layer 3404, etc.

The exterior and interior layers 3404, 3406 may each span the entirety of the appliance 3400, or only certain portions of the appliance 3400. In some embodiments, the exterior and interior layers 3404, 3406 extend from the lingual surface 3408 to the buccal surface 3410 of the appliance 3400, thereby covering the lingual, occlusal, and buccal surfaces of the teeth received within the appliance 3400. Optionally, one or more portions of the exterior layer 3404 and/or interior layer 3406 may also extend over the gingiva. The exterior and interior layers 3404, 3406 may overlap each other such that they cover the same or similar portions of the patient's teeth when the appliance 3400 is worn. The exterior layer 3404 and interior layer 3406 can be coupled to each other (e.g., by one or more discrete attachment points and/or over one or more continuous attachment areas) at the overlapping portions, thereby forming a bilayered shell structure. In some embodiments, the exterior and interior layers 3404, 3406 overlap over the entirety of the appliance 3400 so that the whole appliance 3400 is at least bilayered. Alternatively, the exterior and interior layers 3404, 3406 may not overlap over some portions of the appliance 3400, such that the teeth received within these portions are covered by the exterior layer 3404 without the interior layer 3406, or vice-versa. Some portions of the appliance 3400 may be formed from other materials or components, and thus may not include either of the exterior or interior layers 3404, 3406.

The exterior layer 3404 may be relatively rigid and the interior layer 3406 may be relatively elastic. Consequently, the stiffness of the interior layer 3406 may be less than the stiffness of the exterior layer 3404. The properties (e.g., stiffness) of the appliance 3400 at the bilayered portions may be determined primarily by the properties of the exterior layer 3404, with relatively little contribution from the elastic interior layer 3406. Accordingly, these portions of the appliance 3400 may be relatively rigid and may experience little or no deformation when placed on the patient's teeth. Conversely, portions of the appliance 3400 where there are discontinuities in the exterior layer 3404 may permit greater contributions from the interior layer 3406 and therefore may be relatively flexible and/or deformable, as discussed in further detail below.

The properties of the exterior and interior layer 3404, 3406 can be varied as desired. For example, the interior layer 3406 may have an elastic modulus of about 600 psi, or within a range from about 100 psi to about 8000 psi, or from about 100 psi to about 50,000 psi. The exterior layer 3404 may have an elastic modulus of approximately 100,000 psi, or within a range from approximately 10,000 psi to approximately 700,000 psi. The elastic modulus of the interior layer 3406 may be approximately 100%, 90%, 80%, 70%, 60%, 50%, 40%, 30%, 30%, or 10% of the elastic modulus of the exterior layer 304. In some embodiments, the stiffness of each layer is related to the thickness of the layer. The exterior and interior layers 3404, 3406 may have the same thickness or different thicknesses. For instance, the thickness of the interior layer 3404 may be approximately 0.02 mm, or within a range from approximately 0.01 mm to approximately 1.0 mm. The thickness of the exterior layer 306 may be approximately 0.05 mm, or within a range from approximately 0.02 mm to approximately 1.0 mm. The thickness of the interior layer 3404 may be approximately 100%, 90%, 80%, 70%, 60%, 50%, 40%, 30%, 30%, or 10% of the thickness of the exterior layer 3406.

In alternative embodiments, the exterior layer 3404 may be relatively elastic and the interior layer 3406 may be relatively rigid, such that the stiffness of the exterior layer 3404 is less than the stiffness of the interior layer 3406. It shall be understood that although various embodiments presented herein illustrate a shell with a rigid exterior layer and elastic interior layer, the concepts of the present disclosure are also applicable to alternative configurations of layered appliances, e.g., appliances including a shell with an elastic exterior layer and rigid interior layer.

A layered appliance as described herein can include one or more discontinuities formed in one or more of the layers, e.g., the exterior layer, the interior layer, the elastic layer, the rigid layer, or combinations thereof. In some embodiments, the one or more discontinuities are formed in only a single layer, e.g., the exterior layer only, the interior layer only, the elastic layer only, or the rigid layer only, such that the other layer(s) do not include any discontinuities. Although various embodiments herein describe discontinuities formed in only a rigid exterior layer of a layered orthodontic appliance, it shall be understood that alternative embodiments can include discontinuities formed in other layers, e.g., an elastic interior layer, a rigid interior layer, etc.

A discontinuity can include any suitable number and combination of cuts, flaps, apertures (e.g., openings, windows, gaps, notches), or deformations (e.g., protrusions, indentations, reliefs) formed in any suitable portion of the layer, such as an exterior layer, (e.g., in a buccal, lingual, occlusal, and/or gingival surface). The dimensions (e.g., length, width, depth, surface area, etc.) and/or the shape of the discontinuity can be calculated, for instance, to achieve a specified degree of appliance compliance. A discontinuity may be linear, curved, curvilinear, circular, elliptical, triangular, square, rectangular, polygonal, or any other regular or irregular shape, or suitable portions or combinations thereof. A discontinuity can be oriented along any direction, such as along an occlusal-gingival direction, a mesial-distal direction, or a buccal-lingual direction.

The number, geometry, and configuration of the discontinuities can be selected so as to modulate the local properties (e.g., compliance or stiffness) of the appliance and/or influence the forces imparted onto the patient's teeth via the appliance. The forces may be provided wholly or in part by the interaction of the layer (e.g., an elastic interior layer) with the discontinuity, and may result from deformations, deflections, and/or displacements of the discontinuity and/or interior layer when the appliance is worn on a patient's teeth. The geometry and configuration of the discontinuities described herein can be selected to control the magnitude and/or direction of the forces applied to the teeth.

Figure 34B:
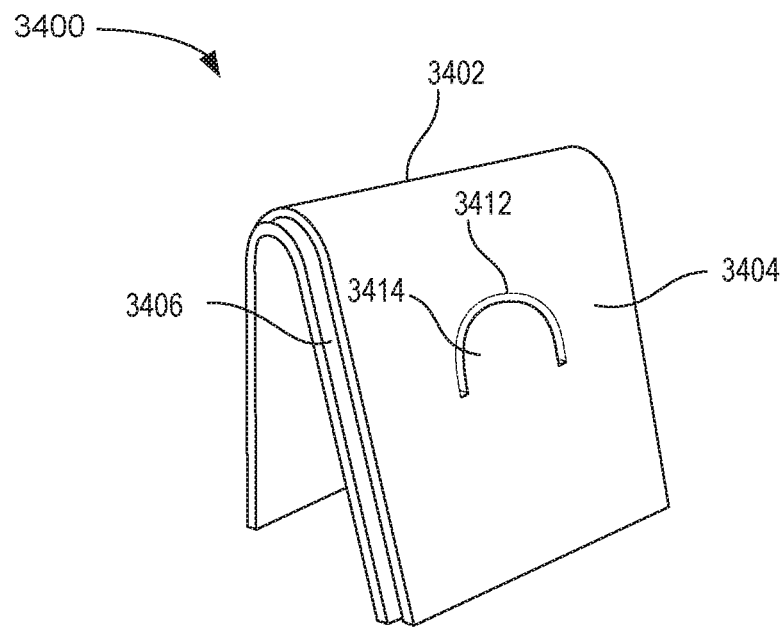
FIGS. 34B through 34I illustrate discontinuities formed in an exterior layer of a layered orthodontic appliance, in accordance with some embodiments.

FIG. 34B illustrates a discontinuity 3412 formed in the exterior layer 3404 of the appliance 3400, in accordance with some embodiments. The discontinuity 3412 can be formed solely in the exterior layer 3404 such that the interior layer 3406 is left intact. The interior layer 3406 may be exposed through the discontinuity 3412. The presence of the discontinuity 3412 may alter the properties of the appliance 3400 at or near the discontinuity 3412. For example, in some embodiments, the exposed interior layer 3406 is less rigid than the exterior layer 3404, such that the local compliance of the appliance 3400 at or near the discontinuity 3412 may be increased compared to other portions of the appliance 3400. In some instances, the discontinuity 3412 may be deformable (e.g., changeable with respect to shape, size) and/or displaceable, e.g., when the appliance is worn, which may also produce an increase in the local compliance of the appliance. The amount of local compliance can be used to control the resulting forces (e.g., magnitude, direction) exerted on the underlying teeth. Furthermore, the interior layer 3406 may interact with the discontinuity 3412, such as by exerting forces on the discontinuity 3412 or on portions of the exterior layer 3404 near the discontinuity 3412. These forces may result wholly or in part from deformation or displacement of the discontinuity 3412 and/or interior layer 3406 when the appliance 3400 is worn, as described in greater detail below. The forces generated by the interaction of the interior layer 3406 and the discontinuity 3412 may be transmitted to the underlying teeth via the shell 3402, thereby causing the repositioning of one or more teeth. The forces can be applied directly to the teeth by the shell 3402. Alternatively, the shell 3402 can apply force indirectly, e.g., via one or more attachments mounted on one or more teeth (not shown). In such instances, the discontinuity 3412 can be shaped to accommodate the attachment.

In FIG. 34B, the discontinuity 3412 is depicted as an arcuate cut forming a semicircular flap 3414 in the exterior layer 3404. Alternatively, other geometries for the cut and flap 3414 can be used (e.g., elliptical, square, rectangular, triangular, polygonal, etc.). The edges of the flap 3414 may be joined to the edges of adjacent portions of the exterior layer 3404 by the underlying interior layer 3406. The flap 3414 may be outwardly and/or inwardly deflectable relative to the surrounding portions of the exterior layer 3404. In some instances, the arcuate cut can extend around a feature formed in the shell 3402, such as a protrusion, indentation, or relief. Optionally, the arcuate cut can be situated adjacent to or near a tooth-mounted attachment when the appliance 3400 is worn by a patient.

Figure 34C:
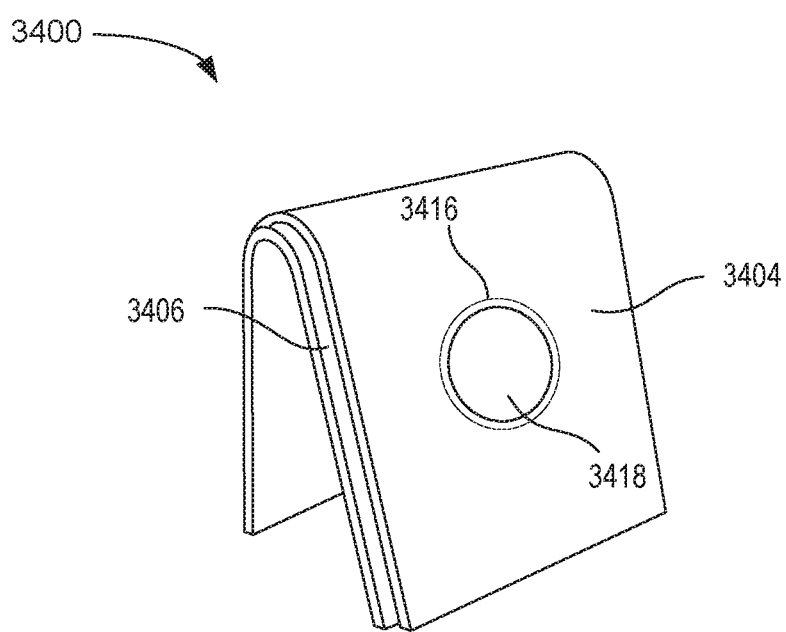

FIGS. 34C through 34F illustrate other exemplary discontinuities that may be provided as part of the appliance 3400, in accordance with some embodiments. FIG. 34C illustrates a discontinuity formed as a closed cut 3416. The closed cut 3416 encloses a region 3418 of the exterior layer 3404, thus separating it from the rest of the exterior layer 3404. The interior layer 3406 may span the closed cut 3416 so as to join the edges of the enclosed region 3418 to the edges of the adjacent portions of the exterior layer 3404. The closed cut 3416 may be a circular cut, as depicted herein, or any other suitable shape. The separated region 3418 defined by the closed cut 3416 may include a feature such as a protrusion, indentation, or relief. The separated region 3418 may be displaceable relative to the surrounding portions of the exterior layer 3404.

Figure 34D:
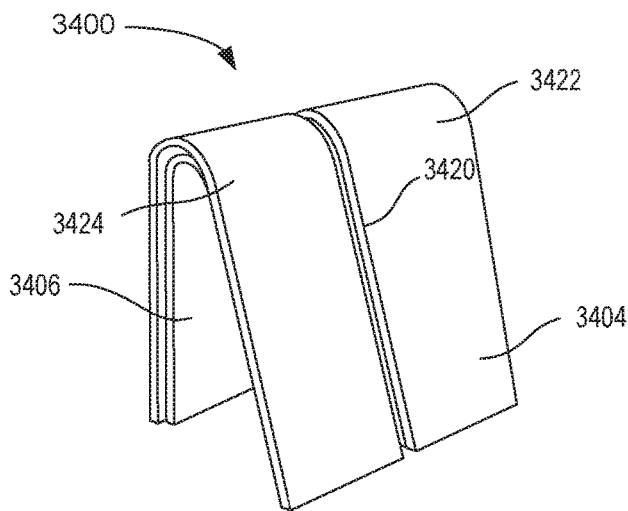

FIG. 34D illustrates a discontinuity formed as an elongate linear cut 3420. The linear cut 3420 may extend from the buccal surface to the lingual surface of the exterior layer 3404. The dimensions of the linear cut 3420 can be varied as desired. For example, the linear cut 3420 may extend from the buccal edge to the lingual edge of the appliance 3400, thus separating the exterior layer 3404 into discrete segments 3422, 3424. The segments 3422, 3424 may be joined to each other by the portions of the interior layer 3406 spanning the linear cut 3420. The segments 3422, 3424 may be displaced relative to each other when the appliance 3400 is placed on the patient's teeth. In some embodiments, the linear cut 3420 is positioned adjacent to or near an interproximal region between teeth, with the segments 3422, 3424 at least partially covering the teeth adjacent to the interproximal region. Accordingly, the segments 3422, 3424 can be shaped to receive teeth or portions thereof.

Figure 34E:
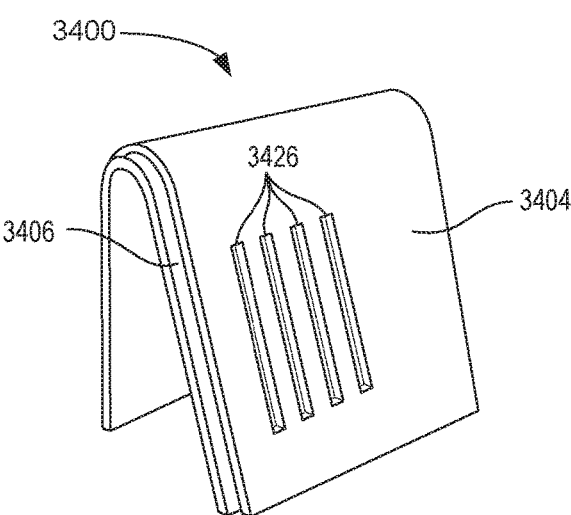

FIG. 34E illustrates a discontinuity formed as a plurality of elongate linear cuts 3426. Any suitable number of linear cuts 3426 can be used. The linear cuts 3426 may have the same or similar dimensions (e.g., length, width). Similar may mean that the variation of the dimension may be no more than 50%, no more than 25%, or no more than 10% of the maximum value of a corresponding dimension in the appliance. Alternatively, some of the cuts 3426 may have different dimensions than other cuts 3426, for example, variations of more than 10%, more than 25%, or more than 50% of the maximum value of a corresponding dimension in the appliance. Some or all of the linear cuts 3426 may be parallel cuts. Conversely, some or all of the linear cuts 3426 may not be parallel to each other. The linear cuts 3426 can be spaced apart from each other by a specified distance. The spacing between the linear cuts 3426 may be uniform or may vary. The portions of the exterior layer 3404 adjacent the linear cuts 3426 may be joined by the interior layer 3406 underlying the cuts 3426. The cuts 3426 may deform (e.g., stretch, widen) when the appliance 3400 is worn by the patient.

Figure 34F:
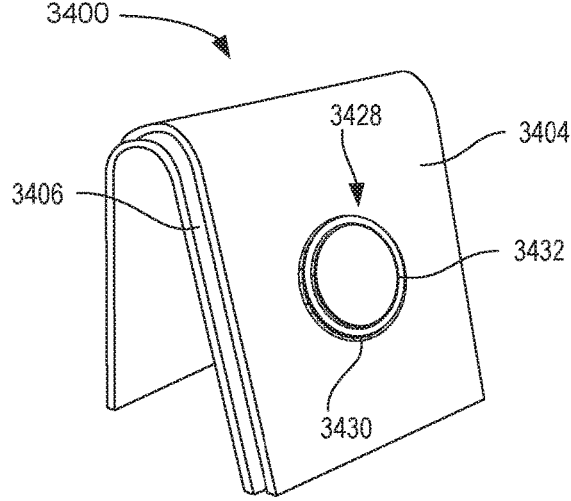

FIG. 34F illustrates a discontinuity formed as an etched shape 3428 in the exterior layer 3404. The shape 3428 can be etched only partially into the exterior surface of the exterior layer 3404, such that the interior layer 3406 is not exposed. Alternatively, the etching may penetrate through the entire depth of the exterior layer 3404 so as to expose the interior layer 3406. The etching of the exterior layer 3404 may reduce the thickness of the exterior layer 3404 at the discontinuity, which may alter the properties (e.g., stiffness) of the appliance 3400 at or near the discontinuity. For instance, the presence of the etched shape 3428 may increase the influence of the interior layer 3406 on the local compliance of the appliance 3400 (e.g., reduce the local compliance).

The etched shape 3428 is depicted herein as a collapsible structure including a ring 3430 and a disk 3432, although other geometries can also be used. The interior layer 3406 may join the ring 3430 and disk 3432. In the collapsed configuration of the etched shape 3428 (e.g., when the appliance 3400 is not being worn by a patient), the ring 3430 and disk 3432 may lie in approximately the same plane as the surrounding portions of the exterior layer 3404. In the expanded configuration of the etched shape 3428 (e.g., when the appliance 3400 is worn by the patient), the ring 3430, disk 3432, and intervening portions of the interior layer 3406 can protrude outwards from the surrounding exterior layer 3404 so as to form a receptacle. The receptacle can be shaped, for instance, to receive an attachment mounted on the underlying tooth, and to exert force onto the tooth via the attachment.

Figure 34G:
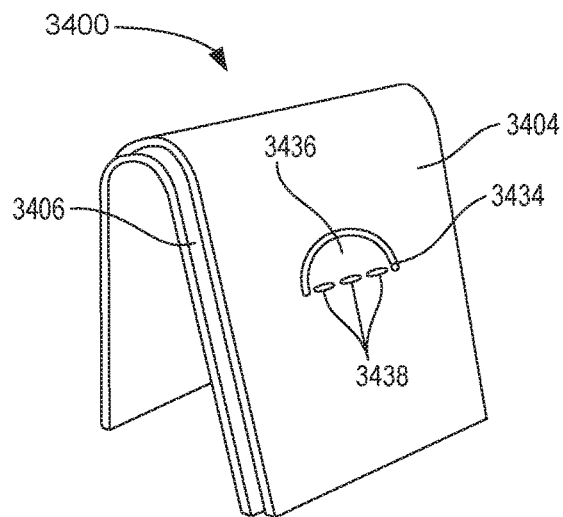
Figure 34H:
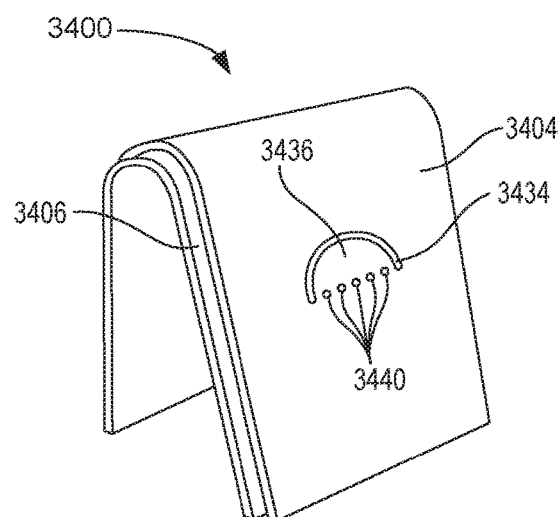
Figure 34I:
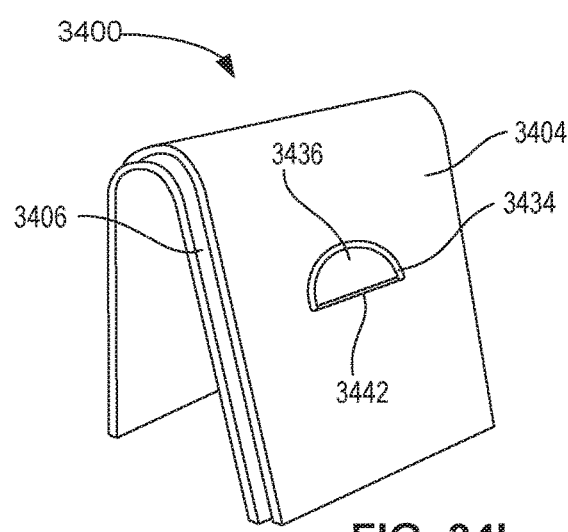

FIGS. 34G through 34I each illustrate a discontinuity formed as a cut 3434 defining a flap 3436 in the exterior layer 3404, similar to the embodiment depicted in FIG. 34B. The flap 3436 can be deflected relative to the surrounding portions of the exterior layer 3404, e.g., to accommodate an underlying tooth surface, shell feature, and/or tooth attachment. In order to increase the movement range of the flap 3436 and/or reduce the magnitude of the forces needed to deflect the flap 3436, it may be beneficial to modify the exterior layer 3404 to reduce the flexing resistance of the material at or near the joint portion of the flap 3436. This may be accomplished by forming one or more discontinuities in the exterior layer 3404 at or near the joint portion. In some embodiments, the discontinuities can be positioned so as to define the joint portion that flexes during deflection of the flap 3436. Any suitable number and combination of discontinuities can be used, and the geometry (e.g., size, shape) and configuration of the discontinuities can be varied as desired in order to provide the appropriate amount of flexing resistance at or near the joint portion. For instance, FIG. 34G illustrates a plurality of perforations 3438 formed in the exterior layer 3404 at the joint portion of the flap 3436. The perforations 3438 may be oval-shaped, as depicted in FIG. 34G, or any other suitable geometry (e.g., circular, square, triangular, polygonal, etc.). As another example, FIG. 34H illustrates a plurality of small circular perforations 3440 formed in the exterior layer 3404 at the joint portion. At least some of the discontinuities presented herein may extend through the entire thickness of the exterior layer 3404, thereby exposing the underlying interior layer 3406. In alternative embodiments, the discontinuities may only extend partially through the exterior layer 3404, thereby reducing the thickness of the material at or near the joint portion. For example, FIG. 34I illustrates a groove 3442 formed in the exterior layer 3404 near the joint portion of the flap 3436. The ends of the groove 3442 may contact the cut 3434. In alternative embodiments, the ends of the groove 3442 may not be in contact with the cut 3434. The groove 3442 can be etched or engraved into the exterior layer 3404 to a depth that is less than the thickness of the exterior layer 3404. The dimensions (e.g., length, width, depth) and shape (e.g., linear, curved, curvilinear) of the groove 3442 can be configured to optimize the flexibility of the flap 3436.

The layered appliances described herein can be worn by a patient so as to apply force onto one or more underlying teeth, and thereby effect various movements of the teeth. The direction and extent of the resultant tooth movements can be determined based on the geometry, configuration, and properties of the discontinuity, interior layer, and/or exterior layer. Furthermore, the appliances described herein may incorporate various features (e.g., protrusions, indentations, grooves, notches, buttons, reliefs) formed in the appliance shell (e.g., in the interior and/or exterior layer) that can engage the teeth at discrete points and/or over continuous regions so as to further influence the magnitude and/or direction of the forces imparted on the teeth. The number, geometry, and configuration of such features can be selected based on the desired movements for the targeted teeth.

Figure 35A:
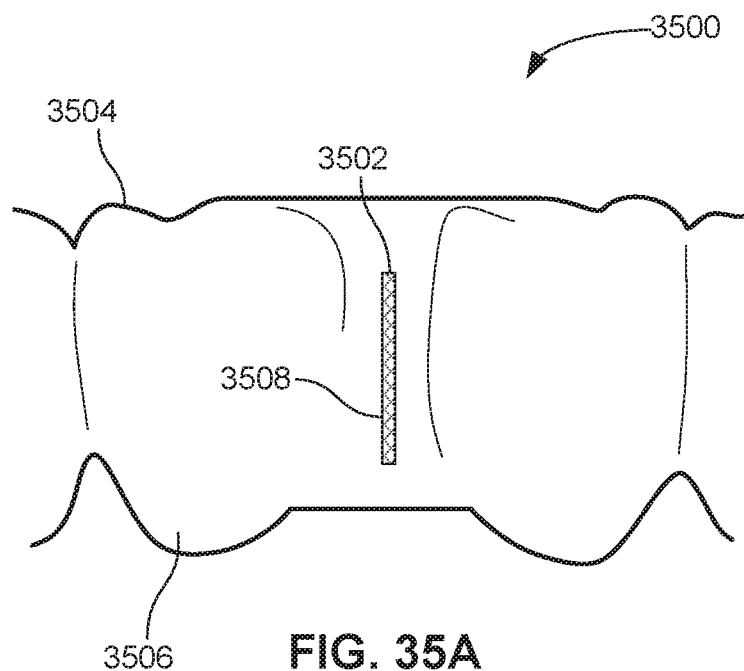
FIG. 35A illustrates a layered orthodontic appliance having a discontinuity, in accordance with some embodiments.
Figure 35B:
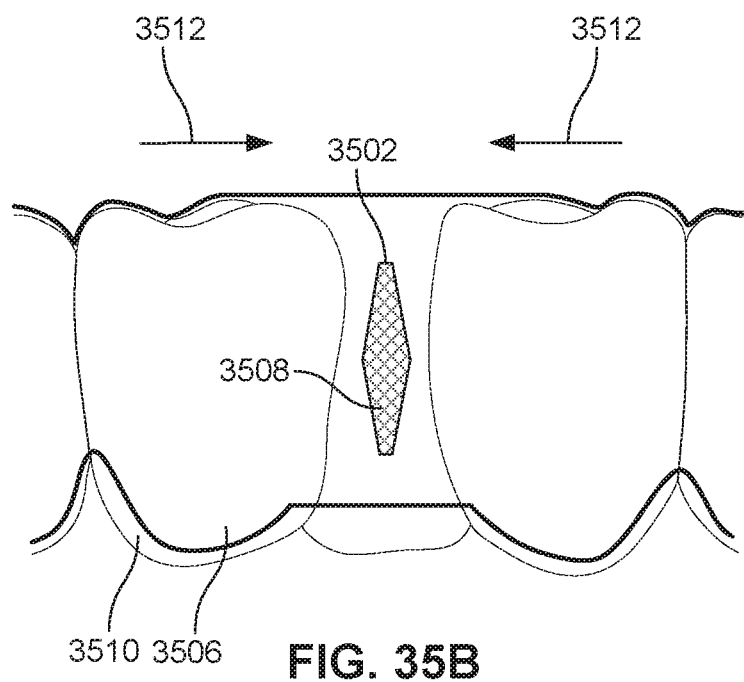
FIG. 35B illustrates the appliance of FIG. 35A when placed over a patient's teeth, in accordance with some embodiments.

FIGS. 35A and 35B illustrate a layered orthodontic appliance 3500 having a discontinuity 3502, in accordance with some embodiments. The appliance 3500 can include a shell 3504 formed from an exterior layer 3506 and elastic interior layer 3508, with a portion of the interior layer 3508 exposed through the discontinuity 3502 (depicted herein as an elongate linear cut). In other embodiments, no portion of the interior layer may be exposed through the discontinuity, e.g., in embodiments where the discontinuity does not penetrate through the entire exterior layer. When the appliance 3500 is placed on a patient's teeth 3510 (depicted in FIG. 35B), the discontinuity 3502 may be deformed by the intentional mismatch between the patient's current tooth arrangement and the tooth arrangement specified by the geometry of the appliance 3500. For instance, the elongate linear cut of the discontinuity 3502 may be widened into an elongate aperture. Additionally, one or more portions of the interior layer 3508 spanning the discontinuity 3502 may also be deformed (e.g., stretched) according to the deformation of the discontinuity 3502. The resistance of the interior layer 3508 to deformation may cause forces to be exerted on the discontinuity 3502 and/or the surrounding portions of the exterior layer 3506. Some or all of these forces may be transmitted to the underlying teeth, thereby eliciting movements of one or more teeth with respect to up to six degrees of freedom of motion (e.g., translation, rotation, intrusion, extrusion, tipping, torqueing, etc.). For example, the interaction of the discontinuity 3502 and interior layer 3508 may produce tooth movements that reduce an interproximal space between teeth (e.g., arrows 3512). Alternatively or additionally, the appliance 3500 may be used to produce other types of tooth movements, such as tooth movements increasing an interproximal space between teeth (e.g., to correct malocclusions, to accommodate an implant or other dental prosthesis, etc.). As the teeth are repositioned, the deformation of the discontinuity 3502 and/or the interior layer 3508 may decrease, thus diminishing the amount of force expressed on the teeth by the appliance 3500.

FIGS. 36A and 36B illustrate cross-sectional views of a layered orthodontic appliance 3600 having a discontinuity 3602, in accordance with some embodiments. The appliance 3600 can include a shell 3604 having an exterior layer 3606 and elastic interior layer 3608. The discontinuity 3602 can be a cut forming a flap in the exterior layer 3606, similar to the embodiments depicted in FIGS. 34B and 34G through 34I. The edges of the cut may be joined by the interior layer 3608. The shell 3604 can include a feature such as a protrusion 3610 (e.g., a button, knob, etc.) situated on the flap and extending into the interior cavity of the appliance 3600. When a tooth 3612 is received within the appliance 3600, the protrusion 3610 and flap may be displaced outwards by the surface topography of the tooth 3612. The elastic interior layer 3608 may resist the displacement by exerting force on the exterior layer 3606 at or near the discontinuity 3602, thereby pulling the protrusion 3610 and flap inwards against the tooth surface (e.g., arrow 3614). The exerted force may be transmitted to the tooth 3612 primarily at the point of contact between the surface of the tooth 3612 and the protrusion 3610. The application of force to the contact point can elicit various movements of the tooth 3612, such as a tipping movement. In some instances, a plurality of protrusions can be used in combination with a plurality of discontinuities so as to provide a plurality of contact points for more precise application of forces to the tooth.

Various different embodiments or configurations may be considered for the layered appliances described herein. For example, an appliance may accommodate various different configurations for elastic and/or rigid layers, including different compositions and/or structures of elastic and/or rigid materials. Material forming a layer may include a single continuous layer of material or multiple layers of the same material, different materials, or a combination of some layers of the same material and one or more layers of different material(s). Properties of the material layer such as resiliency, elasticity, hardness/softness, color, and the like can be determined, at least partially, based on the selected material, layers of material, and/or layer thickness. In some instances, the layer can be configured such that one or more properties are uniform along a length or portion of the layer (or entire layer). Additionally, one or more properties of the layer may vary along a length or portion of the layer (or entire layer). Vary (or variable) may for example mean that the variations of the one or more properties is higher than 10%, higher than 25%, or higher than 50% of the highest value of the corresponding property/properties of the elastic material. For example, a layer may have substantially uniform thickness along a length or portion, or may vary along a length/portion. Substantially uniform may mean that the variations (e.g., the absolute value of the difference between any two values of one property with regard to the appliance) of the one or more properties is no higher than 50%, no higher than 25%, or no higher than 10% of the highest value of the corresponding property/properties of the elastic material. As will be appreciated, characteristics of the layer or layer may be selected so as to affect the force application to the patient's teeth or tooth movement aspects of a particular treatment desired.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, and/or forming one or more discontinuities in a layer of the shell (e.g., by cutting, etching, etching, etc.).

FIG. 37 illustrates a method 3700 for fabricating an orthodontic appliance, in accordance with some embodiments. The method 3700 can be applied to any embodiment of the orthodontic appliances described herein.

In step 3710, a shell having a plurality of cavities shaped to receive teeth is provided. The shell can include a first layer and a second layer having a stiffness less than a stiffness of the first layer, such that the first layer is relatively rigid and the second layer is relatively elastic. For example, the first layer can be an exterior layer of the shell and the second layer can be an interior layer of the shell. Alternatively, the first layer can be an interior layer of the shell and the second layer can be an exterior layer of the shell. The second and first layers can be formed from any suitable material or combination of materials. For example, the first layer and/or second layer can be formed from biocompatible materials suitable for orthodontic use, such as latex. In some instances, the first and second layers are transparent, translucent, or colored, so as to improve the aesthetics of the appliance when worn by a patient. The first layer (e.g., the relatively rigid layer) can be fabricated from materials similar or corresponding to those used for conventional single layered appliance shells, such as polymeric sheets. The materials for the first layer may be more rigid than those typically used for single layered shells. The second layer (e.g., the relatively elastic layer) can be fabricated from any suitable elastic material, and such materials may be provided as strips, bands, sheets, meshes, coatings, layers, or suitable combinations thereof. The characteristics of the elastic material (e.g., length, width, thickness, area, shape, cross-section, stiffness, etc.) may be homogeneous throughout the bulk of the elastic material, or may be variable. For example, different portions of the second layer may have different thicknesses, thereby altering the local compliance of the appliance shell. Furthermore, in some instances, the second layer may have anisotropic characteristics. As an example, the second layer may be relatively compliant along a first direction, and less compliant (or noncompliant) along a second direction. The directionality of the second layer can be used to control the direction of the resultant forces applied to the teeth. Optionally, the second layer can be formed with topological features (e.g., embossing, brushing, texturing, roughening, etc.) to enhance surface friction between the shell and the enamel of the received teeth. Such features can be used, for instance, to improve the ability of the shell to grip onto teeth when worn by the patient.

The shell can be fabricated using any suitable method, such as thermoforming, additive manufacturing, or computer numerical control (CNC) milling. For example, the first and second layers may be thermoformed to form the shell. The layers may be thermoformed simultaneously or sequentially. An interior layer may be thermoformed first and an exterior layer subsequently thermoformed on top of the interior layer. The thermoforming process may directly bond the first and second layers together (e.g., via thermal bonding) without the use of adhesives or other indirect bonding methods. Alternatively or in addition, adhesive agents can be used to couple the first and second layers to each other. In some instances, an exterior layer may be formed first, with an interior layer being subsequently coupled to the exterior layer (e.g., by dipping, spraying, extruding, coating, etc.), or vice-versa. In some embodiments, the shell is fabricated using direct fabrication methods, as discussed further herein. The bilayered shells described herein can be fabricated based on a physical or digital model of the patient's teeth. The model can be generated from dental impressions or scanning (e.g., of the patient's intraoral cavity, of a positive or negative model of the patient's intraoral cavity, or of a dental impression formed from the patient's intraoral cavity).

In step 3720, a discontinuity is formed in the first layer. Any method suitable for creating cuts in the first layer or removing material from the first layer can be used to create one or more discontinuities. For example, the discontinuity can be engraved or etched in the first layer (e.g., using CNC-based or laser-based methods). The discontinuity may be formed without disturbing the second layer. The discontinuity may penetrate through the entire thickness of the first layer so as to expose the underlying second layer, or may penetrate only partially through the first layer so that the second layer is not exposed. In some embodiments, the discontinuity is located only in the first layer, such that the second layer is left intact.

Although the above steps show a method 3700 for fabricating an orthodontic appliance in accordance with embodiments, a person of ordinary skill in the art will recognize many variations based on the teaching described herein. Some of the steps may comprise sub-steps. Many of the steps may be repeated as often as beneficial to the treatment. One or more steps of the method 3700 may be applied to any suitable orthodontic appliance, such as the embodiments described herein. The order of the steps can be varied. For example, in alternative embodiments, a layered orthodontic appliance can be fabricated by first providing a first (e.g., exterior) layer, and forming a discontinuity in the first layer as described above. The first layer can subsequently be coupled to an elastic second (e.g., interior) layer to form a bilayered shell, using any of the techniques discussed herein.

Elastic-Coated Orthodontic Appliance

In some embodiments, an orthodontic appliance of the present disclosure includes a shell covered at least in part by an elastic coating. The shell can be relatively thin and compliant compared to the elastic coating. Consequently, the properties of the coated portions of the appliance may be controlled primarily by the properties of the elastic coating, such that the tooth repositioning forces generated by the appliance are provided wholly or predominantly by the elastic coating. The material properties (e.g., stiffness) of the appliances described herein can be varied via the elastic coating, thus affording different force application to different teeth of the patient's arch and, in some instances, more precise application or delivery of one or more forces to teeth with decreased patient discomfort.

Thus, in one aspect, an orthodontic appliance includes a shell having a plurality of cavities shaped to receive a patient's teeth and comprising an interior surface and an exterior surface, and an elastic coating covering at least a portion of one or more of the interior surface or exterior surface of the shell. A stiffness of a portion of the orthodontic appliance corresponding to the portion of the shell covered with the elastic coating is determined by a stiffness of the elastic coating. In some instances, the stiffness of the portion can be determined mainly by the stiffness of the elastic coating.

The elastic coating may vary in design. For example, the elastic coating can have a variable thickness over the portion of the shell. The stiffness of the elastic coating can be variable over the portion of the shell. The portion can include any part of the shell, such as the entire shell. Various techniques can be used to couple the elastic coating to the shell. In some instances, the elastic coating can be sprayed or extruded onto the portion of the shell. The elastic coating can be formed by attaching discrete pieces of elastic material to the shell. The elastic coating can be transparent, translucent, or opaque. Optionally, the elastic coating can be colored.

The shell may be flexible. The dimensions of the shell can be varied. For example, a thickness of the shell can be less than or equal to about 0.02 mm.

In another aspect, an appliance as described herein may be included in a series of appliances so as to provide an orthodontic system for positioning teeth. Such an orthodontic system can include a plurality of orthodontic appliances each comprising a shell including one or more cavities shaped to receive at least portions of a patient's teeth. The appliances may be successively worn or wearable by the patient to move one or more teeth from a first arrangement to a second arrangement. One or more of the appliances can include an elastic-coated orthodontic appliance as described herein. For example, an elastic-coated appliance of a system can include an appliance shell having a plurality of cavities shaped to receive the patient's teeth and comprising an interior surface and an exterior surface; and an elastic coating covering at least a portion of one or more of the interior surface or exterior surface of the appliance shell, wherein stiffness of a portion of the orthodontic appliance corresponding to the portion of the appliance shell covered with the elastic coating is determined by a stiffness of the elastic coating.

The characteristics of an appliance of an orthodontic system can be varied as necessary in order to impart the desired tooth repositioning forces to a patient's teeth. For instance, the elastic coating can have a variable thickness over the portion of the appliance shell. Alternatively or in addition, the stiffness of the elastic coating can be variable over the portion of the appliance shell. The portion of the appliance shell covered by the elastic coating can include the entire appliance shell. The method for fabricating an appliance can be varied. For example, the elastic coating can be sprayed or extruded onto the portion of the appliance shell. In some embodiments, the elastic coating is formed by attaching discrete pieces of elastic material to the appliance shell. The aesthetics of the elastic coating can be varied as desired, such that the elastic coating can be transparent, translucent, opaque, and/or colored.

A shell of an orthodontic appliance can be manufactured with any suitable characteristics. For example, the appliance shell may be flexible. A thickness of the appliance shell can be less than or equal to 0.02 mm.

In another aspect, a method for creating an orthodontic appliance is provided herein. A method of creating or fabricating an appliance can include providing a shell having a plurality of cavities shaped to receive a patient's teeth and comprising an interior surface and an exterior surface. At least a portion of one or more of the interior surface or exterior surface of the shell may be covered with an elastic coating, such that a stiffness of a portion of the orthodontic appliance corresponding to the portion of the shell covered with the elastic coating is determined by a stiffness of the elastic coating.

A method may permit the design of the elastic coating to be varied. For example, the elastic coating can have a variable thickness over the portion of the shell. The stiffness of the elastic coating can be variable over the portion of the shell. The portion can include the entire shell. Covering at least a portion of the interior and/or exterior surface of the shell with the elastic coating can include spraying or extruding the elastic coating onto the portion of the shell, as well as attaching discrete pieces of elastic material onto the shell. The elastic coating can be transparent, translucent, opaque, and/or colored.

The provided shell may be flexible. A thickness of the shell can be any suitable amount, such as less than or equal to about 0.02 mm.

In another aspect, a method for creating an orthodontic appliance is provided herein. A method of creating or fabricating an appliance can include providing a shell having a plurality of cavities shaped to receive a patient's teeth. At least a portion of one or more of the interior surface or exterior surface of the shell may be covered with an elastic coating. The method can further include removing the shell from the elastic coating in order to form the orthodontic appliance comprising the elastic coating.

The various steps and features of the method can be varied as desired. For example, covering at least a portion of the interior and/or exterior surface of the shell with the elastic coating can include spraying or extruding the elastic coating onto the portion of the shell, as well as attaching discrete pieces of elastic material onto the shell. As another example, removing the shell can comprise dissolving the shell or releasing the shell from the elastic coating.

In another aspect, a method of designing an orthodontic appliance is provided. The method can comprise generating a digital model of the orthodontic appliance. The digital model can comprises a digital representation of a shell having a plurality of cavities shaped to receive a patient's teeth and comprising an interior surface and an exterior surface. The digital model can comprise a digital representation of an elastic coating covering at least a portion of one or more of the interior surface or exterior surface of the shell. A stiffness of a portion of the orthodontic appliance corresponding to the portion of the shell covered with the elastic coating can be determined by a stiffness of the elastic coating. The method can further comprise generating instructions for fabricating the orthodontic appliance comprising the shell and the elastic coating by a direct fabrication technique, based on the digital model.

Various types of direct fabrication techniques are suitable for use with the embodiments herein. For example, the direct fabrication technique can comprise one or more of: vat photopolymerization, material jetting, binder jetting, material extrusion, powder bed fusion, sheet lamination, or directed energy deposition. In some embodiments, the direct fabrication technique comprises a continuous direct fabrication technique. Optionally, the direct fabrication technique comprises a multi-material direct fabrication technique.

The use of direct fabrication as discussed herein permits the various components of the orthodontic appliance to be fabricated concurrently in a single manufacturing step, without requiring additional steps to form and/or couple additional components. For example, in some embodiments, the instructions are configured to cause a fabrication machine to form the elastic coating concurrently with the shell.

In some embodiments, the elastic coating comprises a plurality of portions with differing stiffnesses. The instructions can be configured to cause a fabrication machine to form the elastic coating by one or more of: depositing different materials at the plurality of portions, varying a thickness of the elastic coating at the plurality of portions, varying curing parameters for the elastic coating at the plurality of portions, or forming stiffness-modulating structures at the plurality of portions.

Various embodiments and configurations of appliances can be used with the orthodontic systems and treatment procedures described herein. For example, an orthodontic appliance can include a thin shell covered wholly or in part by a coating of elastic material. The shell may serve primarily as a template for the geometry of the elastic coating, and thus the properties (e.g., stiffness, thickness) of the shell may provide relatively little contribution to the overall properties (e.g., stiffness, thickness) of the appliance. The properties of the appliance may be determined primarily by the properties of the elastic coating. This may mean, for instance, that the elastic coating is responsible for at least 50%, at least 75%, at least 80%, or at least 90%, of the value of the property of the appliance. For example, the elastic modulus of the shell can be approximately 2000 psi, or within a range from approximately 200 psi to approximately 20,000 psi, while the elastic modulus of the coating may be approximately 1000 psi, approximately 4000 psi, or within a range from approximately 200 psi to approximately 20,000 psi. The ratio of the contribution of the elastic coating to the contribution of the shell, e.g., with respect to the properties of the shell such as thickness and/or elastic modulus, may be any suitable value, such as approximately 100:0, 90:10, 80:20, 70:30, 60:40, 50:50, 40:60, 30:70, 20:80, 10:90, or 0:100. The properties of the elastic coating can be selected so as to exert forces on the patient's teeth for eliciting various tooth movements (e.g., translation, rotation, extrusion, intrusion, tipping) as part of an orthodontic treatment procedure.

Figure 38A:
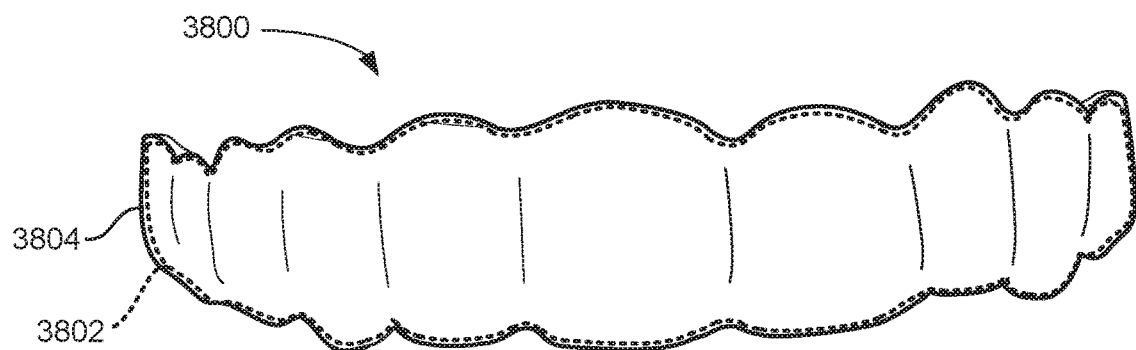
FIG. 38A illustrates an elastic-coated orthodontic appliance, in accordance with some embodiments.
Figure 38B:
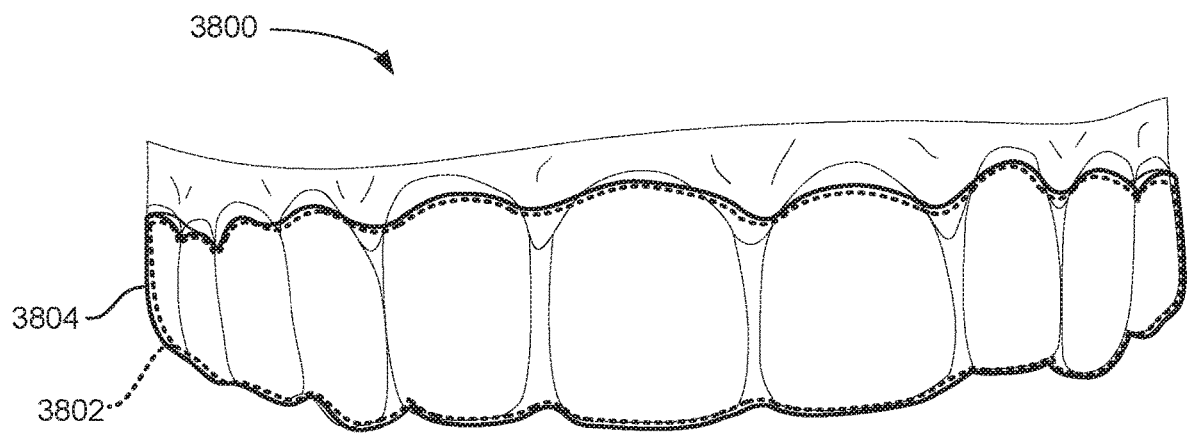
FIG. 38B illustrates the appliance of FIG. 38A placed over the teeth of a patient, in accordance with some embodiments.
Figure 38C:
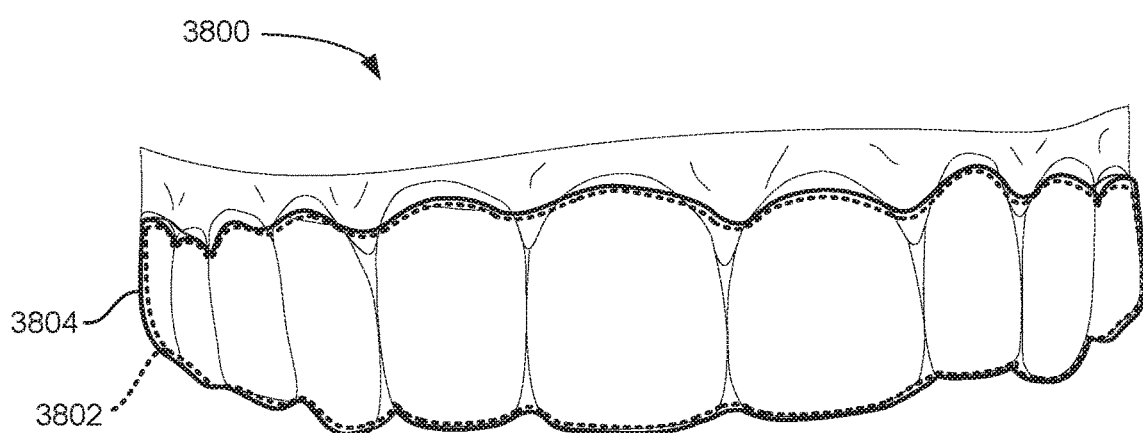
FIG. 38C illustrates the appliance of FIG. 38B after tooth repositioning has occurred, in accordance with some embodiments.

FIGS. 38A through 38C illustrate an elastic-coated orthodontic appliance 3800, in accordance with some embodiments. The appliance 3800 includes a shell 3802 covered by an elastic coating 3804. The shell 3802 can include a plurality of cavities adapted to receive some or all of the teeth of a patient's arch. The elastic coating 3804 can cover a portion of the shell 3802, including one or more of the exterior and/or interior surfaces of the shell 3802. The terms interior surface and exterior surface may be used herein to refer to surfaces adjacent to and away from the received teeth, respectively. The elastic coating 3804 may conform to the surface topography of the shell 3802, so that the tooth arrangement specified by the geometry of the elastic coating is identical or similar to the tooth arrangement of the shell 3802. In some instances, the elastic coating 3804 may form a single continuous layer covering the entirety of the shell 3802. Alternatively, the elastic coating 3804 may cover only some portions of the shell 3802, leaving other portions exposed. For example, the elastic coating 3804 may cover only the exterior surface of the shell 3802 or only the interior surface of the shell 3802.

The shell 3802 can be a flexible shell that is relatively thin and compliant compared to the elastic coating 3804. For instance, the thickness of the shell 3802 can be less than or equal to approximately 0.02 mm, or within a range from approximately 0.01 mm to approximately 0.3 mm, whereas the thickness of the elastic coating 3804 can be greater than or equal to approximately 0.01 mm, or within a range from approximately 0.01 mm to approximately 4 mm. Consequently, the overall properties of the coated portions of the appliance 3800 may be determined mainly by the properties of the elastic coating 3804, rather than by the properties of the shell 3802. As an example, the stiffness of the elastic coating 3804 may dictate the stiffness of the coated portions of the appliance 3800, with minimal or no contribution from the shell 3802. The shell 3802 may serve primarily as a template or "skeleton" for forming the geometry of the elastic coating 3804, and may provide little or no structural support to the overall appliance 3800. In some embodiments, the shell 3802 applies little or no force when deflected by a patient's teeth (e.g., when worn). Alternatively, the overall properties of the coated portions of the appliance 3800 may be determined by any suitable combination of the properties of the elastic coating 3804 and the properties of the shell 3802. For example, the stiffness of the coated portions of the appliance 3800 may be determined partially by the stiffness of the elastic coating 3804 and partially by the stiffness of the shell 3802. The properties of the shell 3802 and/or elastic coating 3804 (e.g., thickness, elastic modulus) can be varied as desired in order to generate the appropriate forces for repositioning teeth. The elastic modulus of the shell 3802 may be approximately 2000 psi, or within a range from approximately 200 psi to approximately 20,000 psi. The elastic modulus of the coating 3804 may be approximately 1000 psi, approximately 4000 psi, or within a range from approximately 200 psi to approximately 20,000 psi. The ratio of the contribution of the coating 3804 to the contribution of the shell 3802, e.g., with respect to the properties of the shell such as thickness and/or elastic modulus, may be any suitable value, such as approximately 100:0, 90:10, 80:20, 70:30, 60:40, 50:50, 40:60, 30:70, 20:80, 10:90, or 0:100.

When the appliance 3800 is worn by a patient (as depicted in FIG. 38B), the shell 3802 may readily deform (e.g., flex, stretch) to accommodate the patient's current tooth arrangement. The deformation may result from an intentional mismatch between the geometry of the appliance 3800 (e.g., the shell 3802 and/or elastic coating 3804) and the patient's current tooth arrangement. The elastic coating 3804 can resist the deformation of the shell 3802, such that the overall extent of deformation of the appliance 3800 is smaller than what would occur if the coating 3804 were not present. The resistance of the elastic coating 3804 to deformation can exert forces onto the underlying teeth, thereby eliciting movements of one or more teeth with respect to up to six degrees of freedom of motion (e.g., translation, rotation, intrusion, extrusion, tipping, torqueing, etc.). Alternatively or in combination, the elastic coating 3804 may apply forces to one or more teeth in order to retain the teeth at their current positions and/or orientations. The repositioning or movements of the teeth may reduce the extent of deformation of the elastic coating 3804 and shell 3802, thus decreasing the amount of force applied to the teeth (as depicted in FIG. 38C).

The properties of the elastic coating (e.g., length, width, thickness, area, shape, cross-section, stiffness, elastic coefficient, etc.) can be used to control the magnitude and/or direction of the forces exerted on the teeth. These properties may be homogeneous or approximately homogeneous throughout the entire coating. Approximately homogeneous may mean that the variations of the properties are no higher than 50%, no higher than 25%, or no higher than 10% of the largest value of this property present in the coating. Alternatively, the coating may be heterogeneous, such that some or all of these properties are variable, e.g., some or all of these properties are higher than 10%, higher than 25%, or higher than 50% of the largest value of the property present in the coating. For instance, the coating can include a plurality of different portions, some of which may have different properties. The portions may span a plurality of teeth, a single tooth, or parts of one or more teeth. A portion may have approximately uniform properties, or may have variable properties. The geometry and configuration of the different portions can be selected based on the targeted tooth movements for the current treatment stage. As an example, portions adjacent to teeth targeted for repositioning may have a greater stiffness than portions adjacent to teeth used for anchoring the appliance. Furthermore, in some instances, the elastic coating can have anisotropic characteristics or properties. For example, at least some portions of the elastic coating may be relatively compliant along a first direction, and less compliant (or noncompliant) along a second direction. The directionality of the elastic coating can be used to control the direction of the resultant forces applied to the teeth.

Figure 39A:
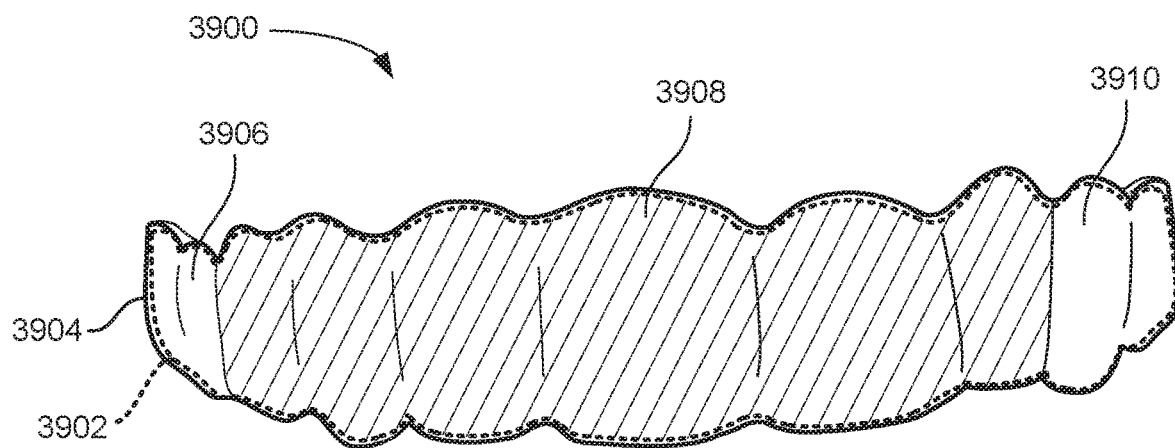
FIG. 39A illustrates an elastic-coated orthodontic appliance with segments, in accordance with some embodiments.
Figure 39B:
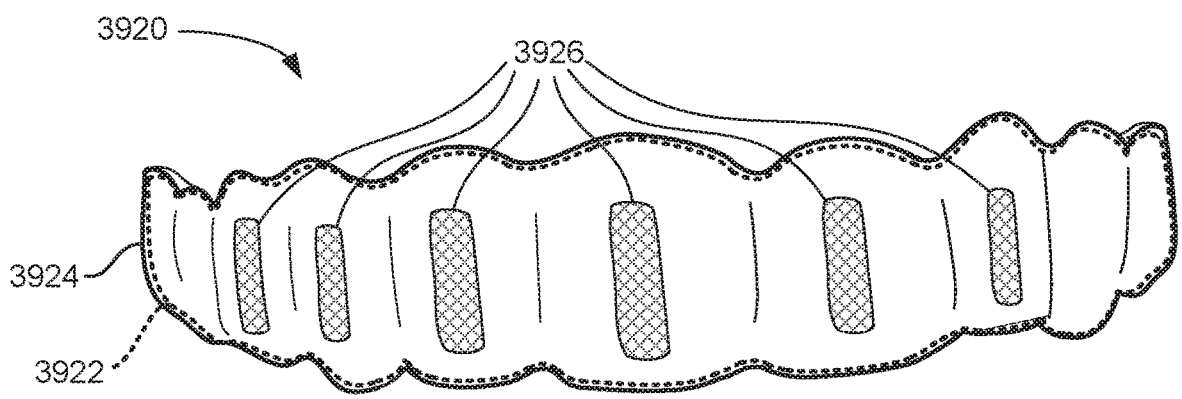
FIG. 39B illustrates an elastic-coated orthodontic appliance with discrete regions, in accordance with some embodiments.
Figure 39C:
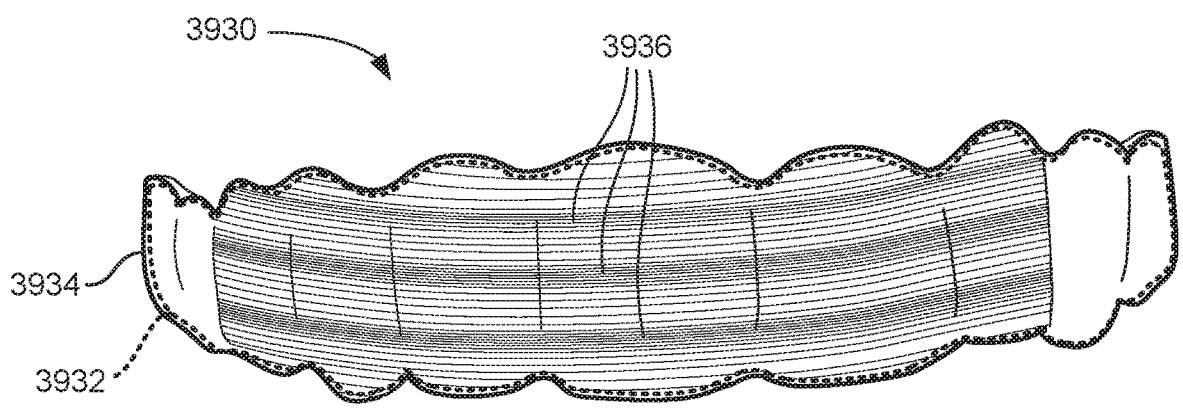
FIG. 39C illustrates an elastic-coated orthodontic appliance with striations, in accordance with some embodiments.

FIG. 39A through 39C illustrate various examples of elastic-coated appliances with heterogeneous properties, in accordance with some embodiments. The appliance 3900 of FIG. 39A includes a shell 3902 covered by an elastic coating 3904 having a plurality of segments 3906, 3908, 3910. In one embodiment, when the appliance 3900 is worn by a patient, the segment 3908 covers a plurality of front teeth, while the segments 3906, 3910 cover a plurality of back teeth. However, it will be appreciated that the coating 3904 can include any number of segments, each covering one or more teeth or parts thereof. The geometry and properties of each segment can be varied as necessary in order to apply the desired forces to the patient's teeth. Some segments of the coating 3904 may have different properties than other segments. This may mean, for example, that the variations in a property are higher than 10%, higher than 25%, or higher than 50% of the maximum value present for the property in the segments. For example, the segment 3908 may have a different thickness, stiffness, etc. compared to the segments 3906, 3910. Conversely, some segments may have the same or similar properties (e.g., segments 3906, 3910). Similar properties may mean, for instance, that the variations in a property are no higher than 50%, no higher than 25%, or no higher than 10% of the maximum value present for the property in the segments.

FIG. 39B illustrates an appliance 3920 in which the shell 3922 is covered by an elastic coating 3924 with a plurality of discrete regions 3926. The properties of the regions 3926 (e.g., stiffness, thickness, etc.) may differ from the properties of the surrounding portions of the coating 3924. In some embodiments, the geometry (e.g., size, surface area, shape), arrangement, and properties of the regions 3926 are designed to facilitate the repositioning of one or more teeth. For instance, although the regions 3926 are depicted in FIG. 39B as covering portions of the buccal surfaces of the teeth, in other embodiments, the regions 3926 may additionally or alternatively cover other portions of the teeth, such as portions of one or more lingual surfaces, one or more occlusal surfaces, one or more interproximal regions, or suitable combinations thereof.

FIG. 39C illustrates an appliance 3930 in which the shell 3932 is covered by an elastic coating 3934 having a plurality of striations 3936. The properties of the elastic coating 3934 may vary according to the striation pattern. For example, in one embodiment, each of the striations 3936 may have an increased thickness compared to other portions of the coating 3934. This may mean, for example, that each of the striations is more than 10%, more than 25%, more than 50%, or more than 100% thicker than the portion of the coating with the least thickness. As another example, the striations 3936 may correspond to bands of stiffer material formed in the coating 3934. The striations 3936 may extend across the entirety of the appliance 3930 or only across certain portions of the appliance 3930. The striations 3936 can be oriented along a mesial-distal direction (as depicted in FIG. 39C), a gingival-occlusal direction, or any other direction suitable for facilitating the desired tooth movements. Similar to the other embodiments provided herein, the geometry (e.g., length, width, spacing, gradient) and properties of the striations 3936 can be determined based on the targeted tooth movements for the appliance 3930.

The elastic-coated appliances described herein may accommodate various different configurations for elastic materials used for the elastic coating, including different compositions and/or structures of elastic materials. Elastic material for the coating may include a single continuous coating of elastic material or multiple coatings of the same elastic material, different materials, or a combination of some coatings of the same material and one or more coatings of different material(s). Properties of the elastic coating such as resiliency, elasticity, hardness/softness, color, and the like can be determined, at least partially, based on the selected material, coatings of material, and/or elastic coating thickness. In some instances, the elastic material or coating can be configured such that one or more properties are uniform along a length or portion of the elastic (or entire elastic). Additionally, one or more properties of the elastic material or coating may vary along a length or portion of the elastic (or entire elastic). This may mean, for example, that the variations in a property may be greater than 10%, greater than 25%, or greater than 50% of the maximum value of the property along the length or portion of the elastic (or entire elastic). For example, an elastic or coating may have substantially uniform thickness along a length or portion, or may vary along a length/portion. As will be appreciated, characteristics of the elastic or coating may be selected so as to affect the force application to the patient's teeth or tooth movement aspects of a particular treatment desired.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more discontinuities in the shell (e.g., by cutting, etching, etc.), and/or covering at least a portion of the shell with an elastic coating.

Figure 40:
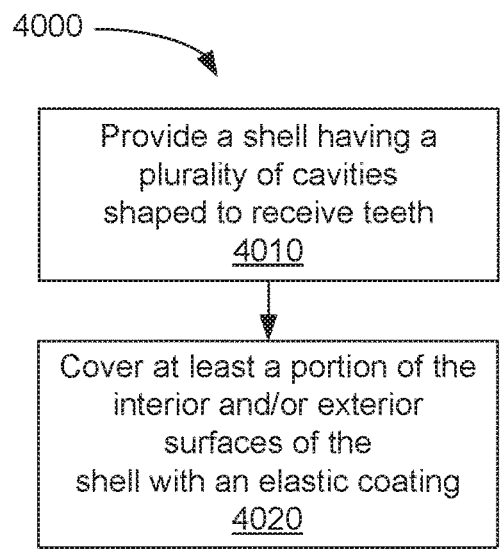
FIG. 40 illustrates a method for creating an orthodontic appliance, in accordance with some embodiments.
Figure 41A:
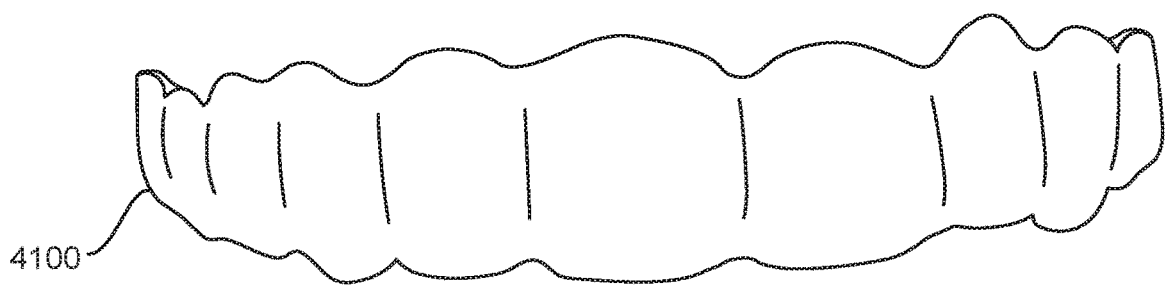
FIGS. 41A and 41B illustrate fabrication of an orthodontic appliance, in accordance with some embodiments.
Figure 41B:
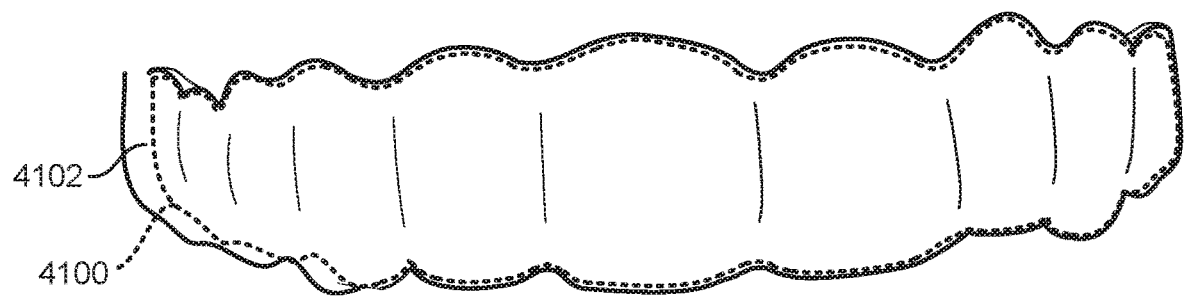

FIG. 40 illustrates a method 4000 for creating an orthodontic appliance, in accordance with some embodiments. The method 4000 can be applied to any embodiment of the orthodontic appliances described herein. FIGS. 41A and 41B illustrate fabrication of an orthodontic appliance, in accordance with some embodiments.

In step 4010, a shell having a plurality of cavities shaped to receive teeth is provided (see, e.g., shell 4100 of FIG. 41A). Exemplary methods for fabricating shells include thermoforming, additive manufacturing (e.g., stereolithography, etc.), or computer numerical control (CNC) milling. For example, the shell can be thermoformed from one or more layers of polymer sheets. Optionally, the shell can be manufactured using direct fabrication, as discussed further herein. The material(s) used for the shell may be translucent or colored. Alternatively, the shell or shell segments can be transparent, opaque, or any other suitable level of optical clarity. In some instances, the shell can be fabricated based on a physical or digital model of the patient's teeth. The model can be generated from dental impressions or scanning (e.g., of the patient's intraoral cavity, of a positive or negative model of the patient's intraoral cavity, or of a dental impression formed from the patient's intraoral cavity).

In step 4020, at least a portion of the interior and/or exterior of the shell (e.g., interior and/or exterior surfaces) is covered with an elastic coating (see, e.g., elastic coating 4102 of FIG. 41B). The elastic coating can be provided as strips, meshes, sheets, or layers, or suitable combinations thereof. Any suitable material or combination of materials can be used for the elastic coating, such as rubber, latex, polyurethane, or other elastomeric or biocompatible materials. The elastic material can have varying levels of optical clarity. In some embodiments, the elastic material is transparent, translucent, or opaque. Optionally, the material may be translucent or colored so as to improve the aesthetics of the appliance when worn by the patient.

The elastic coating can be placed on the shell using any suitable method, including spraying, dipping, extrusion, deposition, painting, sputtering, casting, dip-coating, and the like, or combinations thereof. In some instances, the elastic coating can be coupled to the shell, using suitable adhesives, bonding agents and the like. Alternatively, the elastic coating may have adhesive properties, thus allowing the coating to be directly attached to the shell without the use of additional external agents. The elastic coating may include different portions with differing properties, as discussed above, with different portions being fabricated using different materials and/or techniques. In one embodiment, the elastic coating can be directly fabricated on the shell by using an extrusion system to place one or more layers of material onto the shell. The extruded material can be provided in any suitable form (e.g., a fluid or gel, a solid such as a filament). A fluid material can be cured or fixed as it is dispensed from the extrusion system in order to solidify the elastic coating, e.g., using various energy sources such as ultraviolet, infrared, laser, and/or thermal energy sources. Alternatively or in combination, the elastic coating can be placed or deposited by a manufacturing system configured to attach discrete pieces of material (e.g., bands, strips, layers) to the shell. The fabrication systems presented herein may be computer-controlled systems, thereby permitting fully automated manufacturing of orthodontic appliances.

Although the above steps show a method 4000 for creating an orthodontic appliance in accordance with embodiments, a person of ordinary skill in the art will recognize many variations based on the teaching described herein. Some of the steps may comprise sub-steps. Many of the steps may be repeated as often as is beneficial. One or more steps of the method 4000 may be applied to any suitable orthodontic appliance, such as the embodiments described herein.

Moreover, in some embodiments, the shell is removed from the orthodontic appliance once the elastic coating has been applied (e.g., after the step 4020 has been performed), thereby resulting in an "elastic appliance" that includes the elastic coating without the shell. Optionally, the resultant elastic appliance may include only the elastic coating. Various methods can be used to remove the shell from the elastic coating, e.g., by dissolving the shell, applying a releasing agent allowing the shell to be physically separated from the elastic coating without damaging the elastic coating, or combinations thereof. Accordingly, in such embodiments, the shell serves only as a fabrication template for the geometry of the elastic coating and is therefore not intended for use in the final appliance for treating the patient. The forces applied to the patient's teeth when the elastic appliance is worn can result solely from the deformation of the elastic appliance (e.g., due to mismatch between the patient's current tooth arrangement and the tooth arrangement defined by the geometry elastic coating).

This approach of removing the shell following application of the elastic coating can be advantageous in producing appliances made of elastic materials that would otherwise be relatively difficult to directly fabricate without use of a template. Moreover, the properties of such elastic appliances can be locally varied (e.g., by locally changing the coating thickness, coating material, degree of cure, etc.), thus allowing for appliances with heterogeneous properties, in contrast to conventional sheet-based thermoforming methods which produce relatively homogeneous appliances. Additionally, this technique is compatible with thermoset materials such as thermoset elastomers, which may provide better resistance to stress relaxation than thermoplastic materials (e.g., thermoplastic elastomers) typically used in thermoforming procedures. It shall be understood that any of the embodiments of the orthodontic appliances provided herein can be further modified as described herein to remove the shell and retain only the elastic coating, and the elastic appliances resulting from such modifications are considered part of the present disclosure.

Direct Fabrication of Orthodontic Appliances with Elastics

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively stiff or rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic or compliant portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For example, in the context of the segmented appliances described herein, multi-material fabrication can permit fabrication of the plurality of shell segments concurrently with the fabrication of the elastic material, such that a separate coupling step for the joining the segments to the elastic is not needed. In some embodiments, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object (e.g., an appliance shell, shell segments, interior layer) can be formed from a first material in accordance with any of the direct fabrication methods herein, then a second portion of the object (e.g., one or more elastics or elastic materials, exterior layer, coating) can be formed from a second material in accordance with methods herein, and so on, until the entirety of the object has been formed. The relative arrangement of the first and second portions can be varied as desired, e.g., the first portion can be partially or wholly encapsulated by the second portion of the object.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness.

In some embodiments, direct fabrication allows for the entirety of an orthodontic appliance with elastics and discontinuities (e.g., shell, discontinuities, elastics, and/or other auxiliary components) to be integrally produced in a single step, thus obviating the need for additional steps, e.g., to form a discontinuity in the shell and/or couple an elastic or an auxiliary component to the shell. For example, using direct fabrication techniques, the various types of discontinuities described herein (e.g., cuts, flaps, apertures, deformations, etc.) can be formed concurrently with the forming of the appliance shell, rather than being formed in a separate material removal step. This approach can advantageously improve the accuracy and fidelity with which the discontinuity is formed, as well as avoid the possibility of damage to the appliance shell by the material removal process.

In some embodiments, direct fabrication allows for the entirety of a segmented appliance (e.g., shell segments and elastic material) to be integrally produced in a single step, thus obviating the need for additional steps, e.g., to couple the elastic material to the shell segments. For example, using direct fabrication techniques, the shell segments and elastic material joining the shell segments can be integrally formed as a single piece in a single manufacturing step, thus simplifying the fabrication procedure.

In some embodiments, direct fabrication allows for the entirety of a layered orthodontic appliance (e.g., interior layer, exterior layer, discontinuities) to be integrally produced in a single step, thus obviating the need for additional steps, e.g., to form a discontinuity in a layer. For instance, the various layers of the appliance can be concurrently formed with each other in a single manufacturing step using the direct fabrication techniques herein, without requiring a separate step to couple the layers to each other. Additionally, using direct fabrication techniques, the various types of discontinuities described herein (e.g., cuts, flaps, apertures, deformations, etc.) can be formed concurrently with the forming of the appliance layers, rather than being formed in a separate material removal step. This approach can advantageously improve the accuracy and fidelity with which the discontinuity is formed, as well as avoid the possibility of damage to the appliance shell by the material removal process.

In some embodiments, direct fabrication allows for the entirety of an elastic-coated appliance (e.g., the shell and coating) to be integrally produced in a single step, thus obviating the need for additional steps, e.g., to cover the shell with the elastic coating. Optionally, in embodiments where an elastic appliance including only the elastic coating without the shell is the desired end product, direct fabrication permits such an elastic appliance to be formed directly from the elastic material without forming any shell, thus obviating the need for a separate step to remove the shell from the coating.

Similarly, by using multi-material direct fabrication methods, the various types of elastics described herein (e.g., bands, cords, strips, loops, wires, springs, meshes, membranes, scaffolds, layers, etc.) can be formed integrally as a single piece with the appliance shell, thus simplifying and streamlining the appliance manufacturing process.

In alternative embodiments, if an elastic member or material is to be coupled to the shell after fabrication of the shell, the direct fabrication methods herein can be used to produce appliances with interfaces configured to facilitate coupling to the elastic member or material. In such embodiments, direct fabrication can be used to produce appliance shells or shell segments with grooves, recesses, receptacles, apertures, or other interfacing structures shaped to receive a portion of an elastic member or material to be coupled to the shell or shell segments. Optionally, the geometry (e.g., depth) of the interface can be configured such that the elastic lies below or flush with the exterior surface of the appliance when coupled to the shell or shell segments, e.g., to improve patient comfort and/or reduce the likelihood of the elastic becoming damaged or dislodged during use. Such interfaces can also be implemented to facilitate coupling to other components described herein, such as guide features (e.g., the spring and piston elements discussed herein with respect to FIGS. 8H, 8I, 25A, and 25B) or other prefabricated auxiliary components that are connected to the shell.

In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, or internal structures (e.g., for improving strength with reduced weight and material usage). For instance, appliances with structures including but not limited to biasing features such as perforations (see, e.g., FIGS. 26A through 26D), channels (see, e.g., FIG. 6), telescoping features (see, e.g., FIGS. 8A through 8C), interproximal features (see, e.g., FIGS. 10A through 10C), external features such as fastening features or retention features (see, e.g., FIGS. 14C and 14D), and internal features such as protrusions or complex flap geometries (see, e.g., FIGS. 16A through 16C, FIGS. 15A through 15F) can be easily produced by the direct fabrication methods presented herein. Such structures may be produced integrally as a single piece with the appliance shell via direct fabrication, for example.

In some embodiments, an appliance with an elastic coating having heterogeneous material properties (e.g., thickness, stiffness), such as a plurality of segments with different properties (see, e.g., FIG. 39A), a plurality of discrete regions with different properties (see, e.g., FIG. 39B), and/or patterned properties such as striations (see, e.g., FIG. 39C) can be easily produced by the direct fabrication methods presented herein. In some embodiments, such heterogeneous coatings are produced through the use of multi-material direct fabrication to deposit different types of materials at locations where different properties are desired. For instance, a relatively stiff or rigid material can be deposited at locations where increased stiffness is desired, and a relatively elastic material can be deposited at locations where increased elasticity is desired. Alternatively or in combination, one or more portions of an appliance can be formed from a mixture of a plurality of different materials, and the amounts and/or types of materials used in the mixture can control the amount of stiffness or elasticity of the corresponding appliance portion. Accordingly, appliances with heterogeneous properties as discussed herein can be produced by using different material mixtures to form different portions of the appliance. The multi-material approaches described herein permit the fabrication of heterogeneous appliances without varying the geometry (e.g., thickness) of the appliance. For example, a variable stiffness appliance can be fabricated by forming different portions of the appliance with different materials or mixtures of materials, while maintaining a substantially uniform thickness. The production of an appliance from multiple materials can be performed concurrently in a single manufacturing step, or in a plurality of sequential steps, as discussed above and herein.

Alternatively or in combination, elastic coatings with heterogeneous material properties are produced through the use of direct fabrication techniques that vary the geometry of the coating material at locations where different properties are desired. For example, a direct fabrication process can selectively vary the thickness of the formed material in order to control the resultant stiffness of the coating, e.g., such that stiffer portions of the coating have an increased thickness compared to more elastic portions of the coating. As another example, stiffness-modulating structures such as apertures, slits, perforations, etchings, and the like can be selectively formed at certain locations in the coating in order to reduce the local stiffness at those locations. Direct fabrication permits formation of such structures integrally and concurrently with formation of the coating, such that separate cutting or etching steps are not needed. In yet another example, direct fabrication process parameters such as curing parameters (e.g., curing time, energy, power, spacing, depth) can be selectively varied in order to influence the stiffness and/or other properties of the material. In some embodiments, control over the curing parameters is used to control the degree of crosslinking of the formed material, which in turn contributes to the local stiffness (e.g., increased crosslinking produces increased stiffness, reduced crosslinking produces reduced stiffness).

In some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm. The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Alternatively, appliances with anisotropic properties may be produced, as described above and herein. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In some embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In some embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In some embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more discontinuities in the shell (e.g., by cutting, etching, etc.), and/or coupling one or more elastics to the shell (e.g., by extrusion, additive manufacturing, spraying, thermoforming, adhesives, bonding, fasteners, etc.). Optionally, one or more auxiliary appliance components as described herein (e.g., channels, guide features, fastening features, flaps, receptacles, etc.) are formed separately from and coupled to the appliance shell (e.g., via adhesives, bonding, fasteners, etc.) after the shell has been fabricated.

In some embodiments, the orthodontic appliances herein can be fabricated using a combination of direct and indirect fabrication techniques. For example, different portions of an appliance can be fabricated using different fabrication techniques and assembled in order to form the final appliance.

Digital Design of Orthodontic Appliances with Elastics

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein (e.g., the shell, discontinuities, elastics, layers, coating, and/or other auxiliary components) can be digitally designed and fabricated with the aid of computer-controlled manufacturing devices (e.g., computer numerical control (CNC) milling, computer-controlled additive manufacturing, etc.). The computer-based methods presented herein can improve the accuracy, flexibility, and convenience of appliance fabrication.

Appliance fabrication or design can make use of one or more physical or digital representations of the patient's teeth. Representations of the patient's teeth can include representations of the patient's teeth in a current arrangement, and may further include representations of the patient's teeth repositioned in one or more treatment stages. Treatment stages can include a desired or target arrangement of the patient's teeth, such as a desired final arrangement of teeth. Treatment stages can also include one or more intermediate arrangements of teeth (e.g., planned intermediate arrangements) representing arrangements of the patient's teeth as the teeth progress from a first arrangement (e.g., initial arrangement) toward a second or desired arrangement (e.g., desired final arrangement).

Figure 42:
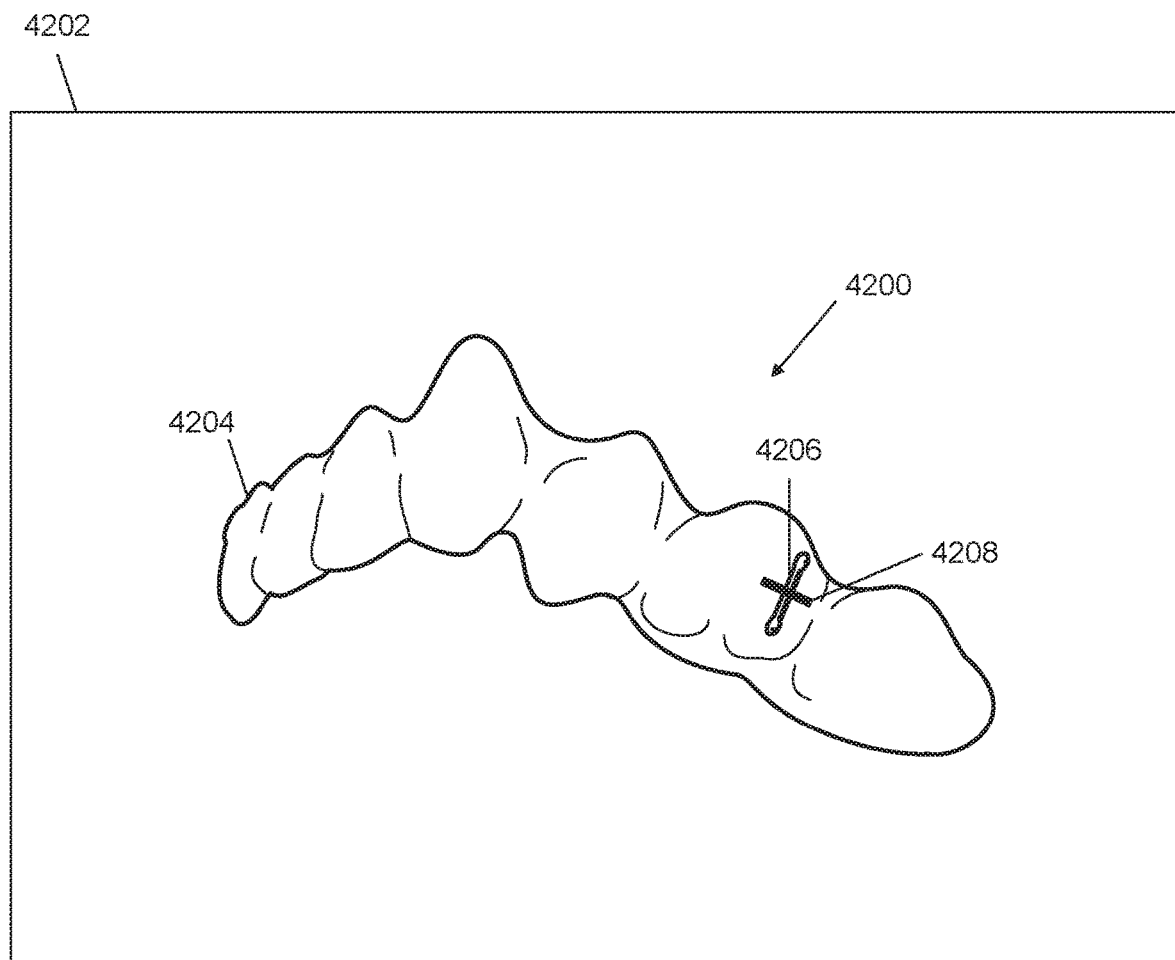
FIG. 42 illustrates a digital model of an orthodontic appliance, in accordance with some embodiments.

FIG. 42 illustrates a digital model 4200 of an orthodontic appliance, in accordance with some embodiments. The digital model 4200 can be shown to a user, e.g., via a user interface shown on a display 4202. In some embodiments, the digital model 4200 includes digital representations of one or more components of the appliance, such as digital representations of the appliance shell 4204, one or more discontinuities 4206, and one or more elastic members 4208. Optionally, the digital model 4200 can include digital representations of one or more auxiliary appliance components (e.g., guide features, retention features, channels, etc.). Alternatively or in combination, the digital model 4200 can include digital representations of one or more interfaces for facilitating coupling of an elastic member 4208 and/or auxiliary component to the shell 4204. The geometries and arrangement of the various components of the digital model 4200 can correspond to the desired geometries and arrangement of the components in the appliance to be fabricated. Accordingly, the digital model 4200 can be used as a basis for generating fabrication instructions for controlling a fabrication machine to produce the orthodontic appliance with the specified components. In embodiments where the fabrication machine is configured to perform one or more of the direct fabrication methods described herein, the fabrication instructions can include instructions for concurrently forming an appliance shell with one or more discontinuities, one or more elastic members, and/or one or more auxiliary components, according to the configuration of the corresponding digital representations of the digital model 4200.

Figure 43:
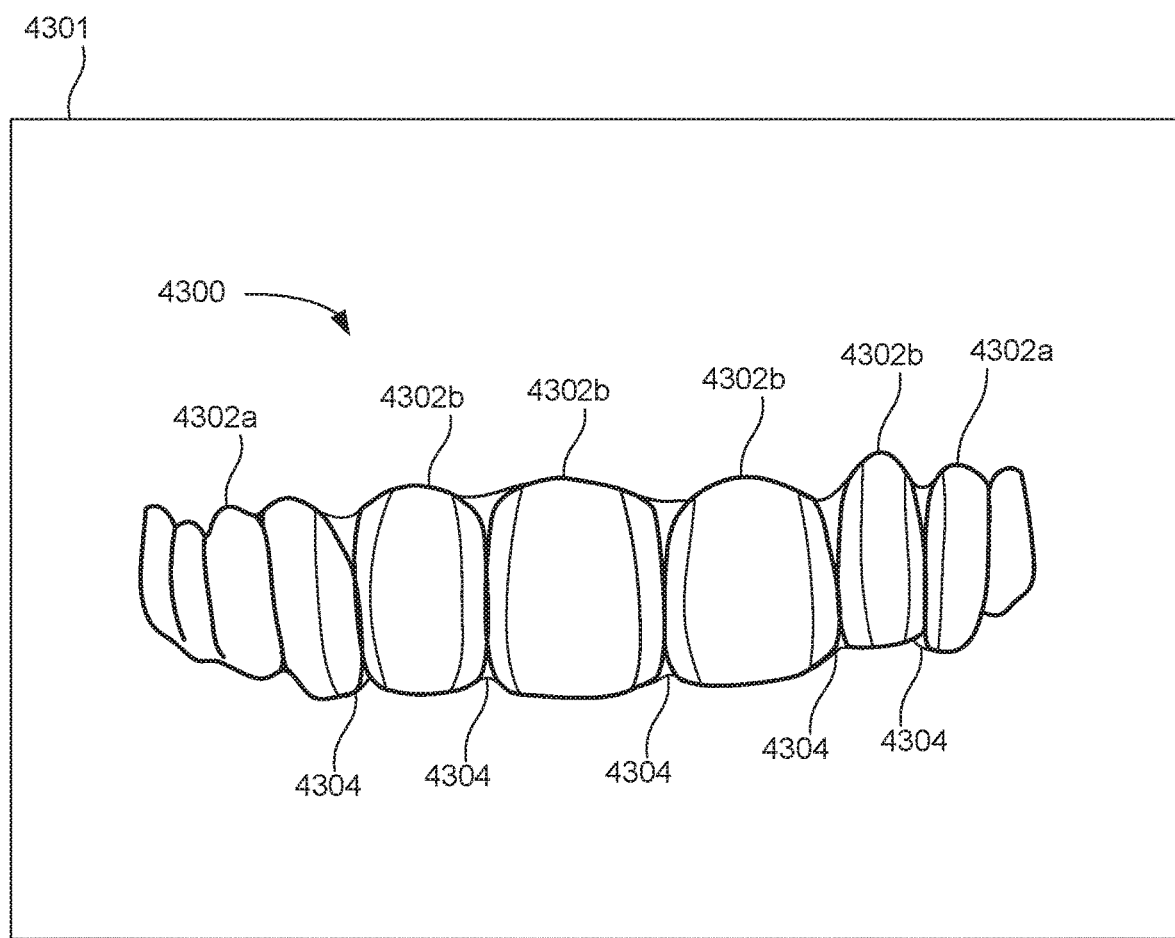
FIG. 43 illustrates a digital model of a segmented orthodontic appliance, in accordance with some embodiments.

FIG. 43 illustrates a digital model 4300 of a segmented orthodontic appliance, in accordance with some embodiments. The digital model 4300 can be shown to a user, e.g., via a user interface shown on a display 4301. In some embodiments, the digital model 4300 includes digital representations of one or more components of the appliance, such as digital representations of a plurality of discrete shell segments 4302a-b and a plurality of discrete elastic segments 4304. Optionally, in embodiments where the elastic segments 4304 are formed separately from and coupled to the shell segments 4302a-b, the digital model 4300 can include digital representations of one or more interfaces for facilitating coupling of the elastics 4304 to the segments 4302a-b. The geometries and arrangement of the various components of the digital model 4300 can correspond to the desired geometries and arrangement of the components in the appliance to be fabricated. Accordingly, the digital model 4300 can be used as a basis for generating fabrication instructions for controlling a fabrication machine to produce the orthodontic appliance with the specified components. In embodiments where the fabrication machine is configured to perform one or more of the direct fabrication methods described herein, the fabrication instructions can include instructions for concurrently forming an appliance shell having a plurality of shell segments joined by a plurality of elastic segments, according to the configuration of the corresponding digital representations of the digital model 4300.

Figure 44:
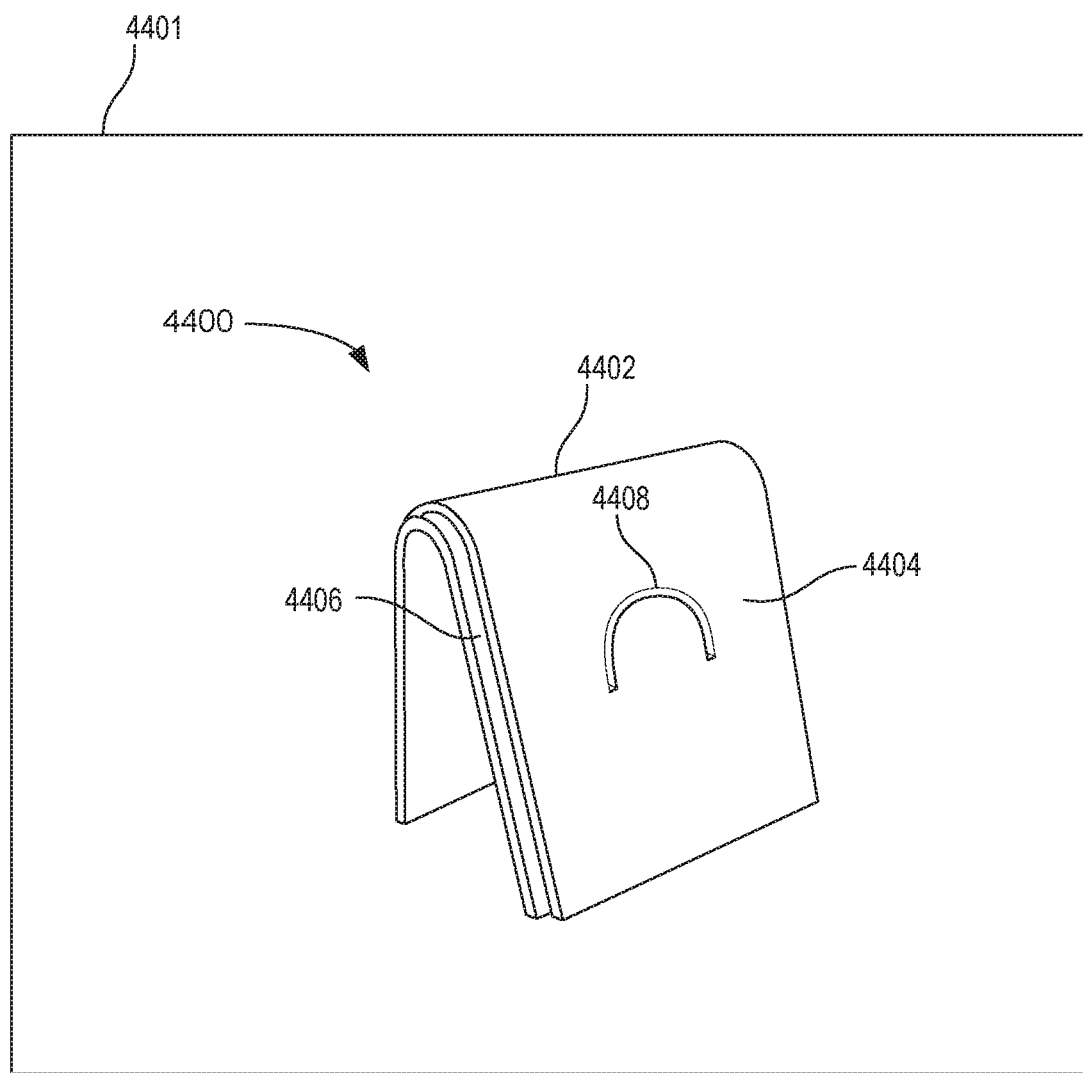
FIG. 44 illustrates a digital model of a layered orthodontic appliance, in accordance with some embodiments.

FIG. 44 illustrates a digital model 4400 of a layered orthodontic appliance, in accordance with some embodiments. The digital model 4400 can be shown to a user, e.g., via a user interface shown on a display 4401. In some embodiments, the digital model 4400 includes digital representations of one or more components of the appliance, such as digital representations of an appliance shell 4401 having an exterior layer 4404 and an interior layer 4406, and one or more discontinuities 4408 formed in the exterior layer 4404 and/or interior layer 4406. The geometries and arrangement of the various components of the digital model 4400 can correspond to the desired geometries and arrangement of the components in the appliance to be fabricated. Accordingly, the digital model 4400 can be used as a basis for generating fabrication instructions for controlling a fabrication machine to produce the orthodontic appliance with the specified components. In embodiments where the fabrication machine is configured to perform one or more of the direct fabrication methods described herein, the fabrication instructions can include instructions for concurrently forming an appliance shell with a plurality of layers and/or discontinuities, according to the configuration of the corresponding digital representations of the digital model 4400.

Figure 45:
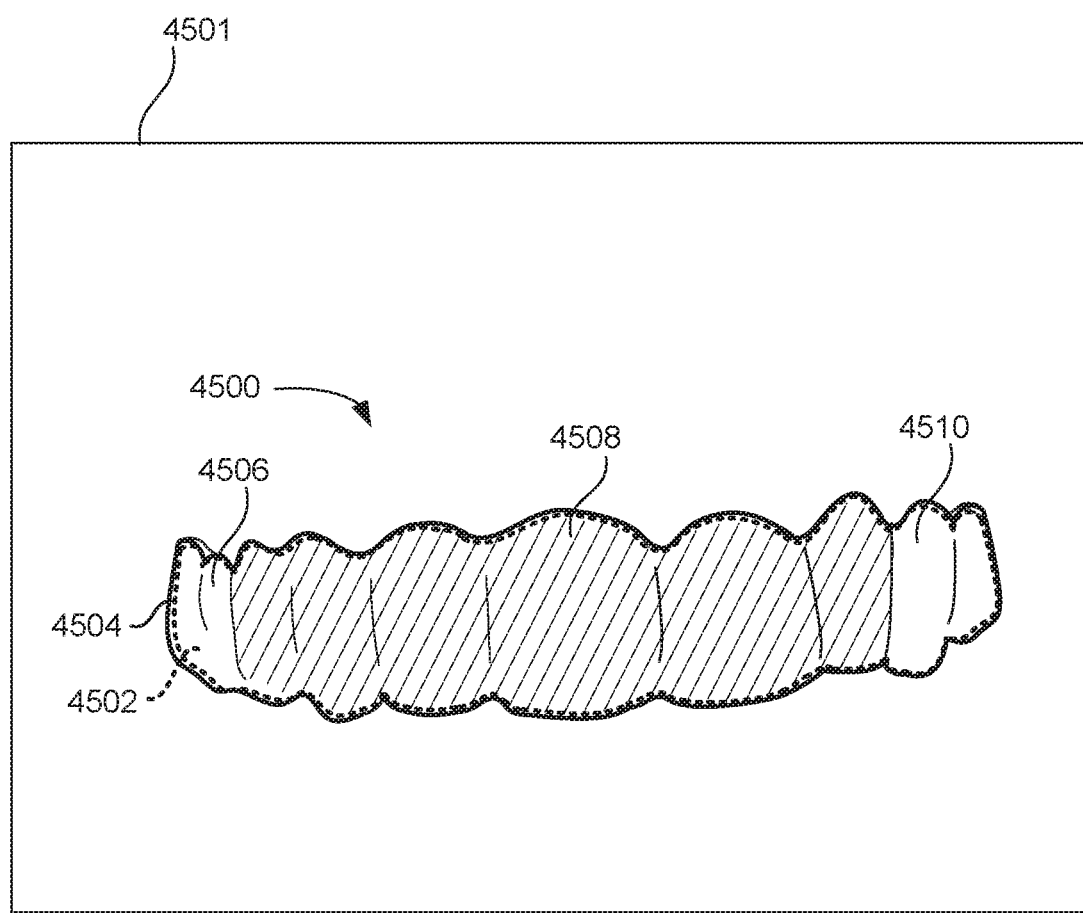
FIG. 45 illustrates a digital model of an elastic-coated orthodontic appliance, in accordance with some embodiments.

FIG. 45 illustrates a digital model 4500 of an elastic-coated orthodontic appliance, in accordance with some embodiments. The digital model 4500 can be shown to a user, e.g., via a user interface shown on a display 4501. In some embodiments, the digital model 4500 includes digital representations of one or more components of the appliance, such as digital representations of an appliance shell 4502 and an elastic coating 4504. Optionally, in embodiments where the elastic coating 4504 has heterogeneous material properties, the digital model 4500 can include digital representations the different portions of the coating 4504 (e.g., portions 4506, 4508, 4510). The geometries and arrangement of the various components of the digital model 4500 can correspond to the desired geometries and arrangement of the components in the appliance to be fabricated. Accordingly, the digital model 4500 can be used as a basis for generating fabrication instructions for controlling a fabrication machine to produce the orthodontic appliance with the specified components. In embodiments where the fabrication machine is configured to perform one or more of the direct fabrication methods described herein, the fabrication instructions can include instructions for concurrently forming an appliance shell with an elastic coating. In alternative embodiments where an elastic appliance is desired, the digital model 4500 can include the digital representation of the coating 4504 without the digital representation of the shell 4502, and the instructions can control the fabrication machine to directly fabricate the coating 4504 from one or more elastic materials without forming the shell in accordance with the digital model 4500.

Figure 46:
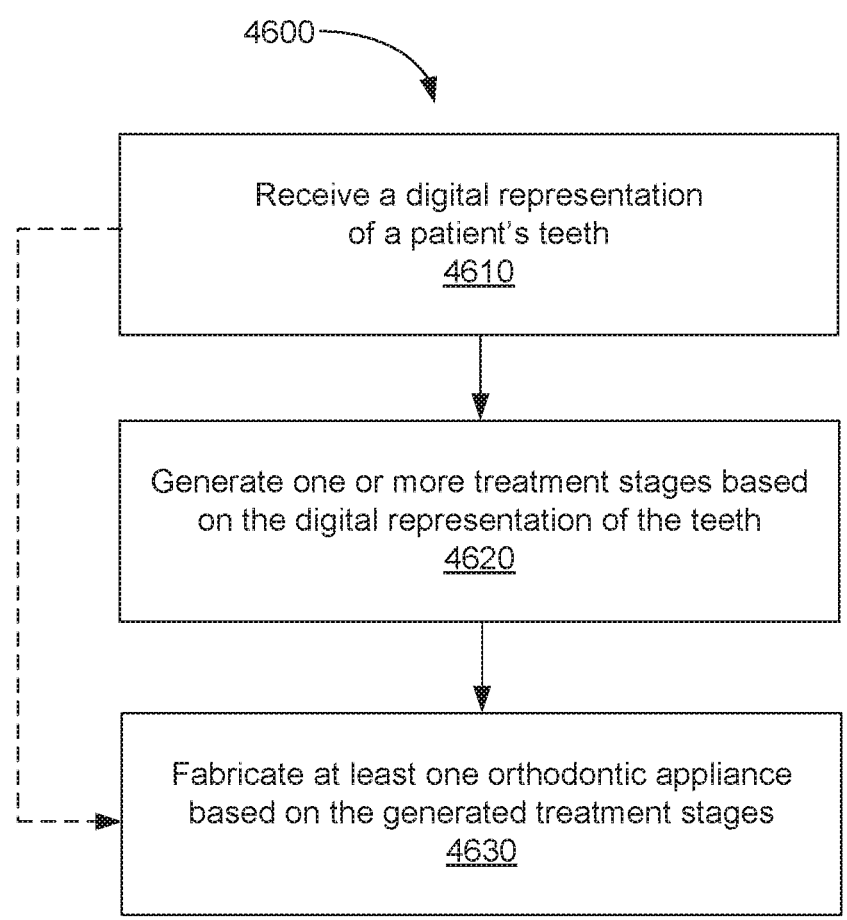
FIG. 46 illustrates a method for digitally planning an orthodontic treatment, in accordance with some embodiments.

FIG. 46 illustrates a method 4600 for digitally planning an orthodontic treatment and/or design or fabrication of an appliance, in accordance with some embodiments. The method 4600 can be applied to any of the treatment procedures described herein and can be performed by any suitable data processing system.

In step 4610, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 4620, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 4630, at least one orthodontic appliance is fabricated based on the generated treatment stages. For example, a set of appliances can be fabricated, each shaped to accommodate a tooth arrangement specified by one of the treatment stages, such that the appliances can be sequentially worn by the patient to incrementally reposition the teeth from the initial arrangement to the target arrangement. Some of the appliances can be shaped to accommodate a tooth arrangement specified by one of the treatment stages. Alternatively or in combination, some of the appliances can be shaped to accommodate a tooth arrangement that is different from the target arrangement for the corresponding treatment stage. For example, as previously described herein, an appliance may have a geometry corresponding to an overcorrected tooth arrangement. Such an appliance may be used to ensure that a suitable amount of force is expressed on the teeth as they approach or attain their desired target positions for the treatment stage. As another example, an appliance can be designed in order to apply a specified force system on the teeth and may not have a geometry corresponding to any current or planned arrangement of the patient's teeth.

The appliances can be fabricated using indirect fabrication and/or direct fabrication, as desired. The appliance set may include one or more of the orthodontic appliances described herein (e.g., orthodontic appliances having at least one discontinuity and/or at least elastic member, segmented appliances, layered appliances, elastic-coated appliances, etc.). The properties (e.g., number, geometry, configuration, material characteristics) of the structures of such appliances (e.g., discontinuities and/or elastic members, shell, shell segments, interior and exterior layers, elastic coating, etc.) can be selected to elicit the tooth movements specified by the corresponding treatment stage. At least some of these properties can be determined via suitable computer software or other digital-based approaches. The fabrication of the appliance may involve creating a digital model of the appliance to be used as input to a computer-controlled fabrication system.

For example, an appliance set may include one or more of the layered appliances described herein. The properties of the interior and exterior layers of these appliances (e.g., geometry, configuration, material characteristics) and the configuration of one or more discontinuities in the exterior layer can be selected to elicit the tooth movements specified by the corresponding treatment stage. In some embodiments, a layered appliance associated with a treatment stage may omit one or more portions of the interior layer or exterior layer. The determination of which portions to omit may be based on the particular tooth movements to be achieved during the treatment stage. For example, when contacting a tooth, the relatively elastic interior layer may produce increased frictional forces compared to the exterior layer. Accordingly, the removal of portions of the interior layer may in some instances facilitate the movement of the tooth relative to the appliance. Conversely, the presence of the interior layer at certain locations may be beneficial in embodiments where increased friction between the tooth surface and the appliance enhances force application onto the tooth.

The design of the appliances provided herein can be determined via suitable computer software or other digital-based approaches. Computer modeling strategies can be used to determine suitable force systems including one or more forces and/or torques to be applied to the teeth to elicit the desired tooth movements. For example, with respect to the layered appliances described herein, the arrangement and properties of the interior and exterior layers and the configuration of one or more discontinuities in the exterior layer can be designed to provide the specified forces and/or torques when the appliance is worn by the patient during an appropriate stage of treatment. As another example, with respect to the elastic-coated appliances described herein, the properties of the shell and/or elastic coating can be then be designed to provide the specified forces and/or torques when the appliance is worn by the patient during an appropriate stage of treatment. Additional examples of digital modeling and force analysis techniques suitable for use with the embodiments provided herein are described in application Ser. Nos. 12/623,340, 12/324,714, and 13/365,167, and in U.S. Pat. No. 8,439,672, the disclosures of which are herein incorporated by reference in their entirety. The digital models created using such methods may be used as input to a computer-controlled fabrication system for fabricating appliances.

Although the above steps show method 4600 of digitally planning an orthodontic treatment and/or design or fabrication of an appliance in accordance with embodiments, a person of ordinary skill in the art will recognize many variations based on the teaching described herein. Some of the steps may comprise sub-steps. Many of the steps may be repeated as often as beneficial to the design and/or fabrication process. One or more steps of the method 4600 may be applied to the fabrication of any orthodontic appliance, such as the embodiments described herein. Some of the steps may be optional, and the order of the steps can be varied. In some instances, staging of various arrangements or treatment stages may not be necessary for design and/or fabrication of an appliance. As illustrated by the dashed line in FIG. 46, design and/or fabrication of an orthodontic appliance, and perhaps a particular orthodontic treatment, may include use of a representation of the patient's teeth (e.g., receive a digital representation of the patient's teeth 4610), followed by design and/or fabrication of an orthodontic appliance based on a representation of the patient's teeth in the arrangement represented by the received representation. For example, a shell may be generated based on the representation of the patient's teeth (e.g., as in step 4610), followed by forming of discontinuities and/or application of elastic members to generate an appliance described in various embodiments herein. As another example, a shell may be generated based on the representation of the patient's teeth, followed by segmentation of the shell and application of elastics to generate an appliance described in various embodiments herein. In another example, a positive or negative model may be generated based on the representation of the patient's teeth (e.g., as in step 4610), followed by thermoforming of the interior and exterior layers onto the positive or negative model to form an appliance shell as described in various embodiments herein. In yet another example, For example, a shell may be generated based on the representation of the patient's teeth (e.g., as in step 4610), then coated with elastic to generate an appliance described in various embodiments herein.

Figure 47:
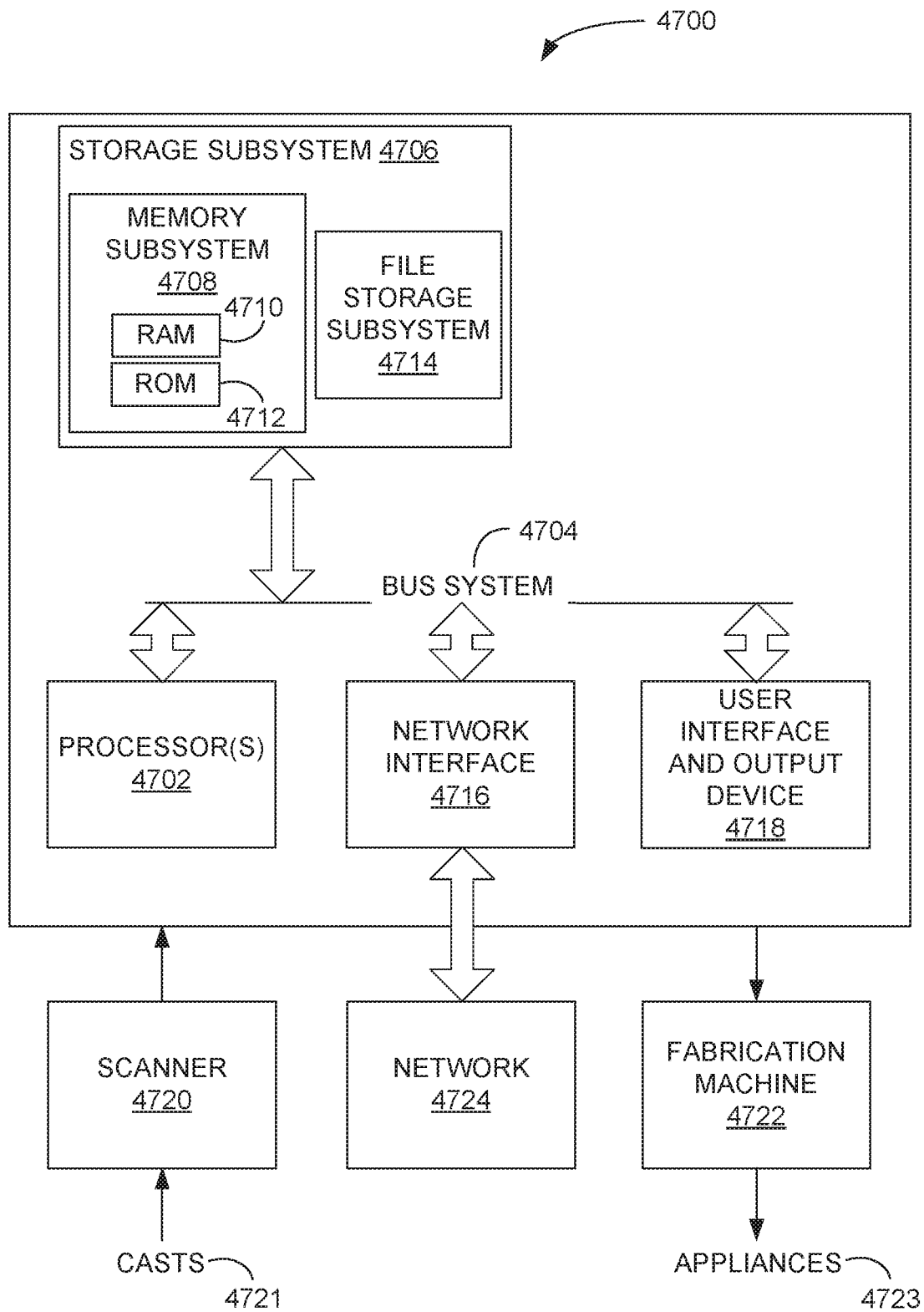
FIG. 47 is a simplified block diagram of a data processing system, in accordance with some embodiments.

FIG. 47 is a simplified block diagram of a data processing system 4700 that may be used in executing methods and processes described herein. The data processing system 4700 typically includes at least one processor 4702 that communicates with one or more peripheral devices via bus subsystem 4704. These peripheral devices typically include a storage subsystem 4706 (memory subsystem 4708 and file storage subsystem 4714), a set of user interface input and output devices 4718, and an interface to outside networks 4716. This interface is shown schematically as "Network Interface" block 4716, and is coupled to corresponding interface devices in other data processing systems via communication network interface 4724. Data processing system 4700 can include, for example, one or more computers, such as a personal computer, workstation, mainframe, laptop, and the like.

The user interface input devices 4718 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 4706 maintains the basic required programming, including computer readable media having instructions (e.g., operating instructions, etc.), and data constructs. The program modules discussed herein are typically stored in storage subsystem 4706. Storage subsystem 4706 typically includes memory subsystem 4708 and file storage subsystem 4714. Memory subsystem 4708 typically includes a number of memories (e.g., RAM 4710, ROM 4712, etc.) including computer readable memory for storage of fixed instructions, instructions and data during program execution, basic input/output system, etc. File storage subsystem 4714 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 4720 includes any means for obtaining a digital representation (e.g., images, surface topography data, etc.) of a patient's teeth (e.g., by scanning physical models of the teeth such as casts 4721, by scanning impressions taken of the teeth, or by directly scanning the intraoral cavity), which can be obtained either from the patient or from treating professional, such as an orthodontist, and includes means of providing the digital representation to data processing system 4700 for further processing. Scanner 4720 may be located at a location remote with respect to other components of the system and can communicate image data and/or information to data processing system 4700, for example, via a network interface 4724. Fabrication system 4722 fabricates appliances 4723 based on a treatment plan, including data set information received from data processing system 4700. Fabrication machine 4722 can, for example, be located at a remote location and receive data set information from data processing system 4700 via network interface 4724.

The data processing aspects of the methods described herein (e.g., the method 4600) can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing steps can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:
1. A method comprising:
   generating a digital model related to a treatment plan to treat a patient's teeth, wherein the digital model comprises:
      a digital representation of the patient's teeth at one or more treatment stages of the treatment plan, a digital representation of a discontinuity to be formed in a shell including a plurality of cavities configured to receive and resiliently reposition the patient's teeth, and a digital representation of an elastic member configured to interact with the discontinuity; and generating, based on the digital model, instructions to fabricate, using an additive manufacturing technique, the elastic member and the shell, including to fabricate at least a part of the shell and the elastic member joined together.

2. The method of claim 1, wherein the additive manufacturing fabrication technique comprises one or more of: vat photopolymerization, material jetting, binder jetting, fused deposition modeling, powder bed fusion, sheet lamination, or directed energy deposition.

3. The method of claim 1, wherein the instructions are configured to cause a fabrication machine to concurrently fabricate the shell and the discontinuity using the additive manufacturing fabrication technique.

4. The method of claim 3, wherein the instructions are configured to cause the fabrication machine to couple the elastic member to the shell after fabricating the shell and the discontinuity.

5. The method of claim 4, wherein the digital model further comprises a digital representation of an interface shaped to facilitate coupling of the elastic member to the at least the part of the shell.

6. The method of claim 1, wherein the instructions are configured to cause a fabrication machine to concurrently fabricate the shell and elastic member using the additive manufacturing fabrication technique.

7. The method of claim 1, wherein the instructions are configured to cause a fabrication machine to fabricate the shell from a first material and the elastic member from a second material, wherein the first material has a greater stiffness than the second material.

8. The method of claim 1, wherein the discontinuity comprises an aperture or cut in the shell.

9. The method of claim 8, wherein a portion of the elastic member spans the aperture or cut.

10. The method of claim 1, wherein the digital model further comprises a digital representation of one or more auxiliary components formed in or coupled to the shell, the one or more auxiliary components comprising one or more of: a channel, a guide feature, a fastening feature, a flap, a receptacle, a retention feature, a telescoping feature, an interproximal feature, or a biasing feature.

11. The method of claim 1, wherein the digital representation of the patient's teeth represents the shell.

12. The method of claim 1, wherein the elastic member is configured to control application of repositioning forces exerted by the shell.

13. The method of claim 1, wherein the elastic member comprises an elastic coating.

14. A method comprising:
gathering a digital model related to a treatment plan to treat a patient's teeth wherein the digital model comprises:
a digital representation of the patient's teeth at a plurality of treatment stages of the treatment plan;
a digital representation of a plurality of discontinuities to be formed in a plurality of shells for each of the plurality of treatment stages, each of the plurality of shells including a plurality of cavities configured to receive and resiliently reposition the patient's teeth; and
a digital representation of a plurality of elastic members configured to interact with the plurality of discontinuities at each of the plurality of treatment stages; and
generating, based on the digital model, instructions to fabricate, using an additive manufacturing technique, a first elastic member of the plurality of elastic members and a first shell of the plurality of shells for a first treatment stage of the plurality of treatment stages, with at least a part of the first shell being joined to the first elastic member when fabricated.

15. The method of claim 14, further comprising: generating, based on the digital model, instructions to fabricate, using the additive manufacturing technique, a second elastic member of the plurality of elastic members and a second shell of the plurality of shells for a second treatment stage of the plurality of treatment stages, with at least a part of the second shell being joined to the second elastic member.

16. The method of claim 15, wherein the first and second treatment stages are successive treatment stages of the treatment plan.

17. The method of claim 15, wherein a first discontinuity of the plurality of discontinuities corresponding to the first shell resides at a first location on the first shell, and a second discontinuity of the plurality of discontinuities corresponding to the second shell resides at a second location on the second shell, and the second location is different than the first location.

18. The method of claim 14, wherein the digital representation of the patient's teeth represents one or more of the plurality of shells.

19. The method of claim 14, wherein the plurality of elastic members are configured to control application of repositioning forces exerted by the plurality of shells.

20. The method of claim 14, wherein the additive manufacturing technique comprises forming the first elastic member and the first shell without using a physical template to define a geometry of the first shell.

21. The method of claim 14, wherein the first elastic member comprises multiple materials and the additive manufacturing technique comprises multi-material direct fabrication.

* * * * *

UNITED STATES PATENT AND TRADEMARK OFFICE
CERTIFICATE OF CORRECTION

PATENT NO. : 10,555,792 B2
APPLICATION NO. : 15/202392
DATED : February 11, 2020
INVENTOR(S) : Avi Kopelman and Jeeyoung Choi It is certified that error appears in the above-identified patent and that said Letters Patent is hereby corrected as shown below:

On the Title Page

Item (60), Related U.S. Application Data: "61/015,170, filed on Jun. 20, 2014," should read -- 62/015,170, filed on Jun. 20, 2014, --

Signed and Sealed this
Thirtieth Day of June, 2020

Andrei Iancu
*Director of the United States Patent and Trademark Office*